US012565528B2

(12) United States Patent
Toms et al.

(10) Patent No.: US 12,565,528 B2
(45) Date of Patent: Mar. 3, 2026

(54) LAG-3 ANTAGONIST THERAPY FOR LUNG CANCER

(71) Applicant: Bristol-Myers Squibb Company, Princeton, NJ (US)

(72) Inventors: Laurence David Toms, Princeton, NJ (US); Paul Andrew Basciano, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 18/759,360

(22) Filed: Jun. 28, 2024

(65) Prior Publication Data

US 2024/0417465 A1 Dec. 19, 2024

Related U.S. Application Data

(63) Continuation of application No. 18/033,200, filed as application No. PCT/US2021/056241 on Oct. 22, 2021, now abandoned.

(60) Provisional application No. 63/110,210, filed on Nov. 5, 2020, provisional application No. 63/104,744, filed on Oct. 23, 2020.

(51) Int. Cl.

| | |
|---|---|
| ***C07K 16/28*** | (2006.01) |
| ***A61K 31/282*** | (2006.01) |
| ***A61K 31/337*** | (2006.01) |
| ***A61K 31/519*** | (2006.01) |
| ***A61K 33/243*** | (2019.01) |
| ***A61K 39/00*** | (2006.01) |
| ***A61P 35/00*** | (2006.01) |

(52) U.S. Cl.

CPC ........ *C07K 16/2803* (2013.01); *A61K 31/282* (2013.01); *A61K 31/337* (2013.01); *A61K 31/519* (2013.01); *A61K 33/243* (2019.01); *A61P 35/00* (2018.01); *C07K 16/2818* (2013.01); *A61K 2039/507* (2013.01); *A61K 2039/545* (2013.01)

(58) Field of Classification Search

CPC ................................................ A61K 2039/505

See application file for complete search history.

(56) References Cited

U.S. PATENT DOCUMENTS

| | | | |
|---|---|---|---|
| 5,545,806 | A | 8/1996 | Lonberg et al. |
| 5,773,578 | A | 6/1998 | Hercend et al. |
| 5,811,097 | A | 9/1998 | Allison et al. |
| 5,874,250 | A | 2/1999 | Hercend et al. |
| 5,976,877 | A | 11/1999 | Hercend et al. |
| 5,977,318 | A | 11/1999 | Linsley et al. |
| 6,051,227 | A | 4/2000 | Allison et al. |
| 6,143,273 | A | 11/2000 | Faure et al. |
| 6,197,524 | B1 | 3/2001 | Romagnani |
| 6,207,156 | B1 | 3/2001 | Kuchroo et al. |
| 6,482,925 | B1 | 11/2002 | El et al. |
| 6,500,422 | B2 | 12/2002 | Biffoni |
| RE38,313 | E | 11/2003 | Faure et al. |
| 6,682,736 | B1 | 1/2004 | Hanson et al. |
| 6,808,710 | B1 | 10/2004 | Wood et al. |
| 6,984,720 | B1 | 1/2006 | Korman et al. |
| 7,034,121 | B2 | 4/2006 | Carreno et al. |
| 7,138,501 | B2 | 11/2006 | Ruben et al. |
| 7,306,906 | B2 | 12/2007 | Maruyama et al. |
| 7,329,737 | B2 | 2/2008 | Sexton et al. |
| 7,488,802 | B2 | 2/2009 | Collins et al. |
| 7,563,441 | B2 | 7/2009 | Graus et al. |
| 7,595,048 | B2 | 9/2009 | Honjo et al. |
| 7,605,238 | B2 | 10/2009 | Korman et al. |
| 7,635,757 | B2 | 12/2009 | Freeman et al. |
| 7,790,160 | B2 | 9/2010 | Von et al. |
| 7,850,965 | B2 | 12/2010 | Jensen et al. |
| 7,943,743 | B2 | 5/2011 | Korman et al. |
| 8,008,449 | B2 | 8/2011 | Korman et al. |
| 8,168,179 | B2 | 5/2012 | Honjo et al. |
| 8,168,757 | B2 | 5/2012 | Finnefrock et al. |
| 8,217,149 | B2 | 7/2012 | Irving et al. |
| 8,354,509 | B2 | 1/2013 | Carven et al. |
| 8,383,796 | B2 | 2/2013 | Korman et al. |
| 8,409,577 | B2 | 4/2013 | Thompson et al. |
| 8,476,419 | B2 | 7/2013 | Thielemans et al. |
| 8,551,481 | B2 | 10/2013 | Pardoll et al. |
| 8,609,089 | B2 | 12/2013 | Langermann et al. |
| 8,686,119 | B2 | 4/2014 | Rotem-Yehudar et al. |

(Continued)

FOREIGN PATENT DOCUMENTS

| | | | |
|---|---|---|---|
| CN | 101490085 | A1 | 7/2009 |
| JP | 2006340714 | A | 12/2006 |

(Continued)

OTHER PUBLICATIONS

Socincski et al. (J. Clin. Oncol. Jun. 10, 2012; 30 (17): 2055-62).*
Lei et al. (Crit. Rev. Oncol. Hematol. Aug. 2022; 176: 103727; pp. 1-9).*
Brahmer et al. (J. Clin. Oncol. Jul. 1, 2010; 28 (19): 3167-75).*
Kondo et al. (Thorac. Cancer. Jan. 12, 2022; 13 (4): 648-52).*
Clinical Trial NCT04623775 (first posted Nov. 10, 2020); pp. 1-25.*
Tawbi et al. (N. Engl. J. Med. Jan. 6, 2022; 386 (1): 24-34).*
Schuler et al. (Nat. Med. Jun. 2024; 30 (6): 1602-11).*
Agrawal, S., et al., "Clinical Pharmacokinetics (PK) of BMS-936558, a Fully Human Anti-pd-1 Monoclonal Antibody," Journal of Clinical Oncology 30(15):1 (2012), ASCO Annual Meeting Website, [retrieved on Jan. 13, 2015]. Retrieved from the Internet: URL:http://www.meetinglibrary.asco.org/content/98623-114.

(Continued)

*Primary Examiner* — Sue X Liu

(74) *Attorney, Agent, or Firm* — Sterne, Kessler, Goldstein & Fox P.L.L.C.

(57) ABSTRACT

The disclosure provides a method of treating a human subject afflicted with lung cancer with a lymphocyte activation gene-3 (LAG-3) antagonist. In some aspects, the method comprises combination of the LAG-3 antagonist with an additional therapeutic agent (e.g., a programmed death-1 pathway inhibitor) and/or anti-cancer therapy (e.g., chemotherapy such as a platinum doublet chemotherapy).

22 Claims, No Drawings

Specification includes a Sequence Listing.

(56) References Cited

U.S. PATENT DOCUMENTS

| | | | |
|---|---|---|---|
| 8,728,474 | B2 | 5/2014 | Honjo et al. |
| 8,779,105 | B2 | 7/2014 | Korman et al. |
| 8,900,587 | B2 | 12/2014 | Carven et al. |
| 9,005,614 | B2 | 4/2015 | Damiano et al. |
| 9,005,629 | B2 | 4/2015 | Pardoll et al. |
| 9,067,999 | B1 | 6/2015 | Honjo et al. |
| 9,073,994 | B2 | 7/2015 | Honjo et al. |
| 9,084,776 | B2 | 7/2015 | Korman et al. |
| 9,102,725 | B2 | 8/2015 | Korman et al. |
| 9,212,224 | B2 | 12/2015 | Cogswell et al. |
| 9,220,776 | B2 | 12/2015 | Sharma et al. |
| 9,273,135 | B2 | 3/2016 | Korman et al. |
| 9,358,289 | B2 | 6/2016 | Korman et al. |
| 9,387,247 | B2 | 7/2016 | Korman et al. |
| 9,393,301 | B2 | 7/2016 | Honjo et al. |
| 9,402,899 | B2 | 8/2016 | Honjo et al. |
| 9,439,962 | B2 | 9/2016 | Honjo et al. |
| 9,492,539 | B2 | 11/2016 | Korman et al. |
| 9,492,540 | B2 | 11/2016 | Korman et al. |
| 9,505,839 | B2 | 11/2016 | Lonberg et al. |
| 9,580,505 | B2 | 2/2017 | Korman et al. |
| 9,580,507 | B2 | 2/2017 | Korman et al. |
| 9,683,048 | B2 | 6/2017 | Freeman et al. |
| 9,856,320 | B2 | 1/2018 | Cogswell |
| 9,987,500 | B2 | 6/2018 | Papadopoulos et al. |
| 10,072,082 | B2 | 9/2018 | Cogswell |
| 10,081,681 | B2 | 9/2018 | Korman et al. |
| 10,138,299 | B2 | 11/2018 | Cogswell |
| 10,188,730 | B2 | 1/2019 | Liang et al. |
| 10,266,591 | B2 | 4/2019 | Lonberg |
| 10,266,594 | B1 | 4/2019 | Cogswell |
| 10,266,595 | B2 | 4/2019 | Cogswell |
| 10,266,596 | B1 | 4/2019 | Cogswell |
| 10,308,714 | B2 | 6/2019 | Cogswell |
| 10,316,090 | B2 | 6/2019 | Cogswell |
| 10,316,091 | B2 | 6/2019 | Cogswell |
| 10,323,092 | B2 | 6/2019 | Cogswell |
| 10,323,093 | B2 | 6/2019 | Cogswell |
| 10,344,089 | B2 | 7/2019 | Thudium |
| 10,358,495 | B2 | 7/2019 | Ullman et al. |
| 10,377,824 | B2 | 8/2019 | Lonberg et al. |
| 10,441,655 | B2 | 10/2019 | Korman et al. |
| 10,577,423 | B2 | 3/2020 | Cogswell et al. |
| 10,584,170 | B2 | 3/2020 | Cogswell et al. |
| 10,604,575 | B2 | 3/2020 | Cogswell et al. |
| 10,988,535 | B2 | 4/2021 | Thudium |
| 10,988,536 | B2 | 4/2021 | Thudium |
| 11,001,630 | B2 | 5/2021 | Thudium |
| 11,072,657 | B2 | 7/2021 | Nathan |
| 11,236,163 | B2 | 2/2022 | Thudium |
| 11,236,164 | B2 | 2/2022 | Thudium |
| 11,236,165 | B2 | 2/2022 | Thudium |
| 11,274,152 | B2 | 3/2022 | Korman et al. |
| 11,345,752 | B2 | 5/2022 | Lonberg et al. |
| 11,512,130 | B2 | 11/2022 | Thudium et al. |
| 11,530,267 | B2 | 12/2022 | Thudium et al. |
| 11,566,073 | B2 | 1/2023 | Edwards et al. |
| 11,723,975 | B2 | 8/2023 | Burton et al. |
| 11,767,361 | B2 | 9/2023 | Tschaika |
| 11,807,686 | B2 | 11/2023 | Novotny, Jr. et al. |
| 11,919,957 | B2 | 3/2024 | Bhagavatheeswaran et al. |
| 12,049,503 | B2 | 7/2024 | Novotny et al. |
| 12,227,576 | B2 | 2/2025 | Edwards et al. |
| 2002/0086014 | A1 | 7/2002 | Korman et al. |
| 2002/0146753 | A1 | 10/2002 | Ditzel et al. |
| 2003/0059937 | A1 | 3/2003 | Ruben et al. |
| 2003/0129601 | A1 | 7/2003 | Cole |
| 2004/0072164 | A1 | 4/2004 | Maruyama et al. |
| 2004/0171551 | A1 | 9/2004 | Triebel |
| 2005/0009136 | A1 | 1/2005 | Nixon et al. |
| 2005/0226876 | A1 | 10/2005 | Graus et al. |
| 2005/0276823 | A1 | 12/2005 | Cini et al. |
| 2006/0083744 | A1 | 4/2006 | Chen et al. |
| 2006/0110383 | A1 | 5/2006 | Honjo et al. |
| 2006/0177442 | A1 | 8/2006 | Von et al. |
| 2006/0240024 | A1 | 10/2006 | Pardoll et al. |
| 2007/0004910 | A1 | 1/2007 | Sexton et al. |
| 2007/0160598 | A1 | 7/2007 | Dennis et al. |
| 2008/0038264 | A1 | 2/2008 | Bodary et al. |
| 2008/0069822 | A1 | 3/2008 | Jensen et al. |
| 2008/0260641 | A1 | 10/2008 | Teeling et al. |
| 2008/0279865 | A1 | 11/2008 | Gomez-Navarro |
| 2009/0055944 | A1 | 2/2009 | Korman et al. |
| 2009/0203538 | A1 | 8/2009 | Sugioka et al. |
| 2009/0217401 | A1 | 8/2009 | Korman et al. |
| 2009/0252741 | A1 | 10/2009 | Liu |
| 2009/0297518 | A1 | 12/2009 | Honjo et al. |
| 2009/0317368 | A1 | 12/2009 | Chen |
| 2010/0055102 | A1 | 3/2010 | Langermann et al. |
| 2010/0196394 | A1 | 8/2010 | Pardoll et al. |
| 2010/0233183 | A1 | 9/2010 | Triebel et al. |
| 2011/0070238 | A1 | 3/2011 | Triebel et al. |
| 2011/0081341 | A1 | 4/2011 | Honjo et al. |
| 2011/0150892 | A1 | 6/2011 | Thudium et al. |
| 2011/0209230 | A1 | 8/2011 | Korman et al. |
| 2013/0017199 | A1 | 1/2013 | Langermann et al. |
| 2013/0122014 | A1 | 5/2013 | Korman et al. |
| 2013/0133091 | A1 | 5/2013 | Korman et al. |
| 2013/0309250 | A1 | 11/2013 | Cogswell et al. |
| 2014/0093511 | A1 | 4/2014 | Lonberg et al. |
| 2014/0212422 | A1 | 7/2014 | Korman et al. |
| 2014/0271684 | A1 | 9/2014 | Li |
| 2014/0294852 | A1 | 10/2014 | Korman et al. |
| 2014/0314714 | A1 | 10/2014 | Honjo et al. |
| 2014/0328833 | A1 | 11/2014 | Korman et al. |
| 2014/0341917 | A1 | 11/2014 | Nastri et al. |
| 2014/0348743 | A1 | 11/2014 | Korman et al. |
| 2015/0079109 | A1 | 3/2015 | Li et al. |
| 2015/0093380 | A1 | 4/2015 | Honjo et al. |
| 2015/0125463 | A1 | 5/2015 | Cogswell et al. |
| 2015/0165025 | A1 | 6/2015 | Korman et al. |
| 2015/0197572 | A1 | 7/2015 | Honjo et al. |
| 2015/0259420 | A1 | 9/2015 | Triebel et al. |
| 2015/0307609 | A1 | 10/2015 | Lonberg et al. |
| 2015/0337038 | A1 | 11/2015 | Korman et al. |
| 2016/0024593 | A1 | 1/2016 | Zheng et al. |
| 2016/0075782 | A1 | 3/2016 | Korman et al. |
| 2016/0090417 | A1 | 3/2016 | Cogswell et al. |
| 2016/0108121 | A1 | 4/2016 | Pardoll et al. |
| 2016/0152720 | A1 | 6/2016 | Kim et al. |
| 2016/0158355 | A1 | 6/2016 | Honjo et al. |
| 2016/0158356 | A1 | 6/2016 | Honjo et al. |
| 2016/0159905 | A1 | 6/2016 | Abdiche et al. |
| 2016/0222116 | A1 | 8/2016 | Korman et al. |
| 2016/0272708 | A1 | 9/2016 | Chen |
| 2016/0326248 | A1 | 11/2016 | Gutierrez et al. |
| 2016/0362495 | A1 | 12/2016 | Korman et al. |
| 2017/0051060 | A1 | 2/2017 | Honjo et al. |
| 2017/0088615 | A1 | 3/2017 | Korman et al. |
| 2017/0101472 | A1 | 4/2017 | Ullman et al. |
| 2017/0137514 | A1 | 5/2017 | Lonberg et al. |
| 2017/0143827 | A1 | 5/2017 | Sadineni et al. |
| 2017/0158767 | A1 | 6/2017 | Korman et al. |
| 2017/0168054 | A1 | 6/2017 | Balko et al. |
| 2017/0260271 | A1 | 9/2017 | Igawa et al. |
| 2018/0066054 | A1 | 3/2018 | Thudium |
| 2018/0086830 | A1 | 3/2018 | Triebel et al. |
| 2018/0244773 | A1 | 8/2018 | Gutierrez et al. |
| 2018/0273624 | A1 | 9/2018 | Cogswell |
| 2018/0282413 | A1 | 10/2018 | Cogswell |
| 2018/0282414 | A1 | 10/2018 | Cogswell |
| 2018/0312590 | A1 | 11/2018 | Cogswell |
| 2018/0319887 | A1 | 11/2018 | Cogswell |
| 2018/0346569 | A1 | 12/2018 | Wang et al. |
| 2018/0371087 | A1 | 12/2018 | Lonberg |
| 2019/0092863 | A1 | 3/2019 | Cogswell |
| 2019/0100589 | A1 | 4/2019 | Cogswell |
| 2019/0100590 | A1 | 4/2019 | Cogswell |
| 2019/0112376 | A1 | 4/2019 | Cogswell |
| 2019/0112377 | A1 | 4/2019 | Cogswell |
| 2019/0135920 | A1 | 5/2019 | Cogswell |
| 2019/0153099 | A1 | 5/2019 | Cogswell |
| 2019/0256594 | A1 | 8/2019 | Lonberg et al. |
| 2019/0276538 | A1 | 9/2019 | Thudium |

(56) References Cited

U.S. PATENT DOCUMENTS

| | | | |
|---|---|---|---|
| 2019/0276539 A1 | 9/2019 | Thudium | |
| 2020/0055938 A1 | 2/2020 | Desai et al. | |
| 2020/0062845 A1 | 2/2020 | Korman et al. | |
| 2020/0062846 A1 | 2/2020 | Honjo et al. | |
| 2020/0062848 A1 | 2/2020 | Korman et al. | |
| 2020/0138945 A1 | 5/2020 | Korman et al. | |
| 2020/0172617 A1 | 6/2020 | Stein et al. | |
| 2020/0231671 A1 | 7/2020 | Thudium | |
| 2020/0308282 A1 | 10/2020 | Cogswell et al. | |
| 2020/0385466 A1 | 12/2020 | Thudium | |
| 2020/0385467 A1 | 12/2020 | Thudium | |
| 2021/0009692 A1 | 1/2021 | Korman et al. | |
| 2021/0122820 A1 | 4/2021 | Gutierrez et al. | |
| 2021/0238287 A1 | 8/2021 | Srivastava et al. | |
| 2021/0283251 A1 | 9/2021 | Burton et al. | |
| 2021/0338813 A1 | 11/2021 | Maurer et al. | |
| 2021/0340250 A1 | 11/2021 | Korman et al. | |
| 2021/0380693 A1 | 12/2021 | Maier et al. | |
| 2022/0017619 A1 | 1/2022 | Nathan | |
| 2022/0185892 A1 | 6/2022 | Korman et al. | |
| 2022/0195040 A1 | 6/2022 | Thudium et al. | |
| 2022/0204612 A1 | 6/2022 | Thudium et al. | |
| 2022/0348653 A1 | 11/2022 | Hedvat et al. | |
| 2022/0411499 A1 | 12/2022 | Srivastava et al. | |
| 2023/0061544 A1 | 3/2023 | Korman et al. | |
| 2023/0077348 A1 | 3/2023 | Lonberg et al. | |
| 2023/0083487 A1 | 3/2023 | Nathan | |
| 2023/0111786 A1 | 4/2023 | Korman et al. | |
| 2023/0265188 A1 | 8/2023 | Srivastava et al. | |
| 2023/0272079 A1 | 8/2023 | Korman et al. | |
| 2023/0322919 A1 | 10/2023 | Thudium et al. | |
| 2024/0002512 A1 | 1/2024 | Cogswell et al. | |
| 2024/0034793 A1 | 2/2024 | Cogswell et al. | |
| 2024/0052035 A1 | 2/2024 | Tschaika | |
| 2024/0066123 A1 | 2/2024 | Burton et al. | |
| 2024/0092911 A1 | 3/2024 | Novotny et al. | |
| 2024/0101666 A1 | 3/2024 | Toms et al. | |
| 2024/0150459 A1 | 5/2024 | Gutierrez et al. | |
| 2024/0190963 A1 | 6/2024 | Bhagavatheeswaran et al. | |
| 2024/0301066 A1 | 9/2024 | Bhagavatheeswaran et al. | |
| 2024/0417471 A1 | 12/2024 | Cogswell et al. | |
| 2024/0417473 A1 | 12/2024 | Srivastava et al. | |
| 2025/0011466 A1 | 1/2025 | Feltquate et al. | |
| 2025/0043006 A1 | 2/2025 | Novotny et al. | |
| 2025/0136684 A1 | 5/2025 | Lonberg et al. | |
| 2025/0145713 A1 | 5/2025 | Edwards et al. | |
| 2025/0152708 A1 | 5/2025 | Burton et al. | |
| 2025/0154254 A1 | 5/2025 | Thudium et al. | |
| 2025/0154257 A1 | 5/2025 | Nathan | |
| 2025/0163152 A1 | 5/2025 | Korman et al. | |
| 2025/0163155 A1 | 5/2025 | Korman et al. | |
| 2025/0179174 A1 | 6/2025 | Moss et al. | |
| 2025/0197495 A1 | 6/2025 | Gutierrez et al. | |
| 2025/0215076 A1 | 7/2025 | Moss et al. | |
| 2025/0257136 A1 | 8/2025 | Cogswell et al. | |
| 2025/0263486 A1 | 8/2025 | Cogswell et al. | |
| 2025/0270322 A1 | 8/2025 | Coggswell et al. | |

FOREIGN PATENT DOCUMENTS

| | | | |
|---|---|---|---|
| WO | WO-9110682 A1 | 7/1991 | |
| WO | WO-9530750 A2 | 11/1995 | |
| WO | WO-9703695 A1 | 2/1997 | |
| WO | WO-9713852 A1 | 4/1997 | |
| WO | WO-9732733 A1 | 9/1997 | |
| WO | WO-9842752 A1 | 10/1998 | |
| WO | WO-9858059 A1 | 12/1998 | |
| WO | WO-0037504 A2 | 6/2000 | |
| WO | WO-0069914 A2 | 11/2000 | |
| WO | WO-0114424 A2 | 3/2001 | |
| WO | WO-200243478 A2 | 6/2002 | |
| WO | WO-03088808 A2 | 10/2003 | |
| WO | WO-03099196 A2 | 12/2003 | |
| WO | WO-2004004771 A1 | 1/2004 | |
| WO | WO-2004039956 A2 | 5/2004 | |
| WO | WO-2004078928 A2 | 9/2004 | |
| WO | WO-2005034733 A2 | 4/2005 | |
| WO | WO-2005059106 A2 | 6/2005 | |
| WO | WO-2005067620 A2 | 7/2005 | |
| WO | WO-2006007850 A1 | 1/2006 | |
| WO | WO-2006121168 A1 | 11/2006 | |
| WO | WO-2006126835 A1 | 11/2006 | |
| WO | WO-2006133396 A2 | 12/2006 | |
| WO | WO-2007005874 A2 | 1/2007 | |
| WO | WO-2007113648 A2 | 10/2007 | |
| WO | WO-2008007648 A1 | 1/2008 | |
| WO | WO-2008073160 A2 | 6/2008 | |
| WO | WO-2008121615 A2 | 10/2008 | |
| WO | WO-2008121616 A2 | 10/2008 | |
| WO | WO-2008132601 A1 | 11/2008 | |
| WO | WO-2008156712 A1 | 12/2008 | |
| WO | WO-2009014708 A2 | 1/2009 | |
| WO | WO-2009044273 A2 | 4/2009 | |
| WO | WO-2009114335 A2 | 9/2009 | |
| WO | WO-2010019570 A2 | 2/2010 | |
| WO | WO-2011008092 A2 | 1/2011 | |
| WO | WO-2011066389 A1 | 6/2011 | |
| WO | WO-2011161699 A2 | 12/2011 | |
| WO | WO-2012009442 A2 | 1/2012 | |
| WO | WO-2012054438 A1 | 4/2012 | |
| WO | WO-2012059858 A1 | 5/2012 | |
| WO | WO-2012122444 A1 | 9/2012 | |
| WO | WO-2012145493 A1 | 10/2012 | |
| WO | WO-2013014668 A1 | 1/2013 | |
| WO | WO-2013063186 A2 | 5/2013 | |
| WO | WO-2013079174 A1 | 6/2013 | |
| WO | WO-2013166118 A2 | 11/2013 | |
| WO | WO-2013173223 A1 | 11/2013 | |
| WO | WO-2013181634 A2 | 12/2013 | |
| WO | WO-2014008218 A1 | 1/2014 | |
| WO | WO-2014140180 A1 | 9/2014 | |
| WO | WO-2014179664 A2 | 11/2014 | |
| WO | WO-2014194302 A2 | 12/2014 | |
| WO | WO-2014206107 A1 | 12/2014 | |
| WO | WO-2015016718 A1 | 2/2015 | |
| WO | WO-2015034820 A1 | 3/2015 | |
| WO | WO-2015035606 A1 | 3/2015 | |
| WO | WO-2015042246 A1 | 3/2015 | |
| WO | WO-2015085847 A1 | 6/2015 | |
| WO | WO-2015094995 A2 | 6/2015 | |
| WO | WO-2015094996 A2 | 6/2015 | |
| WO | WO-2015095404 A2 | 6/2015 | |
| WO | WO-2015112800 A1 | 7/2015 | |
| WO | WO-2015112900 A1 | 7/2015 | |
| WO | WO-2015116539 A1 | 8/2015 | |
| WO | WO-2015138920 A1 | 9/2015 | |
| WO | WO-2015160641 A2 | 10/2015 | |
| WO | WO-2015175340 A1 | 11/2015 | |
| WO | WO-2015176033 A1 | 11/2015 | |
| WO | WO-2015200119 A1 | 12/2015 | |
| WO | WO-2016028672 A1 | 2/2016 | |
| WO | WO-2016039749 A1 | 3/2016 | |
| WO | WO-2016057624 A1 | 4/2016 | |
| WO | WO-2016077518 A1 | 5/2016 | |
| WO | WO-2016100285 A1 | 6/2016 | |
| WO | WO-2016100608 A1 | 6/2016 | |
| WO | WO-2016106159 A1 | 6/2016 | |
| WO | WO-2016110593 A1 | 7/2016 | |
| WO | WO-2016126646 A1 | 8/2016 | |
| WO | WO-2016126858 A2 | 8/2016 | |
| WO | WO-2016127220 A1 | 8/2016 | |
| WO | WO-2016149201 A2 | 9/2016 | |
| WO | WO-2016149351 A1 | 9/2016 | |
| WO | WO-2016168716 A1 | 10/2016 | |
| WO | WO-2016176504 A1 | 11/2016 | |
| WO | WO-2016191751 A1 | 12/2016 | |
| WO | WO-2016196237 A1 | 12/2016 | |
| WO | WO-2016197367 A1 | 12/2016 | |
| WO | WO-2016200782 A1 | 12/2016 | |
| WO | WO-2017004153 A1 | 1/2017 | |
| WO | WO-2017013436 A1 | 1/2017 | |
| WO | WO-2017015560 A2 | 1/2017 | |
| WO | WO-2017019846 A1 | 2/2017 | |
| WO | WO-2017019894 A1 | 2/2017 | |

(56) References Cited

FOREIGN PATENT DOCUMENTS

| | | | | |
|---|---|---|---|---|
| WO | WO-2017020291 A1 | 2/2017 | | |
| WO | WO-2017020858 A1 | 2/2017 | | |
| WO | WO-2017024465 A1 | 2/2017 | | |
| WO | WO-2017024515 A1 | 2/2017 | | |
| WO | WO-2017025016 A1 | 2/2017 | | |
| WO | WO-2017025051 A1 | 2/2017 | | |
| WO | WO-2017025498 A1 | 2/2017 | | |
| WO | WO-2017034916 A1 | 3/2017 | | |
| WO | WO-2017037203 A1 | 3/2017 | | |
| WO | WO-2017040790 A1 | 3/2017 | | |
| WO | WO-2007045996 A1 | 4/2017 | | |
| WO | WO-2017062888 A1 | 4/2017 | | |
| WO | WO-2017066227 A1 | 4/2017 | | |
| WO | WO-2017070585 A1 | 4/2017 | | |
| WO | WO-2017079150 A1 | 5/2017 | | |
| WO | WO-2017086367 A1 | 5/2017 | | |
| WO | WO-2017086419 A1 | 5/2017 | | |
| WO | WO-2017087589 A2 | 5/2017 | | |
| WO | WO-2017087599 A1 | 5/2017 | | |
| WO | WO-2017087678 A2 | 5/2017 | | |
| WO | WO-2017087870 A1 | 5/2017 | | |
| WO | WO-2017087901 A2 | 5/2017 | | |
| WO | WO-2017106061 A1 | 6/2017 | | |
| WO | WO-2017106129 A1 | 6/2017 | | |
| WO | WO-2017123557 A1 | 7/2017 | | |
| WO | WO-2017132508 A1 | 8/2017 | | |
| WO | WO-2017132827 A1 | 8/2017 | | |
| WO | WO-2017133540 A1 | 8/2017 | | |
| WO | WO-2017149143 A1 | 9/2017 | | |
| WO | WO-2017151830 A1 | 9/2017 | | |
| WO | WO-2017176608 A1 | 10/2017 | | |
| WO | WO-2017198741 A1 | 11/2017 | | |
| WO | WO-2017210624 A1 | 12/2017 | | |
| WO | WO-2017210631 A1 | 12/2017 | | |
| WO | WO-2017219995 A1 | 12/2017 | | |
| WO | WO-2017220555 A1 | 12/2017 | | |
| WO | WO-2017220569 A1 | 12/2017 | | |
| WO | WO-2018009505 A1 | 1/2018 | | |
| WO | WO-2018034227 A1 | 2/2018 | | |
| WO | WO-2018044963 A1 | 3/2018 | | |
| WO | WO-2018057506 A1 | 3/2018 | | |
| WO | WO-2018069500 A2 | 4/2018 | | |
| WO | WO-2018071500 A1 | 4/2018 | | |
| WO | WO-2018071824 A1 | 4/2018 | | |
| WO | WO-2018083087 A2 | 5/2018 | | |
| WO | WO-2018085750 A2 | 5/2018 | | |
| WO | WO-2018118848 A1 | 6/2018 | | |
| WO | WO-2018148476 A1 | 8/2018 | | |
| WO | WO-2018152687 A1 | 8/2018 | | |
| WO | WO-2018183171 A1 | 10/2018 | | |
| WO | WO-2018185043 A1 | 10/2018 | | |
| WO | WO-2018185046 A1 | 10/2018 | | |
| WO | WO-2018201096 A1 | 11/2018 | | |
| WO | WO-2018204374 A1 | 11/2018 | | |
| WO | WO-2018208868 A1 | 11/2018 | | |
| WO | WO-2018217940 A2 | 11/2018 | | |
| WO | WO-2018218215 A1 | 11/2018 | | |
| WO | WO-2018222711 A2 | 12/2018 | | |
| WO | WO-2018222718 A1 | 12/2018 | | |
| WO | WO-2018222722 A2 | 12/2018 | | |
| WO | WO-2018223040 A1 | 12/2018 | | |
| WO | WO-2018237153 A1 | 12/2018 | | |
| WO | WO-2019011306 A1 | 1/2019 | | |
| WO | WO-2019018730 A1 | 1/2019 | * | A61K 39/0011 |
| WO | WO-2019070643 A1 | 4/2019 | | |
| WO | WO-2019075468 A1 | 4/2019 | | |
| WO | WO-2019099838 A1 | 5/2019 | | |
| WO | WO-2019147662 A1 | 8/2019 | | |
| WO | WO-2019169123 A1 | 9/2019 | | |
| WO | WO-2019191676 A1 | 10/2019 | | |
| WO | WO-2019200395 A1 | 10/2019 | | |
| WO | WO-2019241098 A1 | 12/2019 | | |
| WO | WO-2020023707 A1 | 1/2020 | | |
| WO | WO-2020055702 A1 | 3/2020 | | |
| WO | WO-2020081928 A1 | 4/2020 | | |
| WO | WO-2020086724 A1 | 4/2020 | | |
| WO | WO-2021055994 A1 | 3/2021 | | |
| WO | WO-2021092380 A1 | 5/2021 | | |
| WO | WO-2021133653 A1 | 7/2021 | | |
| WO | WO-2022047189 A1 | 3/2022 | | |
| WO | WO-2022087402 A1 | 4/2022 | * | A61K 31/282 |

OTHER PUBLICATIONS

Anonymous: "A Phase 1 Dose Escalation and Cohort Expansion Study of the Safety, Tolerability, and Efficacy of Anti-LAG-3 (BMS-986016) in Relapsed or Refractory Chronic Lymphocytic Leukemia and Lymphomas and Multiple Myeloma," ClinicaiTrials.gov Archive Identifier NCT02061761, accessed at https://clinicaltrials.gov/archive/NCT02061761/2014_11_20, accessed on Jun. 16, 2015, 5 pages.

Anonymous: "A Phase 1 Dose Escalation and Cohort Expansion Study of the Safety, Tolerability, and Efficacy of Anti-LAG-3 Monoclonal Antibody (BMS-986016) Administered Alone and in Combination With Anti-PD-1 Monoclonal Antibody (Nivolumab, BMS-936558) in Advanced Solid Tumors," ClinicaiTrials.gov Archive Identifier NCT01968109, accessed at https://clinicaltrials.gov/archive/NCT01968109/2014_01_23, last accessed on Jun. 12, 2015, 5 pages.

ATCC Product Data Sheet, A3.4H2 (ATCC® HB-12319™), American Type Culture Collections, 2013. 2 pages.

ATCC Product Data Sheet, A3.6B10 (ATCC® HB-12318™), American Type Culture Collections, 2013. 2 pages.

Baixeras, E., et al., "Characterization of the Lymphocyte Activation Gene 3-encoded Protein. A New Ligand for Human Leukocyte Antigen Class II Antigens," The Journal of Experimental Medicine 176(2):327-337, Rockefeller University Press, United States (Aug. 1992).

Blackburn, S.D., et al., "Coregulation of CD8+ T cell exhaustion by multiple inhibitory receptors during chronic viral infection," Nature immunology 10(1):29-37, Nature America Inc., United States (Jan. 2009).

Casati, C., et al., "Soluble Human LAG-3 Molecule Amplifies the in Vitro Generation of Type 1 Tumor-specific Immunity," Cancer Research 66(8):4450-4460, American Association for Cancer Research, United States (Apr. 2006).

Cashion, M.P. and Long, T.E., "Biomimetic Design and Performance of Polymerizable Lipids," Accounts of Chemical Research 42(8):1016-1025, American Chemical Society, United States (Aug. 2009).

Chelius, D., et al., "Identification and Characterization of Deamidation Sites in the Conserved Regions of Human Immunoglobulin Gamma Antibodies," Analytical Chemistry 77(18):6004-6011, American Chemical Society, United States (Sep. 2005).

Cleland, J,L., et al., "The Development of Stable Protein Formulations: A Close Look at Protein Aggregation, Deamidation, and Oxidation," Critical Reviews in Therapeutic Drug Carrier Systems 10(4):307-377, CRC Press, United States (Jan. 1993).

Correia, I,R., et al., "Stability of IgG Isotypes in Serum," mAbs 2(3):221-232, Taylor & Francis, United States (May-Jun. 2010).

De Pascalis, R., et al., "Grafting of 'Abbreviated' Complementarity-determining Regions Containing Specificity-determining Residues Essential for Ligand Contact to Engineer a Less Immunogenic Humanized Monoclonal Antibody," Journal of Immunology 169(6):3076-3084, The American Association of Immunologists, United States (Sep. 2002).

Drake, C.G., et al., "Blocking the Regulatory T Cell Molecule LAG-3 Augments in Vivo Anti-tumor Immunity in an Autochthonous Model of Prostate Cancer," Journal of Clinical Oncology 24(18):2573 (Jun. 2006).

El Mir, S. and Triebel, F., "A Soluble Lymphocyte Activation Gene-3 Molecule Used as a Vaccine Adjuvant Elicits Greater Humoral and Cellular Immune Responses to Both Particulate and Soluble Antigens," Journal of Immunology 164(11):5583-5589, American Association of Immunologists, United States (Jun. 2000).

Extended European Search Report for EP Application No. 17177885, Hague, Netherlands, mailed on Nov. 17, 2017.

(56) References Cited

OTHER PUBLICATIONS

Extended European Search Report mailed Feb. 23, 2017 in EP Patent Application No. 16197459.7, European Patent Office, Munich, Germany, 15 pages.
Fishwild, D.M., et al., "High-Avidity Human IgG Kappa Monoclonal Antibodies from a Novel Strain of Minilocus Transgenic Mice," Nature Biotechnology 14(7):845-851, Nature America Publishing, United States (Jul. 1996).
Goding, S,R., et al., "Combination of Adoptive Cell Transfer, Anti-PD-L1 and Anti-LAG-3 Antibodies for the Treatment of Recurrent Tumors," OncoImmunology 2(8), 4 pages (May 2013).
Grosso, J.F., et al., "LAG-3 Regulates CD8+ T Cell Accumulation and Effector Function in Murine Self- and Tumor-tolerance Systems," The Journal of Clinical Investigation 117(11):3383-3392, American Society for Clinical Investigation, United States (Nov. 2007).
Harris, R.J., et al., "Identification of Multiple Sources of Charge Heterogeneity in a Recombinant Antibody," Journal of chromatography. B, Biomedical Sciences and Applications 752(2):233-245, Elsevier, Netherlands (Mar. 2001).
Huang, C,T., et al., "Role of LAG-3 in Regulatory T Cells," Immunity 21(4):503-513, Cell Press, United States (Oct. 2004).
Huard, B., et al., "Characterization of the Major Histocompatibility Complex Class II Binding Site on LAG-3 Protein," Proceedings of the National Academy of Sciences of the United States of America 94(11):5744-5749, National Academy of Sciences, United States (May 1997).
Huard, B., et al., "Cellular expression and tissue distribution of the humanLAG-3-encoded protein, an MHC class II ligand," Immunogenetics 39:213-217, Springer-Verlag, Germany (Jan. 1994).
Huard, B., et al., "Lymphocyte-activation Gene 3/major Histocompatibility Complex Class II Interaction Modulates the Antigenic Response of CD4+ T Lymphocytes," European Journal of Immunology 24(12):3216-3221, Wiley-VCH, Germany (Dec. 1994).
Huard, B., et al., "T Cell Major Histocompatibility Complex Class II Molecules Down-regulate CD4+ T Cell Clone Responses Following LAG-3 Binding," European Journal of Immunology 26(5):1180-1186, Wiley-VCH, Germany (May 1996).
International Preliminary Report on Patentability and Written Opinion for Application Serial No. PCT/US2013/48999, issued on Jan. 6, 2015, 7 pages.
International Preliminary Report on Patentability for Application No. PCT/US2009/053405, mailed on Feb. 15, 2011, 10 pages.
International Preliminary Report on Patentability for Application Serial No. PCT/US2014/056277, issued on Mar. 22, 2016, 10 pages.
International Search Report and written opinion for International Application No. PCT/US2009/053405, Isa/US Alexandria, Virginia, mailed on Mar. 31, 2010, 15 pages.
International Search Report and Written Opinion for International Application No. PCT/US2013/48999, European patent office, Rijswijk, mailed on Sep. 23, 2013, 11 pages.
International Search Report and Written Opinion for International Application No. PCT/US2014/056277, European patent office, Rijswijk, mailed on Feb. 4, 2015, 15 pages.
International Search Report and Written Opinion for International Application No. PCT/US2015/012916, European patent office, Rijswijk, mailed on Jun. 23, 2015, 12 pages.
Iouzalen, N., et al., "LAP, A Lymphocyte Activation Gene-3 (LAG-3)-associated Protein That Binds to a Repeated EP Motif in the Intracellular Region of LAG-3, May Participate in the Down-regulation of the CD3/TCR Activation Pathway," European Journal of Immunology 31(10):2885-2891, Wiley-VCH, Germany (Oct. 2001).
Kocak, E., et al., "Combination Therapy with Anti-CTL Antigen-4 and Anti-4-1BB Antibodies Enhances Cancer Immunity and Reduces Autoimmunity," Cancer Research 66(14):7276-7284, American Association for Cancer Research, United States (Jul. 2006).
Kosky, A,A., et al., "Multivariate Analysis of the Sequence Dependence of Asparagine Deamidation Rates in Peptides," Pharmaceutical Research 26(11):2417-2428, Kluwer Academic/Plenum Publishers, United states (Nov. 2009).
Kroon, D,J., et al., "Identification of Sites of Degradation in a Therapeutic Monoclonal Antibody by Peptide Mapping," Pharmaceutical Research 9(11):1386-1393, Kluwer Academic/Plenum Publishers, United states (Nov. 1992).
Lonberg, N., et al., "Antigen-specific Human Antibodies from Mice Comprising Four Distinct Genetic Modifications," Nature 368(6474):856-859, Nature Publishing Group, United States (Apr. 1994).
Maccallum, R.M., et al., "Antibody-antigen Interactions: Contact Analysis and Binding Site Topography," Journal of Molecular Biology 262(5):732-745, Academic Press, England (Oct. 1996).
Macon-Lemaitre, L. and Triebel, F., "The Negative Regulatory Function of the Lymphocyte-activation Gene-3 Co-receptor (CD223) on Human T Cells," Immunology 115(2):170-178, Blackwell Scientific Publications, England (Jun. 2005).
Pardoll, D., "Chapter 14-Dendritic Cells and Coregulatory Signals: Immune Checkpoint Blockade to Stimulate Immunotherapy," Cancer Immunotherapy Immune Suppression and Tumor Growth, pp. 257-275, Elsevier Inc., United States (Jan. 2007).
Prigent, P., et al., "Lymphocyte Activation Gene-3 Induces Tumor Regression and Antitumor Immune Responses," European Journal of Immunology 29(12):3867-3876, Wiley-VCH, Germany (Dec. 1999).
Reply to Communication from the Examining Division dated Nov. 25, 2016 in European Application No. 13737946.7 filed on Jul. 2, 2013, pp. 115-119.
Robinson, N,E. and Robinson, A,B., "Molecular Clocks," Proceedings of the National Academy of Sciences of the United States of America 98(3):944-949, National Academy of Sciences, United states (Jan. 2001).
Subramanyam, M., et al., "Soluble Human Lymphocyte Activation Gene-3 Modulates Allospecific T Cell Responses," International Immunology 10(5):679-689, University Press, England (May 1998).
Supplementary European Search Report for EP Application No. 09807162.4, European Patent Office, Munich, Germany, mailed on Dec. 21, 2012, 9 pages.
Third Party Observation dated Oct. 7, 2016 for European Application No. 13737946.7 filed on Jul. 2, 2013, 17 pages.
Triebel, F., et al., "LAG-3, A Novel Lymphocyte Activation Gene Closely Related to CD4," The Journal of Experimental Medicine 171(5):1393-1405, Rockefeller University Press, United States (May 1990).
Triebel, F., "LAG-3: A Regulator of T-cell and DC Responses and its Use in Therapeutic Vaccination," Trends in Immunology 24(12):619-622, Elsevier Science Ltd., England (Dec. 2003).
Tsai, P,K., et al., "Origin of the Isoelectric Heterogeneity of Monoclonal Immunoglobulin h1B4," Pharmaceutical Research 10(11):1580-1586, Kluwer Academic/Plenum Publishers, United states (Nov. 1993).
Turnis, M,E., et al., "Combinatorial Immunotherapy: PD-1 May Not Be LAG-ing Behind Any More.," Oncoimmunology 1(7):1172-1174, Taylor & Francis, United States (Oct. 2012).
Vlasak, J., et al., "Identification and Characterization of Asparagine Deamidation in the Light Chain CDRlof a Humanized IgG1 Antibody," Analytical Biochemistry 392(2):145-154, Academic Press, United states (Sep. 2009).
Woo, S,R., et al., "Immune Inhibitory Molecules LAG-3 and PD-1 Synergistically Regulate T-cell Function to Promote Tumoral Immune Escape," Cancer Research 72(4):917-927, American Association for Cancer Research, United states (Feb. 2012).
Workman, C.J. and Vignali, D.A., "Negative Regulation of T Cell Homeostasis by Lymphocyte Activation Gene-3 (CD223)," Journal of Immunology 174(2):688-695, American Association of Immunologists, United States (Jan. 2005).
Workman, C.J., et al., "Phenotypic Analysis of the Murine Cd4-related Glycoprotein, CD223 (LAG-3)," European Journal of Immunology 32(8):2255-2263, Wiley-VCH, Germany (Aug. 2002).
Nivolumab, "Guide to Pharmacology," accessed at http://www.guidetopharmacology.org/GRAC/liganddisplayforward?ligandId=7335, last accessed Sep. 28, 2018, 1 page.

(56) References Cited

OTHER PUBLICATIONS

Xiao, Y., and Freeman G.J., "The Microsatellite Instable Subset of Colorectal Cancer Is a Particularly Good Candidate for Checkpoint Blockade Immunotherapy," Cancer Discovery 5(1):16-18, American Association for Cancer Research, United States (Jan. 2015).
Zhang, F., et al., "Structural Basis of a Novel PD-L1 Nanobody for Immune Checkpoint Blockade, "Cell Discovery, 3:17004, Nature Publishing Group, England (Mar. 2017).
Adib-Conquy, M., et al., "Effect of Amino Acid Substitutions in the Heavy Chain CDR3 of an Autoantibody on Its Reactivity," International Immunology 10(3):341-346, Oxford University Press, England (Mar. 1998).
Beers, R., et al., "Immunotoxins With Increased Activity Against Epidermal Growth Factor Receptor vIII-expressing Cells Produced by Antibody Phage Display," Clinical Cancer Research 6(7):2835-2843, The Association, United States (Jul. 2000).
Brummell, D.A., et al., "Probing the Combining Site of an Anti-Carbohydrate Antibody by Saturation-Mutagenesis: Role of the Heavy-Chain CDR3 Residues," Biochemistry 32(4):1180-1187, American Chemical Society, United States (Feb. 1993).
Camacho, L.H., et al., "Phase I clinical trial of anti-CTLA4 human monoclonal antibody CP-675,206 in patients (pts) with advanced solid malignancies," Journal of Clinical Oncology 22(14S): Abstract 2505, 2004 ASCO Annual Meeting Proceedings (Post-Meeting Edition), $40^{th}$ Annual Meeting, Jun. 5-8, New Orleans, LA, American Society of Clinical Oncology, United States (Jul. 2004).
De Wildt, R.M.T., et al., "Heavy Chain CDR3 Optimization of a Germline Encoded Recombinant Antibody Fragment Predisposed to Bind the ULA Protein," Protein Engineering 10(7):835-841, Oxford University Press, England (Jul. 1997).
Extended European Search Report for EP Application No. 09807162.4, European Patent Office, Netherlands, mailed on Dec. 21, 2012, 9 pages.
Greenberg, P.D. and Riddell, S.R., "Deficient Cellular Immunity-Finding and Fixing the Defects," Science 285(5427):546-551, American Association for the Advancement of Science, United States (Jul. 1999).
Grosso, J.F., et al., "Functionally Distinct LAG-3 and PD-1 Subsets on Activated and Chronically Stimulated CD8 T Cells," The Journal of Immunology 182(11):6659-6669, The American Association of Immunologists, Inc., United States (Jun. 2009).
Hahne, M., et al., "Melanoma Cell Expression of Fas(Apo-1/CD95) Ligand: Implications for Tumor Immune Escape," Science 274(5291):1363-1366, American Association for the Advancement of Science, United States (Nov. 1996).
Hall, B.L., et al., "A Single Amino Acid Mutation in CDR3 of the 3-14-9 L Chain Abolished Expression of the IDA 10-defined Idiotope and Antigen Binding," Journal of Immunology 149(5):1605-1612, American Association of Immunologists, United States (Sep. 1992).
He, Y-F., et al., "Blocking Programmed Death-1 Ligand-PD-1 Interactions by Local Gene Therapy Results in Enhancement of Antitumor Effect of Secondary Lymphoid Tissue Chemokine," The Journal of Immunology 173(8):4919-4928, The American Association of Immunologists, United States (Oct. 2004).
Holliger, P., et al., "'Diabodies': Small Bivalent and Bispecific Antibody Fragments," Proceedings of the National Academy of Sciences USA 90(14):6444-6448, National Academy of Sciences, United States (Jul. 1993).
Howard, M. and Ogarra, A., "Biological Properties of Interleukin 10," Immunology Today 13(6):198-200, Elsevier Science Publishers, England (Jan. 1992).
Hurwitz, A.A., et al., "CTLA-4 Blockade Synergizes With Tumor-derived Granulocyte-macrophage Colony-stimulating Factor for Treatment of an Experimental Mammary Carcinoma," Proceedings of the National Academy of Sciences of the United States of America 95(17):10067-10071, National Academy of Sciences, United States (Aug. 1998).
Hutloff, A., et al., "ICOS is an Inducible T-cell Co-stimulator Structurally and Functionally Related to CD28," Nature 397(6716):263-266, Nature Publishing Group, England (Dec. 1999).
Ito, D., et al., "Effective Priming of Cytotoxic T Lymphocyte Precursors by Subcutaneous Administration of Peptide Antigens in Liposomes Accompanied by Anti-CD40 and Anti-CTLA-4 Antibodies," Immunobiology 201(5):527-540, Elsevier, Netherlands (Apr. 2000).
Kehrl, J.H., et al., "Production of Transforming Growth Factor ß by Human T Lymphocytes and Its Potential Role in the Regulation of T Cell Growth," The Journal of Experimental Medicine 163(5):1037-1050, Rockefeller University Press, United States (1986).
Kelley, R.F. and O'connell, M.P., "Thermodynamic Analysis of an Antibody Functional Epitope," Biochemistry 32(27):6828-6835, American Chemical Society, United States (Jul. 1993).
Komissarov, A.A., et al., "Site-specific Mutagenesis of a Recombinant Anti-single-stranded DNA Fab. Role of Heavy Chain Complementarity-determining Region 3 Residues in Antigen Interaction," 272(43):26864-26870, American Society for Biochemistry and Molecular Biology, United States (Oct. 1997).
Melero, I., et al., "Monoclonal Antibodies Against the 4-1BB T-cell Activation Molecule Eradicate Established Tumors," Nature Medicine 3(6):682-685, Nature Publishing Company, United States (Jun. 1997).
Mokyr, M.B., et al., "Realization of the Therapeutic Potential of CTLA-4 Blockade in Low-dose Chemotherapy-treated Tumor-bearing Mice," Cancer Research 58(23):5301-5304, American Association for Cancer Research, United States (Dec. 1998).
Poljak, R.J., "Production and Structure of Diabodies," Structure 2(12):1121-1123, Cell Press, United States (Dec. 1994).
Ridge J.P., et al., "A Conditioned Dendritic Cell Can Be a Temporal Bridge Between a CD4+ T-helper and a T-killer Cell," Nature 393(6684):474-478, Nature Publishing Group, England (Jun. 1998).
Weinberg, A.D., et al., "Engagement of the OX-40 Receptor in Vivo Enhances Antitumor Immunity," Journal of Immunology 164(4):2160-2169, American Association of Immunologists, United States (Feb. 2000).
Poirier, N., et al., "Antibody-mediated depletion of lymphocyte-activation gene-3 (LAG-$3^+$)-activated T lymphocytes prevents delayed-type hypersensitivity in non-human primates" Clinical and Experimental Immunology 164(2):265-274, British Society for Immunology (May 2011).
Kallewaard, N.L., et al., "Functional Maturation of the Human Antibody Response to Rotavirus," Journal of Immunology 180(6):3980-3989, American Association of Immunologists, United States (Mar. 2008).
Wiens, G.D., et al., "Somatic Mutation in VH complementarity-determining Region 2 and Framework Region 2: Differential Effects on Antigen Binding and Ig selection," Journal of Immunology 159(3):1293-1302, American Association of Immunologists, United States (Aug. 1997).
Khan, T., et al., "Adjustable locks and flexible Keys: Plasticity of Epitope-Paratope Interactions in Germline Antibodies," J Immunol 192:5398-5405, American Association of Immunologists, United States (Jun. 2014).
Torres, M., et al., "The Immunoglobulin constant region contributes to affinity and specificity," Trends in Immunology 29(2): 91-97, Elsevier, Netherlands (Feb. 2007).
Poosarla, V.G., et al., "Computational De Novo Design of Antibodies Binding to a Peptide With High Affinity," Biotechnology and Bioengineering 114(6):1331-1342, Wiley Online Library, United States (Jun. 2017).
Edwards, B.M., et al., "The Remarkable Flexibility of the Human Antibody Repertoire; Isolation of Over One Thousand Different Antibodies to a Single Protein," J. Mol. Biol. 334:103-118, Elsevier, Netherlands (Nov. 2003).
Barber, D.L., et al., "Restoring function in exhausted CD8 T cells during chronic viral infection," Nature 439:682-687, Nature Publishing Group, United Kingdom (Feb. 2006).
Declaration of Jeanette L. Fairhurst in Grounds of Opposition mailed Aug. 20, 2020 in EP Application No. 1516647.8, European Patent Office, Germany, 12 pages.
Dyrberg, T., et al., "Peptides as antigens. Importance of orientation," The Journal of Experimental Medicine 164(4):1344-1349, Rockefeller University Press, United States (Oct. 1986).

(56) References Cited

OTHER PUBLICATIONS

Exhibit 1 in Grounds of Opposition mailed Aug. 20, 2020, in EP Application No. 15156647.8, European Patent Office, Germany, 1 page.
Extended European Search Report mailed Jul. 13, 2015, in EP Application No. 15156647.8, European Patent Office, Germany, 9 pages.
Goldberg, M.V., et al., "LAG-3 in Cancer Immunotherapy," Curr Top Microbiol Immunology 344:269-278, Springer, United States (2011).
Grounds of Opposition mailed Aug. 20, 2020, in EP Application No. 1516647.8, European Patent Office, Germany, 86 pages.
Hong, S., et al., "Progress and Application of Humanization of Monoclonal Antibodies," Chinese Journal of Biologicals 21(1):70-73, Changchun Institute of Biological Products, China (2008).
Hoogenboom, H.R., et al., "Designing and optimizing library selection strategies for generating high-affinity antibodies," TibTech Library 15:62-70, Elsevier, Netherlands (Feb. 1997).
Huard, B., et al., "CD4/major histocompatibility complex class II interaction analyzed with CD4- and lymphocyte activation gene-3 (LAG-3)-Ig fusion proteins," Eur. J. Immunol.25:2718-2721, Wiley-VCH, Germany (Sep. 1995).
Huard, B., et al., "LAG-3 does not define a specific mode of natural killing in human," Immunology Letters 61:109-112, Elsevier, Netherlands (Apr. 1998).
Imakiire, T., et al., "Generation, immunologic characterization and antitumor effects of human monoclonal antibodies for carcinoembryonic antigen," Int J Cancer 108(4):564-570, Wiley Online Publishing, United States (2004).
Jespers, L.S., et al., "Guiding the Selection of Human Antibodies from Phage Display Reperotires to a Single Epitope of an Antigen," Biotechnology 12:899-903, Nature Publishing Group, United Kingdom (Sep. 1994).
Kaufmann, D.E., et al., "Upregulation of CTLA-4 by HIV-specific CD4+ T cells correlates with disease progression and defines a reversible immune dysfunction," Nature Immunology 8(11): 1246-1254, Nature Publishing Group, United Kingdom (Nov. 2007).
Response to communication in European Patent Application No. 15156647.8, dated Mar. 29, 2018, European Patent Office, Germany, 3 pages.
Response to communication in European Patent Application No. 15156647.8, dated Feb. 9, 2016, European Patent Office, Germany, 3 pages.
Perez De La Lastra, J.M., et al., "Epitope mapping of 10 monoclonal antibodies against the pig analogue of human membrane cofactor protein (MCP)," Immunology 96:663-670, Blackwell Science Ltd., United States (Apr. 1999).
Shapira, M., et al., "Immunity and protection against influenza virus by synthetic peptide corresponding to antigenic sites of hemagglutinin," PNAS 81(8): 2461-2465, United States National Academy of Sciences, United States (Apr. 1984).
Office Action issued Apr. 28, 2020 in CN 201710463804.9, State Intellectual Property Office of People's Republic of China, China, 8 pages.
Tanaka, T., et al., "Efficient generation of antibodies to oncoproteins by using synthetic peptide antigens," PNAS 82(10):3400-3404, United States National Academy of Sciences, United States (May 1985).
Workman, C.J., et al., "The CD4-related molecule, LAG-3 (CD223), regulates the expansion of activated T cells," Eur J. Immunol. 33(4):970-979, Wiley Online Library, United States (Apr. 2003).
Agata, Y., et al., "Expression of the PD-1 Antigen on the Surface of Stimulated Mouse T and B lymphocytes," International Immunology 8(5):765-772, Oxford University Press, England (May 1996).
Ascierto, P.A., et al., "Initial Efficacy of Anti-lymphocyte Activation Gene-3 (Anti-LAG-3; BMS-986016) in Combination With Nivolumab (Nivo) in Pts With Melanoma (MEL) Previously Treated With Anti-PD-1/PD-L1 Therapy," Journal of Clinical Oncology 35(15_ suppl):[abstract 9520], American Society of Clinical Oncology, United States (May 2017).
Bennett, F., et al., "Program Death-1 Engagement Upon TCR Activation has Distinct Effects on Costimulation and Cytokine-driven Proliferation: Attenuation of ICOS, IL-4, and IL-21, but not CD28, IL-7, and IL-15 responses," The Journal of Immunology 170(2):711-718, The American Association of Immunologists, United States (Jan. 2003).
Bettini, M., et al., "Cutting Edge: Accelerated Autoimmune Diabetes in the Absence of LAG-3," Journal of Immunology 187(7):3493-3498, American Association of Immunologists, United States (Oct. 2011).
Bird, R.E., et al., "Single-chain Antigen-binding Proteins," Science 242(4877):423-426, Association for the Advancement of Science, United States (Oct. 1988).
Blank, C., et al., "Interaction of PD-L1 on Tumor Cells with PD-1 on Tumor-specific T Cells as a Mechanism of Immune Evasion: Implications for Tumor Immunotherapy," Cancer Immunology Immunotherapy 54(4):307-314, Springer-Verlag, Germany (Apr. 2005).
Brown, J.A., et al., "Blockade of Programmed Death-1 Ligands on Dendritic Cells Enhances T Cell Activation and Cytokine Production," The Journal of Immunology 170(3):1257-1266, The American Association of Immunologists, United States (Feb. 2003).
Camisaschi, C., et al., "LAG-3 Expression Defines a Subset of CD4(+)CD25(High)Foxp3(+) Regulatory T Cells That Are Expanded at Tumor Sites," Journal of Immunology 184(11):6545-6551, American Association of Immunologists, United states (Jun. 2010).
Carter, L.L., et al., "PD-1:PD-L Inhibitory Pathway Affects both CD4(+) and CD8(+) T Cells and is Overcome by IL-2," European Journal of Immunology 32(3):634-643, Wiley-VCH Verlag GmbH, German (Mar. 2002).
Condeelis, J. and Weissleder, R., "In Vivo Imaging in Cancer," Cold Spring Harbor Perspectives in Biology 2(12):a003848, Cold Spring Harbor Laboratory Press, United States (Dec. 2010).
Dong, H. and Chen, L., "B7-H1 Pathway and its Role in the Evasion of Tumor Immunity," Journal of Molecular Medicine 81(5):281-287, Springer, Germany (May 2003).
Dong, H., et al., "B7-H1, a Third Member of the B7 Family, Co-stimulates T-cell Proliferation and Interleukin-10 Secretion," Nature Medicine 5(12):1365-1369, Nature America, United States (Dec. 1999).
Dong, H., et al., "Tumor-associated B7-H1 Promotes T-cell Apoptosis: A Potential Mechanism of Immune Evasion," Nature Medicine 8(8):793-800, Nature Publishing Company, United States (Aug. 2002).
Freeman, G.J., et al., "Engagement of the PD-1 Immunoinhibitory Receptor by a Novel B7 Family Member Leads to Negative Regulation of Lymphocyte Activation," The Journal of Experimental Medicine 192(7):1027-1034, The Rockefeller University Press, United States (Oct. 2000).
Gandhi, M,K., et al., "Expression of LAG-3 by Tumor-infiltrating Lymphocytes Is Coincident With the Suppression of Latent Membrane Antigen-specific CD8+ T-cell Function in Hodgkin Lymphoma Patients," Blood 108(7):2280-2289, American Society of Hematology, United States (Oct. 2006).
GenBank, "Human hPD-1 (hPD-1) mRNA, complete cds," Accession No. U64863.1, accessed on https://www.ncbi.nlm.nih.gov/nuccore/U64863, Oct. 12, 2005.
GenBank, "lymphocyte activation gene 3 protein precursor [*Homo sapiens*]," Accession No. NP_002277.4, accessed on https://www.ncbi.nlm.nih.gov/protein/NP_002277, Oct. 6, 2016.
GenBank, "lymphocyte activation gene 3 protein precursor [*Mus musculus*]," Accession No. NP_032505.1, accessed on https://www.ncbi.nlm.nih.gov/protein/NP032505, Feb. 15, 2015.
GenBank, "RecName: Full=Programmed cell death 1 ligand 1; Short-PD-L1; Short=PDCD1 ligand 1; Short-Programmed death ligand 1; AltName: Full=B7 homolog 1; Short=B7-H1; AltName: CD_antigen-CD274; Flags: Precursor," Accession No. Q9NZQ7.1, accessed on https://www.ncbi.nlm.nih.gov/protein/Q9NZQ7, Nov. 2, 2016.
GenBank, "RecName: Full=Programmed cell death 1 ligand 2; Short=PD-1 ligand 2; Short=PD- L2; Short=PDCD1 ligand 2; Short=Programmed death ligand 2; AltName: Full=Butyrophilin B7-DC; Short=B7-DC; AltName: CD_antigen=CD273; Flags: Pre-

(56) References Cited

OTHER PUBLICATIONS cursor," Accession No. Q9BQ51.2, accessed on https://www.ncbi.nlm.nih.gov/protein/Q9BQ51, Feb. 10, 2021.
Goding, S,R., et al., "Restoring Immune Function of Tumor-specific CD4+ T Cells During Recurrence of Melanoma," Journal of Immunology 190(9):4899-4909, American Association of Immunologists, United states (May 2013).
Gorelik, L., et al., Preclinical Characterization of a Novel Fully Human IgG1 anti-PD-L1 mAb CK-301, American Association for Cancer Research Annual Meeting (AACR), Abstract 4606 (Apr. 2016).
Hamid, O., et al., "Safety and Tumor Responses with Lambrolizumab (Anti-Pd-1) in Melanoma," The New England Journal of Medicine 369(2):134-144, Massachusetts Medical Society, United States of America (Jul. 2013).
Hansen, J.A., et al., "Monoclonal Antibodies Identifying a Novel T-cell Antigen and Ia Antigens of Human Lymphocytes," Immunogenetics 10:247-260, Springer-Verlag (Feb. 1980).
Herbst, R.S., et al., "A Study of MPDL3280A, an Engineered PD-L1 Antibody in Patients with Locally Advanced or Metastatic Tumors," Journal of Clinical Oncology 31(Suppl):Abstract 3000, American Society of Clinical Oncology, United States (2013).
Huston, J.S., et al., "Protein Engineering of Antibody Binding Sites: Recovery of Specific Activity in an Anti-digoxin Single-chain Fv Analogue Produced in *Escherichia coli*," Proceedings of the National Academy of Sciences USA 85(16):5879-5883, National Academy of Sciences, United States (Aug. 1988).
International Search Report and Written Opinion for International Application No. PCT/US2019/056923, European Patent Office, Netherlands, mailed on Jan. 27, 2020.
Ishida, Y., et al., "Induced Expression of PD-1, a Novel Member of the Immunoglobulin Gene Superfamily, Upon Programmed Cell Death," The EMBO Journal 11(11):3887-3895, Oxford University Press, England (Nov. 1992).
Iwai, Y., et al., "Involvement of PD-L1 on Tumor Cells in the Escape from Host Immune System and Tumor Immunotherapy by PD-L1 Blockade," Proceedings of the National Academy of Sciences 99(19):12293-12297, The National Academy of Sciences of the United States (Sep. 2002).
Keir, M,E., et al., "PD-1 and Its Ligands in Tolerance and Immunity," Annual Review of Immunology 26:677-704, Annual Reviews Inc, United states (Apr. 2008).
Khleif, S., et al., "MEDI4736, An Anti-PD-L1 Antibody with Modified Fc Domain: Preclinical Evaluation and Early Clinical Results from a Phase 1 Study in Patients with Advanced Solid Tumors," Abstract 802, in Proceedings from the European Cancer Congress 2013, Amsterdam, The Netherlands (Sep. 27-Oct. 1, 2013).
Konishi, J., et al., "B7-H1 Expression on Non-small Cell Lung Cancer Cells and its Relationship with Tumor-infiltrating Lymphocytes and their PD-1 Expression," Clinical Cancer Research 10(15):5094-5100, American Association for Cancer Research, United States (Aug. 2004).
Anonymous: "History of Changes for Study: NCT01968109, An Investigational Immuno-therapy Study to Assess the Safety, Tolerability and Effectiveness of Anti-LAG-3 With and in the Treatment of Solid Tumors" ClinicalTrials. gov Archive, accessed at https://clinicaltrials.gov/ct2/history/NCT01968109?V_69=View, accessed on Dec. 9, 2019, 10 pages.
Latchman, Y., et al., "PD-L2 is a Second Ligand for PD-1 and Inhibits T Cell Activation," Nature Immunology 2(3):261-268, Nature Publishing Group, United States (Mar. 2001).
Lipson, E., et al., "Initial experience administering BMS-986016, a monoclonal antibody that targets lymphocyte activation gene (LAG)-3, alone and in combination with nivolumab to patients with hematologic and solid malignancies," Journal for Immuno Therapy of Cancer, 4(Suppl 1):P232, BMJ, United Kingdom (Nov. 2016).
Liu, S.Y., et al., "Ongoing Clinical Trials of PD-1 and PD-L1 Inhibitors for Lung Cancer inChina, "Journal of Hematology & Oncology, 10(1):136, Biomed Central, England (Jul. 2017).
Llosa, N.J., et al., "The Vigorous Immune Microenvironment of Microsatellite Instable Colon Cancer Is Balanced by Multiple Counter-inhibitory Checkpoints," Cancer Discovery 5(1):43-51, American Association for Cancer Research, United States (Jan. 2015).
Lyford-Pike, S., et al., "Evidence for a Role of the PD-1:PD-L1 Pathway in Immune Resistance of HPV-associated Head and Neck Squamous Cell Carcinoma," Cancer Research 73(6):1733-1741, American Association for Cancer Research, United States (Mar. 2013).
Matsuzaki, J., et al., "Tumor-infiltrating NY-ESO-1-specific CD8+ T Cells Are Negatively Regulated by LAG-3 and PD-1 in Human Ovarian Cancer," Proceedings of the National Academy of Sciences of the United States of America 107(17):7875-7880, National Academy of Sciences, United states (Apr. 2010).
McCabe, K.E. and Wu, A.M., "Positive Progress in ImmunoPET—not Just a Coincidence," Cancer Biotherapy & Radiopharmaceuticals 25(3):253-261, Mary Ann Liebert, Inc, United States (Jun. 2010).
NCI Drug Dictionary, anti-PD-1 Fusion Protein AMP-224, accessed on Dec. 1, 2016, retrieved from the Internet URL: https://www.cancer.gov/publications/dictionaries/cancer-drug?cdrid=700595.
NCI Drug Dictionary, anti-PD-1 monoclonal antibody MEDI0680, accessed on Dec. 1, 2016, retrieved from the Internet URL: https://www.cancer.gov/publications/dictionaries/cancer-drug?cdrid=756047.
NCI Drug Dictionary, pembrolizumab, accessed on Dec. 1, 2016, retrieved from the Internet URL: https://www.cancer.gov/drugdictionary?cancer-drug?cdrid=695789, 3 pages.
Nielsen, C., et al., "A putative regulatory polymorphism in PD-1 is associated with nephropathy in a population-based cohort of systemic lupus erythematosus patients," Lupus 13(7):510-516, SAGE, England (Jul. 2004).
Nishimura, H., et al., "Autoimmune Dilated Cardiomyopathy in PD-1 Receptor-deficient Mice," Science 291(5502):319-322, American Association for the Advancement of Science, United States (Jan. 2001).
Nishimura, H., et al., "Development of Lupus-like Autoimmune Diseases by Disruption of the PD-1 Gene Encoding an ITIM Motif-carrying Immunoreceptor," Immunity 11(2):141-151, Cell Press, United States (Aug. 1999).
Okazaki, T., et al., "New Regulatory Co-receptors: Inducible co-stimulator and PD-1," Current Opinion in Immunology 14(6):779-782, Elsevier, England (Dec. 2002).
Okazaki, T., et al., "PD-1 and LAG-3 Inhibitory Co-receptors Act Synergistically to Prevent Autoimmunity in Mice," The Journal of Experimental Medicine 208(2):395-407, Rockefeller University Press, United states (Feb. 2011).
Okazaki, T., et al., "PD-1 immunoreceptor Inhibits B Cell Receptor-mediated Signaling by Recruiting src Homology 2-domain-containing Tyrosine Phosphatase 2 to Phosphotyrosine," Proceedings of the National Academy of Sciences 98(24):13866-13871, National Academy of Sciences, United States (Nov. 2001).
Olafsen, T., et al., "ImmunoPET Imaging of B-Cell Lymphoma Using 124I-Anti-CD20 scFv Dimers (Diabodies)," Protein Engineering, Design & Selection 23(4):243-249, Oxford University Press, England (Apr. 2010).
Orchard G.E and Calonje E., "The Effect of Melanin Bleaching on Immunohistochemical Staining in Heavily Pigmented Melanocytic Neoplasms," The American Journal of Dermatopathology 20(4):357-361, Lippincott Williams & Wilkins, United States (Aug. 1998).
Pardoll, D.M., "The Blockade of Immune Checkpoints in Cancer Immunotherapy," Nature Reviews Cancer 12(4):252-264, Nature Publishing Group, England (Mar. 2012).
Prokunina, L. and Alarcon-Riquelme, M., "The Genetic Basis of Systemic Lupus Erythematosus -knowledge of Today and Thoughts for Tomorrow," Human Molecular Genetics 13(1):R143-R148, Oxford University Press, England (Apr. 2004).
Salama, A.D., et al., "Critical Role of the Programmed Death-1 (PD-1) Pathway in Regulation of Experimental Autoimmune Encephalomyelitis," The Journal of Experimental Medicine 198(1):71-78, The Rockefeller University Press, United States (Jul. 2003).
Shen W and Wu W., "Study of Melanin Bleaching After Immunohistochemistry of Melanin-containing Tissues," Applied

(56) References Cited

OTHER PUBLICATIONS immunohistochemistry & molecular morphology : AIMM 23(4):303-307, Lippincott Williams & Wilkins, United States (Apr. 2015).
Sierro, S., et al., "The CD4-like Molecule LAG-3, Biology and Therapeutic Applications," Expert Opinion on Therapeutic Targets 15(1):91-101, Informa Healthcare, England (Jan. 2011).
Sweis R., et al., "Molecular Drivers of the Non-T Cell-Inflamed Tumor Microenvironment in Urothelial Bladder Cancer," Cancer Immunology Research 4(7): 563-568, American Association for Cancer Research, United States (Jul. 2016).
Terme, M., et al., "IL-18 Induces PD-1-dependent Immunosuppression in Cancer," Cancer Research 71(16):5393-5399, American Association for Cancer Research, United States (Aug. 2011).
Thomas, M.L., "Of ITAMs and ITIMs: Turning on and off the B Cell Antigen Receptor," The Journal of Experimental Medicine 181(6):1953-1956, The Rockefeller University Press, United States (Jun. 1995).
Topalian, S.L., et al., "Safety, Activity and Immune Correlates of Anti-PD-1 Antibody in Cancer," The New England Journal of Medicine 366(26):2443-2454, Massachusetts Medical Society, United States (Jun. 2012).
Vivier, E. and Daeron, M., "Immunoreceptor Tyrosine-based Inhibition Motifs," Immunology Today 18(6):286-291, Elsevier, England (Jun. 1997).
Wang, C., et al., "In Vitro Characterization of the Anti-PD-1 Antibody Nivolumab, BMS-936558, and in Vivo Toxicology in Non-human Primates," Cancer Immunology Research 2(9):846-856, American Association for Cancer Research, United States (Sep. 2014).
Ward, E.S., et al., "Binding Activities of a Repertoire of Single Immunoglobulin Variable Domains Secreted from *Escherichia coli,*" Nature 341(6242):544-546, Nature Publishing Group, England (Oct. 1989).
Wherry, E.J., "T Cell Exhaustion," Nature Immunology 12(6):492-499, Nature America Inc, United States (Jun. 2011).
Workman, C,J., et al., "LAG-3 Regulates Plasmacytoid Dendritic Cell Homeostasis," Journal of Immunology 182(4):1885-1891, American Association of Immunologists, United states (Feb. 2009).
Monette, A., et al., "Immune-enriched NSCLC biopsy tissue microarrays demonstrate that proliferating and checkpoint expressing TIL correlate with positive outcome," Journal for immunotherapy of Cancer 4(1): 58, BMJ Journals, United Kingdom (Nov. 2016).
Burova, E., et al., "A novel anti-human LAG-3 antibody in combination with anti-human PD-1 (REGN2810) shows enhanced anti-tumor activity in PD-1 x LAG-3 dual-dehumanized mice and favorable pharmacokinetic and safety profiles in cynomolgus monkeys," Journal for Immunotherapy of Cancer 4(1):P195, BMJ Journals, United Kingdom (2016).
Rizvi, N.A., et al., "Nivolumab in Combination With Platinum-Based Doublet Chemotherapy for First-Line Treatment of Advanced Non-Small-Cell Lung Cancer," Journal of Clinical Oncology 34(25):2969-2979, American Society of Clinical Oncology, United States (Sep. 2016).
Daugherty, A.L. and Mrsny, R.J., "Formulation and Delivery Issues for Monoclonal Antibody Therapeutics," Advanced Drug Delivery Reviews 58(5-6):686-706, Elsevier Science Publishers, Netherlands (Aug. 2006).
Freeman, G.J., et al., "Protect the Killer: CTLs Need Defenses against the Tumor," Nature Medicine 8(8):787-789, Nature Publishing Company, United States (Aug. 2002).
Kakavand, H., et al., "PD-L1 Expression and Tumor-Infiltrating Lymphocytes Define Different Subsets of MAPK Inhibitor-Treated Melanoma Patients," Clinical Cancer Research 21(14):3140-3148, American Association for Cancer Research, United States (Jul. 2015).
Brahmer, J.R., et al., "Safety and Activity of Anti-PD-L1 Antibody in Patients with Advanced Cancer," The New England Journal of Medicine 366(26):2455-2465, Massachusetts Medical Society, United States (Jun. 2012).
Brahmer., J.R., et al., "Phase I Study of Single-agent Anti-programmed Death-1 (MDX-1106) in Refractory Solid Tumors: Safety, Clinical Activity, Pharmacodynamics, and Immunologic Correlates," Journal of Clinical Oncology 28(19):3167-3175, American Society of Clinical Oncology, United States (Jul. 2010).
Clinicaltrials.gov, "Safety Study of Anti-LAG-3 in CLL, HL and NHL," Identifier NCT02061761, accessed at https://clinicaltrials.gov/archive/NCT02061761/2014_08_28, last accessed on Jan. 13, 2015, 4 pages.
Clinicaltrials.gov, "Safety Study of Anti-LAG-3 With and Without Anti-PD-1 in the Treatment of Solid Tumors," Identifier NCT01968109, accessed at https://clinicaltrials.gov/archive/NCT01968109/2014_06_20, last accessed on Jan. 13, 2015, 4 pages.
Drake, C.G., et al., "Breathing New Life into Immunotherapy: Review of Melanoma, Lung and Kidney Cancer," Nature Reviews Clinical Oncology 11(1):24-37, Nature Pub. Group, England (Jan. 2014).
Gillam, W.A., et al., "A phase I study of IMP321 and Gemcitabine as the Front-Line Therapy in Patients with Advanced Pancreatic Adenocarcinoma," Investigational New Drugs 31(3):707-713, Springer, United States (Jun. 2013).
Haycock, G,B., et al., "Geometric Method for Measuring Body Surface Area: a Height-weight Formula Validated in Infants, Children, and Adults," The Journal of Pediatrics 93(1):62-66, Mosby, United States (Jul. 1978).
Hemon, P., et al., "MHC Class II Engagement by its Ligand LAG-3 (CD223) Contributes to Melanoma Resistance to Apoptosis," Journal of Immunology 86(9):5173-5183, American Association of Immunologists, United States (May 2011).
Lipson, E.J., et al., "Durable Cancer Regression Off-treatment and Effective Reinduction Therapy with an Anti-PD-1 Antibody," Clinical Cancer Research 19(2):462-468, The Association, United States (Jan. 2013).
ONO Pharmaceutical Co., Ltd, "A full human anti-PD-1 antibodyONO-4538/BMS-936558", Results from Phase 1 Study in Cancer Patients Published in New England Journal of Medicine (NEJM) and Presented at Annual Meeting of the American Society of Clinical Oncology (ASCO), Jun. 4, 2012, [retrieved on May 24, 2018], Retrieved from the Internet: (URL:https://www.ono.co.jp/jpnw/PDF/n12_0604.pdf), Jun. 12, 2018, with translator certification statement, 8 pages.
Rosenberg, S.A., et al., "Cancer Immunotherapy in Cancer: Principles & Practice of Oncology," 332-344, Lippincott Williams & Wilkins (Oct. 2011).
Sierro et al., "The CD4-Like Molecule LAG-3, Biology and Therapeutic Applications," Expert Opinion on Therapeutic Targets, 15(1):91-101, Taylor & Francis, United States (Jan. 2010).
Wolchok, J.D., et al., "Guidelines for the Evaluation of Immune Therapy Activity in Solid Tumors: Immune-related Response Criteria," Clinical Cancer Research 15(23):7412-7420, The Association, United States (Dec. 2009).
Wolchok, J.D., et al., "Nivolumab Plus Ipilimumab in Advanced Melanoma," The New England Journal of Medicine 369(2):122-133, Massachusetts Medical Society, United States (Jul. 2013).
Clinicaltrials.gov, "Safety Study of Anti-LAG-3 With and Without Anti-PD-1 in the Treatment of Solid Tumors," Identifier NCT01968109, accessed at https://clinicaltrials.gov/archive/NCT01968109/2014_01_23, 5 pages.
Zettl, M., "Abstract 4558: In vitro and in vivo characterization of the PD-1 targeting antibody BI754091," Cancer Research 78(13_suppl): Abstract 4558, American Association for Cancer Research, United States (Jul. 2018).
Clinicaltrials.gov, "Safety Study of Anti-LAG-3 With and Without Anti-PD-1 in the Treatment of Solid Tumors," Identifier NCT01968109, accessed at https://clinicaltrials.gov/archive/NCT01968109/2014_05_07, last accessed on Feb. 10, 2021, 4 pages.
Anonymous: "History of Changes for Study: NCT00730639, A Phase 1b Study of MDX-1106 in Subjects With Advanced or Recurrent Malignancies (MDX1106-03)," ClinicalTrials.gov Archive, accessed at https://clinicaltrials.gov/ct2/history/NCT00730639?V_8=View, accessed on Feb. 5, 2021, 10 pages.

(56) References Cited

OTHER PUBLICATIONS

Ansell, S.M., et al., "Epstein-Barr Virus Infection in Richter's Transformation," American Journal of Hematology 60(2):99-104, Wiley-Blackwell, United States (Feb. 1999).

Berrien-Elliott, M.M., et al., "Durable Adoptive Immunotherapy for Leukemia Produced by Manipulation of Multiple Regulatory Pathways of CD8+ T-cell Tolerance," Cancer Research 73(2):605-616, American Association for Cancer Research, United States (Jan. 2013).

Cheson, B.D., et al., "Revised Response Criteria for Malignant Lymphoma," Journal of Clinical Oncology 25(5):579-586, American Society of Clinical Oncology, United States (Feb. 2007).

Dickinson, J.D., et al., "11q22.3 Deletion in B-chronic Lymphocytic Leukemia is Specifically Associated with Bulky Lymphadenopathy and ZAP-70 Expression but Not Reduced Expression of Adhesion/cell Surface Receptor Molecules," Leukemia & Lymphoma 47(2):231-244, Informa Healthcare, England (Jan. 2006).

Dolcetti, R. and Carbone, A., "Epstein-barr Virus Infection and Chronic Lymphocytic Leukemia: A Possible Progression Factor," Infectious Agents and Cancer 5:22, BioMed Central, England (Dec. 2010).

Fujimoto, S., et al., "Studies on the Physical Surface Area of Japanese. 18. Calculation Formulas in Three Stages Over All Ages," Nihon Eiseigaku Zasshi 23(5):443-450, Nippon Eisei Gakkai,Japan (1968).

Genbank, "Predicted: Macaca mulatta lymphocyte-activation gene 3 (LAG3), transcript variant X1, mRNA," accessed at https://www.ncbi.nlm.nih.gov/nuccore/XM_001108923/, accessed on May 21, 2018.

Green, M.R., et al., "Constitutive AP-1 Activity and EBV Infection Induce PD-L1 in Hodgkin Lymphomas and Posttransplant Lymphoproliferative Disorders: Implications for Targeted Therapy," Clinical Cancer Research 18(6):1611-1618, The Association, United States (Mar. 2012).

Hallek, M., et al., "Guidelines for the Diagnosis and Treatment of Chronic Lymphocytic Leukemia: a Report From the International Workshop on Chronic Lymphocytic Leukemia Updating the National Cancer Institute-working Group 1996 Guidelines," Blood 111(12):5446-5456, American Society of Hematology, United States (Jun. 2008).

Kanakry, J.A., et al., "Plasma Epstein-barr Virus Dna Predicts Outcome in Advanced Hodgkin Lymphoma: Correlative Analysis From a Large North American Cooperative Group Trial," Blood 121(18):3547-3553, American Society of Hematology, United States (May 2013).

Kotaskova, J., et al., "High Expression of Lymphocyte-activation Gene 3 (LAG3) in Chronic Lymphocytic Leukemia Cells Is Associated With Unmutated Immunoglobulin Variable Heavy Chain Region (IGHV) Gene and Reduced Treatment-free Survival," The Journal of Molecular Diagnostics 12(3):328-334, American Society for Investigative Pathology and the Association for Molecular, United States (May 2010).

Manuel, M., et al., "Lymphopenia Combined With Low TCR Diversity (Divpenia) Predicts Poor Overall Survival in Metastatic Breast Cancer Patients," Oncoimmunology 1(4):432-440, Taylor & Francis, United States (Jul. 2012).

Monti, S., et al., "Molecular Profiling of Diffuse Large B-cell Lymphoma Identifies Robust Subtypes Including One Characterized by Host Inflammatory Response," Blood 105(5):1851-1861, American Society of Hematology, United States (Mar. 2005).

Tsimberidou, A.M., et al., "Epstein-barr Virus in Patients With Chronic Lymphocytic Leukemia: a Pilot Study," Leukemia & Lymphoma 47(5):827-836, Informa Healthcare, England (Jan. 2006).

Zhang, J., et al., "Using Gene Co-expression Network Analysis to Predict Biomarkers for Chronic Lymphocytic Leukemia," BMC Bioinformatics 11(9):S5, BioMed Central, England (Oct. 2010).

Mathijssen, R.H., et al., "Flat-Fixed Dosing Versus Body Surface Area Based Dosing of Anticancer Drugs In Adults: Does It Make a Difference ??," Oncologist, 12(8):913-923, AlphaMed Press, United States (Aug. 2007).

Huang, R.-Y., et al., "LAG3 and PD1 Co-Inhibitory Molecules Collaborate to Limit CD8+ T Cell Signaling and Dampen Antitumor Immunity in a Murine Ovarian Cancer Model," Oncotarget, 6(29):27359-27377 (Sep. 2015).

Anonymous, "Relatlimab/Nivolumab Combo Active in Melanoma After PD-1/PD-L1 Therapy," Jan. 1, 2017, accessed at https://www.onclive.com/printer?url=/web-exclusives/relatlimabnivolumab-combo-active-in-melanoma-after-pd1pdl1-therapy, accessed on Oct. 12, 2019, 2 pages.

Ascierto, P.A., et al., "Efficacy of BMS-986016, a monoclonal antibody that targets lymphocyte activation gene 3 (LAG-3), in combination with nivolumab in pts with melanoma who progressed during prior anti-PD-1/PD-L1 therapy (mel prior IO) in all-comer and biomarker-enriched populations," Annals of Oncology 28(S5):LBA18, Elsevier, Netherlands (Sep. 2017).

Camisachi, C., et al., "Alternative activation of human plasmacytoid DCs in vitro and in melanoma lesions: involvement of LAG-3," Journal of Investigative Dermatology 134:1893-1902, Society of Investigative Dermatology, United States (Jul. 2014).

Capelle, M.A.H., et al., "High throughput screening of protein formulation stability: practical considerations," Eur. J. Pharm. Biopharm. 65:131-148, Elsevier, Netherlands (Feb. 2006).

Dudgeon, K., et al., "General strategy for the generation of human antibody variable domains with increased aggregation resistance," Proc. Natl. Acad. Sci. USA 109:10879-10884, National Academy of Sciences, United States (Jul. 2012).

Johnson, L., et al., "Development of a LAG-3 immunohistochemistry assay for melanoma," J. Clin. Pathol. 0:1-8, BMJ Publishing Group, United Kingdom (Sep. 2022).

Kang, Y.K., et al., "Nivolumab in patients with advanced gastric or gastro-oesophageal junction cancer refractory to, or intolerant of, at least two previous chemotherapy regimens (ONO-4538-12, Attraction-2): a randomised, double-blind, placebo-controlled, phase 3 trial," Lancet 390: 2461-2471, Elsevier, Netherlands (Oct. 2017).

Kayser, V., et al., "A screening tool for therapeutic monoclonal antibodies: Identifying the most stable protein and its best formulation based on thioflavin T binding," Biotechnology Journal 7:127-132, Wiley, United States (Jan. 2012).

Taieb, J., et al., "Evolution of checkpoint inhibitors for the treatment of metastatic gastric cancers: Current status and future perspectives," Cancer Treatment Reviews 66:104-113, Elsevier, Netherlands (May 2018).

Turnis, M.E., et al., "Inhibitory receptors as targets for cancer immunotherapy," Eur. J. Immunol. 45:1892-1905, Wiley, United States (Jul. 2015).

U.S. Food Drug Administration, "Highlights of Prescribing Information, OPDIVO (nivolumab) injection, for intravenous use," Reference ID: 3710966, U.S. FDA, 27 pages (2015).

Wang, X., et al., "Potential aggregation prone regions in biotherapeutics: A survey of commercial monoclonal antibodies," MAbs 1(3):254-267, Oxford Academic Press, United Kingdom (May 2009).

Xu-Monette, Z.Y., et al., "PD-1 expression and clinical PD-1 blockade in B-cell lymphomas," Blood 131(1):68-83, American Society of Hematology, United States (Jan. 2018).

Zhang, Y., et al., "[Novel immunotherapeutic anti-Hugh for anti-cancer targets]," BIT's *HU st* Annual International Congress of Genetics, China (2016).

English Machine Translation of Zhang, Y., et al., "[Novel immunotherapeutic anti-Hugh for anti-cancer targets]," BIT's 1$^{st}$ Annual International Congress of Genetics, China (2016).

Demeure, C.E., et al., "T Lymphocytes infiltrating various tumour types express the MHC class II ligand lymphocyte activation gene-3 (LAG-3): role of LAG-3/MHC class II interactions in cell-cell contacts," European Journal of Cancer 37:1709-1718, Elsevier Inc., Netherlands (Sep. 2001).

Patel, S.P., et al., "PD-L1 Expression as a Predictive Biomarker in Cancer Immunotherapy," Molecular Cancer Therapeutics 14(4): 847-856, American Association for Cancer Research, United States (Apr. 2015).

Huang, R.Y., et al., "Compensatory upregulation of PD-1, LAG-3, and CTLA-4 limits the efficacy of single-agent checkpoint blockade in metastatic ovarian cancer," Oncoimmunology 6(1):e1249561, Taylor & Francis, United Kingdom (Oct. 2016).

(56) References Cited

OTHER PUBLICATIONS

Co-Pending U.S. Appl. No. 18/705,171, inventor Srivastava; Shivani et al., filed Apr. 26, 2024 (not yet published).
Clinicaltrials.gov, "Neoadjuvant and Adjuvant Checkpoint Blockade," Identifier NCT02519322, Version 23, accessed at https://www.clinicaltrials.gov/study/NCT02519322?term=NCT02519322&rank=1&tab=history&a=23#version-content-panel, dated Aug. 8, 2018, 15 pages.
Clinicaltrials.gov, "Phase 1 Study of IMP321 (Eftilagimod Alpha) Adjuvant to Anti-PD-1 Therapy in Unresectable or Metastatic Melanoma (TACTI-mel)," Identifier NCT02676869, Version 10, accessed at https://clinicaltrials.gov/study/NCT02676869?term=NCT02676869&rank=1&tab=history&a=10, dated Aug. 20, 2018, 13 pages.
Clinicaltrials.gov, "A Study of Relatlimab Plus Nivolumab Versus Nivolumab Alone in Participants With Advanced Melanoma (Relativity-047)," Identifier NCT03470922, Version 14, accessed at https://clinicaltrials.gov/study/NCT03470922?term=NCT03470922&rank=1&tab=history&a=14, dated Oct. 8, 2018, 51 pages.
Tawbi, H.A., et al., "Relatlimab and Nivolumab versus Nivolumab in Untreated Advanced Melanoma," The New England Journal of Medicine 386(1):24-34, Massachusetts Medical Society, United States (Jan. 2022).
International Search Report and Written Opinion for International Application No. PCT/US2021/056241, European Patent Office, Netherlands, mailed on Apr. 4, 2022, 18 pages.
Andrews, L.P., et al., "Inhibitory Receptors and Ligands Beyond PD-1, PD-L1 and CTLA-4: Breakthroughs or Backups," Nature Immunology 20(11):1425-1434, Nature America Inc., United States (Nov. 2019).
Andrews, L.P., et al., "LAG3 (CD223) as a Cancer Immunotherapy Target," Immunological Reviews 276(1):80-96, Blackwell, United Kingdom (Mar. 2017).
Anonymous: "Investigator-Initiated Phase I Trial of CYT001 for unresectable advanced HCC will be started at Chiba University," News Release, accessed at https://www.cytlimic.com/news/20190809_01_en.html, accessed on Nov. 24, 2021, 1 page.
Bristol-Myers Squibb: "History of Changes for Study: NCT01968109, An Investigational Immuno-therapy Study to Assess the Safety, Tolerability and Effectiveness of Anti-LAG-3 With and in the Treatment of Solid Tumors," ClinicalTrials. gov archive, accessed at https://clinicaltrials.gov/ct2/history/NCT01968109?V_76=View#StudyPageTop, accessed on Nov. 24, 2021, 10 pages.
Budczies, J., et al., "Cutoff Finder: A Comprehensive and Straightforward Web Application Enabling Rapid Biomarker Cutoff Optimization," PloS One 7( 12):e51862, pp. 1-7, Public Library of Sciences, United States (Dec. 2012).
Chen, J., et al., "The Effect of Immune Microenvironment on the Progression and Prognosis of Colorectal Cancer," Medical Oncology 31(8):82, pp. 1-8, Springer, United States (Jul. 2014).
Chen, X., et al., "FcγR-Binding Is an Important Functional Attribute for Immune Checkpoint Antibodies in Cancer Immunotherapy," Frontiers in Immunology 10:292, pp. 1-13, Frontiers Research Foundation, Switzerland (Feb. 2019).
Deng, W.W., et al., "LAG-3 Confers Poor Prognosis and Its Blockade Reshapes Antitumor Response in Head and Neck Squamous Cell Carcinoma," Oncoimmunology 5(11):e1239005, 1-14, Taylor & Francis, United States (Oct. 2016).
Floudas, C.S., et al., "Immunotherapy: Current Status and Future Perspectives," Digestive Diseases and Sciences 64(4):1030-1040, Plenum Publishing Corporation, United States (Apr. 2019).
Ghosh, S., et al., "TSR-033, a Novel Therapeutic Antibody Targeting LAG-3, Enhances T-cell Function and the Activity of PD-1 Blockade in Vitro and in Vivo," Molecular Cancer Therapeutics 18(3):632-641, American Association for Cancer Research Inc., United States (Mar. 2019).
He, Y., et al., "LAG-3 Protein Expression in Non-small Cell Lung Cancer and Its Relationship With PD-1/PD-L1 and Tumor-infiltrating Lymphocytes," Journal of Thoracic Oncology 12(5):814-823, Elsevier, United States (Jan. 2017).
He, Y., et al., "Lymphocyte-activation gene-3, an important immune checkpoint in cancer," Cancer Science 107(9):1193-1197, John Wiley & Sons Australia, Ltd., Australia (Sep. 2016).
Ihara, K., "Immune Checkpoint Inhibitor Therapy for Pediatric Cancers: a Mini Review of Endocrine Adverse Events," Clinical Pediatric Endocrinology 28(3):59-68, Jeff Corporation Co., Japan (2019).
Kang, Y.K., et al., "An Open-label, Phase I Trial of BI 754091 Alone and in Combination With BI 754111 in Asian Patients (Pts) With Advanced Solid Tumors," Journal of Clinical Oncology 38(Suppl_15):3054, 1-3, American Society of Clinical Oncology, United States (May 2020).
Mandala, M., and Rutkowski, P., "Rational Combination of Cancer Immunotherapy in Melanoma," Virchows Archiv 474(4):433-447, Springer International, Germany (Apr. 2019).
Marhelava, K., et al., "Targeting Negative and Positive Immune Checkpoints with Monoclonal Antibodies in Therapy of Cancer," Cancers 11(11):1756, pp. 1-21, MDPI, Switzerland (Nov. 2019).
McDermott, D.F., and Atkins, M.B., "PD-1 as a Potential Target in Cancer Therapy," Cancer Medicine 2(5):662-673, John Wiley & Sons Ltd., United States (Oct. 2013).
Melero, I., et al., "Nivolumab Dose Escalation and Expansion in Patients With Advanced Hepatocellular Carcinoma (HCC): the Checkmate 040 Study," Journal of Clinical Oncology 35(Suppl 4): Abstract 226, 4 pages, 2017 Gastrointestinal Cancers Symposium, American Society of Clinical Oncology, United States (Mar. 2017).
NCT02061761, "Safety Study of Anti-LAG-3 in Relapsed or Refractory Hematologic Malignancies," sponsored by Bristol-Myers Squibb, Version 60, dated Aug. 7, 2020, accessed at https://clinicaltrials.gov/study/NCT02061761?term=NCT02061761&rank=1&tab=history&a-60#version-content-panel/, accessed on Aug. 8, 2024, 12 pages.
NCT02460224, "Safety and Efficacy of LAG525 Single Agent and in Combination With PDR001 in Patients With Advanced Malignancies," sponsored by Novartis Pharmaceuticals, Version 28, dated Jun. 19, 2020, accessed at https://clinicaltrials.gov/study/NCT02460224?term=NCT02460224&rank=1&tab=history&a=28#version-content-panel/, accessed on Aug. 8, 2024, 11 pages.
NCT02676869, "Phase 1 Study of IMP321 (Eftilagimod Alpha) Adjuvant to Anti-PD-1 Therapy in Unresectable or Metastatic Melanoma (TACTI-mel)," sponsored by Immutep Australia Pty. Ltd., Version 12, dated Dec. 17, 2019, accessed at https://clinicaltrials.gov/study/NCT02676869?term=NCT02676869&rank=1&tab=history&a=12#version-content-panel/, accessed on Aug. 8, 2024, 8 pages.
NCT02750514, "An Investigational Immuno-therapy Study to Test Combination Treatments in Patients With Advanced Non-Small Cell Lung Cancer (Fraction-Lung)," sponsored by Bristol-Myers Squibb, Version 42, dated Nov. 15, 2019, accessed at https://clinicaltrials.gov/study/NCT02750514?term=NCT02750514&rank=1&tab=history&a=42#version-content-panel/, accessed on Aug. 8, 2024, 13 pages.
NCT03005782, "Study of REGN3767 (Anti-LAG-3) With or Without REGN2810 (Anti-PD1) in Advanced Cancers," sponsored by Regeneron Pharmaceuticals, Version 11, dated Apr. 28, 2020, accessed at https://clinicaltrials.gov/study/NCT03005782?term=NCT03005782&rank=1&tab=history&a=11#version-content-panel/, accessed on Aug. 8, 2024, 13 pages.
NCT03250832, "Study of TSR-033 With an Anti-programmed Cell Death-1 Receptor (PD-1) in Participants With Advanced Solid Tumors (CITRINO)," sponsored by Tesaro, Inc, Version 18, dated Jul. 24, 2020, accessed at https://clinicaltrials.gov/study/NCT03250832?term=NCT03250832&rank=1&tab=history&a=18#version-content-panel/, accessed on Aug. 8, 2024, 22 pages.
NCT03440437, "A Phase 1/2 Study of FS118 in Patients With Advanced Malignancies," invoX Pharma Limited, Version 5, Feb. 3, 2020, accessed at https://clinicaltrials.gov/study/NCT03440437?term=NCT03440437&rank=1&tab=history&a=5#v ersion-content-panel/, accessed on Aug. 8, 2024, 8 pages.
NCT03470922, "A Study of Relatlimab Plus Nivolumab Versus Nivolumab Alone in Participants With Advanced Melanoma (Relativity-047)," sponsored by Bristol-Myers Squibb, Version 35, dated Aug. 6, 2020, accessed at https://clinicaltrials.gov/study/NCT03470922?term=NCT03470922&rank=1&tab=history&a=35#version-content-panel/, accessed on Aug. 8, 2024, 30 pages.

(56) References Cited

OTHER PUBLICATIONS

NCT03598608, "Study to Evaluate the Safety and Efficacy of a Combination of Favezelimab (MK-4280) and Pembrolizumab (MK-3475) in Participants With Hematologic Malignancies (MK-4280-003)," sponsored by Merck Sharp & Dohme LLC, Version 33, dated May 28, 2020, accessed at https://clinicaltrials.gov/study/NCT03598608?term=NCT03598608&rank=1&tab=history&a=33#version-content-panel/, accessed on Aug. 8, 2024, 16 pages.
NCT03662659, "An Investigational Study of Immunotherapy Combinations With Chemotherapy in Patients With Gastric or Gastroesophageal Junction (GEJ) Cancers," sponsored by Bristol-Myers Squibb, Version 40, dated Jun. 29, 2020, accessed at https://clinicaltrials.gov/study/NCT03662659?term=NCT03662659&rank=1&tab=history&a=40#version-content-panel/, accessed on Aug. 8, 2024, 14 pages.
NCT03697304, "Platform Trial Evaluating Safety and Efficacy of B1 754091 Anti-PD-1 Based Combination Therapies in PD-(L)1 naive and PD-(L)1 Pretreated Patient Populations With Advanced/Metastatic Solid Tumours," sponsored by Boehringer Ingelheim, Version 42, dated Jul. 20, 2020, accessed at https://clinicaltrials.gov/study/NCT03697304?term=NCT03697304&rank=1&tab=history&a=42#version-content-panel/, accessed on Aug. 8, 2024, 13 pages.
NCT03704077, "An Investigational Immuno-therapy Study of Relatlimab Plus Nivolumab Compared to Various Standard-of-Care Therapies in Previously Treated Participants With Recurrent, Advanced or Metastatic Gastric Cancer or Gastroesophageal Junction," sponsored by Bristol-Myers Squibb, Version 9, dated May 17, 2020, accessed at https://clinicaltrials.gov/study/NCT03704077?term=NCT03704077&rank=1&tab=history&a=9#version-content-panel/, accessed on Aug. 8, 2024, 13 pages.
NCT03916627, "Neoadjuvant Cemiplimab for the Treatment of Resectable NSCLC, HCC, and HNSCC in Adult Patients," sponsored by Regeneron Pharmaceuticals, Version 5, dated Nov. 22, 2019, accessed at https://clinicaltrials.gov/study/NCT03916627?term=NCT03916627&rank=1&tab=history&a=5#version-content-panel 5/, accessed on Aug. 8, 2024, 9 pages.
Nguyen, L.T., et al., "Clinical blockade of PD 1 and LAG3—potential mechanisms of action," Nature Reviews Immunology 15(1):45-56, Nature Publishing Group, England (Jan. 2015).
Papadopoulos, K.P., et al., "First-in-human Study of REGN3767 (R3767), a Human LAG-3 Monoclonal Antibody (mAb), Cemiplimab in Patients (pts) with Advanced Malignancies," Journal of Clinical Oncology, 37(Suppl_15): Abstract 2508, 2 pages, 2019 ASCO Annual Meeting, American Society of Clinical Oncology, United States (May 2019).
Papadopoulos, K.P., et al., "First-in-human Study of REGN3767 (R3767), a Human LAG-3 Monoclonal Antibody (mAb), Cemiplimab in Patients (pts) with Advanced Malignancies," presented at 2019 ASCO Annual Meeting, Chicago, IL, United States (Jun. 2019).
Robert, C., et al., "Drug of the year: Programmed Death-1 receptor/Programmed Death-1 ILigand-1 receptor monoclonal antibodies," European Journal of Cancer, 49(14):2968-2971, Pergamon Press, United Kingdom (Jul. 2013).
Saleh, R.R., et al., "Prognostic Value of Lymphocyte-Activation Gene 3 (LAG3) in Cancer: A Meta-Analysis," Frontiers in Oncology 15:9:1040, pp. 1-9, Frontiers Research Foundation, Switzerland (Oct. 2019).
Solinas, C., et al., "LAG3: The Biological Processes That Motivate Targeting This Immune Checkpoint Molecule in Human Cancer," Cancers 11(8):1213, pp. 1-16, MDPI, Switzerland (Aug. 2019).
Tassi, E., et al., "Early Effector T Lymphocytes Coexpress Multiple Inhibitory Receptors in Primary Non-small Cell Lung Cancer," Cancer Research 77(4):851-861, American Association for Cancer Research, United States (Feb. 2017).
Uboha, N.V., et al., "Phase II Study of Spartalizumab (PDR001) and LAG525 in Advanced Solid Tumors and Hematologic Malignancies," Journal of Clinical Oncology, 37(Suppl 15): Abstract 2553, 2019 ASCO Annual Meeting I, Chicago, IL, United States (May 2019).
Waldman, A.D., et al., "A Guide to Cancer Immunotherapy: from T Cell Basic Science to Clinical Practice," Nature Reviews. Immunology 20(11):651-668, Nature Publishing Group, United Kingdom (Nov. 2020).
Woo, S.R., et al., "Differential subcellular localization of the regulatory T-cell protein LAG-3 and the coreceptor CD4," European Journal of Immunology 40(6): 1768-1777, Verlag Chemie GmbH, Germany (Jun. 2010).
Workman, C.J., et al., "Cutting Edge: Molecular Analysis of the Negative Regulatory Function of Lymphocyte Activation Gene-3," Journal of Immunology 169(10):5392-5395, American Association of Immunologists, United States (Nov. 2002).
Workman, C.J., et al., "Lymphocyte Activation Gene-3 (CD223) Regulates the Size of the Expanding T Cell Population Following Antigen Activation in Vivo," Journal of Immunology 172(9):5450-5455, American Association of Immunologists, United States (May 2004).
Xu, F., et al., "Immune Checkpoint Therapy in Liver Cancer," Journal of Experimental & Clinical Cancer Research 37(1):110, pp. 1-12, BioMed Central, United Kingdom (May 2018).
Yau, T., et al., "CheckMate 459; A Randomized, Multi-center Phase III Study of Nivolumab (NIVO) vs Sorafenib (SOR) as first-line (IL) Treatment in Patients (pts) with Advanced Hepatocellular Carcinoma (aHCC),"Annals of Oncology, 30(Suppl 5):v874-v875, Elsevier, Netherlands (Oct. 2019).
Yu, X., et al., "Characterization of a Novel Anti-human Lymphocyte Activation Gene 3 (LAG-3) Antibody for Cancer Immunotherapy," mAbs 11(6):1139-1148, Taylor & Francis, United States (Aug. 2019).
Zhong, W., et al., "Comparison of the Molecular and Cellular Phenotypes of Common Mouse Syngeneic Models with Human Tumors," BMC Genomics, 21:2, pp. 1-17, BioMed Central, United Kingdom (Jan. 2020).
Zhou, G., et al., "Antibodies Against Immune Checkpoint Molecules Restore Functions of Tumor-infiltrating T cells in Hepatocellular Carcinomas," Gastroenterology 153(4):1107-1119.e10, W.B. Saunders, United States (Oct. 2017).
Nagasaki, J., et al., "The critical role of CD4+ T cells in PD-1 blockade against MHC-II-expressing tumors such as classic Hodgkin lymphoma," Blood Adv 4(17):4069-4082, The American Society of Hematology, United States (Sep. 2020).
Brignone, C., et al., "A Soluble Form of Lymphocyte Activation Gene-3 (IMP321) Induces Activation of a Large Range of Human Effector Cytotoxic Cells," The Journal of Immunology 179:4202-4211, The American Association of Immunologists, United States (Sep. 2007).
Desai, J., et al., "Phase 1/2 study investigating safety, tolerability, pharmacokinetics, and preliminary antitumor activity of anti-PD-L1 monoclonal antibody bgb-A333 alone and in combination with anti-PD-1 monoclonal antibody tislelizumab in patients with advanced solid tumors," Journal of Clinical Oncology 36 (15_suppl): Abstract TPS3113, American Society of Clinical Oncology, United States (Jun. 2018).
Gandhi, L., et al., "Pembrolizumab plus Chemotherapy in Metastatic Non-Small-Cell Lung Cancer," The New England Journal of Medicine 378:2078-2092, Massachusetts Medical Society, United States (Apr. 2018).
Gadgeel, S., et al., "Updated Analysis From KEYNOTE-189: Pembrolizumab or Placebo Plus Pemetrexed and Platinum for Previously Untreated Metastatic Nonsquamous Non-Small-Cell Lung Cancer," Journal of Clinical Oncology 38:1505-1517, American Society of Clinical Oncology, United States (Mar. 2020).
Jemal, A., et al., "Global Cancer Statistics," CA: A Cancer Journal for Clinicians 61:69-90, American Cancer Society, United States (Feb. 2011).
Kaplon, H., et al., "Antibodies to watch in 2018," MABS 10(2):183-203, Taylor & Francis, United States (Jan. 2018).
Paz-Ares, L., et al., "Pembrolizumab plus Chemotherapy for Squamous Non-Small-Cell Lung Cancer," The New England Journal of Medicine 379:2040-2051, Massachusetts Medical Society, United States (Sep. 2018).
Peters, S., et al., "LBA4_PR - Nivolumab (NIVO) 1 low-dose ipilimumab (IPI) vs platinum doublet chemotherapy (chemo) as

(56) References Cited

OTHER PUBLICATIONS first-line (1L) treatment (tx) for advanced non-small cell lung cancer (NSCLC): CheckMate 227 part 1 final analysis," Annals of Oncology 30(suppl_5):v913- v914, Elsevier, Netherlands (Oct. 2019).
Reck, M., et al., "Nivolumab (NIVO) + ipilimumab (IPI) + 2 cycles of platinum doublet chemotherapy (chemo) vs 4 cycles chemo as first-line (1L) treatment (tx) for stage IV/recurrent non-small cell lung cancer (NSCLC): CheckMate 9LA," Journal of Clinical Oncology 38(15_suppl):Abstract 9501, American Society of Clinical Oncology, United States (May 2020).
Ribas, A., "Anti-CTLA4 Antibody Clinical Trials in Melanoma," Update on Cancer Therapeutics 2(3):133-139, Elsevier Science Ltd., England (Sep. 2007).
Co-Pending U.S. Appl. No. 19/025,264, Bristol-Myers Squibb Company, inventor Korman; Alan J et al., filed Jan. 16, 2025 (not yet published).
Co-Pending U.S. Appl. No. 19/025,919, Bristol-Myers Squibb Company, inventor Burton; Lori S et al., filed Jan. 16, 2025 (not yet published).
Co-Pending U.S. Appl. No. 19/025,563, E.R. Squibb & Sons, L.L.C., inventor Thudium; Kent B. et al., filed Jan. 16, 2025 (not yet published).
Co-Pending U.S. Appl. No. 19/029,969, Bristol-Myers Squibb Company, inventor Korman; Alan J. et al., filed Jan. 17, 2025 (not yet published).
Co-Pending U.S. Appl. No. 19/030,949, Bristol-Myers Squibb Company, inventor Gutierrez; Andres A. et al., filed Jan. 17, 2025 (not yet published).
Yang, X.-Q., et al., "Comparison of first-line chemotherapy based on irinotecan or other drugs to treat non-small cell lung cancer in stage IIIB/IV: a systematic review and meta-analysis," BMC Cancer 15:949, BioMed Central Ltd., United Kingdom (2015).
Horita, N., et al., "The best platinum regimens for chemo-naive incurable non-small cell lung cancer: network metaanalysis," Scientific Reports 7: 13185, Nature Publishing Group, United Kingdom (Oct. 2017).
Paz-Ares, L., et al., "LBA3: Nivolumab (NIVO) + platinum-doublet chemotherapy (chemo) vs chemo as first-line (1L) treatment (tx) for advanced non-small cell lung cancer (aNSCLC): CheckMate 227—part 2 final analysis," Annals of Oncology 30(suppl_11):xi67-xi68, Elsevier, Netherlands (Dec. 2019).
Socinski, M.A., et al., "Atezolizumab for First-Line Treatment of Metastatic Nonsquamous NSCLC," The New England Journal of Medicine 378(24):2288-2301, Massachusetts Medical Society, United States (Jun. 2018).
Noonan, K.L., "The Influence of the Evolution of First-Line Chemotherapy on Steadily Improving Survival in Advanced Non-Small-Cell Lung Cancer Clinical Trials," Journal of Thoracic Oncology 10(11): 1523-1531, Elsevier, United States (Nov. 2015).
Jett, J.R., and Carr, L.L., "Targeted Therapy for Non-Small Cell Lung Cancer," American Journal of Respiratory and Critical Care Medicine 188: 907-912, The American Thoracic Society, United States (2013).
Huang, X.-e., "Interpretation of NCCN Guidelines: General Therapies on Non-small Cell Lung Cancer (Version 6. 2015)," Journal of Translational Internal Medicine 3(2): 145-150, Springer Nature, Germany (2015).
Feeney, K., et al., "CA224-060: A randomized, open label, phase II trial of relatlimab (anti-LAG-3) and nivolumab with chemotherapy versus nivolumab with chemotherapy as first-line treatment in patients with gastric or gastroesophageal junction adenocarcinoma," Journal of Clinical Oncology 37(15_suppl): abstract TPS4143, American Society of Clinical Oncology, United States (May 2019).
Dasgupta, A., et al., "Progression-free survival as surrogate endpoint for overall survival in NSCLC trials of anti PD-1 and anti PD-L1 agents and the impact of line of treatment," Journal of Clinical Oncology 36(15_suppl): abstract e21135, American Society of Clinical Oncology, United States (Jun. 2018).
Long, G.V., et al., "Assessment of nivolumab exposure and clinical safety of 480 mg every 4 weeks flat-dosing schedule in patients with cancer," Annals of Oncology 29(11):2208-2213, Oxford University Press, United Kingdom (Nov. 2018).
Sanlorenzo, M., et al., "Melanoma immunotherapy," Cancer Biology & Therapy 15(6):665-674, Landes Bioscience, United States (Jun. 2014).
Taube, J.M., et al.., "Differential Expression of Immune-Regulatory Genes Associated with PD-L1 Display in Melanoma: Implications for PD-1 Pathway Blockade," Clinical Cancer Research 21(17):3969-3976, American Association for Cancer Research, United States (Sep. 2015).
Diggs, L.P., and Hsueh, E.C., "Utility of PD-L1 immunohistochemistry assays for predicting PD-1/PD-L1 inhibitor response," Biomarker Research 5:12, pp. 1-6, BioMed Central, United Kingdom (Mar. 2017).
Li, M., et al., "Next generation of anti-PD-L1 Atezolizumab with enhanced anti-tumor efficacy in vivo," Scientific Reports 11(1):5774, pp. 1-11, Nature Publishing Group, United Kingdom (Mar. 2021).
Hammond, M.E.H., et al., "American Society of Clinical Oncology/College Of American Pathologists guideline recommendations for immunohistochemical testing of estrogen and progesterone receptors in breast cancer," Journal of Clinical Oncology 28(16):2784-2795, American Society of Clinical Oncology, United States (Jun. 2010).
Hirsch, F.R., et al., "PD-L1 Immunohistochemistry Assays for Lung Cancer: Results from Phase 1 of the Blueprint PD-L1 Ihc Assay Comparison Project," Journal of Thoracic Oncology 12(2):208-222, Elsevier, United States (Feb. 2017).
Pepinsky, R.B., et al., "Improving the solubility of anti-LINGO-1 monoclonal antibody Li33 by isotype switching and targeted mutagenesis," Protein Science 19(5):954-966, Wiley-Blackwell, United States (May 2010).
Prichard, J., et al., "Predictive Markers of Breast Cancer: Er, Pr, and HER2," in *Handbook of Practical Immunohistochemistry: Frequently Asked Questions,* Chapter 9, Lin, F., et al., eds., pp. 103-117, Springer, United States (2011).
Topalian, S.L., et al., "Mechanism-driven biomarkers to guide immune checkpoint blockade in cancer therapy," Nature Reviews Cancer 16(5):275-287, Nature Publishing Group, United Kingdom (May 2016).
Tumeh, P.C., et al., "PD-1 blockade induces responses by inhibiting adaptive immune resistance," Nature 515(7528):568-571, Nature Publishing Group, United Kingdom (Nov. 2014).
Tsao, M.S., et al., eds., *IASLC Atlas of PD-L1 Immunohistochemistry Testing in Lung Cancer,* 132 pages, Editorial Rx Press, United States (2017).
Co-pending Application, U.S. Appl. No. 18/870,218, inventors Burton, L.S., et al., 371(c) Date: Nov. 27, 2024 (Not yet Published).
Co-pending Application, U.S. Appl. No. 19/141,978, inventors Abaskharoun, M.M., et al., Int'l Filing Date: Dec. 20, 2023 (Not yet Published).
Co-pending Application, U.S. Appl. No. 19/213,805, inventors Edwards, R., et al., filed May 20, 2025 (Not yet Published).
Co-pending Application, U.S. Appl. No. 19/277,809, inventors Srivastava, S., filed Jul. 23, 2025 (Not yet Published).
Takahashi, N., "Recent Progress and Prospects of Medical Therapy for Lung Cancer," Nihon University Journal of Medicine 77(6):375-378, Nihon University, Japan (Dec. 2018).
Xu, Y., et al., "LAG-3 and PD-1/PD-L1 Inhibitors Might Become a Promising Treatment for Small Cell Lung Cancer," Research Square Preprint Version 1, doi: https://doi.org/10.21203/rs.3.rs-41769/v1, pp. 1-16, Research Square, United States (Jul. 2020).

* cited by examiner

LAG-3 ANTAGONIST THERAPY FOR LUNG CANCER

CROSS REFERENCE TO RELATED APPLICATIONS

This application is a continuation of U.S. application Ser. No. 18/033,200, which is the National Stage of International Application No. PCT/US2021/056241, filed Oct. 22, 2021, which claims the priority benefit of U.S. Provisional Application Nos. 63/104,744, filed Oct. 23, 2020, and 63/110,210, filed Nov. 5, 2020, which are incorporated herein by reference in their entireties.

REFERENCE TO SEQUENCE LISTING SUBMITTED ELECTRONICALLY

The content of the electronically submitted sequence listing (Name: 3338_2400003_SequenceListing_ST26.xml; Size: 101,917 Bytes; and Date of Creation: Jun. 26, 2024) is herein incorporated by reference in its entirety.

FIELD OF THE INVENTION

The present disclosure provides methods of treating human subjects afflicted with lung cancer comprising a lymphocyte activation gene-3 (LAG-3) antagonist.

BACKGROUND OF THE INVENTION

Lung cancer, and particularly non-small cell lung cancer (NSCLC) remains the leading cause of cancer-related mortality worldwide, accounting for approximately 18% of all cancer deaths (Jenal A, et al., *CA Cancer J. Clin.* 2011; 61:69-90).

Until recently, the treatment of patients with advanced NSCLC whose tumors did not have a targetable genetic alteration was cytotoxic chemotherapy alone. In spite of treatment, patients with metastatic NSCLC treated with platinum doublet chemotherapy had a median survival of approximately 10 months and a 5-year survival rate of less than 5%. The introduction of immune checkpoint inhibitors targeting the PD-1 signaling pathway in the treatment of patients with NSCLC has had a significant effect on patient survival. The anti-PD-1 antibody pembrolizumab combined with chemotherapy in the front-line setting has demonstrated an improvement in overall survival in NSCLC patients as compared to chemotherapy alone (Gandhi L, et al., *N. Engl. J. Med.* 2018; 378:2078-2092; Paz-Ares L, et al., *N. Engl. J. Med.* 2018; 379:2040-2051). More recently, the anti-PD-1 antibody nivolumab plus the anti-CTLA-4 antibody ipilimumab, as well as nivolumab plus ipilimumab in combination with chemotherapy, also showed benefit over chemotherapy in this setting (Peters S, et al., *Annals of Oncology* 2019; 30 (suppl_5):v851-v934; Reck M, *J. Clin. Oncol.* 2020; (suppl):abstr. 9501). However, despite these advances, the median survival of first line patients with metastatic NSCLC is approximately 22 months in the non-squamous and 15.9 months in the squamous population (Paz-Ares L, et al.; Gadgeel S, et al., *J. Clin. Oncol.* 2020; 38(14):1505-1517).

There is a need for improved methods for treating human subjects afflicted with lung cancer.

SUMMARY OF THE INVENTION

The present disclosure is directed to method of treating a human subject afflicted with lung cancer, the method comprising administering to the subject a lymphocyte activation gene-3 (LAG-3) antagonist and a platinum doublet chemotherapy (PDCT).

In some aspects, the method is a first line therapy.

In some aspects, the method is a second line therapy.

In some aspects, the method is a third line therapy.

In some aspects, the subject has progressed on a prior therapy.

In some aspects, the lung cancer is recurrent following multi-modal therapy for locally advanced lung cancer.

In some aspects, the subject has not received a prior systemic therapy for cancer, the subject has not received a prior systemic therapy for lung cancer, or the subject has not received a prior systemic therapy for advanced or metastatic lung cancer.

In some aspects, the subject is naïve to prior immuno-oncology therapy, the subject is naïve to prior immuno-oncology therapy for lung cancer, or the lung cancer is naïve to prior immuno-oncology therapy.

In some aspects, the lung cancer is unresectable, advanced, recurrent, and/or metastatic.

In some aspects, the subject is afflicted with a Stage IV lung cancer.

In some aspects, the lung cancer is small cell lung cancer.

In some aspects, the lung cancer is non-small cell lung cancer (NSCLC). In some aspects, the NSCLC has a squamous or non-squamous histology.

In some aspects, one or more immune cells in tumor tissue from the subject express LAG-3. In some aspects, at least about 1%, at least about 3%, at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, or about 100% of the immune cells express LAG-3. In some aspects, at least about 1% of the immune cells express LAG-3. In some aspects, the immune cells are tumor-infiltrating lymphocytes. In some aspects, the tumor-infiltrating lymphocytes are $CD8^+$ cells.

In some aspects, one or more tumor cells in tumor tissue from the subject express PD-L1. In some aspects, at least about 1%, at least about 3%, at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, or about 100% of the tumor cells express PD-L1. In some aspects, at least about 1% of the tumor cells express PD-L1.

In some aspects, the LAG-3 antagonist is an anti-LAG-3 antibody.

In some aspects, the anti-LAG-3 antibody is a full-length antibody.

In some aspects, the anti-LAG-3 antibody is a monoclonal, human, humanized, chimeric, or multispecific antibody. In some aspects, the multispecific antibody is a dual-affinity re-targeting antibody (DART), a DVD-Ig, or bispecific antibody.

In some aspects, the anti-LAG-3 antibody is a F(ab')2 fragment, a Fab' fragment, a Fab fragment, a Fv fragment, a scFv fragment, a dsFv fragment, a dAb fragment, or a single chain binding polypeptide.

In some aspects, the anti-LAG-3 antibody is BMS-986016 (relatlimab), IMIP731 (H5L7BW), MK4280 (28G-10, favezelimab), REGN3767 (fianlimab), GSK2831781, humanized BAP050, IMP-701 (LAG525, ieramilimab), aLAG3(0414), aLAG3(0416), Sym022, TSR-033, TSR- 075, XmAb841 (XmAb22841), MGD013 (tebotelimab), B1754111, FS118, P 13B02-30, AVA-017, 25F7, AGEN1746, RO7247669, INCAGNO2385, IBI-110, EMB-02, IBI-323, LBL-007, ABL501, or comprises an antigen binding portion thereof.

In some aspects, the anti-LAG-3 antibody comprises CDR1, CDR2 and CDR3 domains of the heavy chain variable region having the sequence set forth in SEQ ID NO:3, and CDR1, CDR2 and CDR3 domains of the light chain variable region having the sequence set forth in SEQ ID NO:4.

In some aspects, the anti-LAG-3 antibody comprises: (a) a heavy chain variable region CDR1 comprising the sequence set forth in SEQ ID NO:5; (b) a heavy chain variable region CDR2 comprising the sequence set forth in SEQ ID NO: 6; (c) a heavy chain variable region CDR3 comprising the sequence set forth in SEQ ID NO:7; (d) a light chain variable region CDR1 comprising the sequence set forth in SEQ ID NO:8; (e) a light chain variable region CDR2 comprising the sequence set forth in SEQ ID NO:9; and (f) a light chain variable region CDR3 comprising the sequence set forth in SEQ ID NO:10.

In some aspects, the anti-LAG-3 antibody comprises heavy and light chain variable regions comprising the sequences set forth in SEQ ID NOs:3 and 4, respectively.

In some aspects, the anti-LAG-3 antibody comprises heavy and light chains comprising the sequences set forth in SEQ ID NOs:1 and 2, respectively.

In some aspects, the anti-LAG-3 antibody comprises heavy and light chains comprising the sequences set forth in SEQ ID NOs:21 and 2, respectively.

In some aspects, the LAG-3 antagonist is a soluble LAG-3 polypeptide. In some aspects, the soluble LAG-3 polypeptide is a fusion polypeptide. In some aspects, the soluble LAG-3 polypeptide comprises a ligand binding fragment of the LAG-3 extracellular domain. In some aspects, the ligand binding fragment of the LAG-3 extracellular domain comprises an amino acid sequence with at least about 90%, at least about 95%, at least about 98%, at least about 99%, or about 100% sequence identity to SEQ ID NO:22. In some aspects, the soluble LAG-3 polypeptide further comprises a half-life extending moiety. In some aspects, the half-life extending moiety comprises an immunoglobulin constant region or a portion thereof, an immunoglobulin-binding polypeptide, an immunoglobulin G (IgG), albumin-binding polypeptide (ABP), a PASylation moiety, a HESylation moiety, XTEN, a PEGylation moiety, an Fc region, or any combination thereof. In some aspects, the soluble LAG-3 polypeptide is IMP321 (eftilagimod alpha).

In some aspects, the LAG-3 antagonist is formulated for intravenous administration.

In some aspects, the LAG-3 antagonist is administered at a flat dose.

In some aspects, the LAG-3 antagonist is administered at a dose of from at least about 0.25 mg to about 2000 mg, about 0.25 mg to about 1600 mg, about 0.25 mg to about 1200 mg, about 0.25 mg to about 800 mg, about 0.25 mg to about 400 mg, about 0.25 mg to about 100 mg, about 0.25 mg to about 50 mg, about 0.25 mg to about 40 mg, about 0.25 mg to about 30 mg, about 0.25 mg to about 20 mg, about 20 mg to about 2000 mg, about 20 mg to about 1600 mg, about 20 mg to about 1200 mg, about 20 mg to about 800 mg, about 20 mg to about 400 mg, about 20 mg to about 100 mg, about 100 mg to about 2000 mg, about 100 mg to about 1800 mg, about 100 mg to about 1600 mg, about 100 mg to about 1400 mg, about 100 mg to about 1200 mg, about 100 mg to about 1000 mg, about 100 mg to about 800 mg, about 100 mg to about 600 mg, about 100 mg to about 400 mg, about 400 mg to about 2000 mg, about 400 mg to about 1800 mg, about 400 mg to about 1600 mg, about 400 mg to about 1400 mg, about 400 mg to about 1200 mg, or about 400 mg to about 1000 mg.

In some aspects, the LAG-3 antagonist is administered at a dose of about 0.25 mg, about 0.5 mg, about 0.75 mg, about 1 mg, about 1.25 mg, about 1.5 mg, about 1.75 mg, about 2 mg, about 2.25 mg, about 2.5 mg, about 2.75 mg, about 3 mg, about 3.25 mg, about 3.5 mg, about 3.75 mg, about 4 mg, about 4.25 mg, about 4.5 mg, about 4.75 mg, about 5 mg, about 5.25 mg, about 5.5 mg, about 5.75 mg, about 6 mg, about 6.25 mg, about 6.5 mg, about 6.75 mg, about 7 mg, about 7.25 mg, about 7.5 mg, about 7.75 mg, about 8 mg, about 8.25 mg, about 8.5 mg, about 8.75 mg, about 9 mg, about 9.25 mg, about 9.5 mg, about 9.75 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, about 600 mg, about 610 mg, about 620 mg, about 630 mg, about 640 mg, about 650 mg, about 660 mg, about 670 mg, about 680 mg, about 690 mg, about 700 mg, about 710 mg, about 720 mg, about 730 mg, about 740 mg, about 750 mg, about 760 mg, about 770 mg, about 780 mg, about 790 mg, about 800 mg, about 810 mg, about 820 mg, about 830 mg, about 840 mg, about 850 mg, about 860 mg, about 870 mg, about 880 mg, about 890 mg, about 900 mg, about 910 mg, about 920 mg, about 930 mg, about 940 mg, about 950 mg, about 960 mg, about 970 mg, about 980 mg, about 990 mg, about 1000 mg, about 1040 mg, about 1080 mg, about 1100 mg, about 1140 mg, about 1180 mg, about 1200 mg, about 1240 mg, about 1280 mg, about 1300 mg, about 1340 mg, about 1380 mg, about 1400 mg, about 1440 mg, about 1480 mg, about 1500 mg, about 1540 mg, about 1580 mg, about 1600 mg, about 1640 mg, about 1680 mg, about 1700 mg, about 1740 mg, about 1780 mg, about 1800 mg, about 1840 mg, about 1880 mg, about 1900 mg, about 1940 mg, about 1980 mg, or about 2000 mg.

In some aspects, the LAG-3 antagonist is administered at a weight-based dose.

In some aspects, the LAG-3 antagonist is administered at a dose from about 0.003 mg/kg to about 25 mg/kg, about 0.003 mg/kg to about 20 mg/kg, about 0.003 mg/kg to about 15 mg/kg, about 0.003 mg/kg to about 10 mg/kg, about 0.003 mg/kg to about 5 mg/kg, about 0.003 mg/kg to about 1 mg/kg, about 0.003 mg/kg to about 0.9 mg/kg, about 0.003 mg/kg to about 0.8 mg/kg, about 0.003 mg/kg to about 0.7 mg/kg, about 0.003 mg/kg to about 0.6 mg/kg, about 0.003 mg/kg to about 0.5 mg/kg, about 0.003 mg/kg to about 0.4 mg/kg, about 0.003 mg/kg to about 0.3 mg/kg, about 0.003 mg/kg to about 0.2 mg/kg, about 0.003 mg/kg to about 0.1 mg/kg, about 0.1 mg/kg to about 25 mg/kg, about 0.1 mg/kg to about 20 mg/kg, about 0.1 mg/kg to about 15 mg/kg, about 0.1 mg/kg to about 10 mg/kg, about 0.1 mg/kg to about 5 mg/kg, about 0.1 mg/kg to about 1 mg/kg, about 1 mg/kg to about 25 mg/kg, about 1 mg/kg to about 20 mg/kg, about 1 mg/kg to about 15 mg/kg, about 1 mg/kg to about 10 mg/kg, about 1 mg/kg to about 5 mg/kg, about 5 mg/kg to about 25 mg/kg, about 5 mg/kg to about 20 mg/kg, about 5 mg/kg to about 15 mg/kg, about 5 mg/kg to about 10 mg/kg, about 10 mg/kg to about 25 mg/kg, about 10 mg/kg to about 20 mg/kg, about 10 mg/kg to about 15 mg/kg, about 15 mg/kg to about 25 mg/kg, about 15 mg/kg to about 20 mg/kg, or about 20 mg/kg to about 25 mg/kg.

In some aspects, the LAG-3 antagonist is administered at a dose of about 0.003 mg/kg, about 0.004 mg/kg, about 0.005 mg/kg, about 0.006 mg/kg, about 0.007 mg/kg, about 0.008 mg/kg, about 0.009 mg/kg, about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1.0 mg/kg, about 2.0 mg/kg, about 3.0 mg/kg, about 4.0 mg/kg, about 5.0 mg/kg, about 6.0 mg/kg, about 7.0 mg/kg, about 8.0 mg/kg, about 9.0 mg/kg, about 10.0 mg/kg, about 11.0 mg/kg, about 12.0 mg/kg, about 13.0 mg/kg, about 14.0 mg/kg, about 15.0 mg/kg, about 16.0 mg/kg, about 17.0 mg/kg, about 18.0 mg/kg, about 19.0 mg/kg, about 20.0 mg/kg, about 21.0 mg/kg, about 22.0 mg/kg, about 23.0 mg/kg, about 24.0 mg/kg, or about 25.0 mg/kg.

In some aspects, the dose is administered once about every one week, once about every two weeks, once about every three weeks, once about every four weeks, once about every five weeks, once about every six weeks, once about every seven weeks, once about every eight weeks, once about every nine weeks, once about every ten weeks, once about every eleven weeks, or once about every twelve weeks.

In some aspects, the PDCT comprises a platinum agent in combination with a nucleoside analog, an antimetabolite, a taxane, a vinca alkaloid, or a topisomerase inhibitor. In some aspects, the platinum agent is cisplatin, carboplatin, oxaliplatin, satraplatin, picoplatin, nedaplatin, triplatin, lipoplatin, or phenanthriplatin. In some aspects, the platinum agent is cisplatin. In some aspects, the platinum agent is carboplatin. In some aspects, the nucleoside analog is cytarabine, gemcitabine, lamivudine, entecavir, or telbivudine. In some aspects, the nucleoside analog is gemcitabine. In some aspects, the antimetabolite is capecitabine, cladribine, clofarabine, cytarabine, floxuridine, fludarabine, fluorouracil, mercaptopurine, methotrexate, pemetrexed, pentostatin, pralatrexate, or thioguanine. In some aspects, the antimetabolite is pemetrexed. In some aspects, the taxane is paclitaxel, albumin-bound paclitaxel, docetaxel, or cabazitaxel. In some aspects, the vinca alkaloid is vinblastine, vincristine, vinorelbine, vindesine, vincaminol, vineridine, or vinburnine. In some aspects, the vinca alkaloid is vinorelbine or vinblastine. In some aspects, the topoisomerase inhibitor is etoposide, mitoxantrone, doxorubicin, irinotecan, topotecan, or camptothecin. In some aspects, the topoisomerase inhibitor is etoposide. In some aspects, the topoisomerase inhibitor is irinotecan.

In some aspects, the PDCT comprises cisplatin or carboplatin in combination with gemcitabine, pemetrexed, paclitaxel, albumin-bound paclitaxel, docetaxel, vinorelbine, vinblastine, etoposide, or irinotecan.

In some aspects, the PDCT comprises cisplatin or carboplatin in combination with paclitaxel or albumin-bound paclitaxel.

In some aspects, the PDCT comprises cisplatin or carboplatin in combination with pemetrexed.

In some aspects, the method further comprises administering to the subject an additional therapeutic agent. In some aspects, the additional therapeutic agent comprises an anti-cancer agent. In some aspects, the anti-cancer agent comprises a tyrosine kinase inhibitor, an anti-angiogenesis agent, a checkpoint inhibitor, a checkpoint stimulator, a chemotherapeutic agent, an immunotherapeutic agent, a platinum agent, an alkylating agent, a taxane, a nucleoside analog, an antimetabolite, a topisomerase inhibitor, an anthracycline, a vinca alkaloid, or any combination thereof.

In some aspects, the tyrosine kinase inhibitor comprises afatinib, erlotinib, dacomitinib, gefitinib, osimertinib, alectinib, brigatinib, ceritinib, crizotinib, lorlatinib, entrectinib, dabrafenib, trametinib, vemurafenib, larotrectinib, or any combination thereof.

In some aspects, the anti-angiogenesis agent comprises an inhibitor of a vascular endothelial growth factor (VEGF), VEGF receptor (VEGFR), platelet-derived growth factor (PDGF), PDGF receptor (PDGFR), angiopoietin (Ang), tyrosine kinase with Ig-like and EGF-like domains (Tie) receptor, hepatocyte growth factor (HGF), tyrosine-protein kinase Met (c-MET), C-type lectin family 14 member A (CLEC14A), multimerin 2 (MMRN2), shock protein 70-1A (HSP70-IA), a epidermal growth factor (EGF), EGF receptor (EGFR), or any combination thereof.

In some aspects, the anti-angiogenesis agent comprises bevacizumab, ramucirumab, aflibercept, tanibirumab, olaratumab, nesvacumab, AMG780, MEDI3617, vanucizumab, rilotumumab, ficlatuzumab, TAK-701, onartuzumab, emibetuzumab, or any combination thereof.

In some aspects, the checkpoint inhibitor comprises a programmed death-1 (PD-1) pathway inhibitor, a cytotoxic T-lymphocyte-associated protein 4 (CTLA-4) inhibitor, a T cell immunoglobulin and ITIM domain (TIGIT) inhibitor, a T cell immunoglobulin and mucin-domain containing-3 (TIM-3) inhibitor, a $TIM^{-1}$ inhibitor, a TIM-4 inhibitor, a B7-H3 inhibitor, a B7-H4 inhibitor, a B and T cell lymphocyte attenuator (BTLA) inhibitor, a V-domain Ig suppressor of T cell activation (VISTA) inhibitor, an indoleamine 2,3-dioxygenase (IDO) inhibitor, a nicotinamide adenine dinucleotide phosphate oxidase isoform 2 (NOX2) inhibitor, a killer-cell immunoglobulin-like receptor (KIR) inhibitor, an adenosine A2a receptor (A2aR) inhibitor, a transforming growth factor beta (TGF-β) inhibitor, a phosphoinositide 3-kinase (PI3K) inhibitor, a CD47 inhibitor, a CD48 inhibitor, a CD73 inhibitor, a CD 113 inhibitor, a sialic acid-binding immunoglobulin-like lectin-7 (SIGLEC-7) inhibitor, a SIGLEC-9 inhibitor, a SIGLEC-15 inhibitor, a glucocorticoid-induced TNFR-related protein (GITR) inhibitor, a galectin-1 inhibitor, a galectin-9 inhibitor, a carcinoembryonic antigen-related cell adhesion molecule-1 ($CEACAM^{-1}$) inhibitor, a G protein-coupled receptor 56 (GPR56) inhibitor, a glycoprotein A repetitions predominant (GARP) inhibitor, a 2B4 inhibitor, a programmed death-1 homolog (PD1H) inhibitor, a leukocyte-associated immunoglobulin-like receptor 1 (LAIR1) inhibitor, or any combination thereof.

In some aspects, the checkpoint inhibitor comprises a PD-1 pathway inhibitor.

In some aspects, the PD-1 pathway inhibitor is an anti-PD-1 antibody and/or an anti-PD-L1 antibody.

In some aspects, the PD-1 pathway inhibitor is an anti-PD-1 antibody.

In some aspects, the anti-PD-1 antibody is a full-length antibody.

In some aspects, the anti-PD-1 antibody is a monoclonal, human, humanized, chimeric, or multispecific antibody. In some aspects, the multispecific antibody is a DART, a DVD-Ig, or bispecific antibody.

In some aspects, the anti-PD-1 antibody is a F(ab')2 fragment, a Fab' fragment, a Fab fragment, a Fv fragment, a scFv fragment, a dsFv fragment, a dAb fragment, or a single chain binding polypeptide.

In some aspects, the anti-PD-1 antibody is nivolumab, pembrolizumab, PDRO01 (spartalizumab), MEDI-0680, TSR-042, cemiplimab, JS001, PF-06801591, BGB-A317, BI 754091, INCSHR1210, GLS-010, AM-001, STI-1110, AGEN2034, MGA012, BCD-100, IBI308, SSI-361, or comprises an antigen binding portion thereof.

In some aspects, the anti-PD-1 antibody comprises CDR1, CDR2 and CDR3 domains of the heavy chain variable region having the sequence set forth in SEQ ID NO:13, and CDR1, CDR2 and CDR3 domains of the light chain variable region having the sequence set forth in SEQ ID NO:14.

In some aspects, the anti-PD-1 antibody comprises: (a) a heavy chain variable region CDR1 comprising the sequence set forth in SEQ ID NO:15; (b) a heavy chain variable region CDR2 comprising the sequence set forth in SEQ ID NO:16; (c) a heavy chain variable region CDR3 comprising the sequence set forth in SEQ ID NO:17; (d) a light chain variable region CDR1 comprising the sequence set forth in SEQ ID NO: 18; (e) a light chain variable region CDR2 comprising the sequence set forth in SEQ ID NO: 19; and (f) a light chain variable region CDR3 comprising the sequence set forth in SEQ ID NO:20.

In some aspects, the anti-PD-1 antibody comprises heavy and light chain variable regions comprising the sequences set forth in SEQ ID NOs:13 and 14, respectively.

In some aspects, the anti-PD-1 antibody comprises heavy and light chains comprising the sequences as set forth in SEQ ID NOs:11 and 12, respectively.

In some aspects, the PD-1 pathway inhibitor is a soluble PD-L2 polypeptide. In some aspects, the soluble PD-L2 polypeptide is a fusion polypeptide. In some aspects, the soluble PD-L2 polypeptide comprises a ligand binding fragment of the PD-L2 extracellular domain. In some aspects, the soluble PD-L2 polypeptide further comprises a half-life extending moiety. In some aspects, the half-life extending moiety comprises an immunoglobulin constant region or a portion thereof, an immunoglobulin-binding polypeptide, an immunoglobulin G (IgG), albumin-binding polypeptide (ABP), a PASylation moiety, a HESylation moiety, XTEN, a PEGylation moiety, an Fc region, or any combination thereof. In some aspects, the soluble PD-L2 polypeptide is AMP-224.

In some aspects, the PD-1 pathway inhibitor is an anti-PD-L1 antibody.

In some aspects, the anti-PD-L1 antibody is a full-length antibody.

In some aspects, the anti-PD-L1 antibody is a monoclonal, human, humanized, chimeric, or multispecific antibody. In some aspects, the multispecific antibody is a DART, a DVD-Ig, or bispecific antibody.

In some aspects, the anti-PD-L1 antibody is a $F(ab')_2$ fragment, a Fab' fragment, a Fab fragment, a Fv fragment, a scFv fragment, a dsFv fragment, a dAb fragment, or a single chain binding polypeptide.

In some aspects, the anti-PD-L1 antibody is BMS-936559, atezolizumab, durvalumab, avelumab, STI-1014, CX-072, KN035, LY3300054, BGB-A333, ICO 36, FAZ053, CK-301, or comprises an antigen binding portion thereof.

In some aspects, the PD-1 pathway inhibitor is BMS-986189.

In some aspects, the checkpoint inhibitor comprises a CTLA-4 inhibitor.

In some aspects, the CTLA-4 inhibitor is an anti-CTLA-4 antibody.

In some aspects, the anti-CTLA-4 antibody is a full-length antibody.

In some aspects, the anti-CTLA-4 antibody is a monoclonal, human, humanized, chimeric, or multispecific antibody. In some aspects, the multispecific antibody is a DART, a DVD-Ig, or bispecific antibody.

In some aspects, the anti-CTLA-4 antibody is a $F(ab')_2$ fragment, a Fab' fragment, a Fab fragment, a Fv fragment, a scFv fragment, a dsFv fragment, a dAb fragment, or a single chain binding polypeptide.

In some aspects, the anti-CTLA-4 antibody is ipilimumab, tremelimumab, MK-1308, AGEN-1884, or comprises an antigen binding portion thereof.

In some aspects, the checkpoint inhibitor is formulated for intravenous administration.

In some aspects, the LAG-3 antagonist and the checkpoint inhibitor are formulated separately. In some aspects, each checkpoint inhibitor is formulated separately when the checkpoint inhibitor comprises more than one checkpoint inhibitor. In some aspects, the checkpoint inhibitor is administered before the LAG-3 antagonist. In some aspects, the LAG-3 antagonist is administered before the checkpoint inhibitor.

In some aspects, the LAG-3 antagonist and the checkpoint inhibitor are formulated together. In some aspects, two or more checkpoint inhibitors are formulated together when the checkpoint inhibitor comprises more than one checkpoint inhibitor.

In some aspects, the LAG-3 antagonist and the checkpoint inhibitor are administered concurrently.

In some aspects, the checkpoint inhibitor is administered at a flat dose.

In some aspects, the checkpoint inhibitor is administered at a dose of from at least about 0.25 mg to about 2000 mg, about 0.25 mg to about 1600 mg, about 0.25 mg to about 1200 mg, about 0.25 mg to about 800 mg, about 0.25 mg to about 400 mg, about 0.25 mg to about 100 mg, about 0.25 mg to about 50 mg, about 0.25 mg to about 40 mg, about 0.25 mg to about 30 mg, about 0.25 mg to about 20 mg, about 20 mg to about 2000 mg, about 20 mg to about 1600 mg, about 20 mg to about 1200 mg, about 20 mg to about 800 mg, about 20 mg to about 400 mg, about 20 mg to about 100 mg, about 100 mg to about 2000 mg, about 100 mg to about 1800 mg, about 100 mg to about 1600 mg, about 100 mg to about 1400 mg, about 100 mg to about 1200 mg, about 100 mg to about 1000 mg, about 100 mg to about 800 mg, about 100 mg to about 600 mg, about 100 mg to about 400 mg, about 400 mg to about 2000 mg, about 400 mg to about 1800 mg, about 400 mg to about 1600 mg, about 400 mg to about 1400 mg, about 400 mg to about 1200 mg, or about 400 mg to about 1000 mg.

In some aspects, the checkpoint inhibitor is administered at a dose of about 0.25 mg, about 0.5 mg, about 0.75 mg, about 1 mg, about 1.25 mg, about 1.5 mg, about 1.75 mg, about 2 mg, about 2.25 mg, about 2.5 mg, about 2.75 mg, about 3 mg, about 3.25 mg, about 3.5 mg, about 3.75 mg, about 4 mg, about 4.25 mg, about 4.5 mg, about 4.75 mg, about 5 mg, about 5.25 mg, about 5.5 mg, about 5.75 mg, about 6 mg, about 6.25 mg, about 6.5 mg, about 6.75 mg, about 7 mg, about 7.25 mg, about 7.5 mg, about 7.75 mg, about 8 mg, about 8.25 mg, about 8.5 mg, about 8.75 mg, about 9 mg, about 9.25 mg, about 9.5 mg, about 9.75 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, about 600 mg, about 610 mg, about 620 mg, about 630 mg, about 640 mg, about 650 mg, about 660 mg, about 670 mg, about 680 mg, about 690 mg, about 700 mg, about 710 mg, about 720 mg, about 730 mg, about 740 mg, about 750 mg, about 760 mg, about 770 mg, about 780 mg, about 790 mg, about 800 mg, about 810 mg, about 820 mg, about 830 mg, about 840 mg, about 850 mg, about 860 mg, about 870 mg, about 880 mg, about 890 mg, about 900 mg, about 910 mg, about 920 mg, about 930 mg, about 940 mg, about 950 mg, about 960 mg, about 970 mg, about 980 mg, about 990 mg, about 1000 mg, about 1040 mg, about 1080 mg, about 1100 mg, about 1140 mg, about 1180 mg, about 1200 mg, about 1240 mg, about 1280 mg, about 1300 mg, about 1340 mg, about 1380 mg, about 1400 mg, about 1440 mg, about 1480 mg, about 1500 mg, about 1540 mg, about 1580 mg, about 1600 mg, about 1640 mg, about 1680 mg, about 1700 mg, about 1740 mg, about 1780 mg, about 1800 mg, about 1840 mg, about 1880 mg, about 1900 mg, about 1940 mg, about 1980 mg, or about 2000 mg.

In some aspects, the checkpoint inhibitor is administered as a weight-based dose.

In some aspects, the checkpoint inhibitor is administered at a dose from about 0.003 mg/kg to about 25 mg/kg, about 0.003 mg/kg to about 20 mg/kg, about 0.003 mg/kg to about 15 mg/kg, about 0.003 mg/kg to about 10 mg/kg, about 0.003 mg/kg to about 5 mg/kg, about 0.003 mg/kg to about 1 mg/kg, about 0.003 mg/kg to about 0.9 mg/kg, about 0.003 mg/kg to about 0.8 mg/kg, about 0.003 mg/kg to about 0.7 mg/kg, about 0.003 mg/kg to about 0.6 mg/kg, about 0.003 mg/kg to about 0.5 mg/kg, about 0.003 mg/kg to about 0.4 mg/kg, about 0.003 mg/kg to about 0.3 mg/kg, about 0.003 mg/kg to about 0.2 mg/kg, about 0.003 mg/kg to about 0.1 mg/kg, about 0.1 mg/kg to about 25 mg/kg, about 0.1 mg/kg to about 20 mg/kg, about 0.1 mg/kg to about 15 mg/kg, about 0.1 mg/kg to about 10 mg/kg, about 0.1 mg/kg to about 5 mg/kg, about 0.1 mg/kg to about 1 mg/kg, about 1 mg/kg to about 25 mg/kg, about 1 mg/kg to about 20 mg/kg, about 1 mg/kg to about 15 mg/kg, about 1 mg/kg to about 10 mg/kg, about 1 mg/kg to about 5 mg/kg, about 5 mg/kg to about 25 mg/kg, about 5 mg/kg to about 20 mg/kg, about 5 mg/kg to about 15 mg/kg, about 5 mg/kg to about 10 mg/kg, about 10 mg/kg to about 25 mg/kg, about 10 mg/kg to about 20 mg/kg, about 10 mg/kg to about 15 mg/kg, about 15 mg/kg to about 25 mg/kg, about 15 mg/kg to about 20 mg/kg, or about 20 mg/kg to about 25 mg/kg.

In some aspects, the checkpoint inhibitor is administered at a dose of about 0.003 mg/kg, about 0.004 mg/kg, about 0.005 mg/kg, about 0.006 mg/kg, about 0.007 mg/kg, about 0.008 mg/kg, about 0.009 mg/kg, about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1.0 mg/kg, about 2.0 mg/kg, about 3.0 mg/kg, about 4.0 mg/kg, about 5.0 mg/kg, about 6.0 mg/kg, about 7.0 mg/kg, about 8.0 mg/kg, about 9.0 mg/kg, about 10.0 mg/kg, about 11.0 mg/kg, about 12.0 mg/kg, about 13.0 mg/kg, about 14.0 mg/kg, about 15.0 mg/kg, about 16.0 mg/kg, about 17.0 mg/kg, about 18.0 mg/kg, about 19.0 mg/kg, about 20.0 mg/kg, about 21.0 mg/kg, about 22.0 mg/kg, about 23.0 mg/kg, about 24.0 mg/kg, or about 25.0 mg/kg.

In some aspects, the dose is administered once about every one week, once about every two weeks, once about every three weeks, once about every four weeks, once about every five weeks, once about every six weeks, once about every seven weeks, once about every eight weeks, once about every nine weeks, once about every ten weeks, once about every eleven weeks, or once about every twelve weeks.

The present disclosure is directed to a method of treating a human subject afflicted with lung cancer, the method comprising administering to the subject: (a) a dose of about 360 mg of an anti-LAG-3 antibody comprising CDR1, CDR2 and CDR3 domains of the heavy chain variable region having the sequence set forth in SEQ ID NO:3, and CDR1, CDR2 and CDR3 domains of the light chain variable region having the sequence set forth in SEQ ID NO:4, and (b) a dose of about 360 mg of an anti-PD-1 antibody comprising CDR1, CDR2 and CDR3 domains of the heavy chain variable region having the sequence set forth in SEQ ID NO:13, and CDR1, CDR2 and CDR3 domains of the light chain variable region having the sequence set forth in SEQ ID NO:14.

The present disclosure is directed to a method of treating a human subject afflicted with lung cancer, the method comprising administering to the subject: (a) a dose of about 720 mg of an anti-LAG-3 antibody comprising CDR1, CDR2 and CDR3 domains of the heavy chain variable region having the sequence set forth in SEQ ID NO:3, and CDR1, CDR2 and CDR3 domains of the light chain variable region having the sequence set forth in SEQ ID NO:4, (b) a dose of about 360 mg of an anti-PD-1 antibody comprising CDR1, CDR2 and CDR3 domains of the heavy chain variable region having the sequence set forth in SEQ ID NO:13, and CDR1, CDR2 and CDR3 domains of the light chain variable region having the sequence set forth in SEQ ID NO:14.

In some aspects, the method is a first line therapy.

In some aspects, the method is a second line therapy.

In some aspects, the method is a third line therapy.

In some aspects, the subject has progressed on a prior therapy.

In some aspects, the lung cancer is unresectable, advanced, recurrent, and/or metastatic.

In some aspects, the subject is afflicted with a Stage IV lung cancer.

In some aspects, the lung cancer is small cell lung cancer.

In some aspects, the lung cancer is non-small cell lung cancer (NSCLC). In some aspects, the NSCLC has a squamous histology. In some aspects, the NSCLC has a non-squamous histology.

In some aspects, the method further comprises administering a PDCT. In some aspects, the PDCT comprises a platinum agent in combination with a nucleoside analog, an antimetabolite, a taxane, a vinca alkaloid, or a topisomerase inhibitor. In some aspects, the platinum agent is cisplatin, carboplatin, oxaliplatin, satraplatin, picoplatin, nedaplatin, triplatin, lipoplatin, or phenanthriplatin. In some aspects, the platinum agent is cisplatin. In some aspects, the platinum agent is carboplatin. In some aspects, the nucleoside analog is cytarabine, gemcitabine, lamivudine, entecavir, or telbivudine. In some aspects, the nucleoside analog is gemcitabine. In some aspects, the antimetabolite is capecitabine, cladribine, clofarabine, cytarabine, floxuridine, fludarabine, fluorouracil, mercaptopurine, methotrexate, pemetrexed, pentostatin, pralatrexate, or thioguanine. In some aspects, the antimetabolite is pemetrexed. In some aspects, the taxane is paclitaxel, albumin-bound paclitaxel, docetaxel, or cabazitaxel. In some aspects, the vinca alkaloid is vinblastine, vincristine, vinorelbine, vindesine, vincaminol, vineridine, or vinburnine. In some aspects, the vinca alkaloid is vinorelbine or vinblastine. In some aspects, the topoisomerase inhibitor is etoposide, mitoxantrone, doxorubicin, irinotecan, topotecan, or camptothecin. In some aspects, the topoisomerase inhibitor is etoposide. In some aspects, the topoisomerase inhibitor is irinotecan. In some aspects, the PDCT comprises cisplatin or carboplatin in combination with gemcitabine, pemetrexed, paclitaxel, albumin-bound paclitaxel, docetaxel, vinorelbine, vinblastine, etoposide, or irinotecan. In some aspects, the PDCT comprises cisplatin or carboplatin in combination with paclitaxel or albumin-bound paclitaxel. In some aspects, the PDCT comprises cisplatin or carboplatin in combination with pemetrexed.

The present disclosure is directed to a method of treating a human subject afflicted with Stage IV or recurrent NSCLC that has a squamous histology, the method comprising administering to the subject: (a) a dose of about 360 mg of an anti-LAG-3 antibody comprising CDR1, CDR2 and CDR3 domains of the heavy chain variable region having the sequence set forth in SEQ ID NO:3, and CDR1, CDR2 and CDR3 domains of the light chain variable region having the sequence set forth in SEQ ID NO:4, (b) a dose of about 360 mg of an anti-PD-1 antibody comprising CDR1, CDR2 and CDR3 domains of the heavy chain variable region having the sequence set forth in SEQ ID NO:13, and CDR1, CDR2 and CDR3 domains of the light chain variable region having the sequence set forth in SEQ ID NO:14, (c) a PDCT comprising: (i) a dose of carboplatin for a target area under the concentration-time curve of about 6 mg/mL·min, and (ii) a dose of about 200 $mg/m^2$ of paclitaxel, wherein the method is a first line therapy.

The present disclosure is directed to a method of treating a human subject afflicted with Stage IV or recurrent NSCLC that has a squamous histology, the method comprising administering to the subject: (a) a dose of about 720 mg of an anti-LAG-3 antibody comprising CDR1, CDR2 and CDR3 domains of the heavy chain variable region having the sequence set forth in SEQ ID NO:3, and CDR1, CDR2 and CDR3 domains of the light chain variable region having the sequence set forth in SEQ ID NO:4, (b) a dose of about 360 mg of an anti-PD-1 antibody comprising CDR1, CDR2 and CDR3 domains of the heavy chain variable region having the sequence set forth in SEQ ID NO:13, and CDR1, CDR2 and CDR3 domains of the light chain variable region having the sequence set forth in SEQ ID NO:14, (c) a PDCT comprising: (i) a dose of carboplatin for a target area under the concentration-time curve of about 6 mg/mL·min, and (ii) a dose of about 200 $mg/m^2$ of paclitaxel, wherein the method is a first line therapy.

The present disclosure is directed to a method of treating a human subject afflicted with Stage IV or recurrent NSCLC that has a squamous histology, the method comprising administering to the subject: (a) a dose of about 360 mg of an anti-LAG-3 antibody comprising CDR1, CDR2 and CDR3 domains of the heavy chain variable region having the sequence set forth in SEQ ID NO:3, and CDR1, CDR2 and CDR3 domains of the light chain variable region having the sequence set forth in SEQ ID NO:4, (b) a dose of about 360 mg of an anti-PD-1 antibody comprising CDR1, CDR2 and CDR3 domains of the heavy chain variable region having the sequence set forth in SEQ ID NO:13, and CDR1, CDR2 and CDR3 domains of the light chain variable region having the sequence set forth in SEQ ID NO:14, (c) a PDCT comprising: (i) a dose of carboplatin for a target area under the concentration-time curve of about 6 mg/mL·min, and (ii) a dose of about 100 $mg/m^2$ of albumin-bound paclitaxel, wherein the method is a first line therapy.

The present disclosure is directed to a method of treating a human subject afflicted with Stage IV or recurrent NSCLC that has a squamous histology, the method comprising administering to the subject: (a) a dose of about 720 mg of an anti-LAG-3 antibody comprising CDR1, CDR2 and CDR3 domains of the heavy chain variable region having the sequence set forth in SEQ ID NO:3, and CDR1, CDR2 and CDR3 domains of the light chain variable region having the sequence set forth in SEQ ID NO:4, (b) a dose of about 360 mg of an anti-PD-1 antibody comprising CDR1, CDR2 and CDR3 domains of the heavy chain variable region having the sequence set forth in SEQ ID NO:13, and CDR1, CDR2 and CDR3 domains of the light chain variable region having the sequence set forth in SEQ ID NO:14, (c) a PDCT comprising: (i) a dose of carboplatin for a target area under the concentration-time curve of about 6 mg/mL·min, and (ii) a dose of about 100 $mg/m^2$ of albumin-bound paclitaxel, wherein the method is a first line therapy.

The present disclosure is directed to a method of treating a human subject afflicted with Stage IV or recurrent NSCLC that has a non-squamous histology, the method comprising administering to the subject: (a) a dose of about 360 mg of an anti-LAG-3 antibody comprising CDR1, CDR2 and CDR3 domains of the heavy chain variable region having the sequence set forth in SEQ ID NO:3, and CDR1, CDR2 and CDR3 domains of the light chain variable region having the sequence set forth in SEQ ID NO:4, (b) a dose of about 360 mg of an anti-PD-1 antibody comprising CDR1, CDR2 and CDR3 domains of the heavy chain variable region having the sequence set forth in SEQ ID NO:13, and CDR1, CDR2 and CDR3 domains of the light chain variable region having the sequence set forth in SEQ ID NO:14, (c) a PDCT comprising: (i) a dose of carboplatin for a target area under the concentration-time curve of about 5 mg/mL·min or about 6 mg/mL·min, and (ii) a dose of about 500 $mg/m^2$ of pemetrexed, wherein the method is a first line therapy.

The present disclosure is directed to a method of treating a human subject afflicted with Stage IV or recurrent NSCLC that has a non-squamous histology, the method comprising administering to the subject: (a) a dose of about 720 mg of an anti-LAG-3 antibody comprising CDR1, CDR2 and CDR3 domains of the heavy chain variable region having the sequence set forth in SEQ ID NO:3, and CDR1, CDR2 and CDR3 domains of the light chain variable region having the sequence set forth in SEQ ID NO:4, (b) a dose of about 360 mg of an anti-PD-1 antibody comprising CDR1, CDR2 and CDR3 domains of the heavy chain variable region having the sequence set forth in SEQ ID NO:13, and CDR1, CDR2 and CDR3 domains of the light chain variable region having the sequence set forth in SEQ ID NO:14, (c) a PDCT comprising: (i) a dose of carboplatin for a target area under the concentration-time curve of about 5 mg/mL·min or about 6 mg/mL·min, and (ii) a dose of about 500 $mg/m^2$ of pemetrexed, wherein the method is a first line therapy.

The present disclosure is directed to a method of treating a human subject afflicted with Stage IV or recurrent NSCLC that has a non-squamous histology, the method comprising administering to the subject: (a) a dose of about 360 mg of an anti-LAG-3 antibody comprising CDR1, CDR2 and CDR3 domains of the heavy chain variable region having the sequence set forth in SEQ ID NO:3, and CDR1, CDR2 and CDR3 domains of the light chain variable region having the sequence set forth in SEQ ID NO:4, (b) a dose of about 360 mg of an anti-PD-1 antibody comprising CDR1, CDR2 and CDR3 domains of the heavy chain variable region having the sequence set forth in SEQ ID NO:13, and CDR1, CDR2 and CDR3 domains of the light chain variable region having the sequence set forth in SEQ ID NO:14, (c) a PDCT comprising: (i) a dose of about 75 $mg/m^2$ of cisplatin, and (ii) a dose of about 500 $mg/m^2$ of pemetrexed, wherein the method is a first line therapy.

The present disclosure is directed to a method of treating a human subject afflicted with Stage IV or recurrent NSCLC that has a non-squamous histology, the method comprising administering to the subject: (a) a dose of about 720 mg of an anti-LAG-3 antibody comprising CDR1, CDR2, and CDR3 domains of the heavy chain variable region having the sequence set forth in SEQ ID NO:3, and CDR1, CDR2, and CDR3 domains of the light chain variable region having the sequence set forth in SEQ ID NO:4, (b) a dose of about 360 mg of an anti-PD-1 antibody comprising CDR1, CDR2, and CDR3 domains of the heavy chain variable region having the sequence set forth in SEQ ID NO:13, and CDR1, CDR2, and CDR3 domains of the light chain variable region having the sequence set forth in SEQ ID NO:14, (c) a PDCT comprising: (i) a dose of about 75 $mg/m^2$ of cisplatin, and (ii) a dose of about 500 $mg/m^2$ of pemetrexed, wherein the method is a first line therapy.

In some aspects, the lung cancer is recurrent following multi-modal therapy for locally advanced lung cancer.

In some aspects, the subject has not received a prior systemic therapy for cancer, the subject has not received a prior systemic therapy for lung cancer, or the subject has not received a prior systemic therapy for advanced or metastatic lung cancer.

In some aspects, the subject is naïve to prior immuno-oncology therapy, the subject is naïve to prior immuno-oncology therapy for lung cancer, or the lung cancer is naïve to prior immuno-oncology therapy.

In some aspects, one or more immune cells in tumor tissue from the subject express LAG-3. In some aspects, at least about 1%, at least about 3%, at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, or about 100% of the immune cells express LAG-3. In some aspects, at least about 1% of the immune cells express LAG-3. In some aspects, the immune cells are tumor-infiltrating lymphocytes. In some aspects, the tumor-infiltrating lymphocytes are $CD8^+$ cells.

In some aspects, one or more tumor cells in tumor tissue from the subject express PD-L1. In some aspects, at least about 1%, at least about 3%, at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, or about 100% of the tumor cells express PD-L1. In some aspects, at least about 1% of the tumor cells express PD-L1.

In some aspects, (a) the anti-LAG-3 antibody comprises a heavy chain variable region CDR1, CDR2, and CDR3 comprising the sequence set forth in SEQ ID NO:5, SEQ ID NO:6, and SEQ ID NO:7, respectively, and a light chain variable region CDR1, CDR2, and CDR3 comprising the sequence set forth in SEQ ID NO:8, SEQ ID NO:9, and SEQ ID NO:10, respectively, and (b) the anti-PD-1 antibody comprises a heavy chain variable region CDR1, CDR2, and CDR3 comprising the sequence set forth in SEQ ID NO:15, SEQ ID NO:16, and SEQ ID NO:17, respectively, and a light chain variable region CDR1, CDR2, and CDR3 comprising the sequence set forth in SEQ ID NO:18, SEQ ID NO:19, and SEQ ID NO:20, respectively.

In some aspects, the anti-LAG-3 antibody comprises heavy and light chain variable regions comprising the sequences set forth in SEQ ID NOs:3 and 4, respectively, and the anti-PD-1 antibody comprises heavy and light chain variable regions comprising the sequences set forth in SEQ ID NOs:13 and 14, respectively.

In some aspects, the anti-LAG-3 antibody and/or the anti-PD-1 antibody is a full-length antibody.

In some aspects, the anti-LAG-3 antibody and/or anti-PD-1 antibody is a monoclonal, human, humanized, chimeric, or multispecific antibody. In some aspects, the multispecific antibody is a DART, a DVD-Ig, or bispecific antibody.

In some aspects, the anti-LAG-3 antibody and/or anti-PD-1 antibody is a $F(ab')_2$ fragment, a Fab' fragment, a Fab fragment, a Fv fragment, a scFv fragment, a dsFv fragment, a dAb fragment, or a single chain binding polypeptide.

In some aspects, the anti-LAG-3 antibody comprises heavy and light chains comprising the sequences set forth in SEQ ID NOs:1 and 2, respectively, and the anti-PD-1 antibody comprises heavy and light chains comprising the sequences as set forth in SEQ ID NOs:11 and 12, respectively.

In some aspects, the anti-LAG-3 antibody comprises heavy and light chains comprising the sequences set forth in SEQ ID NOs:21 and 2, respectively, and the anti-PD-1 antibody comprises heavy and light chains comprising the sequences as set forth in SEQ ID NOs:11 and 12, respectively.

In some aspects, the method further comprises administering to the subject an additional therapeutic agent. In some aspects, the additional therapeutic agent comprises an anti-cancer agent. In some aspects, the anti-cancer agent comprises a tyrosine kinase inhibitor, an anti-angiogenesis agent, a checkpoint inhibitor, a checkpoint stimulator, a chemotherapeutic agent, an immunotherapeutic agent, a platinum agent, an alkylating agent, a taxane, a nucleoside analog, an antimetabolite, a topisomerase inhibitor, an anthracycline, a vinca alkaloid, or any combination thereof.

In some aspects, the tyrosine kinase inhibitor is afatinib, erlotinib, dacomitinib, gefitinib, osimertinib, alectinib, brigatinib, ceritinib, crizotinib, lorlatinib, entrectinib, dabrafenib, trametinib, vemurafenib, larotrectinib, or any combination thereof.

In some aspects, the anti-angiogenesis agent comprises an inhibitor of a vascular endothelial growth factor (VEGF), VEGF receptor (VEGFR), platelet-derived growth factor (PDGF), PDGF receptor (PDGFR), angiopoietin (Ang), tyrosine kinase with Ig-like and EGF-like domains (Tie) receptor, hepatocyte growth factor (HGF), tyrosine-protein kinase Met (c-MET), C-type lectin family 14 member A (CLEC14A), multimerin 2 (MMRN2), shock protein 70-1A (HSP70-1A), a epidermal growth factor (EGF), EGF receptor (EGFR), or any combination thereof.

In some aspects, the anti-angiogenesis agent comprises bevacizumab, ramucirumab, aflibercept, tanibirumab, olaratumab, nesvacumab, AMG780, MEDI3617, vanucizumab, rilotumumab, ficlatuzumab, TAK-701, onartuzumab, emibetuzumab, or any combination thereof.

In some aspects, the checkpoint inhibitor comprises a programmed death-1 (PD-1) pathway inhibitor, a cytotoxic T-lymphocyte-associated protein 4 (CTLA-4) inhibitor, a T cell immunoglobulin and ITIM domain (TIGIT) inhibitor, a T cell immunoglobulin and mucin-domain containing-3 (TIM-3) inhibitor, a $TIM^{-1}$ inhibitor, a TIM-4 inhibitor, a B7-H3 inhibitor, a B7-H4 inhibitor, a B and T cell lymphocyte attenuator (BTLA) inhibitor, a V-domain Ig suppressor of T cell activation (VISTA) inhibitor, an indoleamine 2,3-dioxygenase (IDO) inhibitor, a nicotinamide adenine dinucleotide phosphate oxidase isoform 2 (NOX2) inhibitor, a killer-cell immunoglobulin-like receptor (KIR) inhibitor, an adenosine A2a receptor (A2aR) inhibitor, a transforming growth factor beta (TGF-0) inhibitor, a phosphoinositide 3-kinase (PI3K) inhibitor, a CD47 inhibitor, a CD48 inhibitor, a CD73 inhibitor, a CD 113 inhibitor, a sialic acid-binding immunoglobulin-like lectin-7 (SIGLEC-7) inhibitor, a SIGLEC-9 inhibitor, a SIGLEC-15 inhibitor, a glucocorticoid-induced TNFR-related protein (GITR) inhibitor, a galectin-1 inhibitor, a galectin-9 inhibitor, a carcinoembryonic antigen-related cell adhesion molecule-1 ($CEACAM^{-1}$) inhibitor, a G protein-coupled receptor 56 (GPR56) inhibitor, a glycoprotein A repetitions predominant (GARP) inhibitor, a 2B4 inhibitor, a programmed death-1 homolog (PD1H) inhibitor, a leukocyte-associated immunoglobulin-like receptor 1 (LAIR1) inhibitor, or any combination thereof.

In some aspects, the PD-1 pathway inhibitor is an anti-PD-L1 antibody.

In some aspects, the anti-PD-L1 antibody is a full-length antibody.

In some aspects, the anti-PD-L1 antibody is a monoclonal, human, humanized, chimeric, or multispecific antibody. In some aspects, the multispecific antibody is a DART, a DVD-Ig, or bispecific antibody.

In some aspects, the anti-PD-L1 antibody is a $F(ab')_2$ fragment, a Fab' fragment, a Fab fragment, a Fv fragment, a scFv fragment, a dsFv fragment, a dAb fragment, or a single chain binding polypeptide.

In some aspects, the anti-PD-L1 antibody is BMS-936559, atezolizumab, durvalumab, avelumab, STI-1014, CX-072, KN035, LY3300054, BGB-A333, ICO 36, FAZ053, CK-301, or comprises an antigen binding portion thereof.

In some aspects, the PD-1 pathway inhibitor is BMS-986189.

In some aspects, the checkpoint inhibitor comprises a CTLA-4 inhibitor.

In some aspects, the CTLA-4 inhibitor is an anti-CTLA-4 antibody.

In some aspects, the anti-CTLA-4 antibody is a full-length antibody.

In some aspects, the anti-CTLA-4 antibody is a monoclonal, human, humanized, chimeric, or multispecific antibody. In some aspects, the multispecific antibody is a DART, a DVD-Ig, or bispecific antibody.

In some aspects, the anti-CTLA-4 antibody is a $F(ab')_2$ fragment, a Fab' fragment, a Fab fragment, a Fv fragment, a scFv fragment, a dsFv fragment, a dAb fragment, or a single chain binding polypeptide.

In some aspects, the anti-CTLA-4 antibody is ipilimumab, tremelimumab, MK-1308, AGEN-1884, or comprises an antigen binding portion thereof.

In some aspects, the anti-LAG-3 antibody and the anti-PD-1 antibody are formulated for intravenous administration.

In some aspects, the checkpoint inhibitor is formulated for intravenous administration.

In some aspects, the anti-LAG-3 antibody and the anti-PD-1 antibody are formulated separately.

In some aspects, the anti-LAG-3 antibody and the anti-PD-1 antibody are formulated together.

In some aspects, the anti-PD-1 antibody is administered before the anti-LAG-3 antibody.

In some aspects, the anti-LAG-3 antibody is administered before the anti-PD-1 antibody.

In some aspects, the LAG-3 antibody and the anti-PD-1 antibody are administered concurrently.

In some aspects, the anti-LAG-3 antibody and the anti-PD-1 antibody are administered about once every three weeks. In some aspects, the anti-LAG-3 antibody and the anti-PD-1 antibody are administered on Day 1 of every three-week cycle. In some aspects, the anti-LAG-3 antibody and the anti-PD-1 antibody are administered intravenously from a single intravenous bag for about 30 minutes.

In some aspects, the PDCT is administered every three weeks. In some aspects, the PDCT is administered for up to about 4 three-week cycles.

The present disclosure is directed to a pharmaceutical composition comprising (a) 360 mg of an anti-LAG-3 antibody and (b) 360 mg of an anti-PD-1 antibody.

The present disclosure is directed to a pharmaceutical composition comprising (a) 720 mg of an anti-LAG-3 antibody and (b) 360 mg of an anti-PD-1 antibody In some aspects, (a) the anti-LAG-3 antibody comprises CDR1, CDR2, and CDR3 domains of the heavy chain variable region having the sequence set forth in SEQ ID NO:3, and CDR1, CDR2, and CDR3 domains of the light chain variable region having the sequence set forth in SEQ ID NO:4, and (b) the anti-PD-1 antibody comprises CDR1, CDR2, and CDR3 domains of the heavy chain variable region having the sequence set forth in SEQ ID NO:13, and CDR1, CDR2, and CDR3 domains of the light chain variable region having the sequence set forth in SEQ ID NO:14.

In some aspects, (a) the anti-LAG-3 antibody comprises a heavy chain variable region CDR1, CDR2, and CDR3 comprising the sequence set forth in SEQ ID NO:5, SEQ ID NO:6, and SEQ ID NO:7, respectively, and a light chain variable region CDR1, CDR2, and CDR3 comprising the sequence set forth in SEQ ID NO:8, SEQ ID NO:9, and SEQ ID NO:10, respectively, and (b) the anti-PD-1 antibody comprises a heavy chain variable region CDR1, CDR2, and CDR3 comprising the sequence set forth in SEQ ID NO:15, SEQ ID NO:16, and SEQ ID NO:17, respectively, and a light chain variable region CDR1, CDR2, and CDR3 comprising the sequence set forth in SEQ ID NO:18, SEQ ID NO:19, and SEQ ID NO:20, respectively.

In some aspects, the anti-LAG-3 antibody comprises heavy and light chain variable regions comprising the sequences set forth in SEQ ID NOs:3 and 4, respectively, and the anti-PD-1 antibody comprises heavy and light chain variable regions comprising the sequences set forth in SEQ ID NOs:13 and 14, respectively.

In some aspects, the anti-LAG-3 antibody and/or the anti-PD-1 antibody is a full-length antibody.

In some aspects, the anti-LAG-3 antibody and/or anti-PD-1 antibody is a monoclonal, human, humanized, chimeric, or multispecific antibody. In some aspects, the multispecific antibody is a DART, a DVD-Ig, or bispecific antibody.

In some aspects, the anti-LAG-3 antibody and/or anti-PD-1 antibody is a $F(ab')_2$ fragment, a Fab' fragment, a Fab fragment, a Fv fragment, a scFv fragment, a dsFv fragment, a dAb fragment, or a single chain binding polypeptide.

In some aspects, the anti-LAG-3 antibody comprises heavy and light chains comprising the sequences set forth in SEQ ID NOs:1 and 2, respectively, and the anti-PD-1 antibody comprises heavy and light chains comprising the sequences as set forth in SEQ ID NOs:11 and 12, respectively.

In some aspects, the anti-LAG-3 antibody comprises heavy and light chains comprising the sequences set forth in SEQ ID NOs:21 and 2, respectively, and the anti-PD-1 antibody comprises heavy and light chains comprising the sequences as set forth in SEQ ID NOs:11 and 12, respectively.

The present disclosure is directed to a kit for treating a human subject afflicted with lung cancer, comprising: (a) 360 mg of an anti-LAG-3 antibody; (b) 360 mg of an anti-PD-1 antibody; and (c) instructions for using the anti-LAG-3 antibody and the anti-PD-1 antibody in a method for treating a human subject afflicted with lung cancer.

The present disclosure is directed to a kit for treating a human subject afflicted with lung cancer, comprising: (a) 720 mg of an anti-LAG-3 antibody; (b) 360 mg of an anti-PD-1 antibody; and (c) instructions for using the anti-LAG-3 antibody and the anti-PD-1 antibody in a method for treating a human subject afflicted with lung cancer.

DETAILED DESCRIPTION OF THE INVENTION

The present disclosure provides a method of treating a human subject afflicted with lung cancer (e.g., non-small cell lung cancer (NSCLC)), the method comprising administering to the subject a LAG-3 antagonist (e.g., an anti-LAG-3 antibody). Some aspects of the present disclosure are directed to a method of treating a human subject afflicted with lung cancer, wherein the method is a first, second, or third line therapy. Some aspects of the present disclosure are directed to a method of treating a human subject afflicted with Stage IV or recurrent lung cancer. The present disclosure is also directed to methods of treating a human subject afflicted with lung cancer comprising an anti-cancer therapy and/or a therapeutic agent in combination with the LAG-3 antagonist, such as a chemotherapy (e.g., platinum doublet chemotherapy) and/or a PD-1 pathway inhibitor (e.g., an anti-PD-1 antibody).

I. Terms

In order that the present disclosure can be more readily understood, certain terms are first defined. As used in this application, except as otherwise expressly provided herein, each of the following terms shall have the meaning set forth below. Additional definitions are set forth throughout the application. It is to be noted that the term "a" or "an" entity refers to one or more of that entity; for example, "a nucleotide sequence," is understood to represent one or more nucleotide sequences. As such, the terms "a" (or "an"), "one or more," and "at least one" can be used interchangeably herein.

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

The terms "about" or "comprising essentially of" refer to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within 1 or more than 1 standard deviation per the practice in the art. Alternatively, "about" or "comprising essentially of" can mean a range of up to 10% or 20% (i.e., ±10% or ±20%). For example, about 3 mg can include any number between 2.7 mg and 3.3 mg (for 10%) or between 2.4 mg and 3.6 mg (for 20%). Furthermore, particularly with respect to biological systems or processes, the terms can mean up to an order of magnitude or up to 5-fold of a value. When particular values or compositions are provided in the application and claims, unless otherwise stated, the meaning of "about" or "comprising essentially of" should be assumed to be within an acceptable error range for that particular value or composition.

As described herein, any concentration range, percentage range, ratio range or integer range is to be understood to include the value of any integer within the recited range and, when appropriate, fractions thereof (such as one-tenth and one-hundredth of an integer), unless otherwise indicated.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 5th ed., 2013, Academic Press; and the Oxford Dictionary Of Biochemistry And Molecular Biology, 2006, Oxford University Press, provide one of skill with a general dictionary of many of the terms used in this disclosure.

Units, prefixes, and symbols are denoted in their Systeme International de Unites (SI) accepted form. Numeric ranges are inclusive of the numbers defining the range.

The headings provided herein are not limitations of the various aspects of the disclosure, which can be had by reference to the specification as a whole. Accordingly, the terms defined immediately below are more fully defined by reference to the specification in its entirety.

An "antagonist" shall include, without limitation, any molecule capable of blocking, reducing, or otherwise limiting an interaction or activity of a target molecule (e.g., LAG-3). In some aspects, the antagonist is an antibody. In other aspects, the antagonist comprises a small molecule. The terms "antagonist" and "inhibitor" are used interchangeably herein.

An "antibody" (Ab) shall include, without limitation, a glycoprotein immunoglobulin which binds specifically to an antigen and comprises at least two heavy (H) chains and two light (L) chains interconnected by disulfide bonds. Each H chain comprises a heavy chain variable region (abbreviated herein as $V_H$) and a heavy chain constant region (abbreviated herein as CH). The heavy chain constant region comprises three constant domains, $C_{H1}$, $C_{H2}$ and $C_{H3}$. Each light chain comprises a light chain variable region (abbreviated herein as $V_L$) and a light chain constant region (abbreviated herein as $C_L$). The light chain constant region comprises one constant domain, $C_L$. The $V_H$ and $V_L$ regions can be further subdivided into regions of hypervariability, termed complementarity determining regions (CDRs), interspersed with regions that are more conserved, termed framework regions (FR). Each $V_H$ and $V_L$ comprises three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (Clq) of the classical complement system. A heavy chain can have the C-terminal lysine or not. Unless specified otherwise herein, the amino acids in the variable regions are numbered using the Kabat numbering system and those in the constant regions are numbered using the EU system.

An immunoglobulin can derive from any of the commonly known isotypes, including but not limited to IgA, secretory IgA, IgG and IgM. IgG subclasses are also well known to those in the art and include but are not limited to human IgG1, IgG2, IgG3 and IgG4. "Isotype" refers to the antibody class or subclass (e.g., IgM or IgG1) that is encoded by the heavy chain constant region genes. The term "antibody" includes, by way of example, both naturally occurring and non-naturally occurring antibodies; monoclonal and polyclonal antibodies; chimeric and humanized antibodies; human or nonhuman antibodies; wholly synthetic antibodies; single chain antibodies; monospecific antibodies; bispecific antibodies; and multi-specific antibodies. A nonhuman antibody can be humanized by recombinant methods to reduce its immunogenicity in humans. Where not expressly stated, and unless the context indicates otherwise, the term "antibody" also includes an antigen-binding fragment or an antigen-binding portion of any of the aforementioned immunoglobulins, and includes a monovalent and a divalent fragment or portion, that retains the ability to bind specifically to the antigen bound by the whole immunoglobulin. Examples of an "antigen-binding portion" or "antigen-binding fragment" include: (1) a Fab fragment (fragment from papain cleavage) or a similar monovalent fragment consisting of the $V_L$, $V_H$, $L_C$ and $C_{H1}$ domains; (2) a $F(ab')_2$ fragment (fragment from pepsin cleavage) or a similar bivalent fragment comprising two Fab fragments linked by a disulfide bridge at the hinge region; (3) a Fd fragment consisting of the $V_H$ and CHi domains; (4) a Fv fragment consisting of the $V_L$ and $V_H$ domains of a single arm; (5) a single domain antibody (dAb) fragment (Ward et al., (1989) Nature 341:544-46), which consists of a $V_H$ domain; (6) a bi-single domain antibody which consists of two $V_H$ domains linked by a hinge (dual-affinity re-targeting antibodies (DARTs)); or (7) a dual variable domain immunoglobulin. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see, e.g., Bird et al. (1988) *Science* 242:423-426; and Huston et al. (1988) *Proc. Natl. Acad. Sci. USA* 85:5879-5883).

An "isolated antibody" refers to an antibody that is substantially free of other antibodies having different antigenic specificities (e.g., an isolated antibody that binds specifically to LAG-3 is substantially free of antibodies that do not bind specifically to LAG-3). An isolated antibody that binds specifically to LAG-3 can, however, have cross-reactivity to other antigens, such as LAG-3 molecules from different species. Moreover, an isolated antibody can be substantially free of other cellular material and/or chemicals.

The term "monoclonal antibody" ("mAb") refers to a non-naturally occurring preparation of antibody molecules of single molecular composition, i.e., antibody molecules whose primary sequences are essentially identical, and which exhibits a single binding specificity and affinity for a particular epitope. A mAb is an example of an isolated antibody. MAbs can be produced by hybridoma, recombinant, transgenic or other techniques known to those skilled in the art.

A "human" antibody (HuMAb) refers to an antibody having variable regions in which both the framework and CDR regions are derived from human germline immunoglobulin sequences. Furthermore, if the antibody contains a constant region, the constant region is also derived from human germline immunoglobulin sequences. The human antibodies of the invention can include amino acid residues not encoded by human germline immunoglobulin sequences (e.g., mutations introduced by random or site-specific mutagenesis in vitro or by somatic mutation in vivo). However, the term "human antibody," as used herein, is not intended to include antibodies in which CDR sequences derived from the germline of another mammalian species, such as a mouse, have been grafted onto human framework sequences. The terms "human" antibodies and "fully human" antibodies and are used synonymously.

A "humanized antibody" refers to an antibody in which some, most or all of the amino acids outside the CDR domains of a non-human antibody are replaced with corresponding amino acids derived from human immunoglobulins. In one aspect of a humanized form of an antibody, some, most or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the antibody to bind to a particular antigen. A "humanized" antibody retains an antigenic specificity similar to that of the original antibody.

A "chimeric antibody" refers to an antibody in which the variable regions are derived from one species and the constant regions are derived from another species, such as an antibody in which the variable regions are derived from a mouse antibody and the constant regions are derived from a human antibody.

An "anti-antigen" antibody refers to an antibody that binds specifically to the antigen. For example, an anti-LAG-3 antibody binds specifically to LAG-3.

"LAG-3" refers to Lymphocyte Activation Gene-3. The term "LAG-3" includes variants, isoforms, homologs, orthologs and paralogs. For example, antibodies specific for a human LAG-3 protein can, in certain cases, cross-react with a LAG-3 protein from a species other than human. In other aspects, the antibodies specific for a human LAG-3 protein can be completely specific for the human LAG-3 protein and not exhibit species or other types of cross-reactivity, or can cross-react with LAG-3 from certain other species, but not all other species (e.g., cross-react with monkey LAG-3 but not mouse LAG-3). The term "human LAG-3" refers to human sequence LAG-3, such as the complete amino acid sequence of human LAG-3 having GenBank Accession No. NP_002277. The term "mouse LAG-3" refers to mouse sequence LAG-3, such as the complete amino acid sequence of mouse LAG-3 having GenBank Accession No. NP_032505. LAG-3 is also known in the art as, for example, CD223. The human LAG-3 sequence can differ from human LAG-3 of GenBank Accession No. NP_002277 by having, e.g., conserved mutations or mutations in non-conserved regions, and the LAG-3 has substantially the same biological function as the human LAG-3 of GenBank Accession No. NP_002277. For example, a biological function of human LAG-3 is having an epitope in the extracellular domain of LAG-3 that is specifically bound by an antibody of the instant disclosure or a biological function of human LAG-3 is binding to MHC Class II molecules.

A particular human LAG-3 sequence will generally be at least about 90% identical in amino acid sequence to human LAG-3 of GenBank Accession No. NP_002277 and contains amino acid residues that identify the amino acid sequence as being human when compared to LAG-3 amino acid sequences of other species (e.g., murine). In certain cases, a human LAG-3 can be at least about 95%, or even at least about 96%, at least about 97%, at least about 98%, at least about 99%, or about 100% identical in amino acid sequence to LAG-3 of GenBank Accession No. NP_002277. In certain aspects, a human LAG-3 sequence will display no more than 10 amino acid differences from the LAG-3 sequence of GenBank Accession No. NP_002277. In certain aspects, the human LAG-3 can display no more than 5, or even no more than 4, 3, 2, or 1 amino acid difference from the LAG-3 sequence of GenBank Accession No. NP_002277.

"Programmed Death-1 (PD-1)" refers to an immunoinhibitory receptor belonging to the CD28 family. PD-1 is expressed predominantly on previously activated T cells in vivo, and binds to two ligands, PD-L1 and PD-L2. The term "PD-1" as used herein includes human PD-1 (hPD-1), variants, isoforms, and species homologs of hPD-1, and analogs having at least one common epitope with hPD-1. The complete hPD-1 sequence can be found under GenBank Accession No. U64863. "PD-1" and "PD-1 receptor" are used interchangeably herein.

"Cytotoxic T-Lymphocyte Antigen-4 (CTLA-4)" refers to an immunoinhibitory receptor belonging to the CD28 family. CTLA-4 is expressed exclusively on T cells in vivo, and binds to two ligands, CD80 and CD86 (also called B7-1 and B7-2, respectively). The term "CTLA-4" as used herein includes human CTLA-4 (hCTLA-4), variants, isoforms, and species homologs of hCTLA-4, and analogs having at least one common epitope with hCTLA-4. The complete hCTLA-4 sequence can be found under GenBank Accession No. AAB59385.

"Programmed Death Ligand-1 (PD-L1)" is one of two cell surface glycoprotein ligands for PD-1 (the other being PD-L2) that downregulate T cell activation and cytokine secretion upon binding to PD-1. The term "PD-L1" as used herein includes human PD-L1 (hPD-L1), variants, isoforms, and species homologs of hPD-L1, and analogs having at least one common epitope with hPD-L1. The complete hPD-L1 sequence can be found under GenBank Accession No. Q9NZQ7.

"Programmed Death Ligand-2 (PD-L2)" as used herein includes human PD-L2 (hPD-L2), variants, isoforms, and species homologs of hPD-L2, and analogs having at least one common epitope with hPD-L2. The complete hPD-L2 sequence can be found under GenBank Accession No. Q9BQ51.

A "patient" as used herein includes any patient who is afflicted with a lung cancer (e.g., NSCLC). The terms "subject" and "patient" are used interchangeably herein.

"Administering" refers to the physical introduction of a therapeutic agent to a subject (e.g., a composition or formulation comprising the therapeutic agent), using any of the various methods and delivery systems known to those skilled in the art. Exemplary routes of administration include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some aspects, the formulation is administered via a non-parenteral route, in some aspects, orally. Other non-parenteral routes include a topical, epidermal or mucosal route of administration, for example, intranasally, vaginally, rectally, sublingually or topically. Administering can also be performed, for example, once, a plurality of times, and/or over one or more extended periods.

"Treatment" or "therapy" of a subject refers to any type of intervention or process performed on, or the administration of an active agent to, the subject with the objective of reversing, alleviating, ameliorating, inhibiting, slowing down progression, development, severity or recurrence of a symptom, complication or condition, or biochemical indicia associated with a disease. Response Evaluation Criteria In Solid Tumors (RECIST) is a measure for treatment efficacy and are established rules that define when tumors respond, stabilize, or progress during treatment. RECIST 1.1 is the current guideline to solid tumor measurement and definitions for objective assessment of change in tumor size for use in adult and pediatric cancer clinical trials.

As used herein, "effective treatment" refers to treatment producing a beneficial effect, e.g., amelioration of at least one symptom of a disease or disorder. A beneficial effect can take the form of an improvement over baseline, i.e., an improvement over a measurement or observation made prior to initiation of therapy according to the method. A beneficial effect can also take the form of arresting, slowing, retarding, or stabilizing of a deleterious progression of a marker of solid tumor. Effective treatment can refer to alleviation of at least one symptom of a solid tumor. Such effective treatment can, e.g., reduce patient pain, reduce the size and/or number of lesions, can reduce or prevent metastasis of a tumor, and/or can slow tumor growth.

The term "effective amount" refers to an amount of an agent that provides the desired biological, therapeutic, and/or prophylactic result. That result can be reduction, amelioration, palliation, lessening, delaying, and/or alleviation of one or more of the signs, symptoms, or causes of a disease, or any other desired alteration of a biological system. In reference to solid tumors, an effective amount comprises an amount sufficient to cause a tumor to shrink and/or to decrease the growth rate of the tumor (such as to suppress tumor growth) or to delay other unwanted cell proliferation. In some aspects, an effective amount is an amount sufficient to prevent or delay tumor recurrence. An effective amount can be administered in one or more administrations. The effective amount of the drug or composition can: (i) reduce the number of cancer cells; (ii) reduce tumor size; (iii) inhibit, retard, slow to some extent and can stop cancer cell infiltration into peripheral organs; (iv) inhibit (i.e., slow to some extent and can stop tumor metastasis; (v) inhibit tumor growth; (vi) prevent or delay occurrence and/or recurrence of tumor; and/or (vii) relieve to some extent one or more of the symptoms associated with the cancer. In one example, an "effective amount" is the amount of anti-LAG-3 antibody alone or the amount of anti-LAG-3 antibody and the amount an additional therapeutic agent (e.g., anti-PD-1 antibody), in combination, clinically proven to affect a significant decrease in cancer or slowing of progression of cancer, such as an advanced solid tumor.

As used herein, the terms "fixed dose," "flat dose," and "flat-fixed dose" are used interchangeably and refer to a dose that is administered to a patient without regard for the weight or body surface area (BSA) of the patient. The fixed or flat dose is therefore not provided as a mg/kg dose, but rather as an absolute amount of the agent (e.g., an amount in g or mg).

The use of the term "fixed dose combination" with regard to a composition of the invention means that two or more different inhibitors as described herein (e.g., an anti-LAG-3 antibody and an anti-PD-1 antibody) in a single composition are present in the composition in particular (fixed) ratios with each other. In some aspects, the fixed dose is based on the weight (e.g., mg) of the inhibitors. In certain aspects, the fixed dose is based on the concentration (e.g., mg/ml) of the inhibitors. In some aspects, the ratio is at least about 1:1, about 1:2, about 1:3, about 1:4, about 1:5, about 1:6, about 1:7, about 1:8, about 1:9, about 1:10, about 1:15, about 1:20, about 1:30, about 1:40, about 1:50, about 1:60, about 1:70, about 1:80, about 1:90, about 1:100, about 1:120, about 1:140, about 1:160, about 1:180, about 1:200, about 200:1, about 180:1, about 160:1, about 140:1, about 120:1, about 100:1, about 90:1, about 80:1, about 70:1, about 60:1, about 50:1, about 40:1, about 30:1, about 20:1, about 15:1, about 10:1, about 9:1, about 8:1, about 7:1, about 6:1, about 5:1, about 4:1, about 3:1, or about 2:1 mg first inhibitor to mg second inhibitor. For example, the 2:1 ratio of a first inhibitor and a second inhibitor can mean that a vial can contain about 720 mg of the first inhibitor and 360 mg of the second inhibitor or about 12 mg/ml of the first inhibitor and 6 mg/ml of the second inhibitor.

The term "weight based dose" as referred to herein means that a dose that is administered to a patient is calculated based on the weight of the patient.

"Dosing interval," as used herein, means the amount of time that elapses between multiple doses of a formulation disclosed herein being administered to a subject. Dosing interval can thus be indicated as ranges.

The term "dosing frequency" as used herein refers to the frequency of administering doses of a formulation disclosed herein in a given time. Dosing frequency can be indicated as the number of doses per a given time, e.g., once a week or once in two weeks, etc.

The terms "about once a week," "once about every week," "once about every two weeks," or any other similar dosing interval terms as used herein means approximate number, and "about once a week" or "once about every week" can include every seven days±two days, i.e., every five days to every nine days. The dosing frequency of "once a week" thus can be every five days, every six days, every seven days, every eight days, or every nine days. "Once about every three weeks" can include every 21 days±3 days, i.e., every 25 days to every 31 days. Similar approximations apply, for example, to once about every two weeks, once about every four weeks, once about every five weeks, once about every six weeks, once about every seven weeks, once about every eight weeks, once about every nine weeks, once about every ten weeks, once about every eleven weeks, and once about every twelve weeks. In some aspects, a dosing interval of once about every six weeks or once about every twelve weeks means that the first dose can be administered any day in the first week, and then the next dose can be administered any day in the sixth or twelfth week, respectively. In other aspects, a dosing interval of once about every six weeks or once about every twelve weeks means that the first dose is administered on a particular day of the first week (e.g., Monday) and then the next dose is administered on the same day of the sixth or twelfth weeks (i.e., Monday), respectively.

An "adverse event" (AE) as used herein is any unfavorable and generally unintended or undesirable sign (including an abnormal laboratory finding), symptom, or disease associated with the use of a medical treatment. For example, an adverse event can be associated with activation of the immune system or expansion of immune system cells (e.g., T cells) in response to a treatment. A medical treatment can have one or more associated AEs and each AE can have the same or different level of severity.

The term "tumor" as used herein refers to any mass of tissue that results from excessive cell growth or proliferation, either benign (non-cancerous) or malignant (cancerous), including pre-cancerous lesions.

The term "biological sample" as used herein refers to biological material isolated from a subject. The biological sample can contain any biological material suitable for analysis, for example, by sequencing nucleic acids in the tumor (or circulating tumor cells) and identifying a genomic alteration in the sequenced nucleic acids. The biological sample can be any suitable biological tissue or fluid such as, for example, tumor tissue, blood, blood plasma, and serum. The biological sample can be a test tissue sample (e.g., a tissue sample comprising tumor cells and tumor-infiltrating inflammatory cells). In one aspect, the sample is a tumor tissue biopsy, e.g., a formalin-fixed, paraffin-embedded (FFPE) tumor tissue or a fresh-frozen tumor tissue or the like. In another aspect, the biological sample is a liquid biopsy that, in some aspects, comprises one or more of blood, serum, plasma, circulating tumor cells, exoRNA, ctDNA, and cfDNA.

By way of example, an "anti-cancer agent" promotes cancer regression in a subject. In preferred aspects, a therapeutically effective amount of the agent promotes cancer regression to the point of eliminating the cancer. "Promoting cancer regression" means that administering an effective amount of the anti-cancer agent, alone or in combination with another agent, results in a reduction in tumor growth or size, necrosis of the tumor, a decrease in severity of at least one disease symptom, an increase in frequency and duration of disease symptom-free periods, or a prevention of impairment or disability due to the disease affliction. In addition, the terms "effective" and "effectiveness" with regard to a treatment includes both pharmacological effectiveness and physiological safety. Pharmacological effectiveness refers to the ability of the agent to promote cancer regression in the patient. Physiological safety refers to the level of toxicity, or other adverse physiological effects at the cellular, organ and/or organism level (adverse effects) resulting from administration of the agent.

By way of example for the treatment of tumors, a therapeutically effective amount of an anti-cancer agent can inhibit cell growth or tumor growth by at least about 20%, at least about 40%, at least about 60%, or at least about 80% relative to untreated subjects. In other aspects of the disclosure, tumor regression can be observed and continue for a period of at least about 20 days, more preferably at least about 40 days, or at least about 60 days. Notwithstanding these measurements of therapeutic effectiveness, evaluation of immunotherapeutic drugs must also make allowance for immune-related response patterns.

As used herein, an "immuno-oncology" therapy or an "I-O" or "IO" therapy refers to a therapy that comprises utilizing an immune response to target and treat a tumor in a subject. As such, as used herein, an I-O therapy is a type of anti-cancer therapy. In some aspects, an I-O therapy comprises administering an antibody to a subject. In some aspects, an I-O therapy comprises administering to a subject an immune cell, e.g., a T cell, e.g., a modified T cell, e.g., a T cell modified to express a chimeric antigen receptor or a particular T cell receptor. In some aspects, the I-O therapy comprises administering a therapeutic vaccine to a subject. In some aspects, the I-O therapy comprises administering a cytokine or a chemokine to a subject. In some aspects, the I-O therapy comprises administering an interleukin to a subject. In some aspects, the I-O therapy comprises administering an interferon to a subject. In some aspects, the I-O therapy comprises administering a colony stimulating factor to a subject.

An "immune response" refers to the action of a cell of the immune system (for example, T lymphocytes, B lymphocytes, natural killer (NK) cells, macrophages, eosinophils, mast cells, dendritic cells and neutrophils) and soluble macromolecules produced by any of these cells or the liver (including antibodies, cytokines, and complement) that results in selective targeting, binding to, damage to, destruction of, and/or elimination from a vertebrate's body of invading pathogens, cells or tissues infected with pathogens, cancerous or other abnormal cells, or, in cases of autoimmunity or pathological inflammation, normal human cells or tissues.

A "tumor-infiltrating inflammatory cell" or "tumor-associated inflammatory cell" is any type of cell that typically participates in an inflammatory response in a subject and which infiltrates tumor tissue. Such cells include tumor-infiltrating lymphocytes (TILs), macrophages, monocytes, eosinophils, histiocytes and dendritic cells.

The term "LAG-3 positive" or "LAG-3 expression positive," relating to LAG-3 expression, refers to tumor tissue (e.g., a test tissue sample) that is scored as expressing LAG-3 based on the proportion (i.e., percentage) of immune cells (e.g., tumor-infiltrating lymphocytes such as CD8+ T cells) expressing LAG-3 (e.g., greater than or equal to 1% expression).

"LAG-3 negative" or "LAG-3 expression negative," refers to tumor tissue (e.g., a test tissue sample) that is not scored as expressing LAG-3 (e.g., less than 1% LAG-3 expression).

The term "PD-1 positive" or "PD-1 expression positive," relating to PD-1 expression, refers to tumor tissue (e.g., a test tissue sample) that is scored as expressing PD-1 based on the proportion (i.e., percentage) of immune cells (e.g., tumor-infiltrating lymphocytes such as CD8+ T cells) expressing PD-1 (e.g., greater than or equal to 1% expression).

"PD-1 negative" or "PD-1 expression negative," refers to tumor tissue (e.g., a test tissue sample) that is not scored as expressing PD-1 (e.g., less than 1% PD-1 expression).

The term "PD-L1 positive" or "PD-L1 expression positive," relating to cell surface PD-L1 expression, refers to tumor tissue (e.g., a test tissue sample) that is scored as expressing PD-L1 based on the proportion (i.e., percentage) of tumor cells expressing PD-L1 (e.g., greater than or equal to 1% expression).

The term "PD-L1 negative" or "PD-L1 expression negative" refers to tumor tissue (e.g., a test tissue sample) that is not scored as expressing PD-L1 (e.g., less than 1% expression).

Various aspects of the invention are described in further detail in the following subsections.

II. Methods of the Disclosure

Provided herein are methods of treating a human subject afflicted with lung cancer, the methods comprising administering to the subject a LAG-3 antagonist (e.g., an anti-LAG-3 antibody) alone or in combination with one or more additional therapeutic agents (e.g., a PD-1 pathway inhibitor such as an anti-PD-1 antibody) and/or therapies (e.g., a chemotherapy such as a platinum doublet chemotherapy).

In some aspects, the method is a first line (2L) therapy.

In some aspects, the method is a second line (2L) therapy.

In some aspects, the method is a third line (3L) therapy.

In some aspects, the subject has progressed on a prior therapy (e.g., a standard of care therapy). Standard of care therapies for different types of cancer are well known by persons of skill in the art. For example, the National Comprehensive Cancer Network (NCCN), an alliance of 21 major cancer centers in the USA, publishes the NCCN Clinical Practice Guidelines in Oncology (NCCN GUIDELINES®) that provide detailed up-to-date information on the standard of care treatments for a wide variety of cancers. See NCCN GUIDELINES®, 2020, www.nccn.org/professionals/physician gls/default.aspx, last accessed Oct. 23, 2020.

In some aspects, the lung cancer is recurrent following multi-modal therapy for locally advanced lung cancer.

In some aspects, the subject has not received a prior systemic therapy for cancer, the subject has not received a prior systemic therapy for lung cancer, or the subject has not received a prior systemic therapy for advanced or metastatic lung cancer.

In some aspects, the subject is naïve to prior immuno-oncology (I-O) therapy. In some aspects, the subject has never received I-O therapy, has received I-O therapy for a cancer other than lung cancer, or has received I-O therapy for a previous lung cancer but not a current lung cancer. In some aspects, the subject is naïve to prior I-O therapy, the subject is naïve to prior I-O therapy for lung cancer, or the lung cancer is naïve to prior I-O therapy. In some aspects, the prior I-O therapy is an antibody. In some aspects, the antibody binds to a checkpoint inhibitor. In some aspects, the prior I-O therapy is an anti-PD-1 antibody and/or the combination of an anti-PD-1 antibody and an anti-CTLA-4 antibody.

In some aspects, a method of the disclosure increases duration of progression-free survival (PFS), objective response rate (ORR), overall survival (OS), or any combination thereof as compared to a standard of care therapy and/or a prior therapy such as disclosed herein.

In some aspects, a method of the disclosure reduces the size of a tumor, inhibits growth of a tumor, eliminates a tumor from the subject, prevents relapse of lung cancer, induces remission of lung cancer, provides a complete response or partial response, or any combination thereof.

In some aspects, the methods of the disclosure comprise administering to the subject a LAG-3 antagonist based on the subject's performance status and/or cancer stage. Performance status and/or cancer stage can be indicated by any one or more systems in the art.

In some aspects, the lung cancer is unresectable, advanced, recurrent, and/or metastatic.

In some aspects, performance status is indicated by Eastern Cooperative Oncology Group performance status (ECOG PS), which utilizes standardized criteria for measuring how disease impacts a patient's daily living abilities. Example definitions for ECOG PS include: "0" for a patient who is fully active and able to carry on all pre-disease performance without restriction; "1" for a patient who is restricted in physically strenuous activity but ambulatory and able to carry out work of a light or sedentary nature; "2" for a patient who is ambulatory and capable of all self-care, up and about more than 50% of waking hours, but unable to carry out any work activities; "3" for a patient who is capable of only limited self-care and is confined to a bed or chair more than 50% of waking hours; and "4" for a patient who is completely disabled, cannot carry on any self-care, and is totally confined to bed or chair.

In some aspects the subject has an ECOG PS of 0, 1, 2, 3, or 4. In some aspects, the subject has an ECOG PS of ≤3. In some aspects, the subject has an ECOG PS of ≤2. In some aspects, the subject has an ECOG PS of ≤1.

In some aspects, lung cancer is staged based on a tumor/node/metastasis (TNM) staging system such as the American Joint Committee on Cancer (AJCC) classification.

There are at least seven stages used for lung cancer: occult (hidden) stage, Stage 0 (carcinoma in situ), Stage I, Stage II, Stage IIIA, Stage IIIB, and Stage IV. In the occult stage, the cancer cannot be seen by imaging or bronchoscopy. In Stage 0, cancer cells are found in the lining of the airways.

In some aspects the subject is afflicted with a Stage 0 lung cancer.

In some aspects, the subject is afflicted with a Stage I lung cancer. Stage I lung cancer is divided in Stage IA and IB. In Stage IA, the tumor is in the lung only and is 3 centimeters or smaller. In Stage IB, the cancer has not spread to the lymph nodes and one or more of the following is true: 1) the tumor is larger than 3 centimeters but not larger than 5 centimeters; 2) the cancer has spread to the main bronchus and is at least 2 centimeters below where the trachea joins the bronchus; 3) cancer has spread to the innermost layer of the membrane that covers the lung; or 4) part of the lung has collapsed or developed pneumonitis (inflammation of the lung) in the area where the trachea joins the bronchus.

In some aspects, the subject is afflicted with a Stage II lung cancer. Stage II is divided into Stage IIA and IIB. In Stage IIA, the cancer has either spread to the lymph nodes or not. If the cancer has spread to the lymph nodes, then the cancer can only have spread to the lymph nodes on the same side of the chest as the tumor, the lymph nodes with cancer are within the lung or near the bronchus, and one or more of the following is true: 1) the tumor is not larger than 5 centimeters; 2) the cancer has spread to the main bronchus and is at least 2 centimeters below where the trachea joins the bronchus; 3) cancer has spread to the innermost layer of the membrane that covers the lung; or 4) part of the lung has collapsed or developed pneumonitis (inflammation of the lung) in the area where the trachea joins the bronchus. The tumor is also considered Stage IIA if the cancer has not spread to the lymph nodes and one or more of the following is true: 1) the tumor is larger than 5 centimeters but not larger than 7 centimeters; 2) the cancer has spread to the main bronchus and is at least 2 centimeters below where the trachea joins the bronchus; 3) cancer has spread to the innermost layer of the membrane that covers the lung; or 4) part of the lung has collapsed or developed pneumonitis (inflammation of the lung) in the area where the trachea joins the bronchus. In stage IIB, the cancer has either spread to the lymph nodes or not. If the cancer has spread to the lymph nodes, then the cancer can only have spread to the lymph nodes on the same side of the chest as the tumor, the lymph nodes with cancer are within the lung or near the bronchus, and one or more of the following is true: 1) the tumor is larger than 5 centimeters but not larger than 7 centimeters; 2) the cancer has spread to the main bronchus and is at least 2 centimeters below where the trachea joins the bronchus; 3) cancer has spread to the innermost layer of the membrane that covers the lung; or 4) part of the lung has collapsed or developed pneumonitis (inflammation of the lung) in the area where the trachea joins the bronchus. The tumor is also considered Stage IIB if the cancer has not spread to the lymph nodes and one or more of the following is true: 1) the tumor is larger than 7 centimeters; 2) the cancer has spread to the main bronchus (and is at least 2 centimeters below where the trachea joins the bronchus), the chest wall, the diaphragm, or the nerve that controls the diaphragm; 3) cancer has spread to the membrane around the heart or lining the chest wall; 4) the whole lung has collapsed or developed pneumonitis (inflammation of the lung); or 5) there are one or more separate tumors in the same lobe of the lung.

In some aspects, the subject is afflicted with a Stage III lung cancer. Stage IIIA is divided into 3 sections. These 3 sections are based on 1) the size of the tumor; 2) where the tumor is found and 3) which (if any) lymph nodes have cancer. In the first type of Stage IIIA, the cancer has spread to the lymph nodes on the same side of the chest as the tumor, and the lymph nodes with the cancer are near the sternum or where the bronchus enters the lung. Additionally: 1) the tumor may be any size; 2) part of the lung (where the trachea joins the bronchus) or the whole lung may have collapsed or developed pneumonitis (inflammation of the lung); 3) there may be one or more separate tumors in the same lobe of the lung; and 4) cancer can have spread to any of the following: a) main bronchus, but not the area where the trachea joins the bronchus, b) chest well, c) diaphragm and the nerve that controls it, d) membrane around the lung or lining the chest wall, e) membrane around the heart. In the second type of Stage IIIA, the cancer has spread to the lymph nodes on the same side of the chest as the tumor, and the lymph nodes with the cancer are within the lung or near the bronchus. Additionally: 1) the tumor may be any size; 2) the whole lung may have collapsed or developed pneumonitis (inflammation of the lung); 3) there may be one or more separate tumors in the any of the lobes of the lung with cancer; and 4) cancer can have spread to any of the following: a) main bronchus, but not the area where the trachea joins the bronchus, b) chest well, c) diaphragm and the nerve that controls it, d) membrane around the lung or lining the chest wall, e) heart or the membrane around it, f) major blood vessels that lead to or from the heart, g) trachea, h) esophagus, i) nerve that controls the larynx (voice box), j) sternum (chest bone) or backbone, or k) carina (where the trachea joins the bronchi). In the third type of Stage IIIA, the cancer has not spread to the lymph nodes, the tumor may be any size, and cancer has spread to any one of the following: a) heart, b) major blood vessels that lead to or from the heart, c) trachea, d) esophagus, e) nerve that controls the larynx (voice box), f) sternum (chest bone) or backbone, or g) carina (where the trachea joins the bronchi). Stage IIIB is divided into 2 sections depending on 1) the size of the tumor, 2) where the tumor is found, and 3) which lymph nodes have cancer. In the first type of Stage IIIB, the cancer has spread to the lymph nodes on the opposite side of the chest as the tumor. Additionally, 1) the tumor may be any size; 2) part of the lung (where the trachea joins the bronchus) or the whole lung may have collapsed or developed pneumonitis (inflammation of the lung); 3) there may be one or more separate tumors in any of the lobs of the lung with cancer; and 4) cancer may have spread to any of the following: a) main bronchus, b) chest well, c) diaphragm and the nerve that controls it, d) membrane around the lung or lining the chest wall, e) heart or the membrane around it, f) major blood vessels that lead to or from the heart, g) trachea, h) esophagus, i) nerve that controls the larynx (voice box), j) sternum (chest bone) or backbone, or k) carina (where the trachea joins the bronchi). In the second type of Stage IIIB, the cancer has spread to lymph nodes on the same side of the chest as the tumor. The lymph nodes with cancer are near the sternum (chest bone) or where the bronchus enters the lung. Additionally, 1) the tumor may be any size; 2) there may be separate tumors in different lobes of the same lung; and 3) cancer has spread to any of the following: a) heart, b) major blood vessels that lead to or from the heart, c) trachea, d) esophagus, e) nerve that controls the larynx (voice box), f) sternum (chest bone) or backbone, or g) carina (where the trachea joins the bronchi).

In some aspects, the subject is afflicted with a Stage IV lung cancer. In Stage IV, the tumor may be any size and the cancer may have spread to the lymph nodes. One or more of the following is true in Stage IV: 1) there are one or more tumors in both lungs; 2) cancer is found in the fluid around the lungs or heart; and 3) cancer has spread to other parts of the body, such as the brain, liver, adrenal glands, kidneys or bone.

In some aspects, the lung cancer is small cell lung cancer (SCLC). In some aspects, staging of SCLC is by TNM staging. In some aspects, rather than TNM staging, SCLC is staged as either limited stage or extensive stage. Limited stage SCLC is confined to one lung and/or the local lymph nodes. Extensive stage SCLC is found in both lungs and/or distant sites in the body.

In some aspects, the lung cancer is non-small cell lung cancer (NSCLC). NSCLC includes NSCLC with a histology that is "not otherwise specified" (NOS), NSCLC with a squamous histology (SQ), and NSCLC with a non-squamous histology (NSQ, including adenocarcinoma, large cell, and undifferentiated carcinoma). In some aspects, the NSCLC has a squamous histology. In some aspects, the NSCLC has a non-squamous histology.

Surgery (i.e., surgical resection), radiation therapy (RT), and chemotherapy are three modalities commonly used to treat NSCLC patients. As a class, NSCLCs are relatively insensitive to chemotherapy and RT, compared to small cell carcinoma. In general, for patients with Stage I or II disease, surgical resection has provided the best chance for cure, with chemotherapy often used both pre-operatively and post-operatively. RT can also be used as adjuvant therapy for patients with resectable NSCLC, the primary local treatment, or as palliative therapy for patients with incurable NSCLC. Patients with advanced or metastatic disease (e.g., Stage IV NSCLC) who have a good performance status (PS) can benefit from chemotherapy.

Specific targeted therapies have also been developed for the treatment of advanced or metastatic NSCLC in subjects with sensitizing mutations in genes for epidermal growth factor receptor (EGFR), anaplastic lymphoma kinase (ALK), ROS-1, neurotrophin receptor tyrosine kinase (NTRK), and B-rapidly accelerated fibrosarcoma proto-oncogene (BRAF, e.g., the BRAF V600E mutation).

In some aspects, the subject has an EGFR, ALK, NTRK, ROS-1, or BRAF mutation sensitive to targeted inhibitor therapy.

In some aspects, the subject has no EGFR, ALK, NTRK, ROS-1, or BRAF mutation sensitive to targeted inhibitor therapy.

In some aspects, one or more immune cells in tumor tissue from the subject express LAG-3 (i.e., tumor tissue from the patient is LAG-3 positive) and/or one or more tumor cells in tumor tissue from the subject express PD-L1 (i.e., tumor tissue from the patient is PD-L1 positive). In some aspects, one or more immune cells in tumor tissue from the subject express LAG-3. In some aspects, at least about 1%, at least about 2%, at least about 3%, at least about 4%, at least about 5%, at least about 7%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, or about 100% of the immune cells express LAG-3. In some aspects, at least about 1% of the immune cells express LAG-3. In some aspects, greater than about 1% of the immune cells express LAG-3. In some aspects, at least about 5% of the immune cells express LAG-3. In some aspects, the immune cells are tumor-infiltrating lymphocytes. In some aspects, the tumor-infiltrating lymphocytes are $CD8^+$ cells. In some aspects, one or more tumor cells in tumor tissue from the subject express PD-L1. In some aspects, at least about 1%, at least about 2%, at least about 3%, at least about 4%, at least about 5%, at least about 7%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, or about 100% of the tumor cells express PD-L1. In some aspects, at least about 1% of the tumor cells express PD-L1. In some aspects, at least about 1% of the tumor cells express PD-L1. In some aspects, greater than about 1% of the tumor cells express PD-L1. In some aspects, at least about 5% of the tumor cells express PD-L1. In some aspects, any of the values of "at least about X %" is "≥X %").

In some aspects, one or more immune cells in tumor tissue from the patient does not express LAG-3 (i.e., tumor tissue from the patient is LAG-3 negative). In some aspects, the tumor tissue is LAG-3 negative when less than about 1% of the immune cells express LAG-3.

In some aspects, one or more immune cells in tumor tissue from the patient does not express PD-1 (i.e., tumor tissue from the patient is PD-1 negative). In some aspects, the tumor tissue is PD-1 negative when less than about 1% of the immune cells express PD-1.

In some aspects, one or more tumor cells in tumor tissue from the patient does not express PD-L1 (i.e., tumor tissue from the patient is PD-L1 negative). In some aspects, the tumor tissue is PD-L1 negative when less than about 1% of the tumor cells express PD-L1.

In some aspects, LAG-3, PD-1, and/or PD-L1 expression in the subject's tumor tissue is determined from a test tissue sample. In some aspects, a test tissue sample includes, but is not limited to, any clinically relevant tissue sample, such as a tumor biopsy, a core biopsy, an incisional biopsy, an excisional biopsy, a surgical specimen, a fine needle aspirate, or a sample of bodily fluid, such as blood, plasma, serum, lymph, ascites fluid, cystic fluid, or urine. In some aspects, the test tissue sample is from a primary tumor. In some aspects, the test tissue sample is from a metastasis. In some aspects, test tissue samples are from multiple time points, for example, before treatment, during treatment, and/or after treatment. In some aspects, test tissue samples are from different locations in the subject, for example, from a primary tumor and from a metastasis.

In some aspects, the test tissue sample is a paraffin-embedded fixed tissue sample. In some aspects, the test tissue sample is a formalin-fixed paraffin embedded (FFPE) tissue sample. In some aspects, the test tissue sample is a fresh tissue (e.g., tumor) sample. In some aspects, the test tissue sample is a frozen tissue sample. In some aspects, the test tissue sample is a fresh frozen (FF) tissue (e.g., tumor) sample. In some aspects, the test tissue sample is a cell isolated from a fluid. In some aspects, the test tissue sample comprises circulating tumor cells (CTCs). In some aspects, the test tissue sample comprises tumor-infiltrating lymphocytes (TILs). In some aspects, the test tissue sample comprises tumor cells and tumor-infiltrating lymphocytes (TILs). In some aspects, the test tissue sample comprises circulating lymphocytes. In some aspects, the test tissue sample is an archival tissue sample. In some aspects, the test tissue sample is an archival tissue sample with known diagnosis, treatment, and/or outcome history. In some aspects, the sample is a block of tissue. In some aspects, the test tissue sample is dispersed cells. In some aspects, the sample size is from about 1 cell to about $1\times10^6$ cells or more. In some aspects, the sample size is about 1 cell to about $1\times10^5$ cells. In some aspects, the sample size is about 1 cell to about 10,000 cells. In some aspects, the sample size is about 1 cell to about 1,000 cells. In some aspects, the sample size is about 1 cells to about 100 cells. In some aspects, the sample size is about 1 cell to about 10 cells. In some aspects, the sample size is a single cell.

In some aspects, LAG-3, PD-1, and/or PD-L1 expression is assessed by performing an assay to detect the presence of LAG-3, PD-1, and/or PD-L1 RNA, respectively. In some aspects, the presence of LAG-3, PD-1, and/or PD-L1 RNA is detected by RT-PCR, in situ hybridization or RNase protection.

In some aspects, LAG-3, PD-1, and/or PD-L1 expression is assessed by performing an assay to detect the presence of LAG-3, PD-1, and/or PD-L1 polypeptide, respectively. In some aspects, the presence of LAG-3, PD-1, and/or PD-L1 polypeptide is detected by immunohistochemistry (IHC), enzyme-linked immunosorbent assay (ELISA), in vivo imaging, or flow cytometry.

II.A. LAG-3 Antagonists

A LAG-3 antagonist for use in the methods of the disclosure includes, but is not limited to, LAG-3 binding agents and soluble LAG-3 polypeptides. LAG-3 binding agents include antibodies that specifically bind to LAG-3 (i.e., an "anti-LAG-3 antibody"). The term "LAG-3 antagonist" as used herein is interchangeable with the term "LAG-3 inhibitor."

In some aspects, the LAG-3 antagonist is an anti-LAG-3 antibody.

Antibodies that bind to LAG-3 have been disclosed, for example, in Int'l Publ. No. WO/2015/042246 and U.S. Publ. Nos. 2014/0093511 and 2011/0150892, each of which is incorporated by reference herein in its entirety.

An exemplary LAG-3 antibody useful in the present disclosure is 25F7 (described in U.S. Publ. No. 2011/0150892). An additional exemplary LAG-3 antibody useful in the present disclosure is BMS-986016 (relatlimab). In some aspects, an anti-LAG-3 antibody useful in the present disclosure cross-competes with 25F7 or BMS-986016. In some aspects, an anti-LAG-3 antibody useful in the present disclosure binds to the same epitope as 25F7 or BMS-986016. In some aspects, an anti-LAG-3 antibody comprises six CDRs of 25F7 or BMS-986016.

Other art-recognized anti-LAG-3 antibodies that can be used in the methods of the disclosure include IMP731 (H5L7BW) described in US 2011/007023, MK-4280 (28G-10, favezelimab) described in WO2016028672 and U.S. Publication No. 2020/0055938, REGN3767 (fianlimab) described in Burova E, et al., J. Immunother. Cancer (2016); 4(Supp. 1):P195 and U.S. Pat. No. 10,358,495, humanized BAP050 described in WO2017/019894, GSK2831781, IMP-701 (LAG525; ieramilimab) described in U.S. Pat. No. 10,711,060 and U.S. Publ. No. 2020/0172617, aLAG3 (0414), aLAG3(0416), Sym022, TSR-033, TSR-075, XmAb841 (previously XmAb22841), MGD013 (tebotelimab), BI754111, FS118, P 13B02-30, AVA-017, AGEN1746, RO7247669, INCAGNO2385, IBI-110, EMB-02, IBI-323, LBL-007, and ABL501. These and other anti-LAG-3 antibodies useful in the claimed invention can be found in, for example: U.S. Pat. No. 10,188,730, WO 2016/028672, WO 2017/106129, WO2017/062888, WO2009/044273, WO2018/069500, WO2016/126858, WO2014/179664, WO2016/200782, WO2015/200119, WO2017/019846, WO2017/198741, WO2017/220555, WO2017/220569, WO2018/071500, WO2017/015560, WO2017/025498, WO2017/087589, WO2017/087901, WO2018/083087, WO2017/149143, WO2017/219995, US2017/0260271, WO2017/086367, WO2017/086419, WO2018/034227, WO2018/185046, WO2018/185043, WO2018/217940, WO19/011306, WO2018/208868, WO2014/140180, WO2018/201096, WO2018/204374, and WO2019/018730. The contents of each of these references are incorporated by reference in their entirety.

Anti-LAG-3 antibodies that can be used in the methods of the disclosure also include isolated antibodies that bind specifically to human LAG-3 and cross-compete for binding to human LAG-3 with any anti-LAG-3 antibody disclosed herein, e.g., relatlimab. In some aspects, the anti-LAG-3 antibody binds the same epitope as any of the anti-LAG-3 antibodies described herein, e.g., relatlimab.

In some aspects, the antibodies that cross-compete for binding to human LAG-3 with, or bind to the same epitope region as, any anti-LAG-3 antibody disclosed herein, e.g., relatlimab, are monoclonal antibodies. For administration to human subjects, these cross-competing antibodies are chimeric antibodies, engineered antibodies, or humanized or human antibodies. Such chimeric, engineered, humanized or human monoclonal antibodies can be prepared and isolated by methods well known in the art.

The ability of antibodies to cross-compete for binding to an antigen indicates that the antibodies bind to the same epitope region of the antigen and sterically hinder the binding of other cross-competing antibodies to that particular epitope region. These cross-competing antibodies are expected to have functional properties very similar those of the reference antibody, e.g., relatlimab, by virtue of their binding to the same epitope region. Cross-competing antibodies can be readily identified based on their ability to cross-compete in standard binding assays such as BIACORE analysis, ELISA assays or flow cytometry (see, e.g., WO 2013/173223).

Anti-LAG-3 antibodies that can be used in the methods of the disclosure also include antigen-binding portions of any of the above full-length antibodies. It has been amply demonstrated that the antigen-binding function of an antibody can be performed by fragments of a full-length antibody.

In some aspects, the anti-LAG-3 antibody is a full-length antibody.

In some aspects, the anti-LAG-3 antibody is a monoclonal, human, humanized, chimeric, or multispecific antibody. In some aspects, the multispecific antibody is a dual-affinity re-targeting antibody (DART), a DVD-Ig, or bispecific antibody.

In some aspects, the anti-LAG-3 antibody is a $F(ab')_2$ fragment, a Fab' fragment, a Fab fragment, a Fv fragment, a scFv fragment, a dsFv fragment, a dAb fragment, or a single chain binding polypeptide.

In some aspects, the anti-LAG-3 antibody is BMS-986016 (relatlimab), IMIP731 (H5L7BW), MK4280 (28G-10, favezelimab), REGN3767 (fianlimab), GSK2831781, humanized BAP050, IMP-701 (LAG525, ieramilimab), aLAG3(0414), aLAG3(0416), Sym022, TSR-033, TSR-075, XmAb841 (XmAb22841), MGD013 (tebotelimab), B1754111, FS118, P 13B02-30, AVA-017, 25F7, AGEN1746, RO7247669, INCAGNO2385, IBI-110, EMB-02, IBI-323, LBL-007, ABL501, or comprises an antigen binding portion thereof.

In some aspects, the anti-LAG-3 antibody is relatlimab.

In some aspects, the methods of the disclosure comprise an anti-LAG-3 antibody comprising CDR1, CDR2 and CDR3 domains of the heavy chain variable region having the sequence set forth in SEQ ID NO:3, and CDR1, CDR2 and CDR3 domains of the light chain variable region having the sequence set forth in SEQ ID NO:4.

In some aspects, the methods of the disclosure comprise an anti-LAG-3 antibody comprising: (a) a heavy chain variable region CDR1 comprising the sequence set forth in SEQ ID NO:5; (b) a heavy chain variable region CDR2 comprising the sequence set forth in SEQ ID NO:6; (c) a heavy chain variable region CDR3 comprising the sequence set forth in SEQ ID NO:7; (d) a light chain variable region CDR1 comprising the sequence set forth in SEQ ID NO:8; (e) a light chain variable region CDR2 comprising the sequence set forth in SEQ ID NO:9; and (f) a light chain variable region CDR3 comprising the sequence set forth in SEQ ID NO:10.

In some aspects, the methods of the disclosure comprise an anti-LAG-3 antibody comprising heavy and light chain variable regions comprising the sequences set forth in SEQ ID NOs:3 and 4, respectively.

In some aspects, the methods of the disclosure comprise an anti-LAG-3 antibody comprising heavy and light chains comprising the sequences set forth in SEQ ID NOs:1 and 2, respectively.

In some aspects, the methods of the disclosure comprise an anti-LAG-3 antibody comprising heavy and light chains comprising the sequences set forth in SEQ ID NOs:21 and 2, respectively.

In some aspects, the anti-LAG-3 antibody is MGD013 (tebotelimab), which is a bispecific PD-1×LAG-3 DART. In some aspects, tebotelimab is administered intravenously at a dose of about 300 mg or about 600 mg once about every 2 or 3 weeks. In some aspects, tebotelimab is administered intravenously at a dose of about 300 mg once about every 2 weeks. In some aspects, tebotelimab is administered intravenously at a dose of about 600 mg once about every 3 weeks.

In some aspects, the anti-LAG-3 antibody is REGN3767 (fianlimab). In some aspects, fianlimab is administered intravenously at a dose of about 1 mg/kg, about 3 mg/kg, about 10 mg/kg, or about 20 mg/kg once about every 3 weeks. In some aspects, fianlimab is administered intravenously at a dose of about 1600 mg once about every 3 weeks.In some aspects, the methods of the disclosure comprise an anti-LAG-3 antibody comprising CDR1, CDR2 and CDR3 domains of the heavy chain variable region having the sequence set forth in SEQ ID NO:25, and CDR1, CDR2 and CDR3 domains of the light chain variable region having the sequence set forth in SEQ ID NO:26.

In some aspects, the methods of the disclosure comprise an anti-LAG-3 antibody comprising: (a) a heavy chain variable region CDR1 comprising the sequence set forth in SEQ ID NO:27; (b) a heavy chain variable region CDR2 comprising the sequence set forth in SEQ ID NO:28; (c) a heavy chain variable region CDR3 comprising the sequence set forth in SEQ ID NO:29; (d) a light chain variable region CDR1 comprising the sequence set forth in SEQ ID NO:30; (e) a light chain variable region CDR2 comprising the sequence DAS; and (f) a light chain variable region CDR3 comprising the sequence set forth in SEQ ID NO:32.

In some aspects, the methods of the disclosure comprise an anti-LAG-3 antibody comprising heavy and light chain variable regions comprising the sequences set forth in SEQ ID NOs:25 and 26, respectively.

In some aspects, the methods of the disclosure comprise an anti-LAG-3 antibody comprising heavy and light chains comprising the sequences as set forth in SEQ ID NOs:23 and 24, respectively.

In some aspects, the anti-LAG-3 antibody is LAG525 (ieramilimab). In some aspects, ieramilimab is administered intravenously at a dose of about 300 mg, about 400 mg, about 500 mg, about 600 mg, about 700 mg, about 800 mg, about 900 mg, about 1000 mg, about 1100 mg, about 1200 mg, or about 1300 mg once about every 2, 3, or 4 weeks.

In some aspects, the methods of the disclosure comprise an anti-LAG-3 antibody comprising CDR1, CDR2 and CDR3 domains of the heavy chain variable region having the sequence set forth in SEQ ID NO:47, and CDR1, CDR2 and CDR3 domains of the light chain variable region having the sequence set forth in SEQ ID NO:49.

In some aspects, the methods of the disclosure comprise an anti-LAG-3 antibody comprising CDR1, CDR2 and CDR3 domains of the heavy chain variable region having the sequence set forth in SEQ ID NO:48, and CDR1, CDR2 and CDR3 domains of the light chain variable region having the sequence set forth in SEQ ID NO:50.

In some aspects, the methods of the disclosure comprise an anti-LAG-3 antibody comprising: (a) a heavy chain variable region CDR1 comprising the sequence set forth in SEQ ID NO:51; (b) a heavy chain variable region CDR2 comprising the sequence set forth in SEQ ID NO:52; (c) a heavy chain variable region CDR3 comprising the sequence set forth in SEQ ID NO:53; (d) a light chain variable region CDR1 comprising the sequence set forth in SEQ IDNO: 54; (e) a light chain variable region CDR2 comprising the sequence set forth in SEQ ID NO:55; and (f) a light chain variable region CDR3 comprising the sequence set forth in SEQ ID NO:56.

In some aspects, the methods of the disclosure comprise an anti-LAG-3 antibody comprising heavy and light chain variable regions comprising the sequences set forth in SEQ ID NOs:47 and 49, respectively.

In some aspects, the methods of the disclosure comprise an anti-LAG-3 antibody comprising heavy and light chain variable regions comprising the sequences set forth in SEQ ID NOs:48 and 50, respectively.

In some aspects, the methods of the disclosure comprise an anti-LAG-3 antibody comprising heavy and light chains comprising the sequences as set forth in SEQ ID NOs:43 and 45, respectively.

In some aspects, the methods of the disclosure comprise an anti-LAG-3 antibody comprising heavy and light chains comprising the sequences as set forth in SEQ ID NOs:44 and 46, respectively.

In some aspects, the anti-LAG-3 antibody is MK4280 (favezelimab). In some aspects, favezelimabis administered intravenously at a dose of about 7 mg, about 21 mg, about 70 mg, about 210 mg, about 700 mg, or about 800 mg once about every 3 weeks or once about every 6 weeks. In some aspects, favezelimab is administered intravenously at a dose of about 200 mg once about every 3 weeks. In some aspects, favezelimab is administered intravenously at a dose of about 800 mg once about every 6 weeks. In some aspects, favezelimab is administered intravenously at a dose of about 800 mg on Day 1, then once about every 3 weeks. In some aspects, favezelimab is administered for up to 35 cycles. In some aspects, favezelimab is administered intravenously at a dose of about 800 mg for about 30 minutes on Day 1 of a three-week cycle for up to 35 cycles.

In some aspects, the methods of the disclosure comprise an anti-LAG-3 antibody comprising CDR1, CDR2 and CDR3 domains of the heavy chain variable region having the sequence set forth in SEQ ID NO:69, and CDR1, CDR2 and CDR3 domains of the light chain variable region having the sequence set forth in SEQ ID NO:70.

In some aspects, the methods of the disclosure comprise an anti-LAG-3 antibody comprising: (a) a heavy chain variable region CDR1 comprising the sequence set forth in SEQ ID NO:71; (b) a heavy chain variable region CDR2 comprising the sequence set forth in SEQ ID NO:72; (c) a heavy chain variable region CDR3 comprising the sequence set forth in SEQ ID NO:73; (d) a light chain variable region CDR1 comprising the sequence set forth in SEQ ID NO:74; (e) a light chain variable region CDR2 comprising the sequence set forth in SEQ ID NO:75; and (f) a light chain variable region CDR3 comprising the sequence set forth in SEQ ID NO:76.

In some aspects, the methods of the disclosure comprise an anti-LAG-3 antibody comprising heavy and light chain variable regions comprising the sequences set forth in SEQ ID NOs:69 and 70, respectively.

In some aspects, the methods of the disclosure comprise an anti-LAG-3 antibody comprising heavy and light chains comprising the sequences as set forth in SEQ ID NOs:67 and 68, respectively.

In some aspects, the LAG-3 antagonist is a soluble LAG-3 polypeptide. In some aspects, the soluble LAG-3 polypeptide is a fusion polypeptide, e.g., a fusion protein comprising the extracellular portion of LAG-3. In some aspects, the soluble LAG-3 polypeptide is a LAG-3-Fc fusion polypeptide capable of binding to MHC Class II. In some aspects, the soluble LAG-3 polypeptide comprises a ligand binding fragment of the LAG-3 extracellular domain. In some aspects, the ligand binding fragment of the LAG-3 extracellular domain comprises an amino acid sequence with at least about 90%, at least about 95%, at least about 98%, at least about 99%, or about 100% sequence identity to SEQ ID NO:22. In some aspects, the soluble LAG-3 polypeptide further comprises a half-life extending moiety. In some aspects, the half-life extending moiety comprises an immunoglobulin constant region or a portion thereof, an immunoglobulin-binding polypeptide, an immunoglobulin G (IgG), albumin-binding polypeptide (ABP), a PASylation moiety, a HESylation moiety, XTEN, a PEGylation moiety, an Fc region, or any combination thereof. In some aspects, the soluble LAG-3 polypeptide is IMP321 (eftilagimod alpha). See, e.g., Brignone C, et al., *J. Immunol.* (2007); 179:4202-4211 and WO2009/044273. In some aspects, eftilagimod alpha is administered at a dose of about 30 mg. In some aspects, eftilagimod alpha is administered subcutaneously at a dose of about 30 mg once about every 2 weeks.

In some aspects, an anti-LAG-3 antibody is used to determine LAG-3 expression. In some aspects, an anti-LAG-3 antibody is selected for its ability to bind to LAG-3 in formalin-fixed, paraffin-embedded (FFPE) tissue specimens. In some aspects, an anti-LAG-3 antibody is capable of binding to LAG-3 in frozen tissues. In some aspects, an anti-LAG-3 antibody is capable of distinguishing membrane bound, cytoplasmic, and/or soluble forms of LAG-3.

In some aspects, an anti-LAG-3 antibody useful for assaying, detecting, and/or quantifying LAG-3 expression in accordance with the methods disclosed herein is the 17B4 mouse IgG1 anti-human LAG-3 monoclonal antibody. See, e.g., Matsuzaki, J et al., PNAS (2010); 107:7875.

In some aspects, the LAG-3 antagonist is formulated for intravenous administration.

In some aspects, the anti-LAG-3 antibody is administered intravenously for about 30 minutes.

In some aspects, the LAG-3 antagonist is administered at a flat dose.

In some aspects, the LAG-3 antagonist is administered at a dose of from at least about 0.25 mg to about 2000 mg, about 0.25 mg to about 1600 mg, about 0.25 mg to about 1200 mg, about 0.25 mg to about 800 mg, about 0.25 mg to about 400 mg, about 0.25 mg to about 100 mg, about 0.25 mg to about 50 mg, about 0.25 mg to about 40 mg, about 0.25 mg to about 30 mg, about 0.25 mg to about 20 mg, about 20 mg to about 2000 mg, about 20 mg to about 1600 mg, about 20 mg to about 1200 mg, about 20 mg to about 800 mg, about 20 mg to about 400 mg, about 20 mg to about 100 mg, about 100 mg to about 2000 mg, about 100 mg to about 1800 mg, about 100 mg to about 1600 mg, about 100 mg to about 1400 mg, about 100 mg to about 1200 mg, about 100 mg to about 1000 mg, about 100 mg to about 800 mg, about 100 mg to about 600 mg, about 100 mg to about 400 mg, about 400 mg to about 2000 mg, about 400 mg to about 1800 mg, about 400 mg to about 1600 mg, about 400 mg to about 1400 mg, about 400 mg to about 1200 mg, or about 400 mg to about 1000 mg.

In some aspects, the LAG-3 antagonist is administered at a dose of about 0.25 mg, about 0.5 mg, about 0.75 mg, about 1 mg, about 1.25 mg, about 1.5 mg, about 1.75 mg, about 2 mg, about 2.25 mg, about 2.5 mg, about 2.75 mg, about 3 mg, about 3.25 mg, about 3.5 mg, about 3.75 mg, about 4 mg, about 4.25 mg, about 4.5 mg, about 4.75 mg, about 5 mg, about 5.25 mg, about 5.5 mg, about 5.75 mg, about 6 mg, about 6.25 mg, about 6.5 mg, about 6.75 mg, about 7 mg, about 7.25 mg, about 7.5 mg, about 7.75 mg, about 8 mg, about 8.25 mg, about 8.5 mg, about 8.75 mg, about 9 mg, about 9.25 mg, about 9.5 mg, about 9.75 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, about 600 mg, about 610 mg, about 620 mg, about 630 mg, about 640 mg, about 650 mg, about 660 mg, about 670 mg, about 680 mg, about 690 mg, about 700 mg, about 710 mg, about 720 mg, about 730 mg, about 740 mg, about 750 mg, about 760 mg, about 770 mg, about 780 mg, about 790 mg, about 800 mg, about 810 mg, about 820 mg, about 830 mg, about 840 mg, about 850 mg, about 860 mg, about 870 mg, about 880 mg, about 890 mg, about 900 mg, about 910 mg, about 920 mg, about 930 mg, about 940 mg, about 950 mg, about 960 mg, about 970 mg, about 980 mg, about 990 mg, about 1000 mg, about 1040 mg, about 1080 mg, about 1100 mg, about 1140 mg, about 1180 mg, about 1200 mg, about 1240 mg, about 1280 mg, about 1300 mg, about 1340 mg, about 1380 mg, about 1400 mg, about 1440 mg, about 1480 mg, about 1500 mg, about 1540 mg, about 1580 mg, about 1600 mg, about 1640 mg, about 1680 mg, about 1700 mg, about 1740 mg, about 1780 mg, about 1800 mg, about 1840 mg, about 1880 mg, about 1900 mg, about 1940 mg, about 1980 mg, or about 2000 mg.

In some aspects, the LAG-3 antagonist is administered at a weight-based dose.

In some aspects, the LAG-3 antagonist is administered at a dose from about 0.003 mg/kg to about 25 mg/kg, about 0.003 mg/kg to about 20 mg/kg, about 0.003 mg/kg to about 15 mg/kg, about 0.003 mg/kg to about 10 mg/kg, about 0.003 mg/kg to about 5 mg/kg, about 0.003 mg/kg to about 1 mg/kg, about 0.003 mg/kg to about 0.9 mg/kg, about 0.003 mg/kg to about 0.8 mg/kg, about 0.003 mg/kg to about 0.7 mg/kg, about 0.003 mg/kg to about 0.6 mg/kg, about 0.003 mg/kg to about 0.5 mg/kg, about 0.003 mg/kg to about 0.4 mg/kg, about 0.003 mg/kg to about 0.3 mg/kg, about 0.003 mg/kg to about 0.2 mg/kg, about 0.003 mg/kg to about 0.1 mg/kg, about 0.1 mg/kg to about 25 mg/kg, about 0.1 mg/kg to about 20 mg/kg, about 0.1 mg/kg to about 15 mg/kg, about 0.1 mg/kg to about 10 mg/kg, about 0.1 mg/kg to about 5 mg/kg, about 0.1 mg/kg to about 1 mg/kg, about 1 mg/kg to about 25 mg/kg, about 1 mg/kg to about 20 mg/kg, about 1 mg/kg to about 15 mg/kg, about 1 mg/kg to about 10 mg/kg, about 1 mg/kg to about 5 mg/kg, about 5 mg/kg to about 25 mg/kg, about 5 mg/kg to about 20 mg/kg, about 5 mg/kg to about 15 mg/kg, about 5 mg/kg to about 10 mg/kg, about 10 mg/kg to about 25 mg/kg, about 10 mg/kg to about 20 mg/kg, about 10 mg/kg to about 15 mg/kg, about 15 mg/kg to about 25 mg/kg, about 15 mg/kg to about 20 mg/kg, or about 20 mg/kg to about 25 mg/kg.

In some aspects, the LAG-3 antagonist is administered at a dose of about 0.003 mg/kg, about 0.004 mg/kg, about 0.005 mg/kg, about 0.006 mg/kg, about 0.007 mg/kg, about 0.008 mg/kg, about 0.009 mg/kg, about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1.0 mg/kg, about 2.0 mg/kg, about 3.0 mg/kg, about 4.0 mg/kg, about 5.0 mg/kg, about 6.0 mg/kg, about 7.0 mg/kg, about 8.0 mg/kg, about 9.0 mg/kg, about 10.0 mg/kg, about 11.0 mg/kg, about 12.0 mg/kg, about 13.0 mg/kg, about 14.0 mg/kg, about 15.0 mg/kg, about 16.0 mg/kg, about 17.0 mg/kg, about 18.0 mg/kg, about 19.0 mg/kg, about 20.0 mg/kg, about 21.0 mg/kg, about 22.0 mg/kg, about 23.0 mg/kg, about 24.0 mg/kg, or about 25.0 mg/kg.

In some aspects, the dose is administered once about every one week, once about every two weeks, once about every three weeks, once about every four weeks, once about every five weeks, once about every six weeks, once about every seven weeks, once about every eight weeks, once about every nine weeks, once about every ten weeks, once about every eleven weeks, or once about every twelve weeks.

In some aspects, a LAG-3 antagonist as described herein is administered as a monotherapy, i.e., the LAG-3 antagonist is not administered in combination with one or more additional therapeutic agents.

In some aspects, a LAG-3 antagonist as described herein is administered as a combination therapy, i.e., the LAG-3 antagonist is administered in combination with one or more additional therapeutic agents and/or anti-cancer therapies.

II.B. Combination Therapy

The additional therapeutic agent and/or anti-cancer therapy can comprise any known therapeutic agent or anti-cancer therapy, including a standard of care in the art for the treatment of a subject afflicted with lung cancer. In some aspects, the LAG-3 antagonist is combined with a therapeutic agent and/or therapy described by the NCCN Guidelines® for treatment of NSCLC. See, e.g., therapeutic agents and therapies described at: www.cancertherapyadvisor.com/home/cancer-topics/lung-cancer/lung-cancer-treatment-regimens-landing-page/non-small-cell-lung-cancer-treatment-regimens/, last accessed Oct. 23, 2020.

II.B.1. Anti-Cancer Therapies

In some aspects, the additional anti-cancer therapy comprises a surgery, a radiation therapy, a chemotherapy, an immunotherapy, or any combination thereof. In some aspects, the additional anti-cancer therapy comprises a chemotherapy, including any chemotherapeutic agent disclosed herein. In some aspects, the chemotherapy comprises platinum doublet chemotherapy.

In some aspects, the PDCT comprises a platinum agent in combination with a nucleoside analog, an antimetabolite, a taxane, a vinca alkaloid, or a topisomerase inhibitor.

In some aspects, the platinum agent is cisplatin, carboplatin, oxaliplatin, satraplatin, picoplatin, nedaplatin, triplatin, lipoplatin, or phenanthriplatin.

In some aspects, the nucleoside analog is cytarabine, gemcitabine, lamivudine, entecavir, or telbivudine. In some aspects, the nucleoside analog is gemcitabine.

In some aspects, the antimetabolite is capecitabine, cladribine, clofarabine, cytarabine, floxuridine, fludarabine, fluorouracil, mercaptopurine, methotrexate, pemetrexed, pentostatin, pralatrexate, or thioguanine. In some aspects, the antimetabolite is pemetrexed.

In some aspects, the taxane is paclitaxel, albumin-bound paclitaxel (also called nab-paclitaxel), docetaxel, or cabazitaxel.

In some aspects, the vinca alkaloid is vinblastine, vincristine, vinorelbine, vindesine, vincaminol, vineridine, or vinburnine. In some aspects, the vinca alkaloid is vinorelbine or vinblastine.

In some aspects, the topoisomerase inhibitor is etoposide, mitoxantrone, doxorubicin, irinotecan, topotecan, or camptothecin. In some aspects, the topoisomerase inhibitor is etoposide. In some aspects, the topoisomerase inhibitor is irinotecan.

In some aspects, the PDCT is administered for about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, or about 24 weeks.

In some aspects, the PDCT is administered about every three weeks for about 1, about 2, about 3, about 4, about 5, about 6, about 7, or about 8 cycles. In some aspects, the PDCT is administered about every three weeks for about 1, about 2, about 3, about 4, about 5, or about 6 cycles. In some aspect, the PDCT is administered about every three weeks for about 1, about 2, about 3, or about 4 cycles.

In some aspects, the PDCT is administered for up to about 4, about 5, or about 6 three-week cycles. In some aspects, the PDCT is administered for up to about 4 three-week cycles.

In some aspects, the platinum agent is cisplatin. In some aspects, cisplatin is administered at a dose of about 25 $mg/m^2$ to about 150 $mg/m^2$, about 50 $mg/m^2$ to about 100 $mg/m^2$, about 75 $mg/m^2$ to about 100 $mg/m^2$, or about 75 $mg/m^2$ to about 80 $mg/m^2$. In some aspects, cisplatin is administered at a dose of about 50 $mg/m^2$, about 55 mg/m2, about 60 $mg/m^2$, about 65 $mg/m^2$, about 70 $mg/m^2$, about 75 $mg/m^2$, about 76 $mg/m^2$, about 77 $mg/m^2$, about 78 $mg/m^2$, about 79 $mg/m^2$, about 80 $mg/m^2$, about 85 $mg/m^2$, about 90 $mg/m^2$, about 95 $mg/m^2$, or about 100 $mg/m^2$. In some aspects, cisplatin is administered intravenously for about 60 minutes. In some aspects, cisplatin is administered on Day 1 of a three-week cycle for up to about 4, about 5, or about 6 cycles.

In some aspects, the platinum agent is carboplatin. In some aspects, carboplatin is administered at a dose for a target area under the concentration-time curve (AUC) of about 1 mg/mL·min to about 10 mg/mL·min. In some aspects, carboplatin is administered in a dose for a target AUC of about 1 mg/mL·min, about 2 mg/mL·min, about 3 mg/mL·min, about 4 mg/mL·min, about 5 mg/mL·min, about 6 mg/mL·min, about 7 mg/mL·min, about 8 mg/mL·min, about 9 mg/mL·min, or about 10 mg/mL·min. In some aspects, carboplatin is administered in a dose for a target AUC of about 2 mg/mL·min. In some aspects, carboplatin is administered in a dose for a target AUC of about 5 mg/mL·min. In some aspects, carboplatin is administered in a dose for a target AUC of about 6 mg/mL·min. In some aspects, carboplatin is administered intravenously for about 30 minutes. In some aspects, carboplatin is administered on Day 1 of a three-week cycle for up to about 4, about 5, or about 6 cycles.

Carboplatin dose can be calculated according to methods known in the art. In some aspects, carboplatin dose is calculated using the Calvert formula as follows:

$$\text{Carboplatin dose (mg)} = \text{target } AUC \times (\text{CrCl } [\text{mL/min}] + 25).$$

The Creatine Clearance (CrCl) calculation in the Calvert formula can be determined using the Cockcroft-Gault formula:

$$\text{Cockcroft-Gault CrCl} = [(140-\text{age}) \times (\text{Weight in kg}) \times (0.85 \text{ if female})]/(72 \times \text{Cr}).$$

The Cockcroft-Gault formula includes a subject's most recent weight (kg) and most recent serum creatinine (Cr) concentration (mg/dL). In some aspects, if calculation of CrC1 by the Cockcroft-Gault formula yields a result of >125 mL/min, then a CrC1 is calculated by an alternative formula per institutional standards or capped at 125 mL/min.

In some aspects, the PDCT comprises cisplatin or carboplatin in combination with gemcitabine, paclitaxel, albumin-bound paclitaxel, docetaxel, pemetrexed, vinorelbine, vinblastine, etoposide, or irinotecan.

In some aspects, the PDCT comprises cisplatin or carboplatin in combination with gemcitabine. In some aspects, gemcitabine is administered at a dose of about 1,000 $mg/m^2$ to about 1,250 $mg/m^2$. In some aspects, gemcitabine is administered at a dose of about 1,000 $mg/m^2$, about 1,050 $mg/m^2$, about 1,100 $mg/m^2$, about 1,150 $mg/m^2$, about 1,200 $mg/m^2$, or about 1,250 $mg/m^2$. In some aspects, gemcitabine is administered intravenously for about 30 minutes. In some aspects, gemcitabine is administered on Days 1, 8, and 15 of a three-week cycle for up to about 4, about 5, or about 6 cycles. In some aspects, gemcitabine is administered on Days 1 and 8 of a three-week cycle for up to about 4, about 5, or about 6 cycles. In some aspects, the PDCT comprises a dose of about 1,000 $mg/m^2$ to about 1,250 $mg/m^2$ gemcitabine administered intravenously for about 30 minutes on Days 1 and 8 of a three-week cycle for about 4 to about 6 cycles and a dose of about 75 $mg/m^2$ to about 80 $mg/m^2$ cisplatin administered intravenously for about 60 minutes on Day 1 of each cycle. In some aspects, the PDCT comprises a dose of about 1,000 $mg/m^2$ gemcitabine administered intravenously for about 30 minutes on Days 1, 8, and 15 of a three-week cycle for about 4 to about 6 cycles and carboplatin administered intravenously for about 30 minutes in a dose for a target AUC of about 5 mg/mL·min on Day 1 of each cycle.

In some aspects, the PDCT comprises cisplatin or carboplatin in combination with paclitaxel or albumin-bound paclitaxel.

In some aspects, the PDCT comprises cisplatin or carboplatin in combination with paclitaxel. In some aspects, paclitaxel is administered at a dose of about 45 $mg/m^2$ to about 200 $mg/m^2$. In some aspects, paclitaxel is administered at a dose of about 45 $mg/m^2$, about 50 $mg/m^2$, about 55 $mg/m^2$, about 60 $mg/m^2$, about 65 $mg/m^2$, about 70 $mg/m^2$, about 75 $mg/m^2$, about 80 $mg/m^2$, about 85 $mg/m^2$, about 90 $mg/m^2$, about 95 $mg/m^2$, about 100 $mg/m^2$, about 105 $mg/m^2$, about 110 $mg/m^2$, about 115 $mg/m^2$, about 120 $mg/m^2$, about 125 $mg/m^2$, about 130 $mg/m^2$, about 135 $mg/m^2$, about 140 $mg/m^2$, about 145 $mg/m^2$, about 150 $mg/m^2$, about 155 $mg/m^2$, about 160 $mg/m^2$, about 165 $mg/m^2$, about 170 $mg/m^2$, about 175 $mg/m^2$, about 180 $mg/m^2$, about 185 $mg/m^2$, about 190 $mg/m^2$, about 195 $mg/m^2$, or about 200 $mg/m^2$. In some aspects, paclitaxel is administered intravenously for about 60 minutes to about 180 minutes. In some aspects, the PDCT comprises a dose of about 200 $mg/m^2$ paclitaxel administered intravenously for about 180 minutes on Day 1 of a three-week cycle for about 4 to about 6 cycles and a dose of about 75 $mg/m^2$ to about 80 $mg/m^2$ cisplatin administered intravenously for about 60 minutes on Day 1 of each cycle. In some aspects, the PDCT comprises a dose of about 135 $mg/m^2$ paclitaxel administered intravenously for about 180 minutes on Day 1 of a three-week cycle for about 4 to about 6 cycles and a dose of about 75 $mg/m^2$ cisplatin administered intravenously for about 60 minutes on Day 1 of each cycle. In some aspects, the PDCT comprises a dose of about 200 $mg/m^2$ paclitaxel administered intravenously for about 180 minutes on Day 1 of a three-week cycle for about 4 to about 6 cycles and carboplatin administered intravenously for about 30 minutes in a dose for a target AUC of about 6 mg/mL·min on Day 1 of each cycle. In some aspects, the PDCT comprises a dose of about 45 $mg/m^2$ to about 50 $mg/m^2$ paclitaxel administered intravenously for about 60 minutes on Day 1 of a one-week cycle for about 7 cycles and carboplatin administered intravenously for about 30 minutes in a dose for a target AUC of about 2 mg/mL·min on Day 1 of each cycle.

In some aspects, the PDCT comprises cisplatin or carboplatin in combination with albumin-bound paclitaxel. In some aspects, albumin-bound paclitaxel is administered at a dose of about 100 mg/$m^2$. In some aspects, albumin-bound paclitaxel is administered intravenously for about 30 minutes. In some aspects, the PDCT comprises a dose of about 100 mg/$m^2$ albumin-bound paclitaxel administered intravenously for about 30 minutes on Days 1, 8, and 15 of a three-week cycle for about 4 cycles and a dose of about 75 mg/$m^2$ to about 80 mg/$m^2$ cisplatin administered intravenously for about 60 minutes on Day 1 of each cycle. In some aspects, the PDCT comprises a dose of about 100 mg/$m^2$ albumin-bound paclitaxel administered intravenously for about 30 minutes on Days 1, 8, and 15 of a three-week cycle for about 4 to about 6 cycles and carboplatin administered intravenously for about 30 minutes in a dose for a target AUC of about 6 mg/mL·min on Day 1 of each cycle.

In some aspects, the PDCT comprises cisplatin or carboplatin in combination with docetaxel. In some aspects, docetaxel is administered at a dose of about 75 mg/$m^2$. In some aspects, docetaxel is administered intravenously for about 60 minutes. In some aspects, the PDCT comprises a dose of about 75 mg/$m^2$ docetaxel administered intravenously for about 60 minutes on Day 1 of a three-week cycle for about 4 to about 6 cycles and a dose of about 75 mg/$m^2$ cisplatin administered intravenously for about 60 minutes on Day 1 of each cycle. In some aspects, the PDCT comprises a dose of about 75 mg/$m^2$ docetaxel administered intravenously for about 60 minutes on Day 1 of a three-week cycle for about 4 to about 6 cycles and carboplatin administered intravenously for about 30 minutes in a dose for a target AUC of about 6 mg/mL·min on Day 1 of each cycle.

In some aspects, the PDCT comprises cisplatin or carboplatin in combination with pemetrexed. In some aspects, pemetrexed is administered at a dose of about 500 mg/$m^2$. In some aspects, pemetrexed is administered intravenously for about 10 minutes. In some aspects, the PDCT comprises a dose of about 500 mg/$m^2$ pemetrexed administered intravenously for about 10 minutes on Day 1 of a three-week cycle for about 4 to about 6 cycles and a dose of about 75 mg/$m^2$ cisplatin administered intravenously for about 60 minutes on Day 1 of each cycle. In some aspects, the PDCT comprises a dose of about 500 mg/$m^2$ pemetrexed administered intravenously for about 10 minutes on Day 1 of a three-week cycle for about 3 cycles and a dose of about 75 mg/$m^2$ cisplatin administered intravenously for about 60 minutes on Day 1 of each cycle. In some aspects, the PDCT comprises a dose of about 500 mg/$m^2$ pemetrexed administered intravenously for about 60 minutes on Day 1 of a three-week cycle for about 4 to about 6 cycles and carboplatin administered intravenously for about 30 minutes in a dose for a target AUC of about 6 mg/mL·min on Day 1 of each cycle. In some aspects, the PDCT comprises a dose of about 500 mg/$m^2$ pemetrexed administered intravenously for about 60 minutes on Day 1 of a three-week cycle for about 4 to about 6 cycles and carboplatin administered intravenously for about 30 minutes in a dose for a target AUC of about 5 mg/mL·min on Day 1 of each cycle.

In some aspects, the PDCT comprises cisplatin or carboplatin in combination with etoposide. In some aspects, etoposide is administered at a dose of about 50 mg/$m^2$ to about 100 mg/$m^2$. In some aspects, etoposide is administered intravenously for about 30 minutes to about 60 minutes. In some aspects, the PDCT comprises a dose of about 100 mg/m2 etoposide administered intravenously for about 60 minutes on Days 1-3 of a three-week cycle for about 4 to about 6 cycles and a dose of about 100 mg/$m^2$ cisplatin administered intravenously for about 60 minutes on Day 1 of each cycle. In some aspects, the PDCT comprises a dose of about 100 mg/$m^2$ etoposide administered intravenously for about 60 minutes on Days 1-3 of a four-week cycle for about 4 cycles and a dose of about 100 mg/$m^2$ cisplatin administered intravenously for about 60 minutes on Day 1 of each cycle. In some aspects, the PDCT comprises a dose of about 50 mg/$m^2$ etoposide administered intravenously for about 60 minutes on Days 1-5 of a four-week cycle for about 2 cycles and a dose of about 50 mg/$m^2$ cisplatin administered intravenously for about 60 minutes on Days 1 and 8 of each cycle. In some aspects, the PDCT comprises a dose of about 100 mg/$m^2$ etoposide administered intravenously for about 30 minutes on Days 1-3 of a three-week cycle for about 4 to about 6 cycles and carboplatin administered intravenously for about 30 minutes in a dose for a target AUC of about 5 mg/mL·min on Day 1 of each cycle.

In some aspects, the PDCT comprises cisplatin and vinorelbine. In some aspects, vinorelbine is administered at a dose of about 25 mg/$m^2$ to about 30 mg/$m^2$. In some aspects, vinorelbine is administered intravenously for about 5 minutes to about 10 minutes. In some aspects, the PDCT comprises a dose of about 25 mg/$m^2$ to about 30 mg/$m^2$ vinorelbine administered intravenously for about 5 minutes to about 10 minutes on Days 1 and 8 of a three-week cycle for about 4 cycles and a dose of about 75 mg/$m^2$ to about 80 mg/$m^2$ cisplatin administered intravenously for about 60 minutes on Day 1 of each cycle. In some aspects, the PDCT comprises a dose of about 25 mg/$m^2$ vinorelbine administered intravenously for about 5 minutes to about 10 minutes on Days 1, 8, 15, and 22 of a four-week cycle for about 4 cycles and a dose of about 50 mg/$m^2$ cisplatin administered intravenously for about 60 minutes on Days 1 and 8 of each cycle. In some aspects, the PDCT comprises a dose of about 30 mg/$m^2$ vinorelbine administered intravenously for about 5 minutes to about 10 minutes on Days 1, 8, 15, and 22 of a four-week cycle for about 4 cycles and a dose of about 100 mg/$m^2$ cisplatin administered intravenously for about 60 minutes on Day 1 of each cycle.

In some aspects, the PDCT comprises cisplatin and vinblastine. In some aspects, vinblastine is administered at a dose of about 5 mg/$m^2$. In some aspects, vinblastine is administered intravenously for about 5 minutes to about 10 minutes. In some aspects, the PDCT comprises a dose of about 5 mg/$m^2$ vinblastine administered intravenously for about 5 minutes to about 10 minutes on Days 1, 8, 15, 22, and 29 of a 35-day cycle and a dose of about 100 mg/$m^2$ cisplatin administered intravenously for about 60 minutes on Days 1 and 29 of the cycle.

In some aspects, the PDCT is administered in combination with bevacizumab (also known as AVASTIN®). In some aspects, bevacizumab is administered intravenously at a dose of about 15 mg/kg on Day 1 of a three-week cycle for about 6 cycles, paclitaxel is administered intravenously at a dose of about 200 mg/$m^2$ for about 180 minutes on Day 1 of each cycle, and carboplatin is administered intravenously for about 30 minutes in a dose for a target AUC of about 6 mg/mL·min on Day 1 of each cycle. In some aspects, bevacizumab is administered intravenously at a dose of about 15 mg/kg on Day 1 of a three-week cycle for about 4 to about 6 cycles, pemetrexed is administered intravenously at a dose of about 500 mg/$m^2$ for about 10 minutes on Day 1 of each cycle, and carboplatin is administered intravenously for about 30 minutes in a dose for a target AUC of about 6 mg/mL·min on Day 1 of each cycle. In some aspects, bevacizumab is administered intravenously at a dose of about 7.5 mg/kg on Day 1 of a three-week cycle for about 4 to about 6 cycles, pemetrexed is administered intravenously at a dose of about 500 $mg/m^2$ for about 10 minutes on Day 1 of each cycle, and cisplatin is administered intravenously at a dose of about 75 $mg/m^2$ for about 60 minutes on Day 1 of each cycle.

II.B.2. Therapeutic Agents

In some aspects, the additional therapeutic agent comprises an anti-cancer agent. In some aspects, the anti-cancer agent comprises a tyrosine kinase inhibitor, an anti-angiogenesis agent, a checkpoint inhibitor, a checkpoint stimulator, a chemotherapeutic agent, an immunotherapeutic agent, a platinum agent, an alkylating agent, a taxane, a nucleoside analog, an antimetabolite, a topisomerase inhibitor, an anthracycline, a vinca alkaloid, or any combination thereof.

In some aspects, the tyrosine kinase inhibitor comprises sorafenib (e.g., sorafenib tosylate, also known as NEXAVAR®), lenvatinib (e.g., lenvatinib mesylate, also known as LENVIMA®), regorafenib (e.g., STIVARGA®), cabozantinib (e.g., cabozantinib S-malate, also known as CABOMETYX®), sunitinib (e.g., sunitinib malate, also known as SUTENT®), brivanib, linifanib, pemigatinib (also known as PEMAZYRE™), everolimus (also known as AFINITOR® or ZORTRESS®), gefitinib (IRESSA®, a small-molecule TKI of EGFR), imatinib (e.g., imatinib mesylate), lapatinib (e.g., lapatinib ditosylate, also known as TYKERB®), nilotinib (e.g., nilotinib hydrochloride, also known as TASIGNA®), pazopanib (e.g., pazopanib hydrochloride, also known as VOTRIENT®), temsirolimus (also known as TORISEL®), erlotinib (e.g., erlotinib hydrochloride, also known as TARCEVA®, a small-molecule TKI of EGFR), afatinib (GILOTRIF®, a small-molecule TKI of EGFR), dacomitinib (VIZIMPRO®, a small-molecule TKI of EGFR), osimeritinib (TAGRISSO®, a small-molecule TKI of EGFR), alectinib (ALECENSA®, a small-molecule TKI of ALK), ceritinib (ZYKADIA®, a small-molecule TKI of ALK and ROS-1), brigatinib (ALUNBRIG®, a small-molecule TKI of ALK), crizotinib (XALKORI®, a small-molecule TKI of ALK and ROS-1), lorlatinib (LORBRENA®, a small-molecule TKI of ALK and ROS-1), entrectinib (ROZLYTREK®, a small-molecule TKI of ROS-1 and NTRK), dabrafenib (TAFINLAR®, a small-molecule TKI of BRAF) trametinib (MEKINIST®, a small-molecule TKI of BRAF), vemurafenib (ZELBORAF®, a small-molecule TKI of BRAF), larotrectinib (ROZLYTREK®, a small-molecule TKI of NTRK), or any combination thereof.

In some aspects, the anti-angiogenesis agent comprises an inhibitor of a vascular endothelial growth factor (VEGF), VEGF receptor (VEGFR), platelet-derived growth factor (PDGF), PDGF receptor (PDGFR), angiopoietin (Ang), tyrosine kinase with Ig-like and EGF-like domains (Tie) receptor, hepatocyte growth factor (HGF), tyrosine-protein kinase Met (c-MET), C-type lectin family 14 member A (CLECi4A), multimerin 2 (MMRN2), shock protein 70-1A (HSP70-IA), a epidermal growth factor (EGF), EGFR, or any combination thereof. In some aspects, the anti-angiogenesis agent comprises bevacizumab (also known as AVASTIN®), ramucirumab (also known as CYRAMZA®), aflibercept (also known as EYLEA® or ZALTRAP®), tanibirumab, olaratumab (also known as LARTRUVO™), nesvacumab, AMG780, MEDI3617, vanucizumab, rilotumumab, ficlatuzumab, TAK-701, onartuzumab, emibetuzumab, or any combination thereof.

In some aspects, the anti-angiogenesis agent is bevacizumab. In some aspects, bevacizumab is administered at a dose of about 15 mg/kg. In some aspects, bevacizumab is administered at a dose of about 15 mg/kg on Day 1 of a three-week cycle.

In some aspects, the checkpoint stimulator comprises an agonist of B7-1, B7-2, CD28, 4-1BB (CD137), 4-1BBL, GITR, inducible T cell co-stimulator (ICOS), ICOS-L, OX40, OX40L, CD70, CD27, CD40, death receptor 3 (DR3), CD28H, or any combination thereof.

In some aspects, the chemotherapeutic agent comprises an alkylating agent, an antimetabolite, an antineoplastic antibiotic, a mitotic inhibitor, a hormone or hormone modulator, a protein tyrosine kinase inhibitor, an epidermal growth factor inhibitor, a proteasome inhibitor, other neoplastic agent, or any combination thereof.

In some aspects, the immunotherapeutic agent comprises an antibody that specifically binds to EGFR (e.g., cetuximab (ERBITUX®)), ALK, ROS-1, NTRK, BRAF, ICOS, CD137 (4-1BB), CD134 (OX40), NKG2A, CD27, CD96, GITR, Herpes Virus Entry Mediator (HVEM), PD-1, PD-L1, CTLA-4, BTLA, TIM-3, A2aR, Killer cell Lectin-like Receptor G1 (KLRG-1), Natural Killer Cell Receptor 2B4 (CD244), CD160, TIGIT, VISTA, KIR, TGFβ, IL-10, IL-8, B7-H4, Fas ligand, CSF1R, CXCR4, mesothelin, $CEACAM^{-1}$, CD52, HER2, MICA, MICB, or any combination thereof.

In some aspects, the platinum agent comprises cisplatin, carboplatin, oxaliplatin, satraplatin, picoplatin, nedaplatin, triplatin (e.g., triplatin tetranitrate), lipoplatin, phenanthriplatin, or any combination thereof.

In some aspects, the alkylating agent comprises altretamine, bendamustine, busulfan, carboplatin, carmustine, chlorambucil, cisplatin, cyclophosphamide, dacarbazine, ifosfamide, lomustine, mechlorethamine, melphalan, oxaliplatin, procarbazine, streptozocin, temozolomide, thiotepa, or any combination thereof.

In some aspects, the taxane comprises paclitaxel, albumin-bound paclitaxel (i.e., nab-paclitaxel), docetaxel, cabazitaxel, or any combination thereof.

In some aspects, the taxane comprises paclitaxel. In some aspects, paclitaxel is administered intravenously at a dose of about 200 $mg/m^2$ to about 225 $mg/m^2$ for about 180 minutes on Day 1 of a three-week cycle for about 4 to about 6 cycles. In some aspects, paclitaxel is administered intravenously at a dose of about 80 $mg/m^2$ for about 60 minutes on Days 1, 8, and 15 of a four-week cycle for about 4 to about 6 cycles.

In some aspects, the taxane comprises albumin-bound paclitaxel. In some aspects, albumin-bound paclitaxel is administered intravenously at a dose of about 260 $mg/m^2$ for about 30 minutes on Day 1 of a three-week cycle for about 4 to about 6 cycles. In some aspects, albumin-bound paclitaxel is administered intravenously at a dose of about 125 $mg/m^2$ for about 30 minutes on Days 1, 8, and 15 of a four-week cycle for about 4 to about 6 cycles.

In some aspects, the taxane comprises docetaxel. In some aspects, docetaxel is administered intravenously at a dose of about 75 $mg/m^2$ for about 60 minutes on Day 1 of a three-week cycle. In some aspects, docetaxel is administered intravenously at a dose of about 75 $mg/m^2$ for about 60 minutes on Day 1 of a three-week cycle for about 4 to about 6 cycles.

In some aspects, the nucleoside analog comprises cytarabine, gemcitabine, lamivudine, entecavir, telbivudine, or any combination thereof.

In some aspects, the nucleoside analog is gemcitabine. In some aspects, gemcitabine is administered intravenously at a dose of about 1,000 $mg/m^2$ to about 1,250 $mg/m^2$ for about 30 minutes on Days 1, 8, and 15 of a four-week cycle. In some aspects, gemcitabine is administered intravenously at a dose of about 1,000 $mg/m^2$ to about 1,250 $mg/m^2$ for about 30 minutes on Days 1, 8, and 15 of a four-week cycle for about 4 to about 6 cycles. In some aspects, gemcitabine is administered intravenously at a dose of about 1,250 $mg/m^2$ for about 30 minutes on Days 1 and 8 of a three-week cycle. In some aspects, gemcitabine is administered intravenously at a dose of about 1,250 $mg/m^2$ for about 30 minutes on Days 1 and 8 of a three-week cycle for about 4 to about 6 cycles.

In some aspects, the antimetabolite comprises capecitabine, cladribine, clofarabine, cytarabine, floxuridine, fludarabine, fluorouracil, mercaptopurine, methotrexate, pemetrexed, pentostatin, pralatrexate, thioguanine, or any combination thereof.

In some aspects, the antimetabolite is pemetrexed. In some aspects, pemetrexed is administered intravenously at a dose of about 500 $mg/m^2$ for about 10 minutes on Day 1 of a three-week cycle. In some aspects, pemetrexed is administered intravenously at a dose of about 500 $mg/m^2$ for about 10 minutes on Day 1 of a three-week cycle for about 4 to about 6 cycles.

In some embodiments, the topoisomerase inhibitor comprises etoposide, mitoxantrone, doxorubicin, irinotecan, topotecan, camptothecin, or any combination thereof.

In some aspects, the anthracycline is doxorubicin, daunorubicin, epirubicin, idarubicin, or any combination thereof.

In some aspects, the vinca alkaloid is vinblastine, vincristine, vinorelbine, vindesine, vincaminol, vineridine, vinburnine, or any combination thereof.

In some aspects, the anti-cancer agent comprises gemcitabine and docetaxel. In some aspects, gemcitabine is administered intravenously at a dose of about 1,000 $mg/m^2$ to about 1,250 $mg/m^2$ for about 30 minutes on Days 1 and 8 of a three-week cycle for about 4 to about 6 cycles and docetaxel is administered intravenously at a dose of about 85 $mg/m^2$ for about 30 minutes to about 60 minutes on Day 8 of each cycle.

In some aspects, the anti-cancer agent comprises gemcitabine and vinorelbine. In some aspects, gemcitabine is administered intravenously at a dose of about 1,000 $mg/m^2$ for about 30 minutes on Days 1 and 8 of a three-week cycle for about 4 to about 6 cycles and vinorelbine is administered intravenously at a dose of about 25 $mg/m^2$ for about 5 minutes to about 10 minutes on Days 1 and 8 of each cycle.

In some aspects, the anti-cancer agent comprises ramucirumab and docetaxel. In some aspects, ramucirumab is administered intravenously at a dose of about 10 mg/kg for about 60 minutes on Day 1 of a three-week cycle and docetaxel is administered intravenously at a dose of about 75 $mg/m^2$ for about 60 minutes on Day 1 of each cycle.

In some aspects, the anti-cancer agent comprises bevacizumab and pemetrexed. In some aspects, bevacizumab is administered intravenously at a dose of about 7.5 mg/kg to about 15 mg/kg for about 10 minutes on Day 1 of a three-week cycle and pemetrexed is administered intravenously at a dose of about 500 $mg/m^2$ for about 10 minutes on Day 1 of each cycle.

II.B.3. Checkpoint Inhibitors

In some aspects, the anti-cancer agent that is administered as an additional therapeutic agent in the methods of the disclosure is a checkpoint inhibitor.

In some aspects, the checkpoint inhibitor comprises a programmed death-1 (PD-1) pathway inhibitor, a cytotoxic T-lymphocyte-associated protein 4 (CTLA-4) inhibitor, a T cell immunoglobulin and ITIM domain (TIGIT) inhibitor, a T cell immunoglobulin and mucin-domain containing-3 (TIM-3) inhibitor, a $TIM^{-1}$ inhibitor, a TIM-4 inhibitor, a B7-H3 inhibitor, a B7-H4 inhibitor, a B and T cell lymphocyte attenuator (BTLA) inhibitor, a V-domain Ig suppressor of T cell activation (VISTA) inhibitor, an indoleamine 2,3-dioxygenase (IDO) inhibitor (e.g., an indoleamine 2,3-dioxygenase 1 (IDO1) inhibitor, epacadostat (INCB24360), navoximod (GDC-0919), or linrodostat (BMS-986205), including a linrodostat salt such as, for example, linrodostat mesylate), a nicotinamide adenine dinucleotide phosphate oxidase isoform 2 (NOX2) inhibitor, a killer-cell immunoglobulin-like receptor (KIR) inhibitor, an adenosine A2a receptor (A2aR) inhibitor, a transforming growth factor beta (TGF-0) inhibitor, a phosphoinositide 3-kinase (PI3K) inhibitor, a CD47 inhibitor, a CD48 inhibitor, a CD73 inhibitor, a CD113 inhibitor, a sialic acid-binding immunoglobulin-like lectin-7 (SIGLEC-7) inhibitor, a SIGLEC-9 inhibitor, a SIGLEC-15 inhibitor, a glucocorticoid-induced TNFR-related protein (GITR) inhibitor, a galectin-1 inhibitor, a galectin-9 inhibitor, a carcinoembryonic antigen-related cell adhesion molecule-1 ($CEACAM^{-1}$) inhibitor, a G protein-coupled receptor 56 (GPR56) inhibitor, a glycoprotein A repetitions predominant (GARP) inhibitor, a 2B4 inhibitor, a programmed death-1 homolog (PD1H) inhibitor, a leukocyte-associated immunoglobulin-like receptor 1 (LAIR1) inhibitor, or any combination thereof.

In some aspects, the checkpoint inhibitor is formulated for intravenous administration.

In some aspects, the LAG-3 antagonist and the checkpoint inhibitor are formulated separately. In some aspects, each checkpoint inhibitor is formulated separately when the checkpoint inhibitor comprises more than one checkpoint inhibitor. In some aspects, the checkpoint inhibitor is administered before the LAG-3 antagonist. In some aspects, the LAG-3 antagonist is administered before the checkpoint inhibitor.

In some aspects, the LAG-3 antagonist and the checkpoint inhibitor are formulated together. In some aspects, two or more checkpoint inhibitors are formulated together when the checkpoint inhibitor comprises more than one checkpoint inhibitor.

In some aspects, the LAG-3 antagonist and the checkpoint inhibitor are administered concurrently.

In some aspects, the checkpoint inhibitor is administered at a flat dose.

In some aspects, the checkpoint inhibitor is administered at a dose of from at least about 0.25 mg to about 2000 mg, about 0.25 mg to about 1600 mg, about 0.25 mg to about 1200 mg, about 0.25 mg to about 800 mg, about 0.25 mg to about 400 mg, about 0.25 mg to about 100 mg, about 0.25 mg to about 50 mg, about 0.25 mg to about 40 mg, about 0.25 mg to about 30 mg, about 0.25 mg to about 20 mg, about 20 mg to about 2000 mg, about 20 mg to about 1600 mg, about 20 mg to about 1200 mg, about 20 mg to about 800 mg, about 20 mg to about 400 mg, about 20 mg to about 100 mg, about 100 mg to about 2000 mg, about 100 mg to about 1800 mg, about 100 mg to about 1600 mg, about 100 mg to about 1400 mg, about 100 mg to about 1200 mg, about 100 mg to about 1000 mg, about 100 mg to about 800 mg, about 100 mg to about 600 mg, about 100 mg to about 400 mg, about 400 mg to about 2000 mg, about 400 mg to about 1800 mg, about 400 mg to about 1600 mg, about 400 mg to about 1400 mg, about 400 mg to about 1200 mg, or about 400 mg to about 1000 mg.

In some aspects, the checkpoint inhibitor is administered at a dose of about 0.25 mg, about 0.5 mg, about 0.75 mg, about 1 mg, about 1.25 mg, about 1.5 mg, about 1.75 mg, about 2 mg, about 2.25 mg, about 2.5 mg, about 2.75 mg, about 3 mg, about 3.25 mg, about 3.5 mg, about 3.75 mg, about 4 mg, about 4.25 mg, about 4.5 mg, about 4.75 mg, about 5 mg, about 5.25 mg, about 5.5 mg, about 5.75 mg, about 6 mg, about 6.25 mg, about 6.5 mg, about 6.75 mg, about 7 mg, about 7.25 mg, about 7.5 mg, about 7.75 mg, about 8 mg, about 8.25 mg, about 8.5 mg, about 8.75 mg, about 9 mg, about 9.25 mg, about 9.5 mg, about 9.75 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, about 600 mg, about 610 mg, about 620 mg, about 630 mg, about 640 mg, about 650 mg, about 660 mg, about 670 mg, about 680 mg, about 690 mg, about 700 mg, about 710 mg, about 720 mg, about 730 mg, about 740 mg, about 750 mg, about 760 mg, about 770 mg, about 780 mg, about 790 mg, about 800 mg, about 810 mg, about 820 mg, about 830 mg, about 840 mg, about 850 mg, about 860 mg, about 870 mg, about 880 mg, about 890 mg, about 900 mg, about 910 mg, about 920 mg, about 930 mg, about 940 mg, about 950 mg, about 960 mg, about 970 mg, about 980 mg, about 990 mg, about 1000 mg, about 1040 mg, about 1080 mg, about 1100 mg, about 1140 mg, about 1180 mg, about 1200 mg, about 1240 mg, about 1280 mg, about 1300 mg, about 1340 mg, about 1380 mg, about 1400 mg, about 1440 mg, about 1480 mg, about 1500 mg, about 1540 mg, about 1580 mg, about 1600 mg, about 1640 mg, about 1680 mg, about 1700 mg, about 1740 mg, about 1780 mg, about 1800 mg, about 1840 mg, about 1880 mg, about 1900 mg, about 1940 mg, about 1980 mg, or about 2000 mg.

In some aspects, the checkpoint inhibitor is administered as a weight-based dose.

In some aspects, the checkpoint inhibitor is administered at a dose from about 0.003 mg/kg to about 25 mg/kg, about 0.003 mg/kg to about 20 mg/kg, about 0.003 mg/kg to about 15 mg/kg, about 0.003 mg/kg to about 10 mg/kg, about 0.003 mg/kg to about 5 mg/kg, about 0.003 mg/kg to about 1 mg/kg, about 0.003 mg/kg to about 0.9 mg/kg, about 0.003 mg/kg to about 0.8 mg/kg, about 0.003 mg/kg to about 0.7 mg/kg, about 0.003 mg/kg to about 0.6 mg/kg, about 0.003 mg/kg to about 0.5 mg/kg, about 0.003 mg/kg to about 0.4 mg/kg, about 0.003 mg/kg to about 0.3 mg/kg, about 0.003 mg/kg to about 0.2 mg/kg, about 0.003 mg/kg to about 0.1 mg/kg, about 0.1 mg/kg to about 25 mg/kg, about 0.1 mg/kg to about 20 mg/kg, about 0.1 mg/kg to about 15 mg/kg, about 0.1 mg/kg to about 10 mg/kg, about 0.1 mg/kg to about 5 mg/kg, about 0.1 mg/kg to about 1 mg/kg, about 1 mg/kg to about 25 mg/kg, about 1 mg/kg to about 20 mg/kg, about 1 mg/kg to about 15 mg/kg, about 1 mg/kg to about 10 mg/kg, about 1 mg/kg to about 5 mg/kg, about 5 mg/kg to about 25 mg/kg, about 5 mg/kg to about 20 mg/kg, about 5 mg/kg to about 15 mg/kg, about 5 mg/kg to about 10 mg/kg, about 10 mg/kg to about 25 mg/kg, about 10 mg/kg to about 20 mg/kg, about 10 mg/kg to about 15 mg/kg, about 15 mg/kg to about 25 mg/kg, about 15 mg/kg to about 20 mg/kg, or about 20 mg/kg to about 25 mg/kg.

In some aspects, the checkpoint inhibitor is administered at a dose of about 0.003 mg/kg, about 0.004 mg/kg, about 0.005 mg/kg, about 0.006 mg/kg, about 0.007 mg/kg, about 0.008 mg/kg, about 0.009 mg/kg, about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1.0 mg/kg, about 2.0 mg/kg, about 3.0 mg/kg, about 4.0 mg/kg, about 5.0 mg/kg, about 6.0 mg/kg, about 7.0 mg/kg, about 8.0 mg/kg, about 9.0 mg/kg, about 10.0 mg/kg, about 11.0 mg/kg, about 12.0 mg/kg, about 13.0 mg/kg, about 14.0 mg/kg, about 15.0 mg/kg, about 16.0 mg/kg, about 17.0 mg/kg, about 18.0 mg/kg, about 19.0 mg/kg, about 20.0 mg/kg, about 21.0 mg/kg, about 22.0 mg/kg, about 23.0 mg/kg, about 24.0 mg/kg, or about 25.0 mg/kg.

In some aspects, the dose of the checkpoint inhibitor is administered every one week, every two weeks, every three weeks, every four weeks, every five weeks, every six weeks, every seven weeks, every eight weeks, every nine weeks, every ten weeks, every eleven weeks, or every twelve weeks.

In some aspects, each dose of the LAG-3 antagonist and/or the checkpoint inhibitor is administered in a constant amount.

In some aspects, each dose of the LAG-3 antagonist and/or the checkpoint inhibitor is administered in a varying amount. For example, in some aspects, the maintenance (or follow-on) dose of the LAG-3 antagonist and/or the checkpoint inhibitor can be higher or the same as the loading dose which is first administered. In some aspects, the maintenance dose of the LAG-3 antagonist and/or the checkpoint inhibitor can be lower or the same as the loading dose.

II.B.3.a. PD-1 Pathway Inhibitors

In some aspects, the checkpoint inhibitor for use in the methods of the disclosure comprises a PD-1 pathway inhibitor.

In some aspects the PD-1 pathway inhibitor is a PD-1 inhibitor and/or a PD-L1 inhibitor.

In some aspects, the PD-1 inhibitor and/or PD-L1 inhibitor is a small molecule.

In some aspects, the PD-1 inhibitor and/or PD-L1 inhibitor is a millamolecule.

In some aspects, the PD-1 inhibitor and/or PD-L1 inhibitor is a macrocyclic peptide.

In certain aspects, the PD-1 inhibitor and/or PD-L1 inhibitor is BMS-986189.

In some aspects, the PD-1 inhibitor is an inhibitor disclosed in International Publication No. WO2014/151634, which is incorporated by reference herein in its entirety.

In some aspects, the PD-1 inhibitor is INCMGA00012 (Insight Pharmaceuticals).

In some aspects, the PD-1 inhibitor comprises a combination of an anti-PD-1 antibody disclosed herein and a PD-1 small molecule inhibitor.

In some aspects, the PD-L1 inhibitor comprises a millamolecule having a formula set forth in formula (I):

(I)

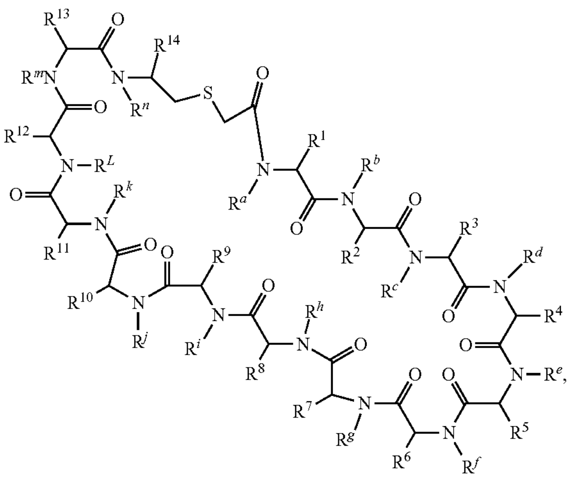

wherein $R^1$-$R^{13}$ are amino acid side chains, $R^a$—$R^n$ are hydrogen, methyl, or form a ring with a vicinal R group, and $R^{14}$ is —C(O)NHR$^{15}$, wherein $R^{15}$ is hydrogen, or a glycine residue optionally substituted with additional glycine residues and/or tails which can improve pharmacokinetic properties. In some aspects, the PD-L1 inhibitor comprises a compound disclosed in International Publication No. WO2014/151634, which is incorporated by reference herein in its entirety. In some aspects, the PD-L1 inhibitor comprises a compound disclosed in International Publication No. WO2016/039749, WO2016/149351, WO2016/077518, WO2016/100285, WO2016/100608, WO2016/126646, WO2016/057624, WO2017/151830, WO2017/176608, WO2018/085750, WO2018/237153, or WO2019/070643, each of which is incorporated by reference herein in its entirety.

In some aspects, the PD-L1 inhibitor comprises a small molecule PD-L1 inhibitor disclosed in International Publication No. WO2015/034820, WO2015/160641, WO2018/044963, WO2017/066227, WO2018/009505, WO2018/183171, WO2018/118848, WO2019/147662, or WO2019/169123, each of which is incorporated by reference herein in its entirety.

In some aspects, the PD-1 pathway inhibitor is a soluble PD-L2 polypeptide. In some aspects, the soluble PD-L2 polypeptide is a fusion polypeptide. In some aspects, the soluble PD-L2 polypeptide comprises a ligand binding fragment of the PD-L2 extracellular domain. In some aspects, the soluble PD-L2 polypeptide further comprises a half-life extending moiety. In some aspects, the half-life extending moiety comprises an immunoglobulin constant region or a portion thereof, an immunoglobulin-binding polypeptide, an immunoglobulin G (IgG), albumin-binding polypeptide (ABP), a PASylation moiety, a HESylation moiety, XTEN, a PEGylation moiety, an Fc region, or any combination thereof. In some aspects, the soluble PD-L2 polypeptide is AMP-224 (see, e.g., US 2013/0017199).

In some aspects, the PD-1 pathway inhibitor is an anti-PD-1 antibody and/or an anti-PD-L1 antibody.

II.B.3.a.i. Anti-PD-1 Antibodies

Anti-PD-1 antibodies that are known in the art can be used in the methods of the disclosure. Various human monoclonal antibodies that bind specifically to PD-1 with high affinity have been disclosed in U.S. Pat. No. 8,008,449. Anti-PD-1 human antibodies disclosed in U.S. Pat. No. 8,008,449 have been demonstrated to exhibit one or more of the following characteristics: (a) bind to human PD-1 with a $K_D$ of $1\times10^{-7}$ M or less, as determined by surface plasmon resonance using a BIACORE biosensor system; (b) do not substantially bind to human CD28, CTLA-4 or ICOS; (c) increase T-cell proliferation in a Mixed Lymphocyte Reaction (MLR) assay; (d) increase interferon-γ production in an MLR assay; (e) increase IL-2 secretion in an MLR assay; (f) bind to human PD-1 and cynomolgus monkey PD-1; (g) inhibit the binding of PD-L1 and/or PD-L2 to PD-1; (h) stimulate antigen-specific memory responses; (i) stimulate antibody responses; and (j) inhibit tumor cell growth in vivo. Anti-PD-1 antibodies usable in the present disclosure include monoclonal antibodies that bind specifically to human PD-1 and exhibit at least one, in some aspects, at least five, of the preceding characteristics.

Other anti-PD-1 monoclonal antibodies that can be used in the methods of the disclosure have been described in, for example, U.S. Pat. Nos. 6,808,710, 7,488,802, 8,168,757 and 8,354,509, US Publication No. 2016/0272708, and PCT Publication Nos. WO 2012/145493, WO 2008/156712, WO 2015/112900, WO 2012/145493, WO 2015/112800, WO 2014/206107, WO 2015/35606, WO 2015/085847, WO 2014/179664, WO 2017/020291, WO 2017/020858, WO 2016/197367, WO 2017/024515, WO 2017/025051, WO 2017/123557, WO 2016/106159, WO 2014/194302, WO 2017/040790, WO 2017/133540, WO 2017/132827, WO 2017/024465, WO 2017/025016, WO 2017/106061, WO 2017/19846, WO 2017/024465, WO 2017/025016, WO 2017/132825, and WO 2017/133540 each of which is incorporated by reference in its entirety.

Anti-PD-1 antibodies that can be used in the methods of the disclosure include nivolumab (also known as OPDIVO®, 5C4, BMS-936558, MDX-1106, and ONO-4538), pembrolizumab (Merck; also known as KEYTRUDA®, lambrolizumab, and MK3475; see WO 2008/156712), PDR001 (Novartis; also known as spartalizumab; see WO 2015/112900 and U.S. Pat. No. 9,683,048), MEDI-0680 (AstraZeneca; also known as AMP-514; see WO 2012/145493), TSR-042 (Tesaro Biopharmaceutical; also known as ANB011 or dostarlimab; see WO 2014/179664), cemiplimab (Regeneron; also known as LIBTAYO® or REGN2810; see WO 2015/112800 and U.S. Pat. No. 9,987,500), JS001 (TAIZHOU JUNSHI PHARMA; also known as toripalimab; see Si-Yang Liu et al., *J. Hematol. Oncol.* 10:136 (2017)), PF-06801591 (Pfizer; also known as sasanlimab; US 2016/0159905), BGB-A317 (Beigene; also known as tislelizumab; see WO 2015/35606 and US 2015/0079109), BI 754091 (Boehringer Ingelheim; see Zettl M et al., *Cancer. Res.* (2018); 78(13 Suppl):Abstract 4558), INCSHR1210 (Jiangsu Hengrui Medicine; also known as SHR-1210 or camrelizumab; see WO 2015/085847; Si-Yang Liu et al., J. *Hematol. Oncol.* 10:136 (2017)), GLS-010 (Wuxi/Harbin Gloria Pharmaceuticals; also known as WBP3055; see Si-Yang Liu et al., *J. Hematol. Oncol.* 10:136 (2017)), AM-0001 (Armo), STI-1110 (Sorrento Therapeutics; see WO 2014/194302), AGEN2034 (Agenus; see WO 2017/040790), MGA012 (Macrogenics, see WO 2017/19846), BCD-100 (Biocad; Kaplon et al., mAbs 10(2):183-203 (2018), IBI308 (Innovent; also known as sintilimab; see WO 2017/024465, WO 2017/025016, WO 2017/132825, and WO 2017/133540), and SSI-361 (Lyvgen Biopharma Holdings Limited, US 2018/0346569).

Anti-PD-1 antibodies that can be used in the methods of the disclosure also include isolated antibodies that bind specifically to human PD-1 and cross-compete for binding to human PD-1 with any anti-PD-1 antibody disclosed herein, e.g., nivolumab (see, e.g., U.S. Pat. Nos. 8,008,449 and 8,779,105; WO 2013/173223). In some aspects, the anti-PD-1 antibody binds the same epitope as any of the anti-PD-1 antibodies described herein, e.g., nivolumab.

In some aspects, the antibodies that cross-compete for binding to human PD-1 with, or bind to the same epitope region as, any anti-PD-1 antibody disclosed herein, e.g., nivolumab, are monoclonal antibodies. For administration to human subjects, these cross-competing antibodies are chimeric antibodies, engineered antibodies, or humanized or human antibodies. Such chimeric, engineered, humanized or human monoclonal antibodies can be prepared and isolated by methods well known in the art.

Anti-PD-1 antibodies that can be used in the methods of the disclosure also include antigen-binding portions of any of the above full-length antibodies.

Anti-PD-1 antibodies that can be used in the methods of the disclosure are antibodies that bind to PD-1 with high specificity and affinity, block the binding of PD-L1 and or PD-L2, and inhibit the immunosuppressive effect of the PD-1 signaling pathway. In any of the compositions or methods disclosed herein, an anti-PD-1 "antibody" includes an antigen-binding portion or fragment that binds to the PD-1 receptor and exhibits the functional properties similar to those of whole antibodies in inhibiting ligand binding and up-regulating the immune system. In certain aspects, the anti-PD-1 antibody or antigen-binding portion thereof cross-competes with nivolumab for binding to human PD-1.

In some aspects, the anti-PD-1 antibody is a full-length antibody. In some aspects, the anti-PD-1 antibody is a monoclonal, human, humanized, chimeric, or multispecific antibody. In some aspects, the multispecific antibody is a DART, a DVD-Ig, or bispecific antibody.

In some aspects, the anti-PD-1 antibody is a $F(ab')_2$ fragment, a Fab' fragment, a Fab fragment, a Fv fragment, a scFv fragment, a dsFv fragment, a dAb fragment, or a single chain binding polypeptide.

In some aspects, the anti-PD-1 antibody is nivolumab, pembrolizumab, PDRO01 (spartalizumab), MEDI-0680, TSR-042, cemiplimab, JS001, PF-06801591, BGB-A317, BI 754091, INCSHR1210, GLS-010, AM-001, STI-1110, AGEN2034, MGA012, BCD-100, IBI308, SSI-361, or comprises an antigen binding portion thereof.

In some aspects, the anti-PD-1 antibody is formulated for intravenous administration.

In some aspects, the anti-PD-1 antibody is administered intravenously for about 30 minutes.

In some aspects, the anti-PD-1 antibody is nivolumab. Nivolumab is a fully human IgG4 (S228P) PD-1 immune checkpoint inhibitor antibody that selectively prevents interaction with PD-1 ligands (PD-L1 and PD-L2), thereby blocking the down-regulation of antitumor T-cell functions (U.S. Pat. No. 8,008,449; Wang et al., 2014 Cancer Immunol Res. 2(9):846-56).

In some aspects, nivolumab is administered at a flat dose of about 240 mg once about every 2 weeks. In some aspects, nivolumab is administered at a flat dose of about 240 mg once about every 3 weeks. In some aspects, nivolumab is administered at a flat dose of about 360 mg once about every 3 weeks. In some aspects, nivolumab is administered at a flat dose of about 480 mg once about every 4 weeks.

In some aspects, nivolumab is administered intravenously at a dose of about 240 mg for about 30 minutes on Day 1 of a two-week cycle.

In some aspects, nivolumab is administered intravenously at a dose of about 480 mg for about 30 minutes on Day 1 of a four-week cycle.

In some aspects, the methods of the disclosure comprise an anti-PD-1 antibody comprising CDR1, CDR2 and CDR3 domains of the heavy chain variable region having the sequence set forth in SEQ ID NO:13, and CDR1, CDR2 and CDR3 domains of the light chain variable region having the sequence set forth in SEQ ID NO:14.

In some aspects, the methods of the disclosure comprise an anti-PD-1 antibody comprising: (a) a heavy chain variable region CDR1 comprising the sequence set forth in SEQ ID NO:15; (b) a heavy chain variable region CDR2 comprising the sequence set forth in SEQ ID NO: 16; (c) a heavy chain variable region CDR3 comprising the sequence set forth in SEQ ID NO: 17; (d) a light chain variable region CDR1 comprising the sequence set forth in SEQ ID NO:18; (e) a light chain variable region CDR2 comprising the sequence set forth in SEQ ID NO:19; and (f) a light chain variable region CDR3 comprising the sequence set forth in SEQ ID NO:20.

In some aspects, the methods of the disclosure comprise an anti-PD-1 antibody comprising heavy and light chain variable regions comprising the sequences set forth in SEQ ID NOs:13 and 14, respectively.

In some aspects, the methods of the disclosure comprise an anti-PD-1 antibody comprising heavy and light chains comprising the sequences as set forth in SEQ ID NOs:11 and 12, respectively.

In some aspects, the methods of the disclosure comprise a combination of relatlimab and nivolumab.

In some aspects, the methods of the disclosure comprise: (a) an anti-LAG-3 antibody comprising CDR1, CDR2 and CDR3 domains of the heavy chain variable region having the sequence set forth in SEQ ID NO:3, and CDR1, CDR2 and CDR3 domains of the light chain variable region having the sequence set forth in SEQ ID NO:4; and (b) an anti-PD-1 antibody comprising CDR1, CDR2 and CDR3 domains of the heavy chain variable region having the sequence set forth in SEQ ID NO:13, and CDR1, CDR2 and CDR3 domains of the light chain variable region having the sequence set forth in SEQ ID NO:14.

In some aspects, the methods of the disclosure comprise: (a) an anti-LAG-3 antibody comprising a heavy chain variable region CDR1, CDR2, and CDR3 comprising the sequence set forth in SEQ ID NO:5, SEQ ID NO:6, and SEQ ID NO:7, respectively, and a light chain variable region CDR1, CDR2, and CDR3 comprising the sequence set forth in SEQ ID NO:8, SEQ ID NO:9, and SEQ ID NO:10, respectively, and (b) an anti-PD-1 antibody comprising a heavy chain variable region CDR1, CDR2, and CDR3 comprising the sequence set forth in SEQ ID NO:15, SEQ ID NO:16, and SEQ ID NO:17, respectively, and a light chain variable region CDR1, CDR2, and CDR3 comprising the sequence set forth in SEQ ID NO:18, SEQ ID NO:19, and SEQ ID NO:20, respectively.

In some aspects, the methods of the disclosure comprise: (a) an anti-LAG-3 antibody comprising heavy and light chain variable regions comprising the sequences set forth in SEQ ID NOs:3 and 4, respectively, and (b) an anti-PD-1 antibody comprising heavy and light chain variable regions comprising the sequences set forth in SEQ ID NOs:13 and 14, respectively.

In some aspects, the methods of the disclosure comprise: (a) an anti-LAG-3 antibody comprising heavy and light chains comprising the sequences set forth in SEQ ID NOs:1 and 2, respectively, and (b) an anti-PD-1 antibody comprises heavy and light chains comprising the sequences as set forth in SEQ ID NOs:11 and 12, respectively.

In some aspects, the methods of the disclosure comprise: (a) an anti-LAG-3 antibody comprising heavy and light chains comprising the sequences set forth in SEQ ID NOs: 21 and 2, respectively, and (b) an anti-PD-1 antibody comprises heavy and light chains comprising the sequences as set forth in SEQ ID NOs:11 and 12, respectively.

In some aspects, the anti-PD-1 antibody is pembrolizumab. Pembrolizumab is a humanized monoclonal IgG4 (S228P) antibody directed against human cell surface receptor PD-1. Pembrolizumab is described, for example, in U.S. Pat. Nos. 8,354,509 and 8,900,587.

In some aspects, pembrolizumab is administered at a flat dose of about 200 mg once about every 2 weeks. In some aspects, pembrolizumab is administered at a flat dose of about 200 mg once about every 3 weeks. In some aspects, pembrolizumab is administered at a flat dose of about 400 mg once about every 6 weeks. In some aspects, pembrolizumab is administered at a flat dose of about 300 mg once about every 4-5 weeks.

In some aspects, pembrolizumab is administered intravenously at a dose of about 200 mg on Day 1, then once about every 3 weeks. In some aspects, pembrolizumab is administered for up to 35 cycles. In some aspects, pembrolizumab is administered intravenously at a dose of about 200 mg for about 30 minutes on Day 1 of a three-week cycle for up to 35 cycles.

In some aspects, pembrolizumab is administered intravenously at a dose of about 200 mg for about 30 minutes on Day 1 of a three-week cycle for up to 35 cycles and pemetrexed is administered intravenously at a dose of about 500 $mg/m^2$ for about 10 minutes on Day 1 of each cycle, followed by maintenance therapy with pemetrexed at a dose of about 500 $mg/m^2$ administered intravenously on Day 1 of a three-week cycle. In some embodiments, the maintenance therapy continues until disease progression or unacceptable toxicity.

In some aspects, pembrolizumab is administered intravenously at a dose of about 200 mg for about 30 minutes on Day 1 of a three week cycle for about 4 to about 6 cycles, pemetrexed is administered intravenously at a dose of about 500 $mg/m^2$ for about 10 minutes on Day 1 of each cycle, and carboplatin is administered intravenously for about 30 minutes in a dose for a target AUC of about 5 mg/mL·min on Day 1 of each cycle.

In some aspects, pembrolizumab is administered intravenously at a dose of about 200 mg for about 30 minutes on Day 1 of a three week cycle for about 4 to about 6 cycles, pemetrexed is administered intravenously at a dose of about 500 $mg/m^2$ for about 10 minutes on Day 1 of each cycle, and cisplatin is administered intravenously at a dose of about 75 $mg/m^2$ for about 60 minutes on Day 1 of each cycle.

In some aspects, pembrolizumab is administered intravenously at a dose of about 200 mg for about 30 minutes on Day 1 of a three week cycle for about 4 cycles, albumin-bound paclitaxel is administered intravenously at a dose of about 100 $mg/m^2$ for about 30 minutes on Days 1, 8, and 15 of each cycle, and carboplatin is administered intravenously for about 30 minutes in a dose for a target AUC of about 6 mg/mL·min on Day 1 of each cycle.

In some aspects, pembrolizumab is administered intravenously at a dose of about 200 mg for about 30 minutes on Day 1 of a three week cycle for about 4 cycles, paclitaxel is administered intravenously at a dose of about 200 $mg/m^2$ for about 180 minutes on Day 1 of each cycle, and carboplatin is administered intravenously for about 30 minutes in a dose for a target AUC of about 6 mg/mL·min on Day 1 of each cycle.

In some aspects, pembrolizumab is administered intravenously at a dose of about 200 mg for about 30 minutes on Day 1 of a three week cycle for about 4 cycles, albumin-bound paclitaxel is administered intravenously at a dose of about 100 $mg/m^2$ for about 30 minutes on Days 1, 8, and 15 of each cycle, and cisplatin is administered intravenously at a dose of about 75 $mg/m^2$ to about 80 $mg/m^2$ for about 60 minutes on Day 1 of each cycle.

In some aspects, pembrolizumab is administered intravenously at a dose of about 200 mg for about 30 minutes on Day 1 of a three week cycle for about 4 cycles, paclitaxel is administered intravenously at a dose of about 200 $mg/m^2$ for about 180 minutes on Day 1 of each cycle, and cisplatin is administered intravenously at a dose of about 75 $mg/m^2$ to about 80 $mg/m^2$ for about 60 minutes on Day 1 of each cycle.

In some aspects, the methods of the disclosure comprise an anti-PD-1 antibody comprising CDR1, CDR2 and CDR3 domains of the heavy chain variable region having the sequence set forth in SEQ ID NO:79, and CDR1, CDR2 and CDR3 domains of the light chain variable region having the sequence set forth in SEQ ID NO:80.

In some aspects, the methods of the disclosure comprise an anti-PD-1 antibody comprising: (a) a heavy chain variable region CDR1 comprising the sequence set forth in SEQ ID NO:81; (b) a heavy chain variable region CDR2 comprising the sequence set forth in SEQ ID NO:82; (c) a heavy chain variable region CDR3 comprising the sequence set forth in SEQ ID NO:83; (d) a light chain variable region CDR1 comprising the sequence set forth in SEQ IDNO: 84; (e) a light chain variable region CDR2 comprising the sequence set forth in SEQ ID NO:85; and (f) a light chain variable region CDR3 comprising the sequence set forth in SEQ ID NO:86.

In some aspects, the methods of the disclosure comprise an anti-PD-1 antibody comprising heavy and light chain variable regions comprising the sequences set forth in SEQ ID NOs:79 and 80, respectively.

In some aspects, the methods of the disclosure comprise an anti-PD-1 antibody comprising heavy and light chains comprising the sequences as set forth in SEQ ID NOs:77 and 78, respectively.

In some aspects, the methods of the disclosure comprise a combination of favezelimab and pembrolizumab. In some aspects, 800 mg of favezelimab and 200 mg of pembrolizumab are administered intravenously on Day 1, then once about every 3 weeks. In some aspects, the combination of favezelimab and pembrolizumab is administered for up to 35 cycles. In some aspects, 800 mg of favezelimab and 200 mg of pembrolizumab are administered intravenously for about 30 minutes on Day 1 of a three-week cycle for up to 35 cycles.

In some aspects, the methods of the disclosure comprise: (a) an anti-LAG-3 antibody comprising CDR1, CDR2 and CDR3 domains of the heavy chain variable region having the sequence set forth in SEQ ID NO:69, and CDR1, CDR2 and CDR3 domains of the light chain variable region having the sequence set forth in SEQ ID NO:70; and (b) an anti-PD-1 antibody comprising CDR1, CDR2 and CDR3 domains of the heavy chain variable region having the sequence set forth in SEQ ID NO:79, and CDR1, CDR2 and CDR3 domains of the light chain variable region having the sequence set forth in SEQ ID NO:80.

In some aspects, the methods of the disclosure comprise: (a) an anti-LAG-3 antibody comprising a heavy chain variable region CDR1, CDR2, and CDR3 comprising the sequence set forth in SEQ ID NO:71, SEQ ID NO:72, and SEQ ID NO:73, respectively, and a light chain variable region CDR1, CDR2, and CDR3 comprising the sequence set forth in SEQ ID NO:74, SEQ ID NO:75, and SEQ ID NO:76, respectively, and (b) an anti-PD-1 antibody comprising a heavy chain variable region CDR1, CDR2, and CDR3 comprising the sequence set forth in SEQ ID NO:81, SEQ ID NO:82, and SEQ ID NO:83, respectively, and a light chain variable region CDR1, CDR2, and CDR3 comprising the sequence set forth in SEQ ID NO:84, SEQ ID NO:85, and SEQ ID NO:86, respectively.

In some aspects, the methods of the disclosure comprise: (a) an anti-LAG-3 antibody comprising heavy and light chain variable regions comprising the sequences set forth in SEQ ID NOs:69 and 70, respectively, and (b) an anti-PD-1 antibody comprising heavy and light chain variable regions comprising the sequences set forth in SEQ ID NOs:79 and 80, respectively.

In some aspects, the methods of the disclosure comprise: (a) an anti-LAG-3 antibody comprising heavy and light chains comprising the sequences set forth in SEQ ID NOs: 67 and 68, respectively, and (b) an anti-PD-1 antibody comprises heavy and light chains comprising the sequences as set forth in SEQ ID NOs:77 and 78, respectively.

In some aspects, the anti-PD-1 antibody is cemiplimab (REGN2810). Cemiplimab is described, for example, in WO 2015/112800 and U.S. Pat. No. 9,987,500.

In some aspects, cemiplimab is administered intravenously at a dose of about 3 mg/kg or about 350 mg once about every 3 weeks.

In some aspects, the methods of the disclosure comprise an anti-PD-1 antibody comprising CDR1, CDR2 and CDR3 domains of the heavy chain variable region having the sequence set forth in SEQ ID NO:35, and CDR1, CDR2 and CDR3 domains of the light chain variable region having the sequence set forth in SEQ ID NO:36.

In some aspects, the methods of the disclosure comprise an anti-PD-1 antibody comprising: (a) a heavy chain variable region CDR1 comprising the sequence set forth in SEQ ID NO:37; (b) a heavy chain variable region CDR2 comprising the sequence set forth in SEQ ID NO:38; (c) a heavy chain variable region CDR3 comprising the sequence set forth in SEQ ID NO:39; (d) a light chain variable region CDR1 comprising the sequence set forth in SEQ ID NO:40; (e) a light chain variable region CDR2 comprising the sequence AAS; and (f) a light chain variable region CDR3 comprising the sequence set forth in SEQ ID NO:42.

In some aspects, the methods of the disclosure comprise an anti-PD-1 antibody comprising heavy and light chain variable regions comprising the sequences set forth in SEQ ID NOs:35 and 36, respectively.

In some aspects, the methods of the disclosure comprise an anti-PD-1 antibody comprising heavy and light chains comprising the sequences as set forth in SEQ ID NOs:33 and 34, respectively.

In some aspects, the methods of the disclosure comprise a combination of fianlimab and cemiplimab.

In some aspects, the methods of the disclosure comprise: (a) an anti-LAG-3 antibody comprising CDR1, CDR2 and CDR3 domains of the heavy chain variable region having the sequence set forth in SEQ ID NO:25, and CDR1, CDR2 and CDR3 domains of the light chain variable region having the sequence set forth in SEQ ID NO:26; and (b) an anti-PD-1 antibody comprising CDR1, CDR2 and CDR3 domains of the heavy chain variable region having the sequence set forth in SEQ ID NO:35, and CDR1, CDR2 and CDR3 domains of the light chain variable region having the sequence set forth in SEQ ID NO:36.

In some aspects, the methods of the disclosure comprise: (a) an anti-LAG-3 antibody comprising a heavy chain variable region CDR1, CDR2, and CDR3 comprising the sequence set forth in SEQ ID NO:27, SEQ ID NO:28, and SEQ ID NO:29, respectively, and a light chain variable region CDR1, CDR2, and CDR3 comprising the sequence set forth in SEQ ID NO:30, the sequence DAS, and the sequence set forth in SEQ ID NO:32, respectively, and (b) an anti-PD-1 antibody comprising a heavy chain variable region CDR1, CDR2, and CDR3 comprising the sequence set forth in SEQ ID NO:37, SEQ ID NO:38, and SEQ ID NO:39, respectively, and a light chain variable region CDR1, CDR2, and CDR3 comprising the sequence set forth in SEQ ID NO:40, the sequence AAS, and the sequence set forth in SEQ ID NO:42, respectively.

In some aspects, the methods of the disclosure comprise: (a) an anti-LAG-3 antibody comprising heavy and light chain variable regions comprising the sequences set forth in SEQ ID NOs:25 and 26, respectively, and (b) an anti-PD-1 antibody comprising heavy and light chain variable regions comprising the sequences set forth in SEQ ID NOs:35 and 36, respectively.

In some aspects, the methods of the disclosure comprise: (a) an anti-LAG-3 antibody comprising heavy and light chains comprising the sequences set forth in SEQ ID NOs: 23 and 24, respectively, and (b) an anti-PD-1 antibody comprises heavy and light chains comprising the sequences as set forth in SEQ ID NOs:33 and 34, respectively.

In some aspects, the anti-PD-1 antibody is spartalizumab (PDRO01). Spartalizumab is described, for example, in WO 2015/112900 and U.S. Pat. No. 9,683,048.

In some aspects, spartalizumab is administered intravenously at a dose of about 300 mg once about every 3 weeks or 400 mg once about every 4 weeks.

In some aspects, the methods of the disclosure comprise an anti-PD-1 antibody comprising CDR1, CDR2 and CDR3 domains of the heavy chain variable region having the sequence set forth in SEQ ID NO:59, and CDR1, CDR2 and CDR3 domains of the light chain variable region having the sequence set forth in SEQ ID NO:60.

In some aspects, the methods of the disclosure comprise an anti-PD-1 antibody comprising: (a) a heavy chain variable region CDR1 comprising the sequence set forth in SEQ ID NO:61; (b) a heavy chain variable region CDR2 comprising the sequence set forth in SEQ ID NO:62; (c) a heavy chain variable region CDR3 comprising the sequence set forth in SEQ ID NO:63; (d) a light chain variable region CDR1 comprising the sequence set forth in SEQ ID NO:64; (e) a light chain variable region CDR2 comprising the sequence set forth in SEQ ID NO:65; and (f) a light chain variable region CDR3 comprising the sequence set forth in SEQ ID NO:66.

In some aspects, the methods of the disclosure comprise an anti-PD-1 antibody comprising heavy and light chain variable regions comprising the sequences set forth in SEQ ID NOs:59 and 60, respectively.

In some aspects, the methods of the disclosure comprise an anti-PD-1 antibody comprising heavy and light chains comprising the sequences as set forth in SEQ ID NOs:57 and 58, respectively.

In some aspects, the methods of the disclosure comprise a combination of ieramilimab and spartalizumab. In some aspects, ieramilimab is administered intravenously at a dose of about 400 mg once about every three weeks and spartalizumab is administered intravenously at a dose of about 300 mg once about every 3 weeks. In some aspects, ieramilimab is administered intravenously at a dose of about 600 mg once about every four weeks and spartalizumab is administered intravenously at a dose of about 400 mg once about every 4 weeks.

In some aspects, the methods of the disclosure comprise: (a) an anti-LAG-3 antibody comprising CDR1, CDR2 and CDR3 domains of the heavy chain variable region having the sequence set forth in SEQ ID NO:47, and CDR1, CDR2 and CDR3 domains of the light chain variable region having the sequence set forth in SEQ ID NO:49; and (b) an anti-PD-1 antibody comprising CDR1, CDR2 and CDR3 domains of the heavy chain variable region having the sequence set forth in SEQ ID NO:59, and CDR1, CDR2 and CDR3 domains of the light chain variable region having the sequence set forth in SEQ ID NO:60.

In some aspects, the methods of the disclosure comprise: (a) an anti-LAG-3 antibody comprising CDR1, CDR2 and CDR3 domains of the heavy chain variable region having the sequence set forth in SEQ ID NO:48, and CDR1, CDR2 and CDR3 domains of the light chain variable region having the sequence set forth in SEQ ID NO:50; and (b) an anti-PD-1 antibody comprising CDR1, CDR2 and CDR3 domains of the heavy chain variable region having the sequence set forth in SEQ ID NO:59, and CDR1, CDR2 and CDR3 domains of the light chain variable region having the sequence set forth in SEQ ID NO:60.

In some aspects, the methods of the disclosure comprise: (a) an anti-LAG-3 antibody comprising a heavy chain variable region CDR1, CDR2, and CDR3 comprising the sequence set forth in SEQ ID NO:51, SEQ ID NO:52, and SEQ ID NO:53, respectively, and a light chain variable region CDR1, CDR2, and CDR3 comprising the sequence set forth in SEQ ID NO:54, SEQ ID NO:55, and SEQ ID NO:56, respectively, and (b) an anti-PD-1 antibody comprising a heavy chain variable region CDR1, CDR2, and CDR3 comprising the sequence set forth in SEQ ID NO:61, SEQ ID NO:62, and SEQ ID NO:63, respectively, and a light chain variable region CDR1, CDR2, and CDR3 comprising the sequence set forth in SEQ ID NO:64, SEQ ID NO:65, and SEQ ID NO:66, respectively.

In some aspects, the methods of the disclosure comprise: (a) an anti-LAG-3 antibody comprising heavy and light chain variable regions comprising the sequences set forth in SEQ ID NOs:47 and 49, respectively, and (b) an anti-PD-1 antibody comprising heavy and light chain variable regions comprising the sequences set forth in SEQ ID NOs:59 and 60, respectively.

In some aspects, the methods of the disclosure comprise: (a) an anti-LAG-3 antibody comprising heavy and light chain variable regions comprising the sequences set forth in SEQ ID NOs:48 and 50, respectively, and (b) an anti-PD-1 antibody comprising heavy and light chain variable regions comprising the sequences set forth in SEQ ID NOs:59 and 60, respectively.

In some aspects, the methods of the disclosure comprise: (a) an anti-LAG-3 antibody comprising heavy and light chains comprising the sequences set forth in SEQ ID NOs: 43 and 45, respectively, and (b) an anti-PD-1 antibody comprises heavy and light chains comprising the sequences as set forth in SEQ ID NOs:57 and 58, respectively.

In some aspects, the methods of the disclosure comprise: (a) an anti-LAG-3 antibody comprising heavy and light chains comprising the sequences set forth in SEQ ID NOs: 44 and 46, respectively, and (b) an anti-PD-1 antibody comprises heavy and light chains comprising the sequences as set forth in SEQ ID NOs:57 and 58, respectively.

Provided herein is a method of treating a human subject afflicted with lung cancer, the method comprising administering to the subject: (a) an anti-LAG-3 antibody, and (b) an anti-PD-1 antibody.

In some aspects, the method further comprises administering to the subject a PDCT.

Provided herein is a method of treating a human subject afflicted with Stage IV or recurrent NSCLC that has a squamous histology, the method comprising administering to the subject: (a) an anti-LAG-3 antibody, (b) an anti-PD-1 antibody, and (c) a PDCT.

Provided herein is a method of treating a human subject afflicted with Stage IV or recurrent NSCLC that has a non-squamous histology, the method comprising administering to the subject: (a) an anti-LAG-3 antibody, (b) an anti-PD-1 antibody, and (c) a PDCT.

The anti-LAG-3 antibody and the anti-PD-1 antibodies can be administered at any of the doses or combinations of doses described herein.

In some aspects, the dose of the anti-LAG-3 antibody is 80 mg.

In some aspects, the dose of the anti-LAG-3 antibody is 160 mg.

In some aspects, the dose of the anti-LAG-3 antibody is 360 mg.

In some aspects, the dose of the anti-LAG-3 antibody is 480 mg.

In some aspects, the dose of the anti-LAG-3 antibody is 720 mg.

In some aspects, the dose of the anti-LAG-3 antibody is 800 mg.

In some aspects, the dose of the anti-LAG-3 antibody is 960 mg.

In some aspects, the dose of the anti-PD-1 antibody is 200 mg.

In some aspects, the dose of the anti-PD-1 antibody is 240 mg.

In some aspects, the dose of the anti-PD-1 antibody is 360 mg.

In some aspects, the dose of the anti-PD-1 antibody is 480 mg.

In some aspects, the dose of the anti-LAG-3 antibody is 80 mg and the dose of the anti-PD-1 antibody is 240 mg.

In some aspects, the dose of the anti-LAG-3 antibody is 160 mg and the dose of the anti-PD-1 antibody is 480 mg.

In some aspects, the dose of the anti-LAG-3 antibody is 360 mg and the dose of the anti-PD-1 antibody is 360 mg.

In some aspects, the dose of the anti-LAG-3 antibody is 480 mg and the dose of the anti-PD-1 antibody is 480 mg.

In some aspects, the dose of the anti-LAG-3 antibody is 720 mg and the dose of the anti-PD-1 antibody is 360 mg.

In some aspects, the dose of the anti-LAG-3 antibody is 800 mg and the dose of the anti-PD-1 antibody is 200 mg.

In some aspects, the dose of the anti-LAG-3 antibody is 960 mg and the dose of the anti-PD-1 antibody is 480 mg.

Provided herein is a method of treating a human subject afflicted with lung cancer, the method comprising administering to the subject: (a) a dose of about 360 mg of an anti-LAG-3 antibody comprising CDR1, CDR2 and CDR3 domains of the heavy chain variable region having the sequence set forth in SEQ ID NO:3, and CDR1, CDR2 and CDR3 domains of the light chain variable region having the sequence set forth in SEQ ID NO:4, and (b) a dose of about 360 mg of an anti-PD-1 antibody comprising CDR1, CDR2 and CDR3 domains of the heavy chain variable region having the sequence set forth in SEQ ID NO:13, and CDR1, CDR2 and CDR3 domains of the light chain variable region having the sequence set forth in SEQ ID NO:14.

Provided herein is a method of treating a human subject afflicted with lung cancer, the method comprising administering to the subject: (a) a dose of about 720 mg of an anti-LAG-3 antibody comprising CDR1, CDR2 and CDR3 domains of the heavy chain variable region having the sequence set forth in SEQ ID NO:3, and CDR1, CDR2 and CDR3 domains of the light chain variable region having the sequence set forth in SEQ ID NO:4, (b) a dose of about 360 mg of an anti-PD-1 antibody comprising CDR1, CDR2 and CDR3 domains of the heavy chain variable region having the sequence set forth in SEQ ID NO:13, and CDR1, CDR2 and CDR3 domains of the light chain variable region having the sequence set forth in SEQ ID NO:14.

Provided herein is a method of treating a human subject afflicted with Stage IV or recurrent NSCLC that has a squamous histology, the method comprising administering to the subject: (a) a dose of about 360 mg of an anti-LAG-3 antibody comprising CDR1, CDR2 and CDR3 domains of the heavy chain variable region having the sequence set forth in SEQ ID NO:3, and CDR1, CDR2 and CDR3 domains of the light chain variable region having the sequence set forth in SEQ ID NO:4, (b) a dose of about 360 mg of an anti-PD-1 antibody comprising CDR1, CDR2 and CDR3 domains of the heavy chain variable region having the sequence set forth in SEQ ID NO:13, and CDR1, CDR2 and CDR3 domains of the light chain variable region having the sequence set forth in SEQ ID NO:14, (c) a PDCT comprising: (i) a dose of carboplatin for a target area under the concentration-time curve of about 6 mg/mL·min, and (ii) a dose of about 200 $mg/m^2$ of paclitaxel, wherein the method is a first line therapy.

Provided herein is a method of treating a human subject afflicted with Stage IV or recurrent NSCLC that has a squamous histology, the method comprising administering to the subject: (a) a dose of about 720 mg of an anti-LAG-3 antibody comprising CDR1, CDR2 and CDR3 domains of the heavy chain variable region having the sequence set forth in SEQ ID NO:3, and CDR1, CDR2 and CDR3 domains of the light chain variable region having the sequence set forth in SEQ ID NO:4, (b) a dose of about 360 mg of an anti-PD-1 antibody comprising CDR1, CDR2 and CDR3 domains of the heavy chain variable region having the sequence set forth in SEQ ID NO:13, and CDR1, CDR2 and CDR3 domains of the light chain variable region having the sequence set forth in SEQ ID NO:14, (c) a PDCT comprising: (i) a dose of carboplatin for a target area under the concentration-time curve of about 6 mg/mL·min, and (ii) a dose of about 200 $mg/m^2$ of paclitaxel, wherein the method is a first line therapy.

Provided herein is a method of treating a human subject afflicted with Stage IV or recurrent NSCLC that has a squamous histology, the method comprising administering to the subject: (a) a dose of about 360 mg of an anti-LAG-3 antibody comprising CDR1, CDR2 and CDR3 domains of the heavy chain variable region having the sequence set forth in SEQ ID NO:3, and CDR1, CDR2 and CDR3 domains of the light chain variable region having the sequence set forth in SEQ ID NO:4, (b) a dose of about 360 mg of an anti-PD-1 antibody comprising CDR1, CDR2 and CDR3 domains of the heavy chain variable region having the sequence set forth in SEQ ID NO:13, and CDR1, CDR2 and CDR3 domains of the light chain variable region having the sequence set forth in SEQ ID NO:14, (c) a PDCT comprising: (i) a dose of carboplatin for a target area under the concentration-time curve of about 6 mg/mL·min, and (ii) a dose of about 100 $mg/m^2$ of albumin-bound paclitaxel, wherein the method is a first line therapy.

Provided herein is a method of treating a human subject afflicted with Stage IV or recurrent NSCLC that has a squamous histology, the method comprising administering to the subject: (a) a dose of about 720 mg of an anti-LAG-3 antibody comprising CDR1, CDR2 and CDR3 domains of the heavy chain variable region having the sequence set forth in SEQ ID NO:3, and CDR1, CDR2 and CDR3 domains of the light chain variable region having the sequence set forth in SEQ ID NO:4, (b) a dose of about 360 mg of an anti-PD-1 antibody comprising CDR1, CDR2 and CDR3 domains of the heavy chain variable region having the sequence set forth in SEQ ID NO:13, and CDR1, CDR2 and CDR3 domains of the light chain variable region having the sequence set forth in SEQ ID NO:14, (c) a PDCT comprising: (i) a dose of carboplatin for a target area under the concentration-time curve of about 6 mg/mL·min, and (ii) a dose of about 100 $mg/m^2$ of albumin-bound paclitaxel, wherein the method is a first line therapy.

Provided herein is a method of treating a human subject afflicted with Stage IV or recurrent NSCLC that has a non-squamous histology, the method comprising administering to the subject: (a) a dose of about 360 mg of an anti-LAG-3 antibody comprising CDR1, CDR2 and CDR3 domains of the heavy chain variable region having the sequence set forth in SEQ ID NO:3, and CDR1, CDR2 and CDR3 domains of the light chain variable region having the sequence set forth in SEQ ID NO:4, (b) a dose of about 360 mg of an anti-PD-1 antibody comprising CDR1, CDR2 and CDR3 domains of the heavy chain variable region having the sequence set forth in SEQ ID NO:13, and CDR1, CDR2 and CDR3 domains of the light chain variable region having the sequence set forth in SEQ ID NO:14, (c) a PDCT comprising: (i) a dose of carboplatin for a target area under the concentration-time curve of about 5 mg/mL·min or about 6 mg/mL·min, and (ii) a dose of about 500 $mg/m^2$ of pemetrexed, wherein the method is a first line therapy.

Provided herein is a method of treating a human subject afflicted with Stage IV or recurrent NSCLC that has a non-squamous histology, the method comprising administering to the subject: (a) a dose of about 720 mg of an anti-LAG-3 antibody comprising CDR1, CDR2 and CDR3 domains of the heavy chain variable region having the sequence set forth in SEQ ID NO:3, and CDR1, CDR2 and CDR3 domains of the light chain variable region having the sequence set forth in SEQ ID NO:4, (b) a dose of about 360 mg of an anti-PD-1 antibody comprising CDR1, CDR2 and CDR3 domains of the heavy chain variable region having the sequence set forth in SEQ ID NO:13, and CDR1, CDR2 and CDR3 domains of the light chain variable region having the sequence set forth in SEQ ID NO:14, (c) a PDCT comprising: (i) a dose of carboplatin for a target area under the concentration-time curve of about 5 mg/mL·min or about 6 mg/mL·min, and (ii) a dose of about 500 $mg/m^2$ of pemetrexed, wherein the method is a first line therapy.

Provided herein is a method of treating a human subject afflicted with Stage IV or recurrent NSCLC that has a non-squamous histology, the method comprising administering to the subject: (a) a dose of about 360 mg of an anti-LAG-3 antibody comprising CDR1, CDR2 and CDR3 domains of the heavy chain variable region having the sequence set forth in SEQ ID NO:3, and CDR1, CDR2 and CDR3 domains of the light chain variable region having the sequence set forth in SEQ ID NO:4, (b) a dose of about 360 mg of an anti-PD-1 antibody comprising CDR1, CDR2 and CDR3 domains of the heavy chain variable region having the sequence set forth in SEQ ID NO:13, and CDR1, CDR2 and CDR3 domains of the light chain variable region having the sequence set forth in SEQ ID NO:14, (c) a PDCT comprising: (i) a dose of about 75 $mg/m^2$ of cisplatin, and (ii) a dose of about 500 $mg/m^2$ of pemetrexed, wherein the method is a first line therapy.

Provided herein is a method of treating a human subject afflicted with Stage IV or recurrent NSCLC that has a non-squamous histology, the method comprising administering to the subject: (a) a dose of about 720 mg of an anti-LAG-3 antibody comprising CDR1, CDR2, and CDR3 domains of the heavy chain variable region having the sequence set forth in SEQ ID NO:3, and CDR1, CDR2, and CDR3 domains of the light chain variable region having the sequence set forth in SEQ ID NO:4, (b) a dose of about 360 mg of an anti-PD-1 antibody comprising CDR1, CDR2, and CDR3 domains of the heavy chain variable region having the sequence set forth in SEQ ID NO:13, and CDR1, CDR2, and CDR3 domains of the light chain variable region having the sequence set forth in SEQ ID NO:14, (c) a PDCT comprising: (i) a dose of about 75 $mg/m^2$ of cisplatin, and (ii) a dose of about 500 $mg/m^2$ of pemetrexed, wherein the method is a first line therapy.

In some aspects, the anti-LAG-3 antibody and the anti-PD-1 antibody are administered about once every three weeks. In some aspects, the anti-LAG-3 antibody and the anti-PD-1 antibody are administered on Day 1 of every three-week cycle.

In some aspects, the anti-LAG-3 antibody is administered intravenously for about 30 minutes.

In some aspects, the anti-PD-1 antibody is administered intravenously for about 30 minutes.

In some aspects, the composition comprising an anti-LAG-3 antibody and an anti-PD-1 antibody is administered intravenously for about 30 minutes.

In some aspects, the anti-LAG-3 antibody and the anti-PD-1 antibody are administered intravenously from a single intravenous bag for about 30 minutes.

In some aspects, a PDCT is administered every three weeks. In some aspects, the PDCT is administered in a three week cycle for up to about 4 cycles.

In some aspects, the anti-LAG-3 antibody and the anti-PD-1 antibody are administered prior to a PDCT.

In some aspects, the PDCT comprises carboplatin and paclitaxel. In some aspects, paclitaxel is administered for about 180 minutes on Day 1 of each cycle followed by carboplatin administered intravenously for about 30 minutes on Day 1 of each cycle. In some aspects, the NSCLC has a squamous histology.

In some aspects, the PDCT comprises carboplatin and albumin-bound paclitaxel. In some aspects, albumin-bound paclitaxel is administered for about 30 minutes on Days 1, 8, and 15 of each cycle followed by carboplatin administered intravenously for about 30 minutes on Day 1 of each cycle. In some aspects, the NSCLC has a squamous histology.

In some aspects, the PDCT comprises carboplatin and pemetrexed. In some aspects, pemetrexed is administered for about 10 minutes on Day 1 of each cycle followed by carboplatin administered intravenously for about 30 minutes on Day 1 of each cycle. In some aspects, pemetrexed is administered at a maintenance dose alone or in combination with the anti-LAG-3 and anti-PD-1 antibodies in subjects who have stable disease or a response following administration of the PDCT for about 4 three-week cycles. In some aspects, the maintenance dose of pemetrexed is 500 $mg/m^2$. In some aspects, the maintenance dose is administered on Day 1 of a three-week cycle. In some aspects, the maintenance dose continues until disease progression or unacceptable toxicity. In some aspects, the NSCLC has a non-squamous histology.

In some aspects, the PDCT comprises cisplatin and pemetrexed. In some aspects, pemetrexed is administered for about 10 minutes on Day 1 of each cycle followed by cisplatin administered intravenously for about 30 minutes on Day 1 of each cycle. In some aspects, pemetrexed is administered at a maintenance dose alone or in combination with the anti-LAG-3 and anti-PD-1 antibodies in subjects who have stable disease or a response following administration of the PDCT for about 4 cycles. In some aspects, the maintenance dose of pemetrexed is 500 $mg/m^2$. In some aspects, the maintenance dose is administered on Day 1 of a three-week cycle. In some aspects, the maintenance dose continues until disease progression or unacceptable toxicity. In some aspects, the NSCLC has a non-squamous histology.

II.B.3.a.ii. Anti-PD-L1 Antibodies

Anti-PD-L1 antibodies that are known in the art can be used in the methods of the disclosure. Examples of anti-PD-L1 antibodies useful in the compositions and methods of the present disclosure include the antibodies disclosed in U.S. Pat. No. 9,580,507. Anti-PD-L1 human monoclonal antibodies disclosed in U.S. Pat. No. 9,580,507 have been demonstrated to exhibit one or more of the following characteristics: (a) bind to human PD-L1 with a $K_D$ of 1×10-7 M or less, as determined by surface plasmon resonance using a BIACORE biosensor system; (b) increase T-cell proliferation in a Mixed Lymphocyte Reaction (MLR) assay; (c) increase interferon-γ production in an MLR assay; (d) increase IL-2 secretion in an MLR assay; (e) stimulate antibody responses; and (f) reverse the effect of T regulatory cells on T cell effector cells and/or dendritic cells. Anti-PD-L1 antibodies usable in the present disclosure include monoclonal antibodies that bind specifically to human PD-L1 and exhibit at least one, in some aspects, at least five, of the preceding characteristics.

Anti-PD-L1 antibodies that can be used in the methods of the disclosure include BMS-936559 (also known as 12A4, MDX-1105; see, e.g., U.S. Pat. No. 7,943,743 and WO 2013/173223), atezolizumab (Roche; also known as TECENTRIQ®; MPDL3280A, RG7446; see U.S. Pat. No. 8,217,149; see, also, Herbst et al. (2013) J Clin Oncol 31(suppl):3000), durvalumab (AstraZeneca; also known as IMFINZI™, MEDI-4736; see WO 2011/066389), avelumab (Pfizer; also known as BAVENCIO®, MSB-0010718C; see WO 2013/079174), STI-1014 (Sorrento; see WO2013/181634), CX-072 (Cytomx; see WO2016/149201), KN035 (3D Med/Alphamab; see Zhang et al., *Cell Discov.* 7:3 (March 2017), LY3300054 (Eli Lilly Co.; see, e.g., WO 2017/034916), BGB-A333 (BeiGene; see Desai et al., JCO 36 (15suppl):TPS3113 (2018)), ICO 36, FAZ053 (Novartis), and CK-301 (Checkpoint Therapeutics; see Gorelik et al., AACR:Abstract 4606 (April 2016)).

Anti-PD-L1 antibodies that can be used in the methods of the disclosure also include isolated antibodies that bind specifically to human PD-L1 and cross-compete for binding to human PD-L1 with any anti-PD-L1 antibody disclosed herein, e.g., atezolizumab, durvalumab, and/or avelumab. In some aspects, the anti-PD-L1 antibody binds the same epitope as any of the anti-PD-L1 antibodies described herein, e.g., atezolizumab, durvalumab, and/or avelumab. In certain aspects, the antibodies that cross-compete for binding to human PD-L1 with, or bind to the same epitope region as, any anti-PD-L1 antibody disclosed herein, e.g., atezolizumab, durvalumab, and/or avelumab, are monoclonal antibodies. For administration to human subjects, these cross-competing antibodies are chimeric antibodies, engineered antibodies, or humanized or human antibodies. Such chimeric, engineered, humanized or human monoclonal antibodies can be prepared and isolated by methods well known in the art.

Anti-PD-L1 antibodies that can be used in the methods of the disclosure also include antigen-binding portions of any of the above full-length antibodies.

Anti-PD-L1 antibodies that can be used in the methods of the disclosure are antibodies that bind to PD-L1 with high specificity and affinity, block the binding of PD-1, and inhibit the immunosuppressive effect of the PD-1 signaling pathway. In any of the compositions or methods disclosed herein, an anti-PD-L1 "antibody" includes an antigen-binding portion or fragment that binds to PD-L1 and exhibits the functional properties similar to those of whole antibodies in inhibiting receptor binding and up-regulating the immune system. In certain aspects, the anti-PD-L1 antibody or antigen-binding portion thereof cross-competes with atezolizumab, durvalumab, and/or avelumab for binding to human PD-L 1.

In some aspects, an anti-PD-L1 antibody is substituted for the anti-PD-1 antibody in any of the methods disclosed herein.

In some aspects, the anti-PD-L1 antibody is a full-length antibody.

In some aspects, the anti-PD-L1 antibody is a monoclonal, human, humanized, chimeric, or multispecific antibody. In some aspects, the multispecific antibody is a DART, a DVD-Ig, or bispecific antibody.

In some aspects, the anti-PD-L1 antibody is a $F(ab')_2$ fragment, a Fab' fragment, a Fab fragment, a Fv fragment, a scFv fragment, a dsFv fragment, a dAb fragment, or a single chain binding polypeptide.

In some aspects, the anti-PD-L1 antibody is BMS-936559, atezolizumab, durvalumab, avelumab, STI-1014, CX-072, KN035, LY3300054, BGB-A333, ICO 36, FAZ053, CK-301, or comprises an antigen binding portion thereof.

In some aspects, the PD-L1 antibody is atezolizumab. Atezolizumab is a fully humanized IgG1 monoclonal anti-PD-L1 antibody. In some aspects, atezolizumab is administered as a flat dose of about 800 mg once about every 2 weeks. In some aspects, atezolizumab is administered as a flat dose of about 840 mg once about every 2 weeks.

In some aspects, atezolizumab is administered intravenously at a dose of about 1,200 mg on Day 1 of a three-week cycle.

In some aspects, atezolizumab is administered intravenously at a dose of about 1,200 mg on Day 1 of a three-week cycle, and bevacizumab is administered at a dose of about 15 mg/kg on Day 1 of each cycle.

In some aspects, atezolizumab is administered intravenously at a dose of about 1,200 mg on Day 1 of a three-week cycle for about 4 to about 6 cycles, bevacizumab is administered at a dose of about 15 mg/kg on Day 1 of each cycle, paclitaxel is administered intravenously at a dose of about 200 $mg/m^2$ for about 180 minutes on Day 1 of each cycle, and carboplatin is administered intravenously for about 30 minutes in a dose for a target AUC of about 6 mg/mL·min on Day 1 of each cycle.

In some aspects, the PD-L1 antibody is durvalumab. Durvalumab is a human IgG1 kappa monoclonal anti-PD-L1 antibody. In some aspects, durvalumab is administered at a dose of about 10 mg/kg once about every 2 weeks. In some aspects, durvalumab is administered at a dose of about 10 mg/kg once about every 2 weeks for up to 12 months. In some aspects, durvalumab is administered as a flat dose of about 800 mg/kg once about every 2 weeks. In some aspects, durvalumab is administered as a flat dose of about 1200 mg/kg once about every 3 weeks.

In some aspects, the PD-L1 antibody is avelumab. Avelumab is a human IgG1 lambda monoclonal anti-PD-L1 antibody. In some aspects, avelumab is administered as a flat dose of about 800 mg once about every 2 weeks.

II.B.3.b. CTLA-4 Inhibitors

In some aspects, the checkpoint inhibitor a disclosed herein comprises a CTLA-4 inhibitor. In some aspects, the CTLA-4 inhibitor is an anti-CTLA-4 antibody.

Anti-CTLA-4 antibodies that can be used in the methods of the disclosure bind to human CTLA-4 and disrupt the interaction of CTLA-4 with a human B7 receptor. Because the interaction of CTLA-4 with B7 transduces a signal leading to inactivation of T-cells bearing the CTLA-4 receptor, disruption of the interaction effectively induces, enhances, or prolongs the activation of such T cells, thereby inducing, enhancing or prolonging an immune response.

Human monoclonal antibodies that bind specifically to CTLA-4 with high affinity have been disclosed in U.S. Pat. Nos. 6,984,720. Other anti-CTLA-4 monoclonal antibodies have been described in, for example, U.S. Pat. Nos. 5,977,318, 6,051,227, 6,682,736, and 7,034,121 and International Publication Nos. WO 2012/122444, WO 2007/113648, WO 2016/196237, and WO 2000/037504, each of which is incorporated by reference herein in its entirety. The anti-CTLA-4 human monoclonal antibodies disclosed in U.S. Pat. No. 6,984,720 have been demonstrated to exhibit one or more of the following characteristics: (a) binds specifically to human CTLA-4 with a binding affinity reflected by an equilibrium association constant ($K_a$) of at least about $10^7$ $M^{-1}$, or about $10^9$ $M^{-1}$, or about $10^{10}$ $M^{-1}$ to $10^{11}$ $M^{-1}$ or higher, as determined by BIACORE analysis; (b) a kinetic association constant ($k_a$) of at least about $10^3$, about $10^4$, or about $10^5$ $m^{-1}$ $s^{-1}$; (c) a kinetic disassociation constant ($k_d$) of at least about $10^3$, about $10^4$, or about $10^5$ $m^{-1}$ $s^{-1}$; and (d) inhibits the binding of CTLA-4 to B7-1 (CD80) and B7-2 (CD86). Anti-CTLA-4 antibodies useful for the present disclosure include monoclonal antibodies that bind specifically to human CTLA-4 and exhibit at least one, at least two, or at least three of the preceding characteristics.

Anti-CTLA-4 antibodies that can be used in the methods of the disclosure include ipilimumab (also known as YERVOY®, MDX-010, 10D1; see U.S. Pat. No. 6,984,720), MK-1308 (Merck), AGEN-1884 (Agenus Inc.; see WO 2016/196237), and tremelimumab (AstraZeneca; also known as ticilimumab, CP-675,206; see WO 2000/037504 and Ribas, *Update Cancer Ther.* 2(3): 133-39 (2007)).

In some aspects, the anti-CTLA-4 antibody binds specifically to human CTLA-4 and cross-competes for binding to human CTLA-4 with any anti-CTLA-4 antibody disclosed herein, e.g., ipilimumab and/or tremelimumab. In some aspects, the anti-CTLA-4 antibody binds the same epitope as any of the anti-CTLA-4 antibodies described herein, e.g., ipilimumab and/or tremelimumab.

In some aspects, the antibodies that cross-compete for binding to human CTLA-4 with, or bind to the same epitope region as, any anti-CTLA-4 antibody disclosed herein, e.g., ipilimumab and/or tremelimumab, are monoclonal antibodies. For administration to human subjects, these cross-competing antibodies are chimeric antibodies, engineered antibodies, or humanized or human antibodies.

Anti-CTLA-4 antibodies that can be used in the methods of the disclosure also include antigen-binding portions of any of the above full-length antibodies.

In some aspects, the anti-CTLA-4 antibody is a full-length antibody. In some aspects, the anti-CTLA-4 antibody is a monoclonal, human, humanized, chimeric, or multispecific antibody. In some aspects, the multispecific antibody is a DART, a DVD-Ig, or bispecific antibody.

In some aspects, the anti-CTLA-4 antibody is a $F(ab')_2$ fragment, a Fab' fragment, a Fab fragment, a Fv fragment, a scFv fragment, a dsFv fragment, a dAb fragment, or a single chain binding polypeptide.

In some aspects, the anti-CTLA-4 antibody is ipilimumab, tremelimumab, MK-1308, AGEN-1884, or comprises an antigen binding portion thereof.

In some aspects, the anti-CTLA-4 antibody is ipilimumab. Ipilimumab is a fully human, IgG1 monoclonal antibody that blocks the binding of CTLA-4 to its B7 ligands, thereby stimulating T cell activation. In some aspects, ipilimumab is administered at a dose of about 3 mg/kg once about every 3 weeks. In some aspects, ipilimumab is administered at a dose of about 10 mg/kg once about every 3 weeks. In some aspects, ipilimumab is administered at a dose of about 10 mg/kg once about every 12 weeks. In some aspects, the ipilimumab is administered for four doses. In some aspects, ipilimumab is administered on Day 1 of each cycle.

IIB.4. Therapies for Sensitizing Mutations

In some aspects, a method of the disclosure comprises treatment of a subject with a mutation sensitive to targeted inhibitor therapy such as a sensitizing mutation in a gene such as EGFR, ALK, ROS-1, NTRK, or BRAF. Such methods can further comprise administration of a targeted inhibitor of the mutated genes, including standard of care therapies for subjects having such mutations who are afflicted with NSCLC.

In some aspects, a method of the disclosure comprises a first line therapy for a subject afflicted with advanced or metastatic NSCLC who has a sensitizing EGFR mutation, comprising administering to the subject afatinib (e.g., 40 mg orally once daily), erlotinib (e.g., 150 mg orally once daily), dacomitinib (e.g., 45 mg orally once daily), gefitinib (e.g., 250 mg orally once daily), or osimertinib (e.g., 80 mg orally once daily).

In some aspects, a method of the disclosure comprises a second or third line therapy for a subject afflicted with advanced or metastatic NSCLC who has a sensitizing EGFR mutation, comprising administering to the subject afatinib and cetuximab (e.g., 40 mg afatinib orally once daily on Days 1-14 and cetuximab at 500 $mg/m^2$ on Day 1 in 2-week cycles) or osimertinib (e.g., 80 mg orally once daily).

In some aspects, a method of the disclosure comprises a first, second, or third line therapy for a subject afflicted with advanced or metastatic NSCLC who has a sensitizing ALK mutation (e.g., ALK rearrangement), comprising administering to the subject alectinib (e.g., 600 mg orally twice daily), brigatinib (e.g., a 4 week cycle of 90 mg orally once daily on Days 1-7, 180 mg orally once daily on days 8-28 followed by 180 mg orally once daily on Days 29-56), ceritinib (e.g., 450 mg orally once daily), or crizotinib (e.g., 250 mg orally twice daily).

In some aspects, a method of the disclosure comprises a second or third line therapy for a subject afflicted with advanced or metastatic NSCLC who has a sensitizing ALK mutation (e.g., ALK rearrangement), comprising administering to the subject lorlatinib (e.g., 100 mg orally once daily).

In some aspects, a method of the disclosure comprises a first line therapy for a subject afflicted with advanced or metastatic NSCLC who has a sensitizing ROS-1 mutation (e.g., ROS-1 rearrangement), comprising administering to the subject ceritinib (e.g., 450 mg orally once daily), crizotinib (e.g., 250 mg orally twice daily), or entrectinib (e.g., 600 mg orally once daily). In some aspects, a method of the disclosure comprises a standard of care second or third line therapy for a subject afflicted with advanced or metastatic NSCLC who has a sensitizing ROS-1 mutation (e.g., ROS-1 rearrangement), wherein the standard of care therapy comprises administering to the subject lorlatinib (e.g., 100 mg orally once daily).

In some aspects, a method of the disclosure comprises a first, second, or third line therapy for a subject afflicted with advanced or metastatic NSCLC who has a sensitizing BRAF mutation (e.g., BRAF V600E), comprising administering to the subject dabrafenib (e.g., 150 mg orally twice daily), dabrafenib and trametinib (e.g., 150 mg orally twice daily and 2 mg orally once daily trametinib), or vemurafenib (e.g., 960 mg orally once daily).

In some aspects, a method of the disclosure comprises a first, second, or third line therapy for a subject afflicted with advanced or metastatic NSCLC who has a sensitizing NTRK mutation (e.g., NTRK gene fusion), comprising administering to the subject entrectinib (e.g., 600 mg orally once daily) or larotrectinib (e.g., 100 mg orally twice daily).

III. Pharmaceutical Compositions

Therapeutic agents of the present disclosure can be constituted in a composition, e.g., a pharmaceutical composition containing an inhibitor, antibody, and/or agent as disclosed herein and a pharmaceutically acceptable carrier. As used herein, a "pharmaceutically acceptable carrier" includes any and all solvents, dispersion media, coatings, antibacterial and antifungal agents, isotonic and absorption delaying agents, and the like that are physiologically compatible.

In some aspects, the carrier for a composition containing an inhibitor, antibody, and/or agent as disclosed herein is suitable for intravenous, intramuscular, subcutaneous, parenteral, spinal or epidermal administration (e.g., by injection or infusion). In some aspects, the carrier is suitable for non-parenteral, e.g., oral, administration. In some aspects, a subcutaneous injection is based on Halozyme Therapeutics' ENHANZE® drug-delivery technology (see U.S. Pat. No. 7,767,429, which is incorporated by reference herein in its entirety). ENHANZE® uses a co-formulation of an antibody with recombinant human hyaluronidase enzyme (rHuPH20), which removes traditional limitations on the volume of biologics and drugs that can be delivered subcutaneously due to the extracellular matrix (see U.S. Pat. No. 7,767,429). A pharmaceutical composition of the disclosure can include one or more pharmaceutically acceptable salts, anti-oxidant, aqueous and non-aqueous carriers, and/or adjuvants such as preservatives, wetting agents, emulsifying agents and dispersing agents. In some aspects, the pharmaceutical composition for the present disclosure can further comprise recombinant human hyaluronidase enzyme, e.g., rHuPH20.

Treatment is continued as long as clinical benefit is observed or until unacceptable toxicity or disease progression occurs. Dosage and frequency vary depending on the half-life of the inhibitor, antibody, and/or agent in the subject. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is typically administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients (i.e., inhibitors, antibodies, and/or agents) in the pharmaceutical compositions of the present disclosure can be varied so as to obtain an amount of the active ingredient which is effective to achieve the desired therapeutic response for a particular patient, composition, and mode of administration, without being unduly toxic to the patient. The selected dosage level will depend upon a variety of pharmacokinetic factors including the activity of the particular compositions of the present disclosure employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A composition of the present disclosure can be administered via one or more routes of administration using one or more of a variety of methods well known in the art. As will be appreciated by the skilled artisan, the route and/or mode of administration will vary depending upon the desired results.

Provided herein is a pharmaceutical composition comprising an anti-LAG-3 antibody and an anti-PD-1 antibody as described herein at any of the doses or combinations of doses described herein.

In some aspects, the pharmaceutical composition is for treating a human subject with lung cancer as described herein.

In some aspects, a method for treating a human subject with lung cancer as described herein comprises administering a pharmaceutical composition as described herein.

In some aspects, the pharmaceutical composition comprises a dose of relatlimab and a dose of an anti-PD-1 antibody as described herein. In some aspects, the anti-PD-1 antibody is nivolumab, pembrolizumab, cemiplimab, or spartalizumab. In some aspects, the anti-PD-1 antibody is nivolumab.

In some aspects, the pharmaceutical composition comprises a dose of favezelimab and a dose of an anti-PD-1 antibody as described herein. In some aspects, the anti-PD-1 antibody is nivolumab, pembrolizumab, cemiplimab, or spartalizumab. In some aspects, the anti-PD-1 antibody is pembrolizumab.

In some aspects, the pharmaceutical composition comprises a dose of fianlimab and a dose of an anti-PD-1 antibody as described herein. In some aspects, the anti-PD-1 antibody is nivolumab, pembrolizumab, cemiplimab, or spartalizumab. In some aspects, the anti-PD-1 antibody is cemiplimab.

In some aspects, the pharmaceutical composition comprises a dose of ieramilimab and a dose of an anti-PD-1 antibody as described herein. In some aspects, the anti-PD-1 antibody is nivolumab, pembrolizumab, cemiplimab, or spartalizumab. In some aspects, the anti-PD-1 antibody is spartalizumab.

In some aspects, the pharmaceutical composition comprises a ratio of anti-LAG-3 antibody to anti-PD-1 antibody of about 1:1, about 1:2, about 1:3, about 1:4, about 1:5, about 1:6, about 1:7, about 1:8, about 1:9, about 1:10, about 1:15, about 1:20, about 1:30, about 1:40, about 1:50, about 1:60, about 1:70, about 1:80, about 1:90, about 1:100, about 1:120, about 1:140, about 1:160, about 1:180, about 1:200, about 200:1, about 180:1, about 160:1, about 140:1, about 120:1, about 100:1, about 90:1, about 80:1, about 70:1, about 60:1, about 50:1, about 40:1, about 30:1, about 20:1, about 15:1, about 10:1, about 9:1, about 8:1, about 7:1, about 6:1, about 5:1, about 4:1, about 3:1, or about 2:1.

In some aspects, the pharmaceutical composition comprises a ratio of anti-LAG-3 antibody to anti-PD-1 antibody of about 1:3.

In some aspects, the pharmaceutical composition comprises a ratio of anti-LAG-3 antibody to anti-PD-1 antibody of about 1:1

In some aspects, the pharmaceutical composition comprises a ratio of anti-LAG-3 antibody to anti-PD-1 antibody of about 2:1.

In some aspects, the pharmaceutical composition comprises a ratio of anti-LAG-3 antibody to anti-PD-1 antibody of about 4:1.

In some aspects, the total amount of anti-LAG-3 and anti-PD-1 antibodies in the pharmaceutical composition is about 20 mg/mL, about 25 mg/mL, about 30 mg/mL, about 35 mg/mL, about 40 mg/mL, about 45 mg/mL, about 50 mg/mL, about 55 mg/mL, about 60 mg/mL, about 65 mg/mL, about 70 mg/mL, about 75 mg/mL, about 80 mg/mL, about 85 mg/mL, about 90 mg/mL, about 95 mg/mL, about 100 mg/mL, about 105 mg/mL, about 110 mg/mL, about 115 mg/mL, about 120 mg/mL, about 125 mg/mL, about 130 mg/mL, about 135 mg/mL, about 140 mg/mL, about 145 mg/mL, about 150 mg/mL, about 155 mg/mL, about 160 mg/mL, about 165 mg/mL, about 170 mg/mL, about 175 mg/mL, about 180 mg/mL, about 185 mg/mL, about 190 mg/mL, about 195 mg/mL, about 200 mg/mL, about 205 mg/mL, about 210 mg/mL, about 215 mg/mL, about 220 mg/mL, about 225 mg/mL, about 230 mg/mL, about 235 mg/mL, about 240 mg/mL, about 245 mg/mL, about 250 mg/mL, about 255 mg/mL, about 260 mg/mL, about 265 mg/mL, about 270 mg/mL, about 275 mg/mL, about 280 mg/mL, about 285 mg/mL, about 290 mg/mL, about 295 mg/mL, about 300 mg/mL, about 305 mg/mL, about 310 mg/mL, about 315 mg/mL, about 320 mg/mL, about 325 mg/mL, about 330 mg/mL, about 335 mg/mL, about 340 mg/mL, about 345 mg/mL, about 350 mg/mL, about 355 mg/mL, about 360 mg/mL, about 365 mg/mL, about 370 mg/mL, about 375 mg/mL, about 380 mg/mL, about 385 mg/mL, about 390 mg/mL, about 395 mg/mL, about 400 mg/mL, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, about 600 mg, about 610 mg, about 620 mg, about 630 mg, about 640 mg, about 650 mg, about 660 mg, about 670 mg, about 680 mg, about 690 mg, about 700 mg, about 710 mg, about 720 mg, about 730 mg, about 740 mg, about 750 mg, about 760 mg, about 770 mg, about 780 mg, about 790 mg, about 800 mg, about 810 mg, about 820 mg, about 830 mg, about 840 mg, about 850 mg, about 860 mg, about 870 mg, about 880 mg, about 890 mg, about 900 mg, about 910 mg, about 920 mg, about 930 mg, about 940 mg, about 950 mg, about 960 mg, about 970 mg, about 980 mg, about 990 mg, about 1000 mg, about 1010 mg, about 1020 mg, about 1030 mg, about 1040 mg, about 1050 mg, about 1060 mg, about 1070 mg, about 1080 mg, about 1090 mg, about 1100 mg, about 1110 mg, about 1120 mg, about 1130 mg, about 1140 mg, about 1150 mg, about 1160 mg, about 1170 mg, about 1180 mg, about 1190 mg, about 1200 mg, about 1210 mg, about 1220 mg, about 1230 mg, about 1240 mg, about 1250 mg, about 1260 mg, about 1270 mg, about 1280 mg, about 1290 mg, about 1300 mg, about 1310 mg, about 1320 mg, about 1330 mg, about 1340 mg, about 1350 mg, about 1360 mg, about 1370 mg, about 1380 mg, about 1390 mg, about 1400 mg, about 1410 mg, about 1420 mg, about 1430 mg, about 1440 mg, about 1450 mg, about 1460 mg, about 1470 mg, about 1480 mg, about 1490 mg, about 1500 mg, about 1510 mg, about 1520 mg, about 1530 mg, about 1540 mg, about 1550 mg, about 1560 mg, about 1570 mg, about 1580 mg, about 1590 mg, about 1600 mg, about 1610 mg, about 1620 mg, about 1630 mg, about 1640 mg, about 1650 mg, about 1660 mg, about 1670 mg, about 1680 mg, about 1690 mg, about 1700 mg, about 1710 mg, about 1720 mg, about 1730 mg, about 1740 mg, about 1750 mg, about 1760 mg, about 1770 mg, or about 1780 mg.

In some aspects, the total amount of anti-LAG-3 and anti-PD-1 antibodies in the pharmaceutical composition is about 25 mg/mL.

In some aspects, the total amount of anti-LAG-3 and anti-PD-1 antibodies in the pharmaceutical composition is about 50 mg/mL.

In some aspects, the total amount of anti-LAG-3 and anti-PD-1 antibodies in the pharmaceutical composition is about 150 mg/mL.

In some aspects, the total amount of anti-LAG-3 and anti-PD-1 antibodies in the pharmaceutical composition is about 50 mg.

In some aspects, the total amount of anti-LAG-3 and anti-PD-1 antibodies in the pharmaceutical composition is about 320 mg.

In some aspects, the total amount of anti-LAG-3 and anti-PD-1 antibodies in the pharmaceutical composition is about 640 mg.

In some aspects, the total amount of anti-LAG-3 and anti-PD-1 antibodies in the pharmaceutical composition is about 720 mg.

In some aspects, the total amount of anti-LAG-3 and anti-PD-1 antibodies in the pharmaceutical composition is about 960 mg.

In some aspects, the total amount of anti-LAG-3 and anti-PD-1 antibodies in the pharmaceutical composition is about 1000 mg.

In some aspects, the total amount of anti-LAG-3 and anti-PD-1 antibodies in the pharmaceutical composition is about 1080 mg.

In some aspects, the total amount of anti-LAG-3 and anti-PD-1 antibodies in the pharmaceutical composition is about 1440 mg.

In some aspects, the pharmaceutical composition comprises about 10 mg/mL, about 12.5 mg/mL, about 15 mg/mL, about 17.5 mg/mL, about 20 mg/mL, about 22.5 mg/mL, about 25 mg/mL, about 27.5 mg/mL, about 30 mg/mL, about 32.5 mg/mL, about 35 mg/mL, about 37.5 mg/mL, about 40 mg/mL, about 42.5 mg/mL, about 45 mg/mL, about 47.5 mg/mL, about 50 mg/mL, about 55 mg/mL, about 60 mg/mL, about 65 mg/mL, about 70 mg/mL, about 75 mg/mL, about 80 mg/mL, about 85 mg/mL, about 90 mg/mL, about 95 mg/mL, about 100 mg/mL, about 105 mg/mL, about 110 mg/mL, about 115 mg/mL, about 120 mg/mL, about 125 mg/mL, 130 mg/mL, about 135 mg/mL, about 140 mg/mL, about 145 mg/mL, about 150 mg/mL, about 155 mg/mL, about 160 mg/mL, about 165 mg/mL, about 170 mg/mL, about 175 mg/mL, about 180 mg/mL, about 185 mg/mL, about 190 mg/mL, about 195 mg/mL, about 200 mg/mL, about 7 mg, about 21 mg, about 40 mg, about 70 mg, about 80 mg, about 160 mg, about 200 mg, about 210 mg, about 300 mg, about 400 mg, about 480 mg, about 500 mg, about 600 mg, about 700 mg, about 800 mg, about 900 mg, about 960 mg, about 1000 mg, about 1100 mg, about 1200 mg, or about 1300 mg of an anti-LAG-3 antibody. In some aspects, the pharmaceutical composition comprises about 5 mg/mL, about 10 mg/mL, about 12.5 mg/mL, about 15 mg/mL, about 17.5 mg/mL, about 20 mg/mL, about 22.5 mg/mL, about 25 mg/mL, about 27.5 mg/ml, about 30 mg/mL, about 32.5 mg/mL, about 35 mg/mL, about 37.5 mg/mL, about 40 mg/mL, about 42.5 mg/mL, about 45 mg/mL, about 47.5 mg/mL, about 50 mg/mL, about 55 mg/mL, about 60 mg/mL, about 65 mg/mL, about 70 mg/mL, about 75 mg/mL, about 80 mg/mL, about 85 mg/mL, about 90 mg/mL, about 95 mg/mL, about 100 mg/mL, about 105 mg/mL, about 110 mg/mL, about 115 mg/mL, about 120 mg/mL, about 125 mg/mL, 130 mg/mL, about 135 mg/mL, about 140 mg/mL, about 145 mg/mL, about 150 mg/mL, about 155 mg/mL, about 160 mg/mL, about 165 mg/mL, about 170 mg/mL, about 175 mg/mL, about 180 mg/mL, about 185 mg/mL, about 190 mg/mL, about 195 mg/mL, about 200 mg/mL, about 10 mg, about 40 mg, about 100 mg, about 200 mg, about 240 mg, about 300 mg, about 350 mg, about 360 mg, about 400 mg, or about 480 mg of an anti-PD-1 antibody.

In some aspects, the pharmaceutical composition comprises about 12.5 mg/mL of an anti-LAG-3 antibody and about 37.5 mg/mL of an anti-PD-1 antibody.

In some aspects, the pharmaceutical composition comprises about 20 mg/mL of an anti-LAG-3 antibody and about 5 mg/mL of an anti-PD-1 antibody.

In some aspects, the pharmaceutical composition comprises about 75 mg/mL of an anti-LAG-3 antibody and about 75 mg/mL of an anti-PD-1 antibody.

In some aspects, the pharmaceutical composition comprises about 100 mg/mL of an anti-LAG-3 antibody and about 50 mg/mL of an anti-PD-1 antibody.

In some aspects, the pharmaceutical composition comprises about 80 mg of an anti-LAG-3 antibody and about 240 mg of an anti-PD-1 antibody.

In some aspects, the pharmaceutical composition comprises about 160 mg of an anti-LAG-3 antibody and about 480 mg of an anti-PD-1 antibody.

In some aspects, the pharmaceutical composition comprises about 360 mg of an anti-LAG-3 antibody and about 360 mg of an anti-PD-1 antibody.

In some aspects, the pharmaceutical composition comprises about 480 mg of an anti-LAG-3 antibody and about 480 mg of an anti-PD-1 antibody.

In some aspects, the pharmaceutical composition comprises about 720 mg of an anti-LAG-3 antibody and about 360 mg of an anti-PD-1 antibody.

In some aspects, the pharmaceutical composition comprises about 800 mg of an anti-LAG-3 antibody and about 200 mg of an anti-PD-1 antibody.

In some aspects, the pharmaceutical composition comprises about 960 mg of an anti-LAG-3 antibody and about 480 mg of an anti-PD-1 antibody.

In some aspects, the pharmaceutical composition comprises from about 5 mM to about 50 mM of histidine, from about 50 mM to about 300 mM of sucrose, from about 5 μM to about 1 mM of diethylenetriaminepentaacetic acid (DTPA) or ethylenediaminetetraacetic acid (EDTA), and from about 0.001% to about 1% (w/v) of polysorbate or poloxamer (e.g., polysorbate 80 (PS80), polysorbate 20 (PS20), poloxamer 188 (PX188), or any combination thereof).

In some aspects, the pharmaceutical composition comprises about 20 mM histidine, about 250 mM sucrose, about 50 μM DTPA, and 0.05% PS80.

In some aspects, the pH of the pharmaceutical composition is from about 5 to about 6.5. In some aspects, the pH is about 5.3 to about 6.3. In some aspects, the pH is 5.8. In some aspects, the pH is 5.7.

Provided herein is a vial, syringe, or intravenous bag comprising a pharmaceutical composition as described herein. In some aspects, the disclosure includes an autoinjector comprising a pharmaceutical composition described herein.

In some aspects, a vial comprises a pharmaceutical composition as described herein, and the vial further comprises a stopper and a seal. In some aspects, the total volume in the vial is about 5 mL, about 6 mL, about 7 mL, about 8 mL, about 9 mL, about 10 mL, about 11 mL, about 12 mL, about 13 mL, about 14 mL, about 15 mL, about 16 mL, about 17 mL, about 18 mL, about 19 mL, or about 20 mL.

IV. Kits

Also within the scope of the present invention are kits for treating a human subject with lung cancer comprising any of the antibodies, therapeutic agents, and/or anti-cancer therapies described herein.

Kits typically include a label indicating the intended use of the contents of the kit and instructions for use. The term "label" includes any writing, or recorded material supplied on or with the kit, or which otherwise accompanies the kit.

Provided herein is a kit for treating a human subject afflicted with lung cancer, comprising: (a) a dose of an anti-LAG-3 antibody; (b) a dose of an anti-PD-1 antibody; and (c) instructions for using the anti-LAG-3 antibody and the anti-PD-1 antibody in a method for treating a human subject afflicted with lung cancer.

The anti-LAG-3 antibody and the anti-PD-1 antibodies can be provided at any of the doses or combinations of doses described herein.

In some aspects, the kit comprises a dose of relatlimab and a dose of an anti-PD-1 antibody as described herein. In some aspects, the anti-PD-1 antibody is nivolumab, pembrolizumab, cemiplimab, or spartalizumab. In some aspects, the anti-PD-1 antibody is nivolumab.

In some aspects, the kit comprises a dose of favezelimab and a dose of an anti-PD-1 antibody as described herein. In some aspects, the anti-PD-1 antibody is nivolumab, pembrolizumab, cemiplimab, or spartalizumab. In some aspects, the anti-PD-1 antibody is pembrolizumab.

In some aspects, the kit comprises fianlimab and an anti-PD-1 antibody as described herein. In some aspects, the anti-PD-1 antibody is nivolumab, pembrolizumab, cemiplimab, or spartalizumab. In some aspects, the anti-PD-1 antibody is cemiplimab.

In some aspects, the kit comprises ieramilimab and an anti-PD-1 antibody as described herein. In some aspects, the anti-PD-1 antibody is nivolumab, pembrolizumab, cemiplimab, or spartalizumab. In some aspects, the anti-PD-1 antibody is spartalizumab.

In some aspects, the kit comprises a ratio of anti-LAG-3 antibody to anti-PD-1 antibody of about 1:1, about 1:2, about 1:3, about 1:4, about 1:5, about 1:6, about 1:7, about 1:8, about 1:9, about 1:10, about 1:15, about 1:20, about 1:30, about 1:40, about 1:50, about 1:60, about 1:70, about 1:80, about 1:90, about 1:100, about 1:120, about 1:140, about 1:160, about 1:180, about 1:200, about 200:1, about 180:1, about 160:1, about 140:1, about 120:1, about 100:1, about 90:1, about 80:1, about 70:1, about 60:1, about 50:1, about 40:1, about 30:1, about 20:1, about 15:1, about 10:1, about 9:1, about 8:1, about 7:1, about 6:1, about 5:1, about 4:1, about 3:1, or about 2:1.

In some aspects, the kit comprises a ratio of anti-LAG-3 antibody to anti-PD-1 antibody of about 1:3.

In some aspects, the kit comprises a ratio of anti-LAG-3 antibody to anti-PD-1 antibody of about 1:1

In some aspects, the kit comprises a ratio of anti-LAG-3 antibody to anti-PD-1 antibody of about 2:1.

In some aspects, the kit comprises a ratio of anti-LAG-3 antibody to anti-PD-1 antibody of about 4:1.

In some aspects, the total amount of anti-LAG-3 and anti-PD-1 antibodies in the kit is about 20 mg/mL, about 25 mg/mL, about 30 mg/mL, about 35 mg/mL, about 40 mg/mL, about 45 mg/mL, about 50 mg/mL, about 55 mg/mL, about 60 mg/mL, about 65 mg/mL, about 70 mg/mL, about 75 mg/mL, about 80 mg/mL, about 85 mg/mL, about 90 mg/mL, about 95 mg/mL, about 100 mg/mL, about 105 mg/mL, about 110 mg/mL, about 115 mg/mL, about 120 mg/mL, about 125 mg/mL, about 130 mg/mL, about 135 mg/mL, about 140 mg/mL, about 145 mg/mL, about 150 mg/mL, about 155 mg/mL, about 160 mg/mL, about 165 mg/mL, about 170 mg/mL, about 175 mg/mL, about 180 mg/mL, about 185 mg/mL, about 190 mg/mL, about 195 mg/mL, about 200 mg/mL, about 205 mg/mL, about 210 mg/mL, about 215 mg/mL, about 220 mg/mL, about 225 mg/mL, about 230 mg/mL, about 235 mg/mL, about 240 mg/mL, about 245 mg/mL, about 250 mg/mL, about 255 mg/mL, about 260 mg/mL, about 265 mg/mL, about 270 mg/mL, about 275 mg/mL, about 280 mg/mL, about 285 mg/mL, about 290 mg/mL, about 295 mg/mL, about 300 mg/mL, about 305 mg/mL, about 310 mg/mL, about 315 mg/mL, about 320 mg/mL, about 325 mg/mL, about 330 mg/mL, about 335 mg/mL, about 340 mg/mL, about 345 mg/mL, about 350 mg/mL, about 355 mg/mL, about 360 mg/mL, about 365 mg/mL, about 370 mg/mL, about 375 mg/mL, about 380 mg/mL, about 385 mg/mL, about 390 mg/mL, about 395 mg/mL, about 400 mg/mL, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, about 600 mg, about 610 mg, about 620 mg, about 630 mg, about 640 mg, about 650 mg, about 660 mg, about 670 mg, about 680 mg, about 690 mg, about 700 mg, about 710 mg, about 720 mg, about 730 mg, about 740 mg, about 750 mg, about 760 mg, about 770 mg, about 780 mg, about 790 mg, about 800 mg, about 810 mg, about 820 mg, about 830 mg, about 840 mg, about 850 mg, about 860 mg, about 870 mg, about 880 mg, about 890 mg, about 900 mg, about 910 mg, about 920 mg, about 930 mg, about 940 mg, about 950 mg, about 960 mg, about 970 mg, about 980 mg, about 990 mg, about 1000 mg, about 1010 mg, about 1020 mg, about 1030 mg, about 1040 mg, about 1050 mg, about 1060 mg, about 1070 mg, about 1080 mg, about 1090 mg, about 1100 mg, about 1110 mg, about 1120 mg, about 1130 mg, about 1140 mg, about 1150 mg, about 1160 mg, about 1170 mg, about 1180 mg, about 1190 mg, about 1200 mg, about 1210 mg, about 1220 mg, about 1230 mg, about 1240 mg, about 1250 mg, about 1260 mg, about 1270 mg, about 1280 mg, about 1290 mg, about 1300 mg, about 1310 mg, about 1320 mg, about 1330 mg, about 1340 mg, about 1350 mg, about 1360 mg, about 1370 mg, about 1380 mg, about 1390 mg, about 1400 mg, about 1410 mg, about 1420 mg, about 1430 mg, about 1440 mg, about 1450 mg, about 1460 mg, about 1470 mg, about 1480 mg, about 1490 mg, about 1500 mg, about 1510 mg, about 1520 mg, about 1530 mg, about 1540 mg, about 1550 mg, about 1560 mg, about 1570 mg, about 1580 mg, about 1590 mg, about 1600 mg, about 1610 mg, about 1620 mg, about 1630 mg, about 1640 mg, about 1650 mg, about 1660 mg, about 1670 mg, about 1680 mg, about 1690 mg, about 1700 mg, about 1710 mg, about 1720 mg, about 1730 mg, about 1740 mg, about 1750 mg, about 1760 mg, about 1770 mg, or about 1780 mg.

In some aspects, the total amount of anti-LAG-3 and anti-PD-1 antibodies in the kit is about 25 mg/mL.

In some aspects, the total amount of anti-LAG-3 and anti-PD-1 antibodies in the kit is about 50 mg/mL.

In some aspects, the total amount of anti-LAG-3 and anti-PD-1 antibodies in the kit is about 150 mg/mL.

In some aspects, the total amount of anti-LAG-3 and anti-PD-1 antibodies in the kit is about 50 mg.

In some aspects, the total amount of anti-LAG-3 and anti-PD-1 antibodies in the kit is about 320 mg.

In some aspects, the total amount of anti-LAG-3 and anti-PD-1 antibodies in the kit is about 640 mg.

In some aspects, the total amount of anti-LAG-3 and anti-PD-1 antibodies in the kit is about 720 mg.

In some aspects, the total amount of anti-LAG-3 and anti-PD-1 antibodies in the kit is about 960 mg.

In some aspects, the total amount of anti-LAG-3 and anti-PD-1 antibodies in the kit is about 1000 mg.

In some aspects, the total amount of anti-LAG-3 and anti-PD-1 antibodies in the kit is about 1080 mg.

In some aspects, the total amount of anti-LAG-3 and anti-PD-1 antibodies in the kit is about 1440 mg.

In some aspects, the kit comprises about 10 mg/mL, about 12.5 mg/mL, about 15 mg/mL, about 17.5 mg/mL, about 20 mg/mL, about 22.5 mg/mL, about 25 mg/mL, about 27.5 mg/mL, about 30 mg/mL, about 32.5 mg/mL, about 35 mg/mL, about 37.5 mg/mL, about 40 mg/mL, about 42.5 mg/mL, about 45 mg/mL, about 47.5 mg/mL, about 50 mg/mL, about 55 mg/mL, about 60 mg/mL, about 65 mg/mL, about 70 mg/mL, about 75 mg/mL, about 80 mg/mL, about 85 mg/mL, about 90 mg/mL, about 95 mg/mL, about 100 mg/mL, about 105 mg/mL, about 110 mg/mL, about 115 mg/mL, about 120 mg/mL, about 125 mg/mL, 130 mg/mL, about 135 mg/mL, about 140 mg/mL, about 145 mg/mL, about 150 mg/mL, about 155 mg/mL, about 160 mg/mL, about 165 mg/mL, about 170 mg/mL, about 175 mg/mL, about 180 mg/mL, about 185 mg/mL, about 190 mg/mL, about 195 mg/mL, about 200 mg/mL, about 7 mg, about 21 mg, about 40 mg, about 70 mg, about 80 mg, about 160 mg, about 200 mg, about 210 mg, about 300 mg, about 400 mg, about 480 mg, about 500 mg, about 600 mg, about 700 mg, about 800 mg, about 900 mg, about 960 mg, about 1000 mg, about 1100 mg, about 1200 mg, or about 1300 mg of an anti-LAG-3 antibody. In some aspects, the kit comprises about 5 mg/mL, about 10 mg/mL, about 12.5 mg/mL, about 15 mg/mL, about 17.5 mg/mL, about 20 mg/mL, about 22.5 mg/mL, about 25 mg/mL, about 27.5 mg/ml, about 30 mg/mL, about 32.5 mg/mL, about 35 mg/mL, about 37.5 mg/mL, about 40 mg/mL, about 42.5 mg/mL, about 45 mg/mL, about 47.5 mg/mL, about 50 mg/mL, about 55 mg/mL, about 60 mg/mL, about 65 mg/mL, about 70 mg/mL, about 75 mg/mL, about 80 mg/mL, about 85 mg/mL, about 90 mg/mL, about 95 mg/mL, about 100 mg/mL, about 105 mg/mL, about 110 mg/mL, about 115 mg/mL, about 120 mg/mL, about 125 mg/mL, 130 mg/mL, about 135 mg/mL, about 140 mg/mL, about 145 mg/mL, about 150 mg/mL, about 155 mg/mL, about 160 mg/mL, about 165 mg/mL, about 170 mg/mL, about 175 mg/mL, about 180 mg/mL, about 185 mg/mL, about 190 mg/mL, about 195 mg/mL, about 200 mg/mL, about 10 mg, about 40 mg, about 100 mg, about 200 mg, about 240 mg, about 300 mg, about 350 mg, about 360 mg, about 400 mg, or about 480 mg of an anti-PD-1 antibody.

In some aspects, the kit comprises about 12.5 mg/mL of an anti-LAG-3 antibody and about 37.5 mg/mL of an anti-PD-1 antibody.

In some aspects, the kit comprises about 20 mg/mL of an anti-LAG-3 antibody and about 5 mg/mL of an anti-PD-1 antibody.

In some aspects, the kit comprises about 75 mg/mL of an anti-LAG-3 antibody and about 75 mg/mL of an anti-PD-1 antibody.

In some aspects, the kit comprises about 100 mg/mL of an anti-LAG-3 antibody and about 50 mg/mL of an anti-PD-1 antibody.

In some aspects, the kit comprises about 80 mg of an anti-LAG-3 antibody and about 240 mg of an anti-PD-1 antibody.

In some aspects, the kit comprises about 160 mg of an anti-LAG-3 antibody and about 480 mg of an anti-PD-1 antibody.

In some aspects, the kit comprises about 360 mg of an anti-LAG-3 antibody and about 360 mg of an anti-PD-1 antibody.

In some aspects, the kit comprises about 480 mg of an anti-LAG-3 antibody and about 480 mg of an anti-PD-1 antibody.

In some aspects, the kit comprises about 720 mg of an anti-LAG-3 antibody and about 360 mg of an anti-PD-1 antibody.

In some aspects, the kit comprises about 800 mg of an anti-LAG-3 antibody and about 200 mg of an anti-PD-1 antibody.

In some aspects, the kit comprises about 960 mg of an anti-LAG-3 antibody and about 480 mg of an anti-PD-1 antibody.

Provided herein is a kit for treating a human subject afflicted with lung cancer, comprising: (a) 360 mg of an anti-LAG-3 antibody; (b) 360 mg of an anti-PD-1 antibody; and (c) instructions for using the anti-LAG-3 antibody and the anti-PD-1 antibody in a method for treating a human subject afflicted with lung cancer.

Provided herein is a kit for treating a human subject afflicted with lung cancer, comprising: (a) 720 mg of an anti-LAG-3 antibody; (b) 360 mg of an anti-PD-1 antibody; and (c) instructions for using the anti-LAG-3 antibody and the anti-PD-1 antibody in a method for treating a human subject afflicted with lung cancer.

Provided herein is a kit for treating a human subject afflicted with lung cancer, comprising: (a) an anti-LAG-3 antibody; (b) an anti-PD-1 antibody; and (c) instructions for preparing each of the antibodies in an amount of 360 mg and using the antibodies in a method for treating a human subject afflicted with lung cancer.

Provided herein is a kit for treating a human subject afflicted with lung cancer, comprising: (a) an anti-LAG-3 antibody; (b) an anti-PD-1 antibody; and (c) instructions for preparing the anti-LAG-3 and anti-PD-1 antibodies in an amount of 720 mg and 360 mg, respectively, and using the antibodies in a method for treating a human subject afflicted with lung cancer.

In some aspects, the anti-LAG-3 and anti-PD-1 antibodies are co-packaged in a single unit dosage form.

In some aspects, the anti-LAG-3 and anti-PD-1 antibodies are packaged as separate unit dosage forms.

In some aspects, 40 mg of the anti-LAG-3 antibody is provided in a unit dosage form.

In some aspects, 80 mg of the anti-LAG-3 antibody is provided in a unit dosage form.

In some aspects, 160 mg of the anti-LAG-3 antibody is provided in a unit dosage form.

In some aspects, 360 mg of the anti-LAG-3 antibody is provided in a unit dosage form.

In some aspects, 480 mg of the anti-LAG-3 antibody is provided in a unit dosage form.

In some aspects, 720 mg of the anti-LAG-3 antibody is provided in a unit dosage form.

In some aspects, 800 mg of the anti-LAG-3 antibody is provided in a unit dosage form.

In some aspects, 960 mg of the anti-LAG-3 antibody is provided in a unit dosage form.

In some aspects, 12.5 mg/mL of the anti-LAG-3 antibody is provided in a unit dosage form.

In some aspects, 20 mg/mL of the anti-LAG-3 antibody is provided in a unit dosage form.

In some aspects, 50 mg/mL of the anti-LAG-3 antibody is provided in a unit dosage form.

In some aspects, 75 mg/mL of the anti-LAG-3 antibody is provided in a unit dosage form.

In some aspects, 100 mg/mL of the anti-LAG-3 antibody is provided in a unit dosage form.

In some aspects, 130 mg/mL of the anti-LAG-3 antibody is provided in a unit dosage form.

In some aspects, 150 mg/mL of the anti-LAG-3 antibody is provided in a unit dosage form.

In some aspects, 175 mg/mL of the anti-LAG-3 antibody is provided in a unit dosage form.

In some aspects, 200 mg/mL of the anti-LAG-3 antibody is provided in a unit dosage form.

In some aspects, 10 mg of the anti-PD-1 antibody is provided in a unit dosage form.

In some aspects, 40 mg of the anti-PD-1 antibody is provided in a unit dosage form.

In some aspects, 100 mg of the anti-PD-1 antibody is provided in a unit dosage form.

In some aspects, 200 mg of the anti-PD-1 antibody is provided in a unit dosage form.

In some aspects, 240 mg of the anti-PD-1 antibody is provided in a unit dosage form.

In some aspects, 360 mg of the anti-PD-1 antibody is provided in a unit dosage form.

In some aspects, 480 mg of the anti-PD-1 antibody is provided in a unit dosage form.

In some aspects, 5 mg/mL of the anti-PD-1 antibody is provided in a unit dosage form.

In some aspects, 10 mg/mL of the anti-PD-1 antibody is provided in a unit dosage form.

In some aspects, 37.5 mg/mL of the anti-PD-1 antibody is provided in a unit dosage form.

In some aspects, 50 mg/mL of the anti-PD-1 antibody is provided in a unit dosage form.

In some aspects, 75 mg/mL of the anti-PD-1 antibody is provided in a unit dosage form.

In some aspects, 100 mg/mL of the anti-PD-1 antibody is provided in a unit dosage form.

In some aspects, 175 mg/mL of the anti-PD-1 antibody is provided in a unit dosage form.

In some aspects, 200 mg/mL of the anti-PD-1 antibody is provided in a unit dosage form.

In some aspects, the unit dosage form comprises from about 5 mM to about 50 mM of histidine, from about 50 mM to about 300 mM of sucrose, from about 5 μM to about 1 mM of diethylenetriaminepentaacetic acid (DTPA) or ethylenediaminetetraacetic acid (EDTA), and from about 0.001% to about 1% (w/v) of polysorbate or poloxamer (e.g., polysorbate 80 (PS80), polysorbate 20 (PS20), poloxamer 188 (PX188), or any combination thereof).

In some aspects, the unit dosage form comprises about 20 mM histidine, about 250 mM sucrose, about 50 μM DTPA, and 0.05% PS80.

In some aspects, the unit dosage form comprises a pH of from about 5 to about 6.5. In some aspects, the pH is about 5.3 to about 6.3. In some aspects, the pH is 5.8. In some aspects, the pH is 5.7.

In some aspects, the unit dosage form is a vial, syringe, or intravenous bag. In some aspects, the unit dosage form is an autoinjector. In some aspects, the unit dosage form is a vial comprising a stopper and a seal. In some aspects, the total volume in the vial is about 5 mL, about 6 mL, about 7 mL, about 8 mL, about 9 mL, about 10 mL, about 11 mL, about 12 mL, about 13 mL, about 14 mL, about 15 mL, about 16 mL, about 17 mL, about 18 mL, about 19 mL, or about 20 mL In some aspects, the kit provides instructions for administering the anti-LAG-3 antibody and/or the anti-PD-1 antibody intravenously for about 30 minutes.

In some aspects, the kit further comprises therapeutic agents for one or more PDCTs as disclosed herein. In some aspects, the therapeutic agents for one or more PDCTs are carboplatin and paclitaxel, carboplatin and albumin-bound paclitaxel, carboplatin and pemetrexed, and/or cisplatin and pemetrexed. In some aspects, the therapeutic agents are carboplatin, cisplatin, paclitaxel, albumin-bound paclitaxel, and pemetrexed.

All of the references cited above, as well as all references cited herein, are incorporated herein by reference in their entireties.

The following examples are offered by way of illustration and not by way of limitation.

EXAMPLES

Example 1

Combination of Anti-LAG-3 and Anti-PD-1 Antibodies with Chemotherapy for Treatment of Lung Cancer A multi-center, randomized trial ("Study A") will evaluate the efficacy and safety of the combination of nivolumab plus relatlimab with chemotherapy versus combination of nivolumab with chemotherapy in adults with untreated Stage IV or recurrent non-small cell lung cancer (NSCLC). The study will be carried out in 2 parts: Part 1, a site-and-subject blind dose safety confirmation; and Part 2, a double-blind, randomized, controlled trial.

Another multi-center, randomized trial ("Study B") will evaluate the efficacy and safety of the combination of nivolumab plus relatlimab with chemotherapy versus combination of pembrolizumab with chemotherapy in adults with untreated Stage IV or recurrent NSCLC.

Patient Inclusion/Exclusion Criteria

Patients will be male and female adults ≥18 years or local age of majority selected based on the following eligibility criteria: (1) histologically confirmed metastatic NSCLC of squamous (SQ) or non-squamous (NSQ) histology with Stage IV A/B (as defined by the 8th International Association for the Study of Lung Cancer Classification) or recurrent disease following multi-modal therapy for locally advanced disease; (2) measurable disease by computed tomography or magnetic resonance imaging per RECIST v1.1 criteria with radiographic tumor assessment performed within 28 days before randomization; (3) no prior systemic anti-cancer treatment given as primary therapy for advanced or metastatic disease; (4) ECOG PS of ≤1 at screening and confirmed prior to randomization; (5) a life expectancy of at least 3 months at the time of first dose; (6) a formalin-fixed paraffin-embedded tissue block containing enough tissue to cut 20 sections or a minimum of 20 unstained slides of tumor tissue from core biopsy, punch biopsy, excisional biopsy, or surgical specimen obtained during screening or prior to enrollment (within 3 months of enrollment if stored at 2-8° C. or within 2 months of enrollment if stored at ambient temperature and with no intervening systemic anti-cancer treatment between time of acquisition and enrollment); and (6) PD-L1 and LAG-3 immunohistochemistry (IHC) results during the screening period prior to randomization (LAG-3 expression on immune cells and PD-L1 expression on tumor cells will be measured using analytically validated assays).

Prior definitive chemoradiation for locally advanced disease is permitted as long as the last administration of chemotherapy or radiotherapy (whichever was given last) occurred at least 6 months prior to enrollment. Prior adjuvant or neoadjuvant chemotherapy for early-stage lung cancer is permitted if completed at least 6 months prior to initiating study treatment. Prior palliative radiotherapy to non-central nervous system (CNS) lesions must have been completed at least 2 weeks prior to treatment. Participants with symptomatic tumor lesions at baseline that may require palliative radiotherapy within 4 weeks of first treatment are strongly encouraged to receive palliative radiotherapy prior to treatment.

Key exclusion criteria will be: (1) women who are pregnant or breastfeeding; (2) participants with EGFR, ALK, or ROS-1 mutations that are sensitive to available targeted inhibitor therapy (all participants with NSQ histology must have been tested for EGFR, ALK or ROS-1 mutation status; participants with NSQ histology and unknown EGFR, ALK, or ROS-1 status are excluded); (3) participants with known BRAF V600E mutations that are sensitive to available targeted inhibitor therapy (participants with unknown or indeterminate BRAF mutation status are eligible); (4) participants with untreated central nervous system metastases; (5) participants with leptomeningeal metastases (carcinomatous meningitis); (6) concurrent malignancy requiring treatment or history of prior malignancy active within 2 years prior to enrollment (i.e., participants with a history of prior malignancy are eligible if treatment was completed at least 2 years before registration and the participant has no evidence of disease); (7) participants with an active, known, or suspected autoimmune disease; (8) prior treatment with an anti-PD-1, anti-PD-L1, anti-PD-L2, anti-LAG-3, or anti-CTLA-4 antibody, or any other antibody or drug specifically targeting T-cell co-stimulation or checkpoint pathways; and (9) participants with history of myocarditis.

Study A Design

Part 1—Dose Safety Confirmation

Up to approximately 120 eligible participants will be randomized 1:1 to experimental Arms A or B. The randomization will be stratified by histology (SQ vs NSQ NSCLC).

Arm A: Nivolumab 360 mg administered every three weeks (Q3W)+relatlimab 720 mg Q3W+4 cycles of histology-based PDCT.

Arm B: Nivolumab 360 mg Q3W+relatlimab 360 mg Q3W+4 cycles of histology-based PDCT.

Histology-based PDCT will be as follows:

NSQ: Carboplatin area under the concentration-time curve (AUC) 5 or 6 or cisplatin 75 $mg/m^{2+}$ pemetrexed 500 $mg/m^2$ (maintenance with pemetrexed permitted following completion of the cycles of PDCT).

SQ: Carboplatin AUC 6+paclitaxel 200 $mg/m^2$ or nab-paclitaxel (i.e., albumin-bound paclitaxel) 100 $mg/m^2$.

Nivolumab plus relatlimab will be administered in a site-and-subject blinded manner, whereas PDCT will be administered as open label.

The safety and tolerability of the combination of nivolumab plus relatlimab 720 mg and PDCT will be evaluated and the safety profile confirmed. The relatlimab 360 mg Q3W dose in Arm B will be evaluated to generate additional safety data at this dose level.

After all treated participants have been followed-up for a minimum of 12 weeks, the Part 1 safety data will be evaluated. In addition, the proportion of treatment-related adverse events (TRAEs) leading to discontinuation within 12 weeks of the first dose will be monitored for each arm separately using Bayesian continuous monitoring.

Part 2—Efficacy and Safety

Part 2 will be a double-blind, randomized, controlled trial that will further evaluate the efficacy and safety of the nivolumab and relatlimab plus chemotherapy combination versus nivolumab plus chemotherapy. Only after the safety of nivolumab plus relatlimab and PDCT has been confirmed in Part 1 of the study can enrollment begin in Part 2 of the study. At this time, participants that are in screening and found to be eligible will be randomized 1:1 into experimental Arm C or control Arm D. Enrollment will end when approximately 400 participants have been randomized. The stratification factors for randomization in Part 2 are PD-L 1 level (≥1% vs≤1% [including non-quantifiable (NQ)]), LAG-3 expression level (≥1% vs<1% [including NQ]), histology (SQ vs NSQ), and gender (male vs female).

Arm C: Nivolumab 360 mg Q3W+relatlimab 720 mg or 360 mg Q3W+4 cycles of histology based PDCT.

Arm D: Nivolumab 360 mg Q3W+placebo Q3W+4 cycles of histology-based PDCT.

Histology-based PDCT is as described for Part 1 of the study.

All participants will be treated until progression, presence of intolerable toxicities, withdrawal of consent, or study end, whichever comes first. Continuous safety evaluations and tumor assessments will guide the decision to treat a participant with additional cycles of study therapy if the participant has confirmed clinical benefit.

Participants will be allowed to continue study treatment until the first occurrence of any of the following situations: (1) progressive disease defined by RECIST v1.1 unless participants meet criteria for treatment beyond progression; (2) clinical deterioration suggesting that no further benefit from treatment is likely; (3) intolerability to therapy; or (4) participant meets criteria for discontinuation of study treatment.

Immunotherapy Dosing

Participants will receive masked nivolumab and relatlimab, followed by chemotherapy on Day 1 of every 3-week cycle. In Arms A, B, and C, nivolumab will be co-administered with relatlimab in a single bag IV over 30 minutes. In order to maintain blinding, Arm D participants will receive nivolumab+placebo (dextrose 5% or normal saline solution 0.9) IV also over 30 minutes. At the time of completion of the 4 cycles of chemotherapy, participants who have not experienced disease progression will continue to receive immunotherapy Q3W starting on Day 1 of the following cycle. There will be no dose escalations or reductions of immunotherapy allowed.

Chemotherapy Dosing

In all 4 study arms, 4 cycles of the histology-based PDCT option selected by the investigator will be administered on Day 1 Q3W. Participants with NSQ histology may also receive optional maintenance therapy with 500 mg/m$^2$ pemetrexed alone on Day 1 of each 3-week cycle until disease progression or unacceptable toxicity.

For PDCT with paclitaxel and carboplatin, participants will receive paclitaxel 200 mg/m$^2$ as a 180-minute IV infusion followed by carboplatin at a dose of AUC 6 as a 30-minute IV infusion on Day 1 of a 3-week cycle, or at doses per the local prescribing information. The infusion time can follow local institutional standards.

For PDCT with nab-paclitaxel and carboplatin, participants will receive nab-paclitaxel 100 mg/m$^2$ as a 30-minute IV infusion on Days 1, 8, and 15 of each 21-day cycle. Carboplatin at a dose of AUC 6 as a 30-minute IV infusion will be administered immediately after nab-paclitaxel on Day 1 of each 3-week cycle or at doses per the local prescribing information. The infusion time can follow local institutional standards.

For PDCT with pemetrexed and cisplatin, participants will receive pemetrexed at a dose of 500 mg/m$^2$ as a 10-minute IV infusion on Day 1 with cisplatin at a dose of 75 mg/m$^2$ infusion as per local standard practice on Day 1 of a 3-week treatment cycle for up to 4 cycles. Cisplatin will be administered to participants at least 30 minutes following the end of the pemetrexed infusion.

For PDCT with pemetrexed and carboplatin, participants will receive pemetrexed at a dose of 500 mg/m$^2$ as a 10-minute IV infusion on Day 1, followed by carboplatin at a dose of AUC 5 or 6 as a 30-minute IV infusion on Day 1 of a 3-week treatment cycle, for up to 4 cycles.

After Cycle 4 of chemotherapy, participants with NSQ histology who have stable disease or response are permitted to receive pemetrexed 500 mg/m$^2$ alone as maintenance therapy until disease progression or unacceptable toxicity.

Study B Design

Study B will be a double-blind, randomized, controlled trial that will further evaluate the safety and efficacy of the nivolumab and relatlimab plus chemotherapy combination versus pembrolizumab plus chemotherapy. Up to approximately 670 eligible participants will be randomized 1:1 to experimental Arm A or control Arm B. The randomization will be stratified by histology (SQ vs NSQ NSCLC), PD-L1 level (≥1% vs <1% [including non-quantifiable (NQ)]), LAG-3 expression level (≥1% vs<1% [including NQ]), and gender (male vs female).

Arm A: Nivolumab 360 mg Q3W+relatlimab 720 mg+4 cycles of histology based PDCT.

Arm B: Pembrolizumab 200 mg Q3W+4 cycles of histology-based PDCT.

Histology-based PDCT is as described for Part 1 of Study A.

All participants will be treated until progression, presence of intolerable toxicities, withdrawal of consent, or for 2 years, whichever comes first. Scans will occur Q6W for 1 year, then Q12W until progression or discontinuation of the study.

Immunotherapy and chemotherapy dosing will be conducted in a manner similar to Study A.

Example 2

Clinical Activity of Anti-LAG-3 Antibody in Combination with Anti-PD-1 Antibody in Patients with Lung Cancer Anti-LAG-3 antibody (relatlimab) in combination with anti-PD-1 antibody (nivolumab) was evaluated as a first line treatment of NSCLC.

A tumor tissue sample was obtained from each patient for determination of LAG-3 expression. Patients were stratified as LAG-3 expressers or non-expressers based on LAG-3 expression in tissue samples of ≥1% or less than 1%, respectively.

Patients were treated with 80 mg of relatlimab once every 2 weeks in combination with 240 mg nivolumab once every 2 weeks.

The best overall response (BOR) summary for all response evaluable subjects is shown in Table 1. The objective response rate (ORR) was defined as the proportion of treated subjects whose BOR was either a complete response (CR) or a partial response (PR) based on blinded independent clinical review (BICR) assessments by RECIST 1.1 Criteria. 2-sided 95% exact confidence intervals were determined by the Clopper-Pearson method.

TABLE 1

Best overall response summary

| Best Overall Response (BOR) (%) | LAG-3 Expressers N = 10 | LAG-3 Non-Expressers N = 5 | LAG-3 Evaluable N = 15 | All Subjects N = 23 |
|---|---|---|---|---|
| Complete Response (CR) | 1 (10.0) | 0 | 1 (6.7) | 1 (4.3) |
| Partial Response (PR) | 5 (50.0) | 1 (20.0) | 6 (40.0) | 6 (26.1) |
| Stable Disease (SD) | 3 (30.0) | 1 (20.0) | 4 (26.7) | 6 (26.1) |
| Stable Disease (≥12 weeks) | 3 (30.0) | 1 (20.0) | 4 (26.7) | 5 (21.7) |
| Progressive Disease (PD) | 1 (10.0) | 1 (20.0) | 2 (13.3) | 7 (30.4) |
| Non-CR/Non-PD | 0 | 0 | 0 | 0 |
| Unable to Determine | 0 | 2 (40.0) | 2 (13.3) | 3 (13.0) |
| Confirmed ORR (A) (%) | 6 (60.0) | 1 (20.0) | 7 (46.7) | 7 (30.4) |

TABLE 1-continued

| Best overall response summary | | | | |
|---|---|---|---|---|
| Best Overall Response (BOR) (%) | LAG-3 Expressers N = 10 | LAG-3 Non-Expressers N = 5 | LAG-3 Evaluable N = 15 | All Subjects N = 23 |
| 95% Confidence Limit | (26.2, 87.8) | (0.5, 71.6) | (21.3, 73.4) | (13.2, 52.9) |
| Confirmed CR + PR + SD (A) (%) | 9 (90.0) | 2 (40.0) | 11 (73.3) | 13 (56.5) |
| 95% Confidence Limit | (55.5, 99.7) | (5.3, 85.3) | (44.9, 92.2) | (34.5, 76.8) |
| Confirmed DCR (12 W) (A) (%) | 9 (90.0) | 2 (40.0) | 11 (73.3) | 12 (52.2) |
| 95% Confidence Limits | (55.5, 99.7) | (5.3, 85.3) | (44.9, 92.2) | (30.6, 73.2) |

(A) = Confirmed Response Only
DCR(12 W) = Disease Control Rate = CR + PR + SD at ≥12 weeks

SEQUENCE LISTING

```
Sequence total quantity: 86
SEQ ID NO: 1           moltype = AA  length = 447
FEATURE                Location/Qualifiers
source                 1..447
                       mol_type = protein
                       note = Heavy Chain Amino Acid Sequence; Anti-LAG-3 mAb
                        (BMS-986016)
                       organism = synthetic construct
SEQUENCE: 1
QVQLQQWGAG LLKPSETLSL TCAVYGGSFS DYYWNWIRQP PGKGLEWIGE INHRGSTNSN  60
PSLKSRVTLS LDTSKNQFSL KLRSVTAADT AVYYCAFGYS DYEYNWFDPW GQGTLVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLGK                                    447

SEQ ID NO: 2           moltype = AA  length = 214
FEATURE                Location/Qualifiers
source                 1..214
                       mol_type = protein
                       note = Light Chain Amino Acid Sequence; Anti-LAG-3 mAb
                        (BMS-986016)
                       organism = synthetic construct
SEQUENCE: 2
EIVLTQSPAT LSLSPGERAT LSCRASQSIS SYLAWYQQKP GQAPRLLIYD ASNRATGIPA  60
RFSGSGSGTD FTLTISSLEP EDFAVYYCQQ RSNWPLTFGQ GTNLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                            214

SEQ ID NO: 3           moltype = AA  length = 120
FEATURE                Location/Qualifiers
source                 1..120
                       mol_type = protein
                       note = Heavy Chain Variable Region (VH) Amino Acid
                        Sequence; Anti-LAG-3 mAb (BMS-986016)
                       organism = synthetic construct
SEQUENCE: 3
QVQLQQWGAG LLKPSETLSL TCAVYGGSFS DYYWNWIRQP PGKGLEWIGE INHRGSTNSN  60
PSLKSRVTLS LDTSKNQFSL KLRSVTAADT AVYYCAFGYS DYEYNWFDPW GQGTLVTVSS  120

SEQ ID NO: 4           moltype = AA  length = 107
FEATURE                Location/Qualifiers
source                 1..107
                       mol_type = protein
                       note = Light Chain Variable Region (VL) Amino Acid
                        Sequence; Anti-LAG-3 mAb (BMS-986016)
                       organism = synthetic construct
SEQUENCE: 4
EIVLTQSPAT LSLSPGERAT LSCRASQSIS SYLAWYQQKP GQAPRLLIYD ASNRATGIPA  60
RFSGSGSGTD FTLTISSLEP EDFAVYYCQQ RSNWPLTFGQ GTNLEIK              107

SEQ ID NO: 5           moltype = AA  length = 5
FEATURE                Location/Qualifiers
source                 1..5
                       mol_type = protein
                       note = Heavy Chain CDR1 Amino Acid Sequence; Anti-LAG-3 mAb
```

-continued

```
                        (BMS-986016)
                       organism = synthetic construct
SEQUENCE: 5
DYYWN                                                                 5

SEQ ID NO: 6           moltype = AA  length = 16
FEATURE                Location/Qualifiers
source                 1..16
                       mol_type = protein
                       note = Heavy Chain CDR2 Amino Acid Sequence; Anti-LAG-3 mAb
                        (BMS-986016)
                       organism = synthetic construct
SEQUENCE: 6
EINHRGSTNS NPSLKS                                                     16

SEQ ID NO: 7           moltype = AA  length = 12
FEATURE                Location/Qualifiers
source                 1..12
                       mol_type = protein
                       note = Heavy Chain CDR3 Amino Acid Sequence; Anti-LAG-3 mAb
                        (BMS-986016)
                       organism = synthetic construct
SEQUENCE: 7
GYSDYEYNWF DP                                                         12

SEQ ID NO: 8           moltype = AA  length = 11
FEATURE                Location/Qualifiers
source                 1..11
                       mol_type = protein
                       note = Light Chain CDR1 Amino Acid Sequence; Anti-LAG-3 mAb
                        (BMS-986016)
                       organism = synthetic construct
SEQUENCE: 8
RASQSISSYL A                                                          11

SEQ ID NO: 9           moltype = AA  length = 7
FEATURE                Location/Qualifiers
source                 1..7
                       mol_type = protein
                       note = Light Chain CDR2 Amino Acid Sequence; Anti-LAG-3 mAb
                        (BMS-986016)
                       organism = synthetic construct
SEQUENCE: 9
DASNRAT                                                               7

SEQ ID NO: 10          moltype = AA  length = 9
FEATURE                Location/Qualifiers
source                 1..9
                       mol_type = protein
                       note = Light Chain CDR3 Amino Acid Sequence; Anti-LAG-3 mAb
                        (BMS-986016)
                       organism = synthetic construct
SEQUENCE: 10
QQRSNWPLT                                                             9

SEQ ID NO: 11          moltype = AA  length = 440
FEATURE                Location/Qualifiers
source                 1..440
                       mol_type = protein
                       note = Heavy Chain Amino Acid Sequence; Anti-PD-1 mAb
                        (BMS-936558)
                       organism = synthetic construct
SEQUENCE: 11
QVQLVESGGG VVQPGRSLRL DCKASGITFS NSGMHWVRQA PGKGLEWVAV IWYDGSKRYY  60
ADSVKGRFTI SRDNSKNTLF LQMNSLRAED TAVYYCATND DYWGQGTLVT VSSASTKGPS  120
VFPLAPCSRS TSESTAALGC LVKDYFPEPV TVSWNSGALT SGVHTFPAVL QSSGLYSLSS  180
VVTVPSSSLG TKTYTCNVDH KPSNTKVDKR VESKYGPPCP PCPAPEFLGG PSVFLFPPKP  240
KDTLMISRTP EVTCVVVDVS QEDPEVQFNW YVDGVEVHNA KTKPREEQFN STYRVVSVLT  300
VLHQDWLNGK EYKCKVSNKG LPSSIEKTIS KAKGQPREPQ VYTLPPSQEE MTKNQVSLTC  360
LVKGFYPSDI AVEWESNGQP ENNYKTTPPV LDSDGSFFLY SRLTVDKSRW QEGNVFSCSV  420
MHEALHNHYT QKSLSLSLGK                                                 440

SEQ ID NO: 12          moltype = AA  length = 213
FEATURE                Location/Qualifiers
source                 1..213
                       mol_type = protein
                       note = Light Chain Amino Acid Sequence; Anti-PD-1 mAb
                        (BMS-936558)
                       organism = synthetic construct
```

```
SEQUENCE: 12
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ SSNWPRTFGQ GTKVEIKRTV AAPSVFIFPP  120
SDEQLKSGTA SVVCLLNNFY PREAKVQWKV DNALQSGNSQ ESVTEQDSKD STYSLSSTLL  180
SKADYEKHKV YACEVTHQGL SSPVTKSFNR GEC                               213

SEQ ID NO: 13          moltype = AA  length = 113
FEATURE                Location/Qualifiers
source                 1..113
                       mol_type = protein
                       note = Heavy Chain Variable Region (VH) Amino Acid
                        Sequence; Anti-PD-1 (BMS-936558)
                       organism = synthetic construct
SEQUENCE: 13
QVQLVESGGG VVQPGRSLRL DCKASGITFS NSGMHWVRQA PGKGLEWVAV IWYDGSKRYY  60
ADSVKGRFTI SRDNSKNTLF LQMNSLRAED TAVYYCATND DYWGQGTLVT VSS         113

SEQ ID NO: 14          moltype = AA  length = 107
FEATURE                Location/Qualifiers
source                 1..107
                       mol_type = protein
                       note = Light Chain Variable Region (VL) Amino Acid
                        Sequence; Anti-PD-1 mAb (BMS-936558)
                       organism = synthetic construct
SEQUENCE: 14
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ SSNWPRTFGQ GTKVEIK                107

SEQ ID NO: 15          moltype = AA  length = 5
FEATURE                Location/Qualifiers
source                 1..5
                       mol_type = protein
                       note = Heavy Chain CDR1 Amino Acid Sequence; Anti-PD-1 mAb
                        (BMS-936558)
                       organism = synthetic construct
SEQUENCE: 15
NSGMH                                                              5

SEQ ID NO: 16          moltype = AA  length = 17
FEATURE                Location/Qualifiers
source                 1..17
                       mol_type = protein
                       note = Heavy Chain CDR2 Amino Acid Sequence; Anti-PD-1 mAb
                        (BMS-936558)
                       organism = synthetic construct
SEQUENCE: 16
VIWYDGSKRY YADSVKG                                                 17

SEQ ID NO: 17          moltype = AA  length = 4
FEATURE                Location/Qualifiers
source                 1..4
                       mol_type = protein
                       note = Heavy Chain CDR3 Amino Acid Sequence; Anti-PD-1 mAb
                        (BMS-936558)
                       organism = synthetic construct
SEQUENCE: 17
NDDY                                                               4

SEQ ID NO: 18          moltype = AA  length = 11
FEATURE                Location/Qualifiers
source                 1..11
                       mol_type = protein
                       note = Light Chain CDR1 Amino Acid Sequence; Anti-PD-1 mAb
                        (BMS-936558)
                       organism = synthetic construct
SEQUENCE: 18
RASQSVSSYL A                                                       11

SEQ ID NO: 19          moltype = AA  length = 7
FEATURE                Location/Qualifiers
source                 1..7
                       mol_type = protein
                       note = Light Chain CDR2 Amino Acid Sequence; Anti-PD-1 mAb
                        (BMS-936558)
                       organism = synthetic construct
SEQUENCE: 19
DASNRAT                                                            7

SEQ ID NO: 20          moltype = AA  length = 9
```

-continued

```
FEATURE                Location/Qualifiers
source                 1..9
                       mol_type = protein
                       note = Light Chain CDR3 Amino Acid Sequence; Anti-PD-1 mAb
                        (BMS-936558)
                       organism = synthetic construct
SEQUENCE: 20
QQSSNWPRT                                                          9

SEQ ID NO: 21          moltype = AA  length = 446
FEATURE                Location/Qualifiers
source                 1..446
                       mol_type = protein
                       note = Heavy Chain Amino Acid Sequence; Anti-LAG-3 mAb
                        (BMS-986016)
                       organism = synthetic construct
SEQUENCE: 21
QVQLQQWGAG LLKPSETLSL TCAVYGGSFS DYYWNWIRQP PGKGLEWIGE INHRGSTNSN  60
PSLKSRVTLS LDTSKNQFSL KLRSVTAADT AVYYCAFGYS DYEYNWFDPW GQGTLVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLG                                       446

SEQ ID NO: 22          moltype = AA  length = 525
FEATURE                Location/Qualifiers
source                 1..525
                       mol_type = protein
                       note = Lymphocyte Activation Gene 3 Protein Amino Acid
                        Sequence
                       organism = synthetic construct
SEQUENCE: 22
MWEAQFLGLL FLQPLWVAPV KPLQPGAEVP VVWAQEGAPA QLPCSPTIPL QDLSLLRRAG  60
VTWQHQPDSG PPAAAPGHPL APGPHPAAPS SWGPRPRRYT VLSVGPGGLR SGRLPLQPRV  120
QLDERGRQRG DFSLWLRPAR RADAGEYRAA VHLRDRALSC RLRLRLGQAS MTASPPGSLR  180
ASDWVILNCS FSRPDRPASV HWFRNRGQGR VPVRESPHHH LAESFLFLPQ VSPMDSGPWG  240
CILTYRDGFN VSIMYNLTVL GLEPPTPLTV YAGAGSRVGL PCRLPAGVGT RSFLTAKWTP  300
PGGGPDLLVT GDNGDFTLRL EDVSQAQAGT YTCHIHLQEQ QLNATVTLAI ITVTPKSFGS  360
PGSLGKLLCE VTPVSGQERF VWSSLDTPSQ RSFSGPWLEA QEAQLLSQPW QCQLYQGERL  420
LGAAVYFTEL SSPGAQRSGR APGALPAGHL LLFLILGVLS LLLLVTGAFG FHLWRRQWRP  480
RRFSALEQGI HPPQAQSKIE ELEQEPEPEP EPEPEPEPEP EPEQL                  525

SEQ ID NO: 23          moltype = AA  length = 449
FEATURE                Location/Qualifiers
source                 1..449
                       mol_type = protein
                       note = Heavy Chain Amino Acid Sequence; Anti-LAG-3 mAb
                        (REGN3767)
                       organism = synthetic construct
SEQUENCE: 23
QVQLVESGGG VVQPGRSLRL SCVASGFTFS SYGMHWVRQA PGKGLEWVAI IWYDGSNKYY  60
ADSVKGRFTI SRDNSKNTQY LQMNSLRAED TAVYYCASVA TSGDFDYYGM DVWGQGTTVT  120
VSSASTKGPS VFPLAPCSRS TSESTAALGC LVKDYFPEPV TVSWNSGALT SGVHTFPAVL  180
QSSGLYSLSS VVTVPSSSLG TKTYTCNVDH KPSNTKVDKR VESKYGPPCP PCPAPPVAGP  240
SVFLFPPKPK DTLMISRTPE VTCVVVDVSQ EDPEVQFNWY VDGVEVHNAK TKPREEQFNS  300
TYRVVSVLTV LHQDWLNGKE YKCKVSNKGL PSSIEKTISK AKGQPREPQV YTLPPSQEEM  360
TKNQVSLTCL VKGFYPSDIA VEWESNGQPE NNYKTTPPVL DSDGSFFLYS RLTVDKSRWQ  420
EGNVFSCSVM HEALHNHYTQ KSLSLSLGK                                    449

SEQ ID NO: 24          moltype = AA  length = 214
FEATURE                Location/Qualifiers
source                 1..214
                       mol_type = protein
                       note = Light Chain Amino Acid Sequence; Anti-LAG-3 mAb
                        (REGN3767)
                       organism = synthetic construct
SEQUENCE: 24
EIVLTQSPAT LSLSPGERTT LSCRASQRIS TYLAWYQQKP GQAPRLLIYD ASKRATGIPA  60
RFSGSGSGTG FTLTISSLEP EDFAVYYCQQ RSNWPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                               214

SEQ ID NO: 25          moltype = AA  length = 123
FEATURE                Location/Qualifiers
source                 1..123
                       mol_type = protein
                       note = Heavy Chain Variable Region (VH) Amino Acid
```

```
                         Sequence; Anti-LAG-3 mAb (REGN3767)
                        organism = synthetic construct
SEQUENCE: 25
QVQLVESGGG VVQPGRSLRL SCVASGFTFS SYGMHWVRQA PGKGLEWVAI IWYDGSNKYY  60
ADSVKGRFTI SRDNSKNTQY LQMNSLRAED TAVYYCASVA TSGDFDYYGM DVWGQGTTVT  120
VSS                                                               123

SEQ ID NO: 26           moltype = AA  length = 107
FEATURE                 Location/Qualifiers
source                  1..107
                        mol_type = protein
                        note = Light Chain Variable Region (VL) Amino Acid
                         Sequence; Anti-LAG-3 mAb (REGN3767)
                        organism = synthetic construct
SEQUENCE: 26
EIVLTQSPAT LSLSPGERTT LSCRASQRIS TYLAWYQQKP GQAPRLLIYD ASKRATGIPA  60
RFSGSGSGTG FTLTISSLEP EDFAVYYCQQ RSNWPLTFGG GTKVEIK                107

SEQ ID NO: 27           moltype = AA  length = 8
FEATURE                 Location/Qualifiers
source                  1..8
                        mol_type = protein
                        note = Heavy Chain CDR1 Amino Acid Sequence; Anti-LAG-3 mAb
                         (REGN3767)
                        organism = synthetic construct
SEQUENCE: 27
GFTFSSYG                                                          8

SEQ ID NO: 28           moltype = AA  length = 8
FEATURE                 Location/Qualifiers
source                  1..8
                        mol_type = protein
                        note = Heavy Chain CDR2 Amino Acid Sequence; Anti-LAG-3 mAb
                         (REGN3767)
                        organism = synthetic construct
SEQUENCE: 28
IWYDGSNK                                                          8

SEQ ID NO: 29           moltype = AA  length = 16
FEATURE                 Location/Qualifiers
source                  1..16
                        mol_type = protein
                        note = Heavy Chain CDR3 Amino Acid Sequence; Anti-LAG-3 mAb
                         (REGN3767)
                        organism = synthetic construct
SEQUENCE: 29
ASVATSGDFD YYGMDV                                                 16

SEQ ID NO: 30           moltype = AA  length = 6
FEATURE                 Location/Qualifiers
source                  1..6
                        mol_type = protein
                        note = Light Chain CDR1 Amino Acid Sequence; Anti-LAG-3 mAb
                         (REGN3767)
                        organism = synthetic construct
SEQUENCE: 30
QRISTY                                                            6

SEQ ID NO: 31           moltype =   length =
SEQUENCE: 31
000

SEQ ID NO: 32           moltype = AA  length = 9
FEATURE                 Location/Qualifiers
source                  1..9
                        mol_type = protein
                        note = Light Chain CDR3 Amino Acid Sequence; Anti-LAG-3 mAb
                         (REGN3767)
                        organism = synthetic construct
SEQUENCE: 32
QQRSNWPLT                                                         9

SEQ ID NO: 33           moltype = AA  length = 444
FEATURE                 Location/Qualifiers
source                  1..444
                        mol_type = protein
                        note = Heavy Chain Amino Acid Sequence; Anti-PD-1 mAb
                         (REGN2810)
                        organism = synthetic construct
```

```
SEQUENCE: 33
EVQLLESGGV LVQPGGSLRL SCAASGFTFS NFGMTWVRQA PGKGLEWVSG ISGGGRDTYF  60
ADSVKGRFTI SRDNSKNTLY LQMNSLKGED TAVYYCVKWG NIYFDYWGQG TLVTVSSAST  120
KGPSVFPLAP CSRSTSESTA ALGCLVKDYF PEPVTVSWNS GALTSGVHTF PAVLQSSGLY  180
SLSSVVTVPS SSLGTKTYTC NVDHKPSNTK VDKRVESKYG PPCPPCPAPE FLGGPSVFLF  240
PPKPKDTLMI SRTPEVTCVV VDVSQEDPEV QFNWYVDGVE VHNAKTKPRE EQFNSTYRVV  300
SVLTVLHQDW LNGKEYKCKV SNKGLPSSIE KTISKAKGQP REPQVYTLPP SQEEMTKNQV  360
SLTCLVKGFY PSDIAVEWES NGQPENNYKT TPPVLDSDGS FFLYSRLTVD KSRWQEGNVF  420
SCSVMHEALH NHYTQKSLSL SLGK                                        444

SEQ ID NO: 34          moltype = AA  length = 214
FEATURE                Location/Qualifiers
source                 1..214
                       mol_type = protein
                       note = Light Chain Amino Acid Sequence; Anti-PD-1 mAb
                        (REGN2810)
                       organism = synthetic construct
SEQUENCE: 34
DIQMTQSPSS LSASVGDSIT ITCRASLSIN TFLNWYQQKP GKAPNLLIYA ASSLHGGVPS  60
RFSGSGSGTD FTLTIRTLQP EDFATYYCQQ SSNTPFTFGP GTVVDFRRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 35          moltype = AA  length = 117
FEATURE                Location/Qualifiers
source                 1..117
                       mol_type = protein
                       note = Heavy Chain Variable Region (VH) Amino Acid
                        Sequence; Anti-PD-1 mAb (REGN2810)
                       organism = synthetic construct
SEQUENCE: 35
EVQLLESGGV LVQPGGSLRL SCAASGFTFS NFGMTWVRQA PGKGLEWVSG ISGGGRDTYF  60
ADSVKGRFTI SRDNSKNTLY LQMNSLKGED TAVYYCVKWG NIYFDYWGQG TLVTVSS     117

SEQ ID NO: 36          moltype = AA  length = 107
FEATURE                Location/Qualifiers
source                 1..107
                       mol_type = protein
                       note = Light Chain Variable Region (VL) Amino Acid
                        Sequence; Anti-PD-1 mAb (REGN2810)
                       organism = synthetic construct
SEQUENCE: 36
DIQMTQSPSS LSASVGDSIT ITCRASLSIN TFLNWYQQKP GKAPNLLIYA ASSLHGGVPS  60
RFSGSGSGTD FTLTIRTLQP EDFATYYCQQ SSNTPFTFGP GTVVDFR                107

SEQ ID NO: 37          moltype = AA  length = 8
FEATURE                Location/Qualifiers
source                 1..8
                       mol_type = protein
                       note = Heavy Chain CDR1 Amino Acid Sequence; Anti-PD-1 mAb
                        (REGN2810)
                       organism = synthetic construct
SEQUENCE: 37
GFTFSNFG                                                          8

SEQ ID NO: 38          moltype = AA  length = 8
FEATURE                Location/Qualifiers
source                 1..8
                       mol_type = protein
                       note = Heavy Chain CDR2 Amino Acid Sequence; Anti-PD-1 mAb
                        (REGN2810)
                       organism = synthetic construct
SEQUENCE: 38
ISGGGRDT                                                          8

SEQ ID NO: 39          moltype = AA  length = 10
FEATURE                Location/Qualifiers
source                 1..10
                       mol_type = protein
                       note = Heavy Chain CDR3 Amino Acid Sequence; Anti-PD-1 mAb
                        (REGN2810)
                       organism = synthetic construct
SEQUENCE: 39
VKWGNIYFDY                                                        10

SEQ ID NO: 40          moltype = AA  length = 6
FEATURE                Location/Qualifiers
source                 1..6
                       mol_type = protein
```

-continued

```
                        note = Light Chain CDR1 Amino Acid Sequence; Anti-PD-1 mAb
                         (REGN2810)
                        organism = synthetic construct
SEQUENCE: 40
LSINTF                                                      6

SEQ ID NO: 41           moltype =   length =
SEQUENCE: 41
000

SEQ ID NO: 42           moltype = AA  length = 9
FEATURE                 Location/Qualifiers
source                  1..9
                        mol_type = protein
                        note = Light Chain CDR3 Amino Acid Sequence; Anti-PD-1 mAb
                         (REGN2810)
                        organism = synthetic construct
SEQUENCE: 42
QQSSNTPFT                                                   9

SEQ ID NO: 43           moltype = AA  length = 451
FEATURE                 Location/Qualifiers
source                  1..451
                        mol_type = protein
                        note = Heavy Chain Amino Acid Sequence; Anti-LAG-3 mAb
                         (LAG525)
                        organism = synthetic construct
SEQUENCE: 43
QVQLVQSGAE VKKPGASVKV SCKASGFTLT NYGMNWVRQA RGQRLEWIGW INTDTGEPTY  60
ADDFKGRFVF SLDTSVSTAY LQISSLKAED TAVYYCARNP PYYYGTNNAE AMDYWGQGTT  120
VTVSSASTKG PSVFPLAPCS RSTSESTAAL GCLVKDYFPE PVTVSWNSGA LTSGVHTFPA  180
VLQSSGLYSL SSVVTVPSSS LGTKTYTCNV DHKPSNTKVD KRVESKYGPP CPPCPAPEFL  240
GGPSVFLFPP KPKDTLMISR TPEVTCVVVD VSQEDPEVQF NWYVDGVEVH NAKTKPREEQ  300
FNSTYRVVSV LTVLHQDWLN GKEYKCKVSN KGLPSSIEKT ISKAKGQPRE PQVYTLPPSQ  360
EEMTKNQVSL TCLVKGFYPS DIAVEWESNG QPENNYKTTP PVLDSDGSFF LYSRLTVDKS  420
RWQEGNVFSC SVMHEALHNH YTQKSLSLSL G                          451

SEQ ID NO: 44           moltype = AA  length = 451
FEATURE                 Location/Qualifiers
source                  1..451
                        mol_type = protein
                        note = Heavy Chain Amino Acid Sequence; Anti-LAG-3 mAb
                         (LAG525)
                        organism = synthetic construct
SEQUENCE: 44
QVQLVQSGAE VKKPGASVKV SCKASGFTLT NYGMNWVRQA PGQGLEWMGW INTDTGEPTY  60
ADDFKGRFVF SLDTSVSTAY LQISSLKAED TAVYYCARNP PYYYGTNNAE AMDYWGQGTT  120
VTVSSASTKG PSVFPLAPCS RSTSESTAAL GCLVKDYFPE PVTVSWNSGA LTSGVHTFPA  180
VLQSSGLYSL SSVVTVPSSS LGTKTYTCNV DHKPSNTKVD KRVESKYGPP CPPCPAPEFL  240
GGPSVFLFPP KPKDTLMISR TPEVTCVVVD VSQEDPEVQF NWYVDGVEVH NAKTKPREEQ  300
FNSTYRVVSV LTVLHQDWLN GKEYKCKVSN KGLPSSIEKT ISKAKGQPRE PQVYTLPPSQ  360
EEMTKNQVSL TCLVKGFYPS DIAVEWESNG QPENNYKTTP PVLDSDGSFF LYSRLTVDKS  420
RWQEGNVFSC SVMHEALHNH YTQKSLSLSL G                          451

SEQ ID NO: 45           moltype = AA  length = 214
FEATURE                 Location/Qualifiers
source                  1..214
                        mol_type = protein
                        note = Light Chain Amino Acid Sequence; Anti-LAG-3 mAb
                         (LAG525)
                        organism = synthetic construct
SEQUENCE: 45
DIQMTQSPSS LSASVGDRVT ITCSSSQDIS NYLNWYLQKP GQSPQLLIYY TSTLHLGVPS  60
RFSGSGSGTE FTLTISSLQP DDFATYYCQQ YYNLPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                       214

SEQ ID NO: 46           moltype = AA  length = 214
FEATURE                 Location/Qualifiers
source                  1..214
                        mol_type = protein
                        note = Light Chain Amino Acid Sequence; Anti-LAG-3 mAb
                         (LAG525)
                        organism = synthetic construct
SEQUENCE: 46
DIQMTQSPSS LSASVGDRVT ITCSSSQDIS NYLNWYQQKP GKAPKLLIYY TSTLHLGIPP  60
RFSGSGYGTD FTLTINNIES EDAAYYFCQQ YYNLPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                       214
```

-continued

```
SEQ ID NO: 47          moltype = AA  length = 125
FEATURE                Location/Qualifiers
source                 1..125
                       mol_type = protein
                       note = Heavy Chain Variable Region (VH) Amino Acid
                        Sequence; Anti-LAG-3 mAb (LAG525)
                       organism = synthetic construct
SEQUENCE: 47
QVQLVQSGAE VKKPGASVKV SCKASGFTLT NYGMNWVRQA RGQRLEWIGW INTDTGEPTY  60
ADDFKGRFVF SLDTSVSTAY LQISSLKAED TAVYYCARNP PYYYGTNNAE AMDYWGQGTT  120
VTVSS                                                             125

SEQ ID NO: 48          moltype = AA  length = 125
FEATURE                Location/Qualifiers
source                 1..125
                       mol_type = protein
                       note = Heavy Chain Variable Region (VH) Amino Acid
                        Sequence; Anti-LAG-3 mAb (LAG525)
                       organism = synthetic construct
SEQUENCE: 48
QVQLVQSGAE VKKPGASVKV SCKASGFTLT NYGMNWVRQA PGQGLEWMGW INTDTGEPTY  60
ADDFKGRFVF SLDTSVSTAY LQISSLKAED TAVYYCARNP PYYYGTNNAE AMDYWGQGTT  120
VTVSS                                                             125

SEQ ID NO: 49          moltype = AA  length = 107
FEATURE                Location/Qualifiers
source                 1..107
                       mol_type = protein
                       note = Light Chain Variable Region (VL) Amino Acid
                        Sequence; Anti-LAG-3 mAb (LAG525)
                       organism = synthetic construct
SEQUENCE: 49
DIQMTQSPSS LSASVGDRVT ITCSSSQDIS NYLNWYLQKP GQSPQLLIYY TSTLHLGVPS  60
RFSGSGSGTE FTLTISSLQP DDFATYYCQQ YYNLPWTFGQ GTKVEIK                107

SEQ ID NO: 50          moltype = AA  length = 107
FEATURE                Location/Qualifiers
source                 1..107
                       mol_type = protein
                       note = Light Chain Variable Region (VL) Amino Acid
                        Sequence; Anti-LAG-3 mAb (LAG525)
                       organism = synthetic construct
SEQUENCE: 50
DIQMTQSPSS LSASVGDRVT ITCSSSQDIS NYLNWYQQKP GKAPKLLIYY TSTLHLGIPP  60
RFSGSGYGTD FTLTINNIES EDAAYYFCQQ YYNLPWTFGQ GTKVEIK                107

SEQ ID NO: 51          moltype = AA  length = 5
FEATURE                Location/Qualifiers
source                 1..5
                       mol_type = protein
                       note = Heavy Chain CDR1 Amino Acid Sequence; Anti-LAG-3 mAb
                        (LAG525)
                       organism = synthetic construct
SEQUENCE: 51
NYGMN                                                             5

SEQ ID NO: 52          moltype = AA  length = 17
FEATURE                Location/Qualifiers
source                 1..17
                       mol_type = protein
                       note = Heavy Chain CDR2 Amino Acid Sequence; Anti-LAG-3 mAb
                        (LAG525)
                       organism = synthetic construct
SEQUENCE: 52
WINTDTGEPT YADDFKG                                                17

SEQ ID NO: 53          moltype = AA  length = 16
FEATURE                Location/Qualifiers
source                 1..16
                       mol_type = protein
                       note = Heavy Chain CDR3 Amino Acid Sequence; Anti-LAG-3 mAb
                        (LAG525)
                       organism = synthetic construct
SEQUENCE: 53
NPPYYYGTNN AEAMDY                                                 16

SEQ ID NO: 54          moltype = AA  length = 11
FEATURE                Location/Qualifiers
```

-continued

```
source                  1..11
                        mol_type = protein
                        note = Light Chain CDR1 Amino Acid Sequence; Anti-LAG-3 mAb
                         (LAG525)
                        organism = synthetic construct
SEQUENCE: 54
SSSQDISNYL N                                                 11

SEQ ID NO: 55           moltype = AA  length = 7
FEATURE                 Location/Qualifiers
source                  1..7
                        mol_type = protein
                        note = Light Chain CDR2 Amino Acid Sequence; Anti-LAG-3 mAb
                         (LAG525)
                        organism = synthetic construct
SEQUENCE: 55
YTSTLHL                                                      7

SEQ ID NO: 56           moltype = AA  length = 9
FEATURE                 Location/Qualifiers
source                  1..9
                        mol_type = protein
                        note = Light Chain CDR3 Amino Acid Sequence; Anti-LAG-3 mAb
                         (LAG525)
                        organism = synthetic construct
SEQUENCE: 56
QQYYNLPWT                                                    9

SEQ ID NO: 57           moltype = AA  length = 443
FEATURE                 Location/Qualifiers
source                  1..443
                        mol_type = protein
                        note = Heavy Chain Amino Acid Sequence; Anti-PD-1 mAb
                         (PDR001)
                        organism = synthetic construct
SEQUENCE: 57
EVQLVQSGAE VKKPGESLRI SCKGSGYTFT TYWMHWVRQA TGQGLEWMGN IYPGTGGSNF  60
DEKFKNRVTI TADKSTSTAY MELSSLRSED TAVYYCTRWT TGTGAYWGQG TTVTVSSAST  120
KGPSVFPLAP CSRSTSESTA ALGCLVKDYF PEPVTVSWNS GALTSGVHTF PAVLQSSGLY  180
SLSSVVTVPS SSLGTKTYTC NVDHKPSNTK VDKRVESKYG PPCPPCPAPE FLGGPSVFLF  240
PPKPKDTLMI SRTPEVTCVV VDVSQEDPEV QFNWYVDGVE VHNAKTKPRE EQFNSTYRVV  300
SVLTVLHQDW LNGKEYKCKV SNKGLPSSIE KTISKAKGQP REPQVYTLPP SQEEMTKNQV  360
SLTCLVKGFY PSDIAVEWES NGQPENNYKT TPPVLDSDGS FFLYSRLTVD KSRWQEGNVF  420
SCSVMHEALH NHYTQKSLSL SLG                                    443

SEQ ID NO: 58           moltype = AA  length = 220
FEATURE                 Location/Qualifiers
source                  1..220
                        mol_type = protein
                        note = Light Chain Amino Acid Sequence; Anti-PD-1 mAb
                         (PDR001)
                        organism = synthetic construct
SEQUENCE: 58
EIVLTQSPAT LSLSPGERAT LSCKSSQSLL DSGNQKNFLT WYQQKPGQAP RLLIYWASTR  60
ESGVPSRFSG SGSGTDFTFT ISSLEAEDAA TYYCQNDYSY PYTFGQGTKV EIKRTVAAPS  120
VFIFPPSDEQ LKSGTASVVC LLNNFYPREA KVQWKVDNAL QSGNSQESVT EQDSKDSTYS  180
LSSTLTLSKA DYEKHKVYAC EVTHQGLSSP VTKSFNRGEC                   220

SEQ ID NO: 59           moltype = AA  length = 117
FEATURE                 Location/Qualifiers
source                  1..117
                        mol_type = protein
                        note = Heavy Chain Variable Region (VH) Amino Acid
                         Sequence; Anti-PD-1 mAb (PDR001)
                        organism = synthetic construct
SEQUENCE: 59
EVQLVQSGAE VKKPGESLRI SCKGSGYTFT TYWMHWVRQA TGQGLEWMGN IYPGTGGSNF  60
DEKFKNRVTI TADKSTSTAY MELSSLRSED TAVYYCTRWT TGTGAYWGQG TTVTVSS     117

SEQ ID NO: 60           moltype = AA  length = 113
FEATURE                 Location/Qualifiers
source                  1..113
                        mol_type = protein
                        note = Light Chain Variable Region (VL) Amino Acid
                         Sequence; Anti-PD-1 mAb (PDR001)
                        organism = synthetic construct
SEQUENCE: 60
EIVLTQSPAT LSLSPGERAT LSCKSSQSLL DSGNQKNFLT WYQQKPGQAP RLLIYWASTR  60
ESGVPSRFSG SGSGTDFTFT ISSLEAEDAA TYYCQNDYSY PYTFGQGTKV EIK         113
```

-continued

```
SEQ ID NO: 61          moltype = AA  length = 5
FEATURE                Location/Qualifiers
source                 1..5
                       mol_type = protein
                       note = Heavy Chain CDR1 Amino Acid Sequence; Anti-PD-1 mAb
                        (PDR001)
                       organism = synthetic construct
SEQUENCE: 61
TYWMH                                                                5

SEQ ID NO: 62          moltype = AA  length = 17
FEATURE                Location/Qualifiers
source                 1..17
                       mol_type = protein
                       note = Heavy Chain CDR2 Amino Acid Sequence; Anti-PD-1 mAb
                        (PDR001)
                       organism = synthetic construct
SEQUENCE: 62
NIYPGTGGSN FDEKFKN                                                   17

SEQ ID NO: 63          moltype = AA  length = 8
FEATURE                Location/Qualifiers
source                 1..8
                       mol_type = protein
                       note = Heavy Chain CDR3 Amino Acid Sequence; Anti-PD-1 mAb
                        (PDR001)
                       organism = synthetic construct
SEQUENCE: 63
WTTGTGAY                                                             8

SEQ ID NO: 64          moltype = AA  length = 17
FEATURE                Location/Qualifiers
source                 1..17
                       mol_type = protein
                       note = Light Chain CDR1 Amino Acid Sequence; Anti-PD-1 mAb
                        (PDR001)
                       organism = synthetic construct
SEQUENCE: 64
KSSQSLLDSG NQKNFLT                                                   17

SEQ ID NO: 65          moltype = AA  length = 7
FEATURE                Location/Qualifiers
source                 1..7
                       mol_type = protein
                       note = Light Chain CDR2 Amino Acid Sequence; Anti-PD-1 mAb
                        (PDR001)
                       organism = synthetic construct
SEQUENCE: 65
WASTRES                                                              7

SEQ ID NO: 66          moltype = AA  length = 9
FEATURE                Location/Qualifiers
source                 1..9
                       mol_type = protein
                       note = Light Chain CDR3 Amino Acid Sequence; Anti-PD-1 mAb
                        (PDR001)
                       organism = synthetic construct
SEQUENCE: 66
QNDYSYPYT                                                            9

SEQ ID NO: 67          moltype = AA  length = 446
FEATURE                Location/Qualifiers
source                 1..446
                       mol_type = protein
                       note = Heavy Chain Amino Acid Sequence; Anti-LAG-3 mAb
                        (MK4280)
                       organism = synthetic construct
SEQUENCE: 67
QMQLVQSGPE VKKPGTSVKV SCKASGYTFT DYNVDWVRQA RGQRLEWIGD INPNDGGTIY  60
AQKFQERVTI TVDKSTSTAY MELSSLRSED TAVYYCARNY RWFGAMDHWG QGTTVTVSSA  120
STKGPSVFPL APCSRSTSES TAALGCLVKD YFPEPVTVSW NSGALTSGVH TFPAVLQSSG  180
LYSLSSVVTV PSSSLGTKTY TCNVDHKPSN TKVDKRVESK YGPPCPPCPA PEFLGGPSVF  240
LFPPKPKDTL MISRTPEVTC VVVDVSQEDP EVQFNWYVDG VEVHNAKTKP REEQFNSTYR  300
VVSVLTVLHQ DWLNGKEYKC KVSNKGLPSS IEKTISKAKG QPREPQVYTL PPSQEEMTKN  360
QVSLTCLVKG FYPSDIAVEW ESNGQPENNY KTTPPVLDSD GSFFLYSRLT VDKSRWQEGN  420
VFSCSVMHEA LHNHYTQKSL SLSLGK                                       446

SEQ ID NO: 68          moltype = AA  length = 218
```

-continued

```
FEATURE                Location/Qualifiers
source                 1..218
                       mol_type = protein
                       note = Light Chain Amino Acid Sequence; Anti-LAG-3 mAb
                        (MK4280)
                       organism = synthetic construct
SEQUENCE: 68
DIVMTQTPLS LSVTPGQPAS ISCKASQSLD YEGDSDMNWY LQKPGQPPQL LIYGASNLES  60
GVPDRFSGSG SGTDFTLKIS RVEAEDVGVY YCQQSTEDPR TFGGGTKVEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 69          moltype = AA  length = 119
FEATURE                Location/Qualifiers
source                 1..119
                       mol_type = protein
                       note = Heavy Chain Variable Region (VH) Amino Acid
                        Sequence; Anti-LAG-3 mAb (MK4280)
                       organism = synthetic construct
SEQUENCE: 69
QMQLVQSGPE VKKPGTSVKV SCKASGYTFT DYNVDWVRQA RGQRLEWIGD INPNDGGTIY  60
AQKFQERVTI TVDKSTSTAY MELSSLRSED TAVYYCARNY RWFGAMDHWG QGTTVTVSS   119

SEQ ID NO: 70          moltype = AA  length = 111
FEATURE                Location/Qualifiers
source                 1..111
                       mol_type = protein
                       note = Light Chain Variable Region (VL) Amino Acid
                        Sequence; Anti-LAG-3 Anti-LAG-3 mAb (MK4280)
                       organism = synthetic construct
SEQUENCE: 70
DIVMTQTPLS LSVTPGQPAS ISCKASQSLD YEGDSDMNWY LQKPGQPPQL LIYGASNLES  60
GVPDRFSGSG SGTDFTLKIS RVEAEDVGVY YCQQSTEDPR TFGGGTKVEI K           111

SEQ ID NO: 71          moltype = AA  length = 5
FEATURE                Location/Qualifiers
source                 1..5
                       mol_type = protein
                       note = Heavy Chain CDR1 Amino Acid Sequence; Anti-LAG-3 mAb
                        (MK4280)
                       organism = synthetic construct
SEQUENCE: 71
DYNVD                                                              5

SEQ ID NO: 72          moltype = AA  length = 17
FEATURE                Location/Qualifiers
source                 1..17
                       mol_type = protein
                       note = Heavy Chain CDR2 Amino Acid Sequence; Anti-LAG-3 mAb
                        (MK4280)
                       organism = synthetic construct
SEQUENCE: 72
DINPNDGGTI YAQKFQE                                                 17

SEQ ID NO: 73          moltype = AA  length = 10
FEATURE                Location/Qualifiers
source                 1..10
                       mol_type = protein
                       note = Heavy Chain CDR3 Amino Acid Sequence; Anti-LAG-3 mAb
                        (MK4280)
                       organism = synthetic construct
SEQUENCE: 73
NYRWFGAMDH                                                         10

SEQ ID NO: 74          moltype = AA  length = 15
FEATURE                Location/Qualifiers
source                 1..15
                       mol_type = protein
                       note = Light Chain CDR1 Amino Acid Sequence; Anti-LAG-3 mAb
                        (MK4280)
                       organism = synthetic construct
SEQUENCE: 74
KASQSLDYEG DSDMN                                                   15

SEQ ID NO: 75          moltype = AA  length = 7
FEATURE                Location/Qualifiers
source                 1..7
                       mol_type = protein
                       note = Light Chain CDR2 Amino Acid Sequence; Anti-LAG-3 mAb
```

-continued

```
                        (MK4280)
                       organism = synthetic construct
SEQUENCE: 75
GASNLES                                                        7

SEQ ID NO: 76          moltype = AA  length = 9
FEATURE                Location/Qualifiers
source                 1..9
                       mol_type = protein
                       note = Light Chain CDR3 Amino Acid Sequence; Anti-LAG-3 mAb
                        (MK4280)
                       organism = synthetic construct
SEQUENCE: 76
QQSTEDPRT                                                      9

SEQ ID NO: 77          moltype = AA  length = 447
FEATURE                Location/Qualifiers
source                 1..447
                       mol_type = protein
                       note = Heavy Chain Amino Acid Sequence; Anti-PD-1 mAb
                        (MK3475)
                       organism = synthetic construct
SEQUENCE: 77
QVQLVQSGVE VKKPGASVKV SCKASGYTFT NYYMYWVRQA PGQGLEWMGG INPSNGGTNF  60
NEKFKNRVTL TTDSSTTTAY MELKSLQFDD TAVYYCARRD YRFDMGFDYW GQGTTVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLGK                                  447

SEQ ID NO: 78          moltype = AA  length = 218
FEATURE                Location/Qualifiers
source                 1..218
                       mol_type = protein
                       note = Light Chain Amino Acid Sequence; Anti-PD-1 mAb
                        (MK3475)
                       organism = synthetic construct
SEQUENCE: 78
EIVLTQSPAT LSLSPGERAT LSCRASKGVS TSGYSYLHWY QQKPGQAPRL LIYLASYLES  60
GVPARFSGSG SGTDFTLTIS SLEPEDFAVY YCQHSRDLPL TFGGGTKVEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                       218

SEQ ID NO: 79          moltype = AA  length = 120
FEATURE                Location/Qualifiers
source                 1..120
                       mol_type = protein
                       note = Heavy Chain Variable Region (VH) Amino Acid
                        Sequence; Anti-PD-1 mAb (MK3475)
                       organism = synthetic construct
SEQUENCE: 79
QVQLVQSGVE VKKPGASVKV SCKASGYTFT NYYMYWVRQA PGQGLEWMGG INPSNGGTNF  60
NEKFKNRVTL TTDSSTTTAY MELKSLQFDD TAVYYCARRD YRFDMGFDYW GQGTTVTVSS  120

SEQ ID NO: 80          moltype = AA  length = 111
FEATURE                Location/Qualifiers
source                 1..111
                       mol_type = protein
                       note = Light Chain Variable Region (VL) Amino Acid
                        Sequence; Anti-PD-1 mAb (MK3475)
                       organism = synthetic construct
SEQUENCE: 80
EIVLTQSPAT LSLSPGERAT LSCRASKGVS TSGYSYLHWY QQKPGQAPRL LIYLASYLES  60
GVPARFSGSG SGTDFTLTIS SLEPEDFAVY YCQHSRDLPL TFGGGTKVEI K          111

SEQ ID NO: 81          moltype = AA  length = 5
FEATURE                Location/Qualifiers
source                 1..5
                       mol_type = protein
                       note = Heavy Chain CDR1 Amino Acid Sequence; Anti-PD-1 mAb
                        (MK3475)
                       organism = synthetic construct
SEQUENCE: 81
NYYMY                                                          5

SEQ ID NO: 82          moltype = AA  length = 17
FEATURE                Location/Qualifiers
```

-continued

```
source                1..17
                      mol_type = protein
                      note = Heavy Chain CDR2 Amino Acid Sequence; Anti-PD-1 mAb
                       (MK4280)
                      organism = synthetic construct
SEQUENCE: 82
GINPSNGGTN FNEKFKN                                                   17

SEQ ID NO: 83         moltype = AA  length = 11
FEATURE               Location/Qualifiers
source                1..11
                      mol_type = protein
                      note = Heavy Chain CDR3 Amino Acid Sequence; Anti-PD-1 mAb
                       (MK3475)
                      organism = synthetic construct
SEQUENCE: 83
RDYRFDMGFD Y                                                         11

SEQ ID NO: 84         moltype = AA  length = 15
FEATURE               Location/Qualifiers
source                1..15
                      mol_type = protein
                      note = Light Chain CDR1 Amino Acid Sequence; Anti-PD-1 mAb
                       (MK3475)
                      organism = synthetic construct
SEQUENCE: 84
RASKGVSTSG YSYLH                                                     15

SEQ ID NO: 85         moltype = AA  length = 7
FEATURE               Location/Qualifiers
source                1..7
                      mol_type = protein
                      note = Light Chain CDR2 Amino Acid Sequence; Anti-PD-1 mAb
                       (MK3475)
                      organism = synthetic construct
SEQUENCE: 85
LASYLES                                                              7

SEQ ID NO: 86         moltype = AA  length = 9
FEATURE               Location/Qualifiers
source                1..9
                      mol_type = protein
                      note = Light Chain CDR3 Amino Acid Sequence; Anti-PD-1 mAb
                       (MK3475)
                      organism = synthetic construct
SEQUENCE: 86
QHSRDLPLT                                                            9
```

What is claimed is:

1. A method of treating a non-small cell lung cancer (NSCLC) in a human subject, the method comprising administering to the subject:

(a) about 360 mg of an anti-LAG-3 antibody comprising a heavy chain variable region CDR1, CDR2, and CDR3 comprising the sequences set forth in SEQ ID NO:5, SEQ ID NO: 6, and SEQ ID NO:7, respectively, and a light chain variable region CDR1, CDR2, and CDR3 comprising the sequences set forth in SEQ ID NO:8, SEQ ID NO:9, and SEQ ID NO:10, respectively, (b) about 360 mg of an anti-PD-1 antibody comprising a heavy chain variable region CDR1, CDR2, and CDR3 comprising the sequences set forth in SEQ ID NO:15, SEQ ID NO: 16, and SEQ ID NO: 17, respectively, and a light chain variable region CDR1, CDR2, and CDR3 comprising the sequences set forth in SEQ ID NO:18, SEQ ID NO: 19, and SEQ ID NO:20, respectively, and (c) a platinum doublet chemotherapy (PDCT) comprising: (i) cisplatin, carboplatin, or nedaplatin, and (ii) gemcitabine, pemetrexed, paclitaxel, albumin-bound paclitaxel, docetaxel, vinorelbine, vinblastine, etoposide, or irinotecan, wherein the anti-LAG-3 antibody and the anti-PD-1 antibody are administered in a cycle of once every three weeks.

2. The method of claim 1, wherein the PDCT comprises: (i) cisplatin or carboplatin, and (ii) paclitaxel, albumin-bound paclitaxel, or pemetrexed.

3. The method of claim 2, wherein the PDCT is administered in a cycle of once every three weeks.

4. The method of claim 3, wherein the PDCT is administered for four cycles.

5. The method of claim 1, wherein the NSCLC has a squamous histology.

6. The method of claim 1, wherein the NSCLC has a non-squamous histology.

7. The method of claim 1, wherein the NSCLC is unresectable, advanced, recurrent, and/or metastatic.

8. The method of claim 1, wherein the NSCLC is a stage IV NSCLC.

9. The method of claim 1, wherein the method is a first line therapy.

10. The method of claim 1, wherein one or more immune cells in tumor tissue from the subject express LAG-3 and/or one or more tumor cells in tumor tissue from the subject express PD-L1.

11. The method of claim 10, wherein:

(a) at least about 1% of the immune cells express LAG-3, and/or (b) at least about 1% of the tumor cells express PD-L1.

12. The method of claim 10, wherein at least about 1% of the tumor cells express PD-L1.

13. The method of claim 10, wherein at least about 1% to about 50% of the tumor cells express PD-L1.

14. The method of claim 1, wherein the anti-LAG-3 antibody and the anti-PD-1 antibody are formulated together.

15. The method of claim 1, wherein the anti-LAG-3 antibody and the anti-PD-1 antibody are formulated separately.

16. The method of claim 1, wherein the anti-LAG-3 antibody and the anti-PD-1 antibody are administered to the subject intravenously from a single intravenous bag for about 30 minutes.

17. The method of claim 1, wherein:

(a) the anti-LAG-3 antibody comprises heavy and light chain variable regions comprising the sequences set forth in SEQ ID NOs: 3 and 4, respectively, and the anti-PD-1 antibody comprises heavy and light chain variable regions comprising the sequences set forth in SEQ ID NOs: 13 and 14, respectively, (b) the anti-LAG-3 antibody comprises heavy and light chains comprising the sequences set forth in SEQ ID NOs: 1 and 2, respectively, and the anti-PD-1 antibody comprises heavy and light chains comprising the sequences set forth in SEQ ID NOs: 11 and 12, respectively, (c) the anti-LAG-3 antibody comprises heavy and light chains comprising the sequences set forth in SEQ ID NOs: 21 and 2, respectively, and the anti-PD-1 antibody comprises heavy and light chains comprising the sequences set forth in SEQ ID NOs: 11 and 12, respectively, or, (d) the anti-LAG-3 antibody comprises relatlimab and the anti-PD-1 antibody comprises nivolumab.

18. A method of treating a Stage IV or recurrent NSCLC that has a squamous histology in a human subject, the method comprising administering to the subject:

(a) about 360 mg of an anti-LAG-3 antibody comprising a heavy chain variable region CDR1, CDR2, and CDR3 comprising the sequences set forth in SEQ ID NO:5, SEQ ID NO: 6, and SEQ ID NO:7, respectively, and a light chain variable region CDR1, CDR2, and CDR3 comprising the sequences set forth in SEQ ID NO:8, SEQ ID NO:9, and SEQ ID NO:10, respectively, (b) about 360 mg of an anti-PD-1 antibody comprising a heavy chain variable region CDR1, CDR2, and CDR3 comprising the sequences set forth in SEQ ID NO:15, SEQ ID NO: 16, and SEQ ID NO: 17, respectively, and a light chain variable region CDR1, CDR2, and CDR3 comprising the sequences set forth in SEQ ID NO:18, SEQ ID NO: 19, and SEQ ID NO:20, respectively, and (c) a PDCT comprising:

(i) carboplatin for a target area under the concentration-time curve of about 6 mg/mL·min, and (ii) about 200 $mg/m^2$ of paclitaxel or about 100 $mg/m^2$ of albumin-bound paclitaxel, wherein the anti-LAG-3 antibody and the anti-PD-1 antibody are formulated together, wherein the anti-LAG-3 antibody, the anti-PD-1 antibody, and the PDCT are administered in a cycle of once every three weeks, and the PDCT is administered for four cycles, and wherein the method is a first line therapy.

19. The method of claim 18, wherein:

(a) the anti-LAG-3 antibody comprises heavy and light chain variable regions comprising the sequences set forth in SEQ ID NOs: 3 and 4, respectively, and the anti-PD-1 antibody comprises heavy and light chain variable regions comprising the sequences set forth in SEQ ID NOs: 13 and 14, respectively, (b) the anti-LAG-3 antibody comprises heavy and light chains comprising the sequences set forth in SEQ ID NOs: 1 and 2, respectively, and the anti-PD-1 antibody comprises heavy and light chains comprising the sequences set forth in SEQ ID NOs: 11 and 12, respectively, (c) the anti-LAG-3 antibody comprises heavy and light chains comprising the sequences set forth in SEQ ID NOs: 21 and 2, respectively, and the anti-PD-1 antibody comprises heavy and light chains comprising the sequences set forth in SEQ ID NOs: 11 and 12, respectively, or (d) the anti-LAG-3 antibody comprises relatlimab and the anti-PD-1 antibody comprises nivolumab.

20. A method of treating a Stage IV or recurrent NSCLC that has a non-squamous histology in a human subject, the method comprising administering to the subject:

(a) about 360 mg of an anti-LAG-3 antibody comprising a heavy chain variable region CDR1, CDR2, and CDR3 comprising the sequences set forth in SEQ ID NO:5, SEQ ID NO: 6, and SEQ ID NO:7, respectively, and a light chain variable region CDR1, CDR2, and CDR3 comprising the sequences set forth in SEQ ID NO:8, SEQ ID NO:9, and SEQ ID NO:10, respectively, (b) about 360 mg of an anti-PD-1 antibody comprising a heavy chain variable region CDR1, CDR2, and CDR3 comprising the sequences set forth in SEQ ID NO:15, SEQ ID NO: 16, and SEQ ID NO:17, respectively, and a light chain variable region CDR1, CDR2, and CDR3 comprising the sequences set forth in SEQ ID NO:18, SEQ ID NO: 19, and SEQ ID NO:20, respectively, and (c) a PDCT comprising:

(i) carboplatin for a target area under the concentration-time curve of about 5 mg/mL·min or about 6 mg/mL·min or about 75 $mg/m^2$ of cisplatin, and (ii) about 500 $mg/m^2$ of pemetrexed, wherein at least about 1% of tumor cells in tumor tissue from the subject express PD-L1, wherein the anti-LAG-3 antibody and the anti-PD-1 antibody are formulated together, wherein the anti-LAG-3 antibody, the anti-PD-1 antibody, and the PDCT are administered in a cycle of once every three weeks, and the PDCT is administered for four cycles, and wherein the method is a first line therapy.

21. The method of claim 20, wherein about 1% to about 50% of the tumor cells express PD-L1.

22. The method of claim 20, wherein:

(a) the anti-LAG-3 antibody comprises heavy and light chain variable regions comprising the sequences set forth in SEQ ID NOs: 3 and 4, respectively, and the anti-PD-1 antibody comprises heavy and light chain variable regions comprising the sequences set forth in SEQ ID NOs: 13 and 14, respectively, (b) the anti-LAG-3 antibody comprises heavy and light chains comprising the sequences set forth in SEQ ID NOs: 1 and 2, respectively, and the anti-PD-1 antibody comprises heavy and light chains comprising the sequences set forth in SEQ ID NOs: 11 and 12, respectively, (c) the anti-LAG-3 antibody comprises heavy and light chains comprising the sequences set forth in SEQ ID NOs: 21 and 2, respectively, and the anti-PD-1 antibody comprises heavy and light chains comprising the sequences set forth in SEQ ID NOs: 11 and 12, respectively, or (d) the anti-LAG-3 antibody comprises relatlimab and the anti-PD-1 antibody comprises nivolumab.

* * * * *